US011344615B2

(12) United States Patent
Kinney

(10) Patent No.: US 11,344,615 B2
(45) Date of Patent: May 31, 2022

(54) NUCLEIC ACIDS ENCODING CHIMERIC DENGUE/ZIKA VIRUSES OPTIMIZED FOR GROWTH AND STABILITY IN VERO CELLS

(71) Applicant: The U.S.A., as represented by the Secretary, Department of Health and Human Services, Bethesda, MD (US)

(72) Inventor: Claire Y. H. Kinney, Fort Collins, CO (US)

(73) Assignee: The United States of America, as represented by the Secretary, Department of Health and Human Services, Bethesda, MD (US)

(*) Notice: Subject to any disclaimer, the term of this patent is extended or adjusted under 35 U.S.C. 154(b) by 715 days.

(21) Appl. No.: 16/316,005

(22) PCT Filed: Jul. 6, 2017

(86) PCT No.: PCT/US2017/040820

§ 371 (c)(1),
(2) Date: Jan. 7, 2019

(87) PCT Pub. No.: WO2018/009604

PCT Pub. Date: Jan. 11, 2018

(65) Prior Publication Data

US 2021/0290749 A1 Sep. 23, 2021

Related U.S. Application Data

(60) Provisional application No. 62/359,812, filed on Jul. 8, 2016.

(51) Int. Cl.

*A61K 39/12* (2006.01)
*C07K 14/005* (2006.01)

(Continued)

(52) U.S. Cl.

CPC ........... *A61K 39/12* (2013.01); *C07K 14/005* (2013.01); *C07K 14/1825* (2013.01); *C12N 7/00* (2013.01);

(Continued)

(58) Field of Classification Search

CPC ........... A61K 39/12; A61K 2039/5252; A61K 2039/5256; C07K 14/005; C07K 14/1816;

(Continued)

(56) References Cited

U.S. PATENT DOCUMENTS 8,715,689 B2 5/2014 Kinney et al.
10,744,194 B2 * 8/2020 Barbero Calzado ... A61K 39/12

(Continued)

FOREIGN PATENT DOCUMENTS

WO WO 01/60847 8/2001

OTHER PUBLICATIONS

Huang, C. Y.-H., et al., Jun. 2005, Chimeric Dengue 2 PDK-53/West Nile NY99 Viruses Retain the Phenotypic Attenuation Markers of the Candidate PDK-53 Vaccine Virus and Protect Mice against Lethal Challenge with West Nile Virus, J. Virol. 79(12)7300-7310.*

(Continued)

*Primary Examiner* — Jeffrey S Parkin

(74) *Attorney, Agent, or Firm* — Klarquist Sparkman, LLP

(57) ABSTRACT

Chimeric flaviviruses that include non-coding regions, non-structural proteins, a capsid (C) protein and a portion of a premembrane (prM) signal sequence from an attenuated or wild-type dengue serotype 2 virus (DENV-2), and a portion of a prM signal sequence, a prM protein and at least a portion of an envelope (E) protein from a Zika virus (ZIKV) are described. Also described are immunogenic composi- (Continued)

tions and methods for eliciting an immune response in a subject, such as an immune response directed against ZIKV.

27 Claims, 3 Drawing Sheets

Specification includes a Sequence Listing.

(51) Int. Cl.
*C12N 7/00* (2006.01)
*C07K 14/18* (2006.01)
*A61K 39/00* (2006.01)

(52) U.S. Cl.
CPC ................. *A61K 2039/5252* (2013.01); *A61K 2039/5256* (2013.01); *C07K 14/1816* (2013.01); *C12N 2770/24122* (2013.01); *C12N 2770/24134* (2013.01); *C12N 2770/24141* (2013.01); *C12N 2770/24144* (2013.01)

(58) Field of Classification Search
CPC .................. C07K 14/1825; C12N 7/00; C12N 2770/24144; C12N 2770/24141; C12N 2770/24122; C12N 2770/24134; C12N 2770/24121; C12N 2770/24143; C12N 2770/24164
See application file for complete search history.

(56) References Cited

U.S. PATENT DOCUMENTS

| | | | | |
|---|---|---|---|---|
| 10,947,277 | B2 * | 3/2021 | Chang | C12N 15/86 |
| 2017/0114330 | A1 | 4/2017 | Kinney | |

OTHER PUBLICATIONS

Azevedo, A. S., et al., Mar. 2013, The Synergistic Effect of Combined Immunization with a DNA Vaccine and Chimeric Yellow Fever/Dengue Virus Leads to Strong Protection against Dengue, PLoS ONE 8(3):e58357 (pp. 1-10).*

Barrett et al., "Vero Cell Platform in Vaccine Production: Moving towards Cell Culture-Based Viral Vaccines," *Expert Rev. Vaccines*, vol. 8:607-618, 2009.

Cohen, "The race for a Zika vaccine is on," *Science*, vol. 351:543-544, 2016.

Durbin, "Vaccine Development for Zika Virus—Timelines and Strategies," *Semin. Reprod. Med.*, vol. 34:299-304, 2016.

Huang et al., "Chimeric Dengue 2 PDK-53/West Nile NY99 Viruses Retain the Phenotypic Attenuation Markers of the Candidate PDK-53 Vaccine Virus and Protect Mice against Lethal Challenge with West Nile Virus," *J. Virol.*, vol. 79:7300-7310, 2005.

Shan et al., "A Live-Attenuated Zika Virus Vaccine Candidate Induces Sterilizing Immunity in Mouse Models," *Nat. Med.*, vol. 23:763-767, 2017.

Shan et al., "Zika Virus: Diagnosis, Therapeutics, and Vaccine," *ACS Infect. Dis.*, vol. 2:170-172, 2016.

* cited by examiner

C6/36 Growth Curve
Geometric Mean Titer
10.00
9.00
8.00
7.00
6.00
5.00
4.00
3.00
2.00
1.00
0.00
0
1
2
3
4
5
6
7
8
9
10
12
Days post-infection
1
2
3
4
5
1 ZIKV PRVABC
2 D2/ZK-V5
3 DEN2 16681
4 DEN 2 PDK-53
5 D2/ZK-P5

Vero Growth Curve
Geometric Mean Titer
8.00
7.00
6.00
5.00
4.00
3.00
2.00
1.00
0
1
2
3
4
5
6
7
8
9
10
12
Days post-infection
1
2
3
4
1 ZIKV PRVABC59
2 Den2 16681
3 D2/ZK-P5
4 D2/ZK-V5

SEQUENCE LISTING

<160> NUMBER OF SEQ ID NOS: 26

<210> SEQ ID NO 1
<211> LENGTH: 10768
<212> TYPE: DNA
<213> ORGANISM: Artificial Sequence
<220> FEATURE:
<223> OTHER INFORMATION: Synthetic construct

<400> SEQUENCE: 1

```
agttgttagt ctacgtggac cgacaaagac agattctttg agggagctaa gctcaatgta     60

gttctaacag tttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatccg cgggtactag tgtcggaatt    420

gttggcctcc tgctgaccac agctatggca gcggaggtca ctagacgtgg gagtgcatac    480

tatatgtact tggacagaaa cgatgctggg gaggccatat cttttccaac cacattgggg    540

atgaataagt gttatataca gatcatggat cttggacaca tgtgtgatgc caccatgagc    600

tatgaatgcc ctatgctgga tgagggggtg gaaccagatg acgtcgattg ttggtgcaac    660

acgacgtcaa cttgggttgt gtacggaacc tgccatcaca aaaaaggtga agcacggaga    720

agtagaagag ctgtgacgct cccctcccat tccactagga agctgcaaac gcggtcgcaa    780

acctggttgg aatcaagaga atacacaaag cacttgatta gagtcgaaaa ttggatattc    840

aggaaccctg gcttcgcgtt agcagcagct gccatcgctt ggcttttggg aagctcaacg    900

agccaaaaag tcatatactt ggtcatgata ctgctgattg ccccggcata cagcatcagg    960

tgcataggag tcagcaatag ggactttgtg gaaggtatgt caggtgggac ttgggttgat   1020

attgtcttgg aacatggagg ttgtgtcacc gtaatggcac aggacaaacc gactgtcgac   1080

atagagctgg ttacaacaac agtcagcaac atggcggagg taagatccta ctgctatgag   1140

gcatcaatat cagacatggc ttcggacagc cgctgcccaa cacaaggtga agcctacctt   1200

gacaagcaat cagacactca atatgtctgc aaaagaacgt tagtggacag aggctgggga   1260

aatggatgtg gactttttgg caaagggagt ctggtgacat gcgctaagtt tgcatgctcc   1320

aagaaaatga ccgggaagag catccagcca gagaatctgg agtaccggat aatgctgtca   1380

gttcatggct cccagcacag tgggatgatc gttaatgaca caggacatga aactgatgag   1440

aatagagcga aggttgagat aacgcccaat tcaccaagag ccgaagccac cctgggggt    1500

tttggaagcc taggacttga ttgtgaaccg aggacaggcc ttgacttttc agatttgtat   1560

tacttgacta tgaataacaa gcactggttg gttcacaagg agtggttcca cgacattcca   1620

ttaccttggc acgctggggc agacaccgga actccacact ggaacaacaa agaagcactg   1680

gtagagttca aggacgcaca tgccaaaagg caaactgtcg tggttctagg gagtcaagaa   1740

ggagcagttc acacggccct tgctggagct ctggaggctg agatggatgg tgcaaaggga   1800

aggctgtcct ctggccactt gaaatgtcgc ctgaaaatgg ataaacttag attgaagggc   1860

gtgtcatact ccttgtgtac cgcagcgttc acattcacca agatcccggc tgaaacactg   1920

cacgggacag tcacagtgga ggtacagtac gcagggacag atggaccttg caaggttcca   1980

gctcagatgg cggtggacat gcaaactctg accccagttg ggaggttgat aaccgctaac   2040
```

-continued

```
cccgtaatca ctgaaagcac tgagaactct aagatgatgc tggaacttga tccaccattt   2100

ggggactctt acattgtcat aggagtcggg gagaagaaga tcacccacca ctggcacagg   2160

agtggcagca ccattggaaa agcatttgaa gccactgtga gaggtgccaa gagaatggca   2220

gtcttgggag acacagcctg ggactttgga tcagttggag gcgctctcaa ctcattgggc   2280

aagggcatcc atcaaatttt tggagcagct ttcaaatcat tgtttggagg aatgtcctgg   2340

ttctcacaaa ttctcattgg aacgttgctg atgtggttgg gtctgaacac aaagaatgga   2400

tctatttccc ttatgtgctt ggccgccggc attgtgacac tgtatttggg agtcatggtg   2460

caggccgata gtggttgcgt tgtgagctgg aaaaacaaag aactgaaatg tggcagtggg   2520

attttcatca cagacaacgt gcacacatgg acagaacaat acaagttcca accagaatcc   2580

ccttcaaaac tagcttcagc tatccagaaa gcccatgaag aggacatttg tggaatccgc   2640

tcagtaacaa gactggagaa tctgatgtgg aaacaaataa caccagaatt gaatcacatt   2700

ctatcagaaa atgaggtgaa gttaactatt atgacaggag acatcaaagg aatcatgcag   2760

gcaggaaaac gatctctgcg gcctcagccc actgagctga agtattcatg gaaaacatgg   2820

ggcaaagcaa aaatgctctc tacagagtct cataaccaga cctttctcat tgatggcccc   2880

gaaacagcag aatgccccaa cacaaataga gcttggaatt cgttggaagt tgaagactat   2940

ggctttggag tattcaccac caatatatgg ctaaaattga aagaaaaaca ggatgtattc   3000

tgcgactcaa aactcatgtc agcggccata aaagacaaca gagccgtcca tgccgatatg   3060

ggttattgga tagaaagtgc actcaatgac acatggaaga tagagaaagc ctctttcatt   3120

gaagttaaaa actgccactg gccaaaatca cacaccctct ggagcaatgg agtgctagaa   3180

agtgagatga taattccaaa gaatctcgct ggaccagtgt ctcaacacaa ctatagacca   3240

ggctaccata cacaaataac aggaccatgg catctaggta agcttgagat ggactttgat   3300

ttctgtgatg gaacaacagt ggtagtgact gaggactgcg gaaatagagg accctctttg   3360

agaacaacca ctgcctctgg aaaactcata acagaatggt gctgccgatc ttgcacatta   3420

ccaccgctaa gatacagagg tgaggatggg tgctggtacg ggatggaaat cagaccattg   3480

aaggagaaag aagagaattt ggtcaactcc ttggtcacag ctggacatgg gcaggtcgac   3540

aacttttcac taggagtctt gggaatggca ttgttcctgg aggaaatgct taggacccga   3600

gtaggaacga aacatgcaat actactagtt gcagtttctt ttgtgacatt gatcacaggg   3660

aacatgtcct ttagagacct gggaagagtg atggttatgg taggcgccac tatgacggat   3720

gacataggta tgggcgtgac ttatcttgcc ctactagcag ccttcaaagt cagaccaact   3780

tttgcagctg gactactctt gagaaagctg acctccaagg aattgatgat gactactata   3840

ggaattgtac tcctctccca gagcaccata ccagagacca ttcttgagtt gactgatgcg   3900

ttagccttag gcatgatggt cctcaaaatg gtgagaaata tggaaaagta tcaattggca   3960

gtgactatca tggctatctt gtgcgtccca aacgcagtga tattacaaaa cgcatggaaa   4020

gtgagttgca caatattggc agtggtgtcc gtttccccac tgttcttaac atcctcacag   4080

caaaaaacag attggatacc attagcattg acgatcaaag gtctcaatcc aacagctatt   4140

tttctaacaa ccctctcaag aaccagcaag aaaaggagct ggccattaaa tgaggctatc   4200

atggcagtcg ggatggtgag cattttagcc agttctctcc taaaaaatga tattcccatg   4260

acaggaccat tagtggctgg agggctcctc actgtgtgct acgtgctcac tggacgatcg   4320

gccgatttgg aactggagag agcagccgat gtcaaatggg aagaccaggc agagatatca   4380
```

```
ggaagcagtc caatcctgtc aataacaata tcagaagatg gtagcatgtc gataaaaaat   4440
gaagaggaag aacaaacact gaccatactc attagaacag gattgctggt gatctcagga   4500
ctttttcctg tatcaatacc aatcacggca gcagcatggt acctgtggga agtgaagaaa   4560
caacgggccg gagtattgtg ggatgttcct tcacccccac ccatgggaaa ggctgaactg   4620
gaagatggag cctatagaat taagcaaaaa gggattcttg gatattccca gatcggagcc   4680
ggagtttaca aagaaggaac attccataca atgtggcatg tcacacgtgg cgctgttcta   4740
atgcataaag gaaagaggat tgaaccatca tgggcggacg tcaagaaaga cctaatatca   4800
tatggaggag gctggaagtt agaaggagaa tggaaggaag gagaagaagt ccaggtattg   4860
gcactggagc ctggaaaaaa tccaagagcc gtccaaacga aacctggtct tttcaaaacc   4920
aacgccggaa caataggtgc tgtatctctg gacttttctc ctggaacgtc aggatctcca   4980
attatcgaca aaaaaggaaa agttgtgggt ctttatggta atggtgttgt tacaaggagt   5040
ggagcatatg tgagtgctat agcccagact gaaaaaagca ttgaagacaa cccagagatc   5100
gaagatgaca ttttccgaaa gagaagactg accatcatgg acctccaccc aggagcggga   5160
aagacgaaga gataccttcc ggccatagtc agagaagcta taaaacgggg tttgagaaca   5220
ttaatcttgg cccccactag agttgtggca gctgaaatgg aggaagccct tagaggactt   5280
ccaataagat accagacccc agccatcaga gctgtgcaca ccgggcggga gattgtggac   5340
ctaatgtgtc atgccacatt taccatgagg ctgctatcac cagttagagt gccaaactac   5400
aacctgatta tcatggacga agcccatttc acagacccag caagtatagc agctagagga   5460
tacatctcaa ctcgagtgga gatgggtgag gcagctggga tttttatgac agccactccc   5520
ccgggaagca gagacccatt tcctcagagc aatgcaccaa tcatagatga agaaagagaa   5580
atccctgaac gctcgtggaa ttccggacat gaatgggtca cggattttaa agggaagact   5640
gtttggttcg ttccaagtat aaaagcagga aatgatatag cagcttgcct gaggaaaaat   5700
ggaaagaaag tgatacaact cagtaggaag acctttgatt ctgagtatgt caagactaga   5760
accaatgatt gggacttcgt ggttacaact gacatttcag aaatgggtgc caatttcaag   5820
gctgagaggg ttatagaccc cagacgctgc atgaaaccag tcatactaac agatggtgaa   5880
gagcgggtga ttctggcagg acctatgcca gtgacccact ctagtgcagc acaaagaaga   5940
gggagaatag gaagaaatcc aaaaaatgag aatgaccagt acatatacat gggggaacct   6000
ctggaaaatg atgaagactg tgcacactgg aaagaagcta aaatgctcct agataacatc   6060
aacacgccag aaggaatcat tcctagcatg ttcgaaccag agcgtgaaaa ggtggatgcc   6120
attgatggcg aataccgctt gagaggagaa gcaaggaaaa cctttgtaga cttaatgaga   6180
agaggagacc taccagtctg gttggcctac agagtggcag ctgaaggcat caactacgca   6240
gacagaaggt ggtgttttga tggagtcaag aacaaccaaa tcctagaaga aaacgtggaa   6300
gttgaaatct ggacaaaaga aggggaaagg aagaaattga aacccagatg gttggatgct   6360
aggatctatt ctgacccact ggcgctaaaa gaatttaagg aatttgcagc cggaagaaag   6420
tctctgaccc tgaacctaat cacagaaatg ggtaggctcc caaccttcat gactcagaag   6480
gcaagagacg cactggacaa cttagcagtg ctgcacacgg ctgaggcagg tggaagggcg   6540
tacaaccatg ctctcagtga actgccggag accctggaga cattgctttt actgacactt   6600
ctggctacag tcacgggagg gatcttttta ttcttgatga gcgcaagggg catagggaag   6660
atgaccctgg gaatgtgctg cataatcacg gctagcatcc tcctatggta cgcacaaata   6720
cagccacact ggatagcagc ttcaataata ctggagtttt ttctcatagt tttgcttatt   6780
```

```
ccagaacctg aaaaacagag aacaccccaa gacaaccaac tgacctacgt tgtcatagcc   6840
atcctcacag tggtggccgc aaccatggca aacgagatgg gtttcctaga aaaaacgaag   6900
aaagatctcg gattgggaag cattgcaacc cagcaacccg agagcaacat cctggacata   6960
gatctacgtc ctgcatcagc atggacgctg tatgccgtgg ccacaacatt tgttacacca   7020
atgttgagac atagcattga aaattcctca gtgaatgtgt ccctaacagc tatagccaac   7080
caagccacag tgttaatggg tctcgggaaa ggatggccat tgtcaaagat ggacatcgga   7140
gttccccttc tcgccattgg atgctactca caagtcaacc ccataactct cacagcagct   7200
cttttcttat tggtagcaca ttatgccatc atagggccag gactccaagc aaaagcaacc   7260
agagaagctc agaaaagagc agcggcgggc atcatgaaaa acccaactgt cgatggaata   7320
acagtgattg acctagatcc aataccttat gatccaaagt ttgaaaagca gttgggacaa   7380
gtaatgctcc tagtcctctg cgtgactcaa gtattgatga tgaggactac atgggctctg   7440
tgtgaggctt taaccttagc taccgggccc atctccacat tgtgggaagg aaatccaggg   7500
aggttttgga acactaccat tgcggtgtca atggctaaca tttttagagg gagttacttg   7560
gccggagctg gacttctctt ttctattatg aagaacacaa ccaacacaag aaggggaact   7620
ggcaacatag gagagacgct tggagagaaa tggaaaagcc gattgaacgc attgggaaaa   7680
agtgaattcc agatctacaa gaaaagtgga atccaggaag tggatagaac cttagcaaaa   7740
gaaggcatta aaagaggaga aacggaccat cacgctgtgt cgcgaggctc agcaaaactg   7800
agatggttcg ttgagagaaa catggtcaca ccagaaggga aagtagtgga cctcggttgt   7860
ggcagaggag gctggtcata ctattgtgga ggactaaaga atgtaagaga agtcaaaggc   7920
ctaacaaaag gaggaccagg acacgaagaa cccatcccca tgtcaacata tgggtggaat   7980
ctagtgcgtc ttcaaagtgg agttgacgtt ttcttcatcc cgccagaaaa gtgtgacaca   8040
ttattgtgtg acatagggga gtcatcacca aatcccacag tggaagcagg acgaacactc   8100
agagtcctta acttagtaga aaattggttg aacaacaaca ctcaattttg cataaaggtt   8160
ctcaacccat atatgccctc agtcatagaa aaaatggaag cactacaaag gaaatatgga   8220
ggagccttag tgaggaatcc actctcacga aactccacac atgagatgta ctgggtatcc   8280
aatgcttccg ggaacatagt gtcatcagtg aacatgattt caaggatgtt gatcaacaga   8340
tttacaatga gatacaagaa agccacttac gagccggatg ttgacctcgg aagcggaacc   8400
cgtaacatcg ggattgaaag tgagatacca aacctagata taattgggaa aagaatagaa   8460
aaaataaagc aagagcatga aacatcatgg cactatgacc aagaccaccc atacaaaacg   8520
tgggcatacc atggtagcta tgaaacaaaa cagactggat cagcatcatc catggtcaac   8580
ggagtggtca ggctgctgac aaaaccttgg gacgtcgtcc ccatggtgac acagatggca   8640
atgacagaca cgactccatt tggacaacag cgcgttttta aagagaaagt ggacacgaga   8700
acccaagaac cgaaagaagg cacgaagaaa ctaatgaaaa taacagcaga gtggctttgg   8760
aaagaattag ggaagaaaaa gacacccagg atgtgcacca gagaagaatt cacaagaaag   8820
gtgagaagca atgcagcctt gggggccata ttcactgatg agaacaagtg gaagtcggca   8880
cgtgaggctg ttgaagatag taggttttgg gagctggttg acaaggaaag gaatctccat   8940
cttgaaggaa agtgtgaaac atgtgtgtac aacatgatgg gaaaaagaga gaagaagcta   9000
ggggaattcg gcaaggcaaa aggcagcaga gccatatggt acatgtggct tggagcacgc   9060
ttcttagagt ttgaagccct aggattctta aatgaagatc actggttctc cagagagaac   9120
```

```
tccctgagtg gagtggaagg agaagggctg cacaagctag gttacattct aagagacgtg   9180

agcaagaaag agggaggagc aatgtatgcc gatgacaccg caggatggga tacaagaatc   9240

acactagaag acctaaaaaa tgaagaaatg gtaacaaacc acatggaagg agaacacaag   9300

aaactagccg aggccatttt caaactaacg taccaaaaca aggtggtgcg tgtgcaaaga   9360

ccaacaccaa gaggcacagt aatggacatc atatcgagaa gagaccaaag aggtagtgga   9420

caagttggca cctatggact caatactttc accaatatgg aagcccaact aatcagacag   9480

atggagggag aaggagtctt taaaagcatt cagcacctaa caatcacaga agaaatcgct   9540

gtgcaaaact ggttagcaag agtggggcgc gaaaggttat caagaatggc catcagtgga   9600

gatgattgtg ttgtgaaacc tttagatgac aggttcgcaa gcgctttaac agctctaaat   9660

gacatgggaa agattaggaa agacatacaa caatgggaac cttcaagagg atggaatgat   9720

tggacacaag tgcccttctg ttcacaccat ttccatgagt taatcatgaa agacggtcgc   9780

gtactcgttg ttccatgtag aaaccaagat gaactgattg gcagagcccg aatctcccaa   9840

ggagcagggt ggtctttgcg ggagacggcc tgtttgggga agtcttacgc ccaaatgtgg   9900

agcttgatgt acttccacag acgcgacctc aggctggcgg caaatgctat ttgctcggca   9960

gtaccatcac attgggttcc aacaagtcga acaacctggt ccatacatgc taaacatgaa  10020

tggatgacaa cggaagacat gctgacagtc tggaacaggg tgtggattca agaaaaccca  10080

tggatggaag acaaaactcc agtggaatca tgggaggaaa tcccatactt ggggaaaaga  10140

gaagaccaat ggtgcggctc attgattggg ttaacaagca gggccacctg ggcaaagaac  10200

atccaagcag caataaatca agttagatcc cttataggca atgaagaata cacagattac  10260

atgccatcca tgaaaagatt cagaagagaa gaggaagaag caggagttct gtggtagaaa  10320

gcaaaactaa catgaaacaa ggctagaagt caggtcggat taagccatag tacggaaaaa  10380

actatgctac ctgtgagccc cgtccaagga cgttaaaaga agtcaggcca tcataaatgc  10440

catagcttga gtaaactatg cagcctgtag ctccacctga gaaggtgtaa aaaatccggg  10500

aggccacaaa ccatggaagc tgtacgcatg gcgtagtgga ctagcggtta gaggagaccc  10560

ctcccttaca aatcgcagca acaatggggg cccaaggcga gatgaagctg tagtctcgct  10620

ggaaggacta gaggttagag gagacccccc cgaaacaaaa aacagcatat tgacgctggg  10680

aaagaccaga gatcctgctg tctcctcagc atcattccag gcacagaacg ccagaaaatg  10740

gaatggtgct gttgaatcaa caggttct                                     10768
```

<210> SEQ ID NO 2
<211> LENGTH: 3406
<212> TYPE: PRT
<213> ORGANISM: Artificial Sequence
<220> FEATURE:
<223> OTHER INFORMATION: Synthetic polypeptide

<400> SEQUENCE: 2

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
```

-continued

```
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Thr Ser Val Gly Ile Val Gly Leu Leu
            100                 105                 110

Leu Thr Thr Ala Met Ala Ala Glu Val Thr Arg Arg Gly Ser Ala Tyr
        115                 120                 125

Tyr Met Tyr Leu Asp Arg Asn Asp Ala Gly Glu Ala Ile Ser Phe Pro
    130                 135                 140

Thr Thr Leu Gly Met Asn Lys Cys Tyr Ile Gln Ile Met Asp Leu Gly
145                 150                 155                 160

His Met Cys Asp Ala Thr Met Ser Tyr Glu Cys Pro Met Leu Asp Glu
                165                 170                 175

Gly Val Glu Pro Asp Asp Val Asp Cys Trp Cys Asn Thr Thr Ser Thr
            180                 185                 190

Trp Val Val Tyr Gly Thr Cys His His Lys Lys Gly Glu Ala Arg Arg
        195                 200                 205

Ser Arg Arg Ala Val Thr Leu Pro Ser His Ser Thr Arg Lys Leu Gln
    210                 215                 220

Thr Arg Ser Gln Thr Trp Leu Glu Ser Arg Glu Tyr Thr Lys His Leu
225                 230                 235                 240

Ile Arg Val Glu Asn Trp Ile Phe Arg Asn Pro Gly Phe Ala Leu Ala
                245                 250                 255

Ala Ala Ala Ile Ala Trp Leu Leu Gly Ser Ser Thr Ser Gln Lys Val
            260                 265                 270

Ile Tyr Leu Val Met Ile Leu Leu Ile Ala Pro Ala Tyr Ser Ile Arg
        275                 280                 285

Cys Ile Gly Val Ser Asn Arg Asp Phe Val Glu Gly Met Ser Gly Gly
    290                 295                 300

Thr Trp Val Asp Ile Val Leu Glu His Gly Gly Cys Val Thr Val Met
305                 310                 315                 320

Ala Gln Asp Lys Pro Thr Val Asp Ile Glu Leu Val Thr Thr Thr Val
                325                 330                 335

Ser Asn Met Ala Glu Val Arg Ser Tyr Cys Tyr Glu Ala Ser Ile Ser
            340                 345                 350

Asp Met Ala Ser Asp Ser Arg Cys Pro Thr Gln Gly Glu Ala Tyr Leu
        355                 360                 365

Asp Lys Gln Ser Asp Thr Gln Tyr Val Cys Lys Arg Thr Leu Val Asp
    370                 375                 380

Arg Gly Trp Gly Asn Gly Cys Gly Leu Phe Gly Lys Gly Ser Leu Val
385                 390                 395                 400

Thr Cys Ala Lys Phe Ala Cys Ser Lys Lys Met Thr Gly Lys Ser Ile
                405                 410                 415

Gln Pro Glu Asn Leu Glu Tyr Arg Ile Met Leu Ser Val His Gly Ser
            420                 425                 430

Gln His Ser Gly Met Ile Val Asn Asp Thr Gly His Glu Thr Asp Glu
        435                 440                 445

Asn Arg Ala Lys Val Glu Ile Thr Pro Asn Ser Pro Arg Ala Glu Ala
    450                 455                 460

Thr Leu Gly Gly Phe Gly Ser Leu Gly Leu Asp Cys Glu Pro Arg Thr
465                 470                 475                 480

Gly Leu Asp Phe Ser Asp Leu Tyr Tyr Leu Thr Met Asn Asn Lys His
                485                 490                 495
```

```
Trp Leu Val His Lys Glu Trp Phe His Asp Ile Pro Leu Pro Trp His
            500                 505                 510

Ala Gly Ala Asp Thr Gly Thr Pro His Trp Asn Asn Lys Glu Ala Leu
        515                 520                 525

Val Glu Phe Lys Asp Ala His Ala Lys Arg Gln Thr Val Val Val Leu
    530                 535                 540

Gly Ser Gln Glu Gly Ala Val His Thr Ala Leu Ala Gly Ala Leu Glu
545                 550                 555                 560

Ala Glu Met Asp Gly Ala Lys Gly Arg Leu Ser Ser Gly His Leu Lys
                565                 570                 575

Cys Arg Leu Lys Met Asp Lys Leu Arg Leu Lys Gly Val Ser Tyr Ser
            580                 585                 590

Leu Cys Thr Ala Ala Phe Thr Phe Thr Lys Ile Pro Ala Glu Thr Leu
        595                 600                 605

His Gly Thr Val Thr Val Glu Val Gln Tyr Ala Gly Thr Asp Gly Pro
    610                 615                 620

Cys Lys Val Pro Ala Gln Met Ala Val Asp Met Gln Thr Leu Thr Pro
625                 630                 635                 640

Val Gly Arg Leu Ile Thr Ala Asn Pro Val Ile Thr Glu Ser Thr Glu
                645                 650                 655

Asn Ser Lys Met Met Leu Glu Leu Asp Pro Pro Phe Gly Asp Ser Tyr
            660                 665                 670

Ile Val Ile Gly Val Gly Glu Lys Lys Ile Thr His His Trp His Arg
        675                 680                 685

Ser Gly Ser Thr Ile Gly Lys Ala Phe Glu Ala Thr Val Arg Gly Ala
    690                 695                 700

Lys Arg Met Ala Val Leu Gly Asp Thr Ala Trp Asp Phe Gly Ser Val
705                 710                 715                 720

Gly Gly Ala Leu Asn Ser Leu Gly Lys Gly Ile His Gln Ile Phe Gly
                725                 730                 735

Ala Ala Phe Lys Ser Leu Phe Gly Gly Met Ser Trp Phe Ser Gln Ile
            740                 745                 750

Leu Ile Gly Thr Leu Leu Met Trp Leu Gly Leu Asn Thr Lys Asn Gly
        755                 760                 765

Ser Ile Ser Leu Met Cys Leu Ala Ala Gly Ile Val Thr Leu Tyr Leu
    770                 775                 780

Gly Val Met Val Gln Ala Asp Ser Gly Cys Val Val Ser Trp Lys Asn
785                 790                 795                 800

Lys Glu Leu Lys Cys Gly Ser Gly Ile Phe Ile Thr Asp Asn Val His
                805                 810                 815

Thr Trp Thr Glu Gln Tyr Lys Phe Gln Pro Glu Ser Pro Ser Lys Leu
            820                 825                 830

Ala Ser Ala Ile Gln Lys Ala His Glu Glu Asp Ile Cys Gly Ile Arg
        835                 840                 845

Ser Val Thr Arg Leu Glu Asn Leu Met Trp Lys Gln Ile Thr Pro Glu
    850                 855                 860

Leu Asn His Ile Leu Ser Glu Asn Glu Val Lys Leu Thr Ile Met Thr
865                 870                 875                 880

Gly Asp Ile Lys Gly Ile Met Gln Ala Gly Lys Arg Ser Leu Arg Pro
                885                 890                 895

Gln Pro Thr Glu Leu Lys Tyr Ser Trp Lys Thr Trp Gly Lys Ala Lys
            900                 905                 910
```

```
Met Leu Ser Thr Glu Ser His Asn Gln Thr Phe Leu Ile Asp Gly Pro
        915                 920                 925

Glu Thr Ala Glu Cys Pro Asn Thr Asn Arg Ala Trp Asn Ser Leu Glu
    930                 935                 940

Val Glu Asp Tyr Gly Phe Gly Val Phe Thr Thr Asn Ile Trp Leu Lys
945                 950                 955                 960

Leu Lys Glu Lys Gln Asp Val Phe Cys Asp Ser Lys Leu Met Ser Ala
                965                 970                 975

Ala Ile Lys Asp Asn Arg Ala Val His Ala Asp Met Gly Tyr Trp Ile
            980                 985                 990

Glu Ser Ala Leu Asn Asp Thr Trp  Lys Ile Glu Lys Ala  Ser Phe Ile
        995                 1000                 1005

Glu Val  Lys Asn Cys His Trp  Pro Lys Ser His Thr  Leu Trp Ser
    1010                 1015                 1020

Asn Gly  Val Leu Glu Ser Glu  Met Ile Ile Pro Lys  Asn Leu Ala
    1025                 1030                 1035

Gly Pro  Val Ser Gln His Asn  Tyr Arg Pro Gly Tyr  His Thr Gln
    1040                 1045                 1050

Ile Thr  Gly Pro Trp His Leu  Gly Lys Leu Glu Met  Asp Phe Asp
    1055                 1060                 1065

Phe Cys  Asp Gly Thr Thr Val  Val Val Thr Glu Asp  Cys Gly Asn
    1070                 1075                 1080

Arg Gly  Pro Ser Leu Arg Thr  Thr Thr Ala Ser Gly  Lys Leu Ile
    1085                 1090                 1095

Thr Glu  Trp Cys Cys Arg Ser  Cys Thr Leu Pro Pro  Leu Arg Tyr
    1100                 1105                 1110

Arg Gly  Glu Asp Gly Cys Trp  Tyr Gly Met Glu Ile  Arg Pro Leu
    1115                 1120                 1125

Lys Glu  Lys Glu Glu Asn Leu  Val Asn Ser Leu Val  Thr Ala Gly
    1130                 1135                 1140

His Gly  Gln Val Asp Asn Phe  Ser Leu Gly Val Leu  Gly Met Ala
    1145                 1150                 1155

Leu Phe  Leu Glu Glu Met Leu  Arg Thr Arg Val Gly  Thr Lys His
    1160                 1165                 1170

Ala Ile  Leu Leu Val Ala Val  Ser Phe Val Thr Leu  Ile Thr Gly
    1175                 1180                 1185

Asn Met  Ser Phe Arg Asp Leu  Gly Arg Val Met Val  Met Val Gly
    1190                 1195                 1200

Ala Thr  Met Thr Asp Asp Ile  Gly Met Gly Val Thr  Tyr Leu Ala
    1205                 1210                 1215

Leu Leu  Ala Ala Phe Lys Val  Arg Pro Thr Phe Ala  Ala Gly Leu
    1220                 1225                 1230

Leu Leu  Arg Lys Leu Thr Ser  Lys Glu Leu Met Met  Thr Thr Ile
    1235                 1240                 1245

Gly Ile  Val Leu Leu Ser Gln  Ser Thr Ile Pro Glu  Thr Ile Leu
    1250                 1255                 1260

Glu Leu  Thr Asp Ala Leu Ala  Leu Gly Met Met Val  Leu Lys Met
    1265                 1270                 1275

Val Arg  Asn Met Glu Lys Tyr  Gln Leu Ala Val Thr  Ile Met Ala
    1280                 1285                 1290

Ile Leu  Cys Val Pro Asn Ala  Val Ile Leu Gln Asn  Ala Trp Lys
    1295                 1300                 1305

Val Ser  Cys Thr Ile Leu Ala  Val Val Ser Val Ser  Pro Leu Phe
```

```
    1310                1315                1320

Leu Thr  Ser Ser Gln Gln Lys  Thr Asp Trp Ile Pro  Leu Ala Leu
    1325                1330                1335

Thr Ile  Lys Gly Leu Asn Pro  Thr Ala Ile Phe Leu  Thr Thr Leu
    1340                1345                1350

Ser Arg  Thr Ser Lys Lys Arg  Ser Trp Pro Leu Asn  Glu Ala Ile
    1355                1360                1365

Met Ala  Val Gly Met Val Ser  Ile Leu Ala Ser Ser  Leu Leu Lys
    1370                1375                1380

Asn Asp  Ile Pro Met Thr Gly  Pro Leu Val Ala Gly  Gly Leu Leu
    1385                1390                1395

Thr Val  Cys Tyr Val Leu Thr  Gly Arg Ser Ala Asp  Leu Glu Leu
    1400                1405                1410

Glu Arg  Ala Ala Asp Val Lys  Trp Glu Asp Gln Ala  Glu Ile Ser
    1415                1420                1425

Gly Ser  Ser Pro Ile Leu Ser  Ile Thr Ile Ser Glu  Asp Gly Ser
    1430                1435                1440

Met Ser  Ile Lys Asn Glu Glu  Glu Glu Gln Thr Leu  Thr Ile Leu
    1445                1450                1455

Ile Arg  Thr Gly Leu Leu Val  Ile Ser Gly Leu Phe  Pro Val Ser
    1460                1465                1470

Ile Pro  Ile Thr Ala Ala Ala  Trp Tyr Leu Trp Glu  Val Lys Lys
    1475                1480                1485

Gln Arg  Ala Gly Val Leu Trp  Asp Val Pro Ser Pro  Pro Pro Met
    1490                1495                1500

Gly Lys  Ala Glu Leu Glu Asp  Gly Ala Tyr Arg Ile  Lys Gln Lys
    1505                1510                1515

Gly Ile  Leu Gly Tyr Ser Gln  Ile Gly Ala Gly Val  Tyr Lys Glu
    1520                1525                1530

Gly Thr  Phe His Thr Met Trp  His Val Thr Arg Gly  Ala Val Leu
    1535                1540                1545

Met His  Lys Gly Lys Arg Ile  Glu Pro Ser Trp Ala  Asp Val Lys
    1550                1555                1560

Lys Asp  Leu Ile Ser Tyr Gly  Gly Gly Trp Lys Leu  Glu Gly Glu
    1565                1570                1575

Trp Lys  Glu Gly Glu Glu Val  Gln Val Leu Ala Leu  Glu Pro Gly
    1580                1585                1590

Lys Asn  Pro Arg Ala Val Gln  Thr Lys Pro Gly Leu  Phe Lys Thr
    1595                1600                1605

Asn Ala  Gly Thr Ile Gly Ala  Val Ser Leu Asp Phe  Ser Pro Gly
    1610                1615                1620

Thr Ser  Gly Ser Pro Ile Ile  Asp Lys Lys Gly Lys  Val Val Gly
    1625                1630                1635

Leu Tyr  Gly Asn Gly Val Val  Thr Arg Ser Gly Ala  Tyr Val Ser
    1640                1645                1650

Ala Ile  Ala Gln Thr Glu Lys  Ser Ile Glu Asp Asn  Pro Glu Ile
    1655                1660                1665

Glu Asp  Asp Ile Phe Arg Lys  Arg Arg Leu Thr Ile  Met Asp Leu
    1670                1675                1680

His Pro  Gly Ala Gly Lys Thr  Lys Arg Tyr Leu Pro  Ala Ile Val
    1685                1690                1695

Arg Glu  Ala Ile Lys Arg Gly  Leu Arg Thr Leu Ile  Leu Ala Pro
    1700                1705                1710
```

```
Thr Arg  Val Val Ala Ala Glu  Met Glu Glu Ala Leu  Arg Gly Leu
    1715                 1720                 1725

Pro Ile  Arg Tyr Gln Thr Pro  Ala Ile Arg Ala Val  His Thr Gly
    1730                 1735                 1740

Arg Glu  Ile Val Asp Leu Met  Cys His Ala Thr Phe  Thr Met Arg
    1745                 1750                 1755

Leu Leu  Ser Pro Val Arg Val  Pro Asn Tyr Asn Leu  Ile Ile Met
    1760                 1765                 1770

Asp Glu  Ala His Phe Thr Asp  Pro Ala Ser Ile Ala  Ala Arg Gly
    1775                 1780                 1785

Tyr Ile  Ser Thr Arg Val Glu  Met Gly Glu Ala Ala  Gly Ile Phe
    1790                 1795                 1800

Met Thr  Ala Thr Pro Pro Gly  Ser Arg Asp Pro Phe  Pro Gln Ser
    1805                 1810                 1815

Asn Ala  Pro Ile Ile Asp Glu  Glu Arg Glu Ile Pro  Glu Arg Ser
    1820                 1825                 1830

Trp Asn  Ser Gly His Glu Trp  Val Thr Asp Phe Lys  Gly Lys Thr
    1835                 1840                 1845

Val Trp  Phe Val Pro Ser Ile  Lys Ala Gly Asn Asp  Ile Ala Ala
    1850                 1855                 1860

Cys Leu  Arg Lys Asn Gly Lys  Lys Val Ile Gln Leu  Ser Arg Lys
    1865                 1870                 1875

Thr Phe  Asp Ser Glu Tyr Val  Lys Thr Arg Thr Asn  Asp Trp Asp
    1880                 1885                 1890

Phe Val  Val Thr Thr Asp Ile  Ser Glu Met Gly Ala  Asn Phe Lys
    1895                 1900                 1905

Ala Glu  Arg Val Ile Asp Pro  Arg Arg Cys Met Lys  Pro Val Ile
    1910                 1915                 1920

Leu Thr  Asp Gly Glu Glu Arg  Val Ile Leu Ala Gly  Pro Met Pro
    1925                 1930                 1935

Val Thr  His Ser Ser Ala Ala  Gln Arg Arg Gly Arg  Ile Gly Arg
    1940                 1945                 1950

Asn Pro  Lys Asn Glu Asn Asp  Gln Tyr Ile Tyr Met  Gly Glu Pro
    1955                 1960                 1965

Leu Glu  Asn Asp Glu Asp Cys  Ala His Trp Lys Glu  Ala Lys Met
    1970                 1975                 1980

Leu Leu  Asp Asn Ile Asn Thr  Pro Glu Gly Ile Ile  Pro Ser Met
    1985                 1990                 1995

Phe Glu  Pro Glu Arg Glu Lys  Val Asp Ala Ile Asp  Gly Glu Tyr
    2000                 2005                 2010

Arg Leu  Arg Gly Glu Ala Arg  Lys Thr Phe Val Asp  Leu Met Arg
    2015                 2020                 2025

Arg Gly  Asp Leu Pro Val Trp  Leu Ala Tyr Arg Val  Ala Ala Glu
    2030                 2035                 2040

Gly Ile  Asn Tyr Ala Asp Arg  Arg Trp Cys Phe Asp  Gly Val Lys
    2045                 2050                 2055

Asn Asn  Gln Ile Leu Glu Glu  Asn Val Glu Val Glu  Ile Trp Thr
    2060                 2065                 2070

Lys Glu  Gly Glu Arg Lys Lys  Leu Lys Pro Arg Trp  Leu Asp Ala
    2075                 2080                 2085

Arg Ile  Tyr Ser Asp Pro Leu  Ala Leu Lys Glu Phe  Lys Glu Phe
    2090                 2095                 2100
```

```
Ala Ala  Gly Arg Lys Ser Leu  Thr Leu Asn Leu Ile  Thr Glu Met
    2105                 2110                 2115

Gly Arg  Leu Pro Thr Phe Met  Thr Gln Lys Ala Arg  Asp Ala Leu
    2120                 2125                 2130

Asp Asn  Leu Ala Val Leu His  Thr Ala Glu Ala Gly  Gly Arg Ala
    2135                 2140                 2145

Tyr Asn  His Ala Leu Ser Glu  Leu Pro Glu Thr Leu  Glu Thr Leu
    2150                 2155                 2160

Leu Leu  Leu Thr Leu Leu Ala  Thr Val Thr Gly Gly  Ile Phe Leu
    2165                 2170                 2175

Phe Leu  Met Ser Ala Arg Gly  Ile Gly Lys Met Thr  Leu Gly Met
    2180                 2185                 2190

Cys Cys  Ile Ile Thr Ala Ser  Ile Leu Leu Trp Tyr  Ala Gln Ile
    2195                 2200                 2205

Gln Pro  His Trp Ile Ala Ala  Ser Ile Ile Leu Glu  Phe Phe Leu
    2210                 2215                 2220

Ile Val  Leu Leu Ile Pro Glu  Pro Glu Lys Gln Arg  Thr Pro Gln
    2225                 2230                 2235

Asp Asn  Gln Leu Thr Tyr Val  Val Ile Ala Ile Leu  Thr Val Val
    2240                 2245                 2250

Ala Ala  Thr Met Ala Asn Glu  Met Gly Phe Leu Glu  Lys Thr Lys
    2255                 2260                 2265

Lys Asp  Leu Gly Leu Gly Ser  Ile Ala Thr Gln Gln  Pro Glu Ser
    2270                 2275                 2280

Asn Ile  Leu Asp Ile Asp Leu  Arg Pro Ala Ser Ala  Trp Thr Leu
    2285                 2290                 2295

Tyr Ala  Val Ala Thr Thr Phe  Val Thr Pro Met Leu  Arg His Ser
    2300                 2305                 2310

Ile Glu  Asn Ser Ser Val Asn  Val Ser Leu Thr Ala  Ile Ala Asn
    2315                 2320                 2325

Gln Ala  Thr Val Leu Met Gly  Leu Gly Lys Gly Trp  Pro Leu Ser
    2330                 2335                 2340

Lys Met  Asp Ile Gly Val Pro  Leu Leu Ala Ile Gly  Cys Tyr Ser
    2345                 2350                 2355

Gln Val  Asn Pro Ile Thr Leu  Thr Ala Ala Leu Phe  Leu Leu Val
    2360                 2365                 2370

Ala His  Tyr Ala Ile Ile Gly  Pro Gly Leu Gln Ala  Lys Ala Thr
    2375                 2380                 2385

Arg Glu  Ala Gln Lys Arg Ala  Ala Ala Gly Ile Met  Lys Asn Pro
    2390                 2395                 2400

Thr Val  Asp Gly Ile Thr Val  Ile Asp Leu Asp Pro  Ile Pro Tyr
    2405                 2410                 2415

Asp Pro  Lys Phe Glu Lys Gln  Leu Gly Gln Val Met  Leu Leu Val
    2420                 2425                 2430

Leu Cys  Val Thr Gln Val Leu  Met Met Arg Thr Thr  Trp Ala Leu
    2435                 2440                 2445

Cys Glu  Ala Leu Thr Leu Ala  Thr Gly Pro Ile Ser  Thr Leu Trp
    2450                 2455                 2460

Glu Gly  Asn Pro Gly Arg Phe  Trp Asn Thr Thr Ile  Ala Val Ser
    2465                 2470                 2475

Met Ala  Asn Ile Phe Arg Gly  Ser Tyr Leu Ala Gly  Ala Gly Leu
    2480                 2485                 2490

Leu Phe  Ser Ile Met Lys Asn  Thr Thr Asn Thr Arg  Arg Gly Thr
```

```
    2495                2500                2505

Gly Asn Ile Gly Glu Thr Leu Gly Glu Lys Trp Lys Ser Arg Leu
    2510                2515                2520

Asn Ala Leu Gly Lys Ser Glu Phe Gln Ile Tyr Lys Lys Ser Gly
    2525                2530                2535

Ile Gln Glu Val Asp Arg Thr Leu Ala Lys Glu Gly Ile Lys Arg
    2540                2545                2550

Gly Glu Thr Asp His His Ala Val Ser Arg Gly Ser Ala Lys Leu
    2555                2560                2565

Arg Trp Phe Val Glu Arg Asn Met Val Thr Pro Glu Gly Lys Val
    2570                2575                2580

Val Asp Leu Gly Cys Gly Arg Gly Gly Trp Ser Tyr Tyr Cys Gly
    2585                2590                2595

Gly Leu Lys Asn Val Arg Glu Val Lys Gly Leu Thr Lys Gly Gly
    2600                2605                2610

Pro Gly His Glu Glu Pro Ile Pro Met Ser Thr Tyr Gly Trp Asn
    2615                2620                2625

Leu Val Arg Leu Gln Ser Gly Val Asp Val Phe Phe Ile Pro Pro
    2630                2635                2640

Glu Lys Cys Asp Thr Leu Leu Cys Asp Ile Gly Glu Ser Ser Pro
    2645                2650                2655

Asn Pro Thr Val Glu Ala Gly Arg Thr Leu Arg Val Leu Asn Leu
    2660                2665                2670

Val Glu Asn Trp Leu Asn Asn Asn Thr Gln Phe Cys Ile Lys Val
    2675                2680                2685

Leu Asn Pro Tyr Met Pro Ser Val Ile Glu Lys Met Glu Ala Leu
    2690                2695                2700

Gln Arg Lys Tyr Gly Gly Ala Leu Val Arg Asn Pro Leu Ser Arg
    2705                2710                2715

Asn Ser Thr His Glu Met Tyr Trp Val Ser Asn Ala Ser Gly Asn
    2720                2725                2730

Ile Val Ser Ser Val Asn Met Ile Ser Arg Met Leu Ile Asn Arg
    2735                2740                2745

Phe Thr Met Arg Tyr Lys Lys Ala Thr Tyr Glu Pro Asp Val Asp
    2750                2755                2760

Leu Gly Ser Gly Thr Arg Asn Ile Gly Ile Glu Ser Glu Ile Pro
    2765                2770                2775

Asn Leu Asp Ile Ile Gly Lys Arg Ile Glu Lys Ile Lys Gln Glu
    2780                2785                2790

His Glu Thr Ser Trp His Tyr Asp Gln Asp His Pro Tyr Lys Thr
    2795                2800                2805

Trp Ala Tyr His Gly Ser Tyr Glu Thr Lys Gln Thr Gly Ser Ala
    2810                2815                2820

Ser Ser Met Val Asn Gly Val Val Arg Leu Leu Thr Lys Pro Trp
    2825                2830                2835

Asp Val Val Pro Met Val Thr Gln Met Ala Met Thr Asp Thr Thr
    2840                2845                2850

Pro Phe Gly Gln Gln Arg Val Phe Lys Glu Lys Val Asp Thr Arg
    2855                2860                2865

Thr Gln Glu Pro Lys Glu Gly Thr Lys Lys Leu Met Lys Ile Thr
    2870                2875                2880

Ala Glu Trp Leu Trp Lys Glu Leu Gly Lys Lys Lys Thr Pro Arg
    2885                2890                2895
```

```
Met Cys  Thr Arg Glu Glu Phe  Thr Arg Lys Val Arg  Ser Asn Ala
    2900                 2905                 2910

Ala Leu  Gly Ala Ile Phe Thr  Asp Glu Asn Lys Trp  Lys Ser Ala
    2915                 2920                 2925

Arg Glu  Ala Val Glu Asp Ser  Arg Phe Trp Glu Leu  Val Asp Lys
    2930                 2935                 2940

Glu Arg  Asn Leu His Leu Glu  Gly Lys Cys Glu Thr  Cys Val Tyr
    2945                 2950                 2955

Asn Met  Met Gly Lys Arg Glu  Lys Lys Leu Gly Glu  Phe Gly Lys
    2960                 2965                 2970

Ala Lys  Gly Ser Arg Ala Ile  Trp Tyr Met Trp Leu  Gly Ala Arg
    2975                 2980                 2985

Phe Leu  Glu Phe Glu Ala Leu  Gly Phe Leu Asn Glu  Asp His Trp
    2990                 2995                 3000

Phe Ser  Arg Glu Asn Ser Leu  Ser Gly Val Glu Gly  Glu Gly Leu
    3005                 3010                 3015

His Lys  Leu Gly Tyr Ile Leu  Arg Asp Val Ser Lys  Lys Glu Gly
    3020                 3025                 3030

Gly Ala  Met Tyr Ala Asp Asp  Thr Ala Gly Trp Asp  Thr Arg Ile
    3035                 3040                 3045

Thr Leu  Glu Asp Leu Lys Asn  Glu Glu Met Val Thr  Asn His Met
    3050                 3055                 3060

Glu Gly  Glu His Lys Lys Leu  Ala Glu Ala Ile Phe  Lys Leu Thr
    3065                 3070                 3075

Tyr Gln  Asn Lys Val Val Arg  Val Gln Arg Pro Thr  Pro Arg Gly
    3080                 3085                 3090

Thr Val  Met Asp Ile Ile Ser  Arg Arg Asp Gln Arg  Gly Ser Gly
    3095                 3100                 3105

Gln Val  Gly Thr Tyr Gly Leu  Asn Thr Phe Thr Asn  Met Glu Ala
    3110                 3115                 3120

Gln Leu  Ile Arg Gln Met Glu  Gly Glu Gly Val Phe  Lys Ser Ile
    3125                 3130                 3135

Gln His  Leu Thr Ile Thr Glu  Glu Ile Ala Val Gln  Asn Trp Leu
    3140                 3145                 3150

Ala Arg  Val Gly Arg Glu Arg  Leu Ser Arg Met Ala  Ile Ser Gly
    3155                 3160                 3165

Asp Asp  Cys Val Val Lys Pro  Leu Asp Asp Arg Phe  Ala Ser Ala
    3170                 3175                 3180

Leu Thr  Ala Leu Asn Asp Met  Gly Lys Ile Arg Lys  Asp Ile Gln
    3185                 3190                 3195

Gln Trp  Glu Pro Ser Arg Gly  Trp Asn Asp Trp Thr  Gln Val Pro
    3200                 3205                 3210

Phe Cys  Ser His His Phe His  Glu Leu Ile Met Lys  Asp Gly Arg
    3215                 3220                 3225

Val Leu  Val Val Pro Cys Arg  Asn Gln Asp Glu Leu  Ile Gly Arg
    3230                 3235                 3240

Ala Arg  Ile Ser Gln Gly Ala  Gly Trp Ser Leu Arg  Glu Thr Ala
    3245                 3250                 3255

Cys Leu  Gly Lys Ser Tyr Ala  Gln Met Trp Ser Leu  Met Tyr Phe
    3260                 3265                 3270

His Arg  Arg Asp Leu Arg Leu  Ala Ala Asn Ala Ile  Cys Ser Ala
    3275                 3280                 3285
```

```
Val Pro  Ser His Trp Val Pro  Thr Ser Arg Thr Thr  Trp Ser Ile
    3290                 3295                 3300

His Ala  Lys His Glu Trp Met  Thr Thr Glu Asp Met  Leu Thr Val
    3305                 3310                 3315

Trp Asn  Arg Val Trp Ile Gln  Glu Asn Pro Trp Met  Glu Asp Lys
    3320                 3325                 3330

Thr Pro  Val Glu Ser Trp Glu  Glu Ile Pro Tyr Leu  Gly Lys Arg
    3335                 3340                 3345

Glu Asp  Gln Trp Cys Gly Ser  Leu Ile Gly Leu Thr  Ser Arg Ala
    3350                 3355                 3360

Thr Trp  Ala Lys Asn Ile Gln  Ala Ala Ile Asn Gln  Val Arg Ser
    3365                 3370                 3375

Leu Ile  Gly Asn Glu Glu Tyr  Thr Asp Tyr Met Pro  Ser Met Lys
    3380                 3385                 3390

Arg Phe  Arg Arg Glu Glu Glu  Glu Ala Gly Val Leu  Trp
    3395                 3400                 3405
```

<210> SEQ ID NO 3
<211> LENGTH: 10768
<212> TYPE: DNA
<213> ORGANISM: Artificial Sequence
<220> FEATURE:
<223> OTHER INFORMATION: Synthetic construct

<400> SEQUENCE: 3

```
agttgttagt ctacgtggac cgacaaagac agattctttg agggagctaa gctcaatgta     60

gttctaacag ttttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatccg cgggtatgat cgtcggaatt    420

gttggcctcc tgctgaccac agctatggca gcggaggtca ctagacgtgg gagtgcatac    480

tatatgtact tggacagaaa cgatgctggg gaggccatat cttttccaac cacattgggg    540

atgaataagt gttatataca gatcatggat cttggacaca tgtgtgatgc caccatgagc    600

tatgaatgcc ctatgctgga tgagggggtg gaaccagatg acgtcgattg ttggtgcaac    660

acgacgtcaa cttgggttgt gtacggaacc tgccatcaca aaaaaggtga agcacggaga    720

agtagaagag ctgtgacgct cccctcccat tccactagga agctgcaaac gcggtcgcaa    780

acctggttgg aatcaagaga atacacaaag cacttgatta gagtcgaaaa ttggatattc    840

aggaaccctg gcttcgcgtt agcagcagct gccatcgctt ggcttttggg aagctcaacg    900

agccaaaaag tcatatactt ggtcatgata ctgctgattg ccccggcata cagcatcagg    960

tgcataggag tcagcaatag ggactttgtg gaaggtatgt caggtgggac ttgggttgat   1020

attgtcttgg aacatggagg ttgtgtcacc gtaatggcac aggacaaacc gactgtcgac   1080

atagagctgg ttacaacaac agtcagcaac atggcggagg taagatccta ctgctatgag   1140

gcatcaatat cagacatggc ttcggacagc cgctgcccaa cacaaggtga agcctacctt   1200

gacaagcaat cagacactca atatgtctgc aaaagaacgt tagtggacag aggctgggga   1260

aatggatgtg gactttttgg caaagggagt ctggtgacat gcgctaagtt tgcatgctcc   1320

aagaaaatga ccgggaagag catccagcca gagaatctgg agtaccggat aatgctgtca   1380
```

```
gttcatggct cccagcacag tgggatgatc gttaatgaca caggacatga aactgatgag   1440
aatagagcga aggttgagat aacgcccaat tcaccaagag ccgaagccac cctgggggt    1500
tttggaagcc taggacttga ttgtgcaccg aggacaggcc ttgacttttc agatttgtat   1560
tacttgacta tgaataacaa gcactggttg gttcacaagg agtggttcca cgacattcca   1620
ttaccttggc acgctggggc agacaccgga actccacact ggaacaacaa agaagcactg   1680
gtagagttca aggacgcaca tgccaaaagg caaactgtcg tggttctagg gagtcaagaa   1740
ggagcagttc acacggccct tgctggagct ctggaggctg agatggatgg tgcaaaggga   1800
aggctgtcct ctggccactt gaaatgtcgc ctgaaaatgg ataaacttag attgaagggc   1860
gtgtcatact ccttgtgtac cgcagcgttc acattcacca agatcccggc tgaaacactg   1920
cacgggacag tcacagtgga ggtacagtac gcagggacag atggaccttg caaggttcca   1980
gctcagatgg cggtggacat gcaaactctg accccagttg ggaggttgat aaccgctaac   2040
cccgtaatca ctgaaagcac tgagaactct aagatgatgc tggaacttga tccaccattt   2100
ggggactctt acattgtcat aggagtcggg gagaagaaga tcacccacca ctggcacagg   2160
agtggcagca ccattggaaa agcatttgaa gccactgtga gaggtgccaa gagaatggca   2220
gtcttgggag acacagcctg ggactttgga tcagttggag gcgctctcaa ctcattgggc   2280
aagggcatcc atcaaatttt tggagcagct ttcaaatcat tgtttggagg aatgtcctgg   2340
ttctcacaaa ttctcattgg aacgttgctg atgtggttgg gtctgaacac aaagaatgga   2400
tctatttccc ttatgtgctt ggccgccggc attgtgacac tgtatttggg agtcatggtg   2460
caggccgata gtggttgcgt tgtgagctgg aaaaacaaag aactgaaatg tggcagtggg   2520
attttcatca cagacaacgt gcacacatgg acagaacaat acaagttcca accagaatcc   2580
ccttcaaaac tagcttcagc tatccagaaa gcccatgaag aggacatttg tggaatccgc   2640
tcagtaacaa gactggagaa tctgatgtgg aaacaaataa caccagaatt gaatcacatt   2700
ctatcagaaa atgaggtgaa gttaactatt atgacaggag acatcaaagg aatcatgcag   2760
gcaggaaaac gatctctgcg gcctcagccc actgagctga agtattcatg gaaaacatgg   2820
ggcaaagcaa aaatgctctc tacagagtct cataaccaga cctttctcat tgatggcccc   2880
gaaacagcag aatgccccaa cacaaataga gcttggaatt cgttggaagt tgaagactat   2940
ggctttggag tattcaccac caatatatgg ctaaaattga aagaaaaaca ggatgtattc   3000
tgcgactcaa aactcatgtc agcggccata aaagacaaca gagccgtcca tgccgatatg   3060
ggttattgga tagaaagtgc actcaatgac acatggaaga tagagaaagc ctctttcatt   3120
gaagttaaaa actgccactg gccaaaatca cacaccctct ggagcaatgg agtgctagaa   3180
agtgagatga taattccaaa gaatctcgct ggaccagtgt ctcaacacaa ctatagacca   3240
ggctaccata cacaaataac aggaccatgg catctaggta agcttgagat ggactttgat   3300
ttctgtgatg gaacaacagt ggtagtgact gaggactgcg gaaatagagg accctctttg   3360
agaacaacca ctgcctctgg aaaactcata acagaatggt gctgccgatc ttgcacatta   3420
ccaccgctaa gatacagagg tgaggatggg tgctggtacg ggatggaaat cagaccattg   3480
aaggagaaag aagagaattt ggtcaactcc ttggtcacag ctggacatgg gcaggtcgac   3540
aacttttcac taggagtctt gggaatggca ttgttcctgg aggaagtgct taggacccga   3600
gtaggaacga aacatgcaat actactagtt gcagtttctt ttgtgacatt gatcacaggg   3660
aacatgtcct ttagagacct gggaagagtg atggttatgg taggcgccac tatgacggat   3720
```

-continued

```
gacataggta tgggcgtgac ttatcttgcc ctactagcag ccttcaaagt cagaccaact   3780
tttgcagctg gactactctt gagaaagctg acctccaagg aattgatgat gactactata   3840
ggaattgtac tcctctccca gagcaccata ccagagacca ttcttgagtt gactgatgcg   3900
ttagccttag gcatgatggt cctcaaaatg gtgagaaata tggaaaagta tcaattggca   3960
gtgactatca tggctatctt gtgcgtccca aacgcagtga tattacaaaa cgcatggaaa   4020
gtgagttgca caatattggc agtggtgtcc gtttccccac tgttcttaac atcctcacag   4080
caaaaaacag attggatacc attagcattg acgatcaaag gtctcaatcc aacagctatt   4140
tttctaacaa ccctctcaag aaccagcaag aaaaggagct ggccattaaa tgaggctatc   4200
atggcagtcg ggatggtgag cattttagcc agttctctcc taaaaaatga tattcccatg   4260
acaggaccat tagtggctgg agggctcctc actgtgtgct acgtgctcac tggacgatcg   4320
gccgatttgg aactggagag agcagccgat gtcaaatggg aagaccaggc agagatatca   4380
ggaagcagtc caatcctgtc aataacaata tcagaagatg gtagcatgtc gataaaaaat   4440
gaagaggaag aacaaacact gaccatactc attagaacag gattgctggt gatctcagga   4500
ctttttcctg tatcaatacc aatcacggca gcagcatggt acctgtggga agtgaagaaa   4560
caacgggccg gagtattgtg ggatgttcct tcacccccac ccatgggaaa ggctgaactg   4620
gaagatggag cctatagaat taagcaaaaa gggattcttg gatattccca gatcggagcc   4680
ggagtttaca aagaaggaac attccataca atgtggcatg tcacacgtgg cgctgttcta   4740
atgcataaag gaaagaggat tgaaccatca tgggcggacg tcaagaaaga cctaatatca   4800
tatggaggag gctggaagtt agaaggagaa tggaaggaag gagaagaagt ccaggtattg   4860
gcactggagc ctggaaaaaa tccaagagcc gtccaaacga aacctggtct tttcaaaacc   4920
aacgccggaa caataggtgc tgtatctctg gacttttctc ctggaacgtc aggatctcca   4980
attatcgaca aaaaaggaaa agttgtgggt ctttatggta atggtgttgt tacaaggagt   5040
ggagcatatg tgagtgctat agcccagact gaaaaaagca ttgaagacaa cccagagatc   5100
gaagatgaca ttttccgaaa gagaagactg accatcatgg acctccaccc aggagcggga   5160
aagacgaaga gataccttcc ggccatagtc agagaagcta taaaacgggg tttgagaaca   5220
ttaatcttgg cccccactag agttgtggca gctgaaatgg aggaagccct tagaggactt   5280
ccaataagat accagacccc agccatcaga gctgtgcaca ccgggcggga gattgtggac   5340
ctaatgtgtc atgccacatt taccatgagg ctgctatcac cagttagagt gccaaactac   5400
aacctgatta tcatggacga agcccatttc acagacccag caagtatagc agctagagga   5460
tacatctcaa ctcgagtgga gatgggtgag gcagctggga tttttatgac agccactccc   5520
ccgggaagca gagacccatt tcctcagagc aatgcaccaa tcatagatga agaaagagaa   5580
atccctgaac gctcgtggaa ttccggacat gaatgggtca cggattttaa agggaagact   5640
gtttggttcg ttccaagtat aaaagcagga aatgatatag cagcttgcct gaggaaaaat   5700
ggaaagaaag tgatacaact cagtaggaag acctttgatt ctgagtatgt caagactaga   5760
accaatgatt gggacttcgt ggttacaact gacatttcag aaatgggtgc caatttcaag   5820
gctgagaggg ttatagaccc cagacgctgc atgaaaccag tcatactaac agatggtgaa   5880
gagcgggtga ttctggcagg acctatgcca gtgacccact ctagtgcagc acaaagaaga   5940
gggagaatag gaagaaatcc aaaaaatgag aatgaccagt acatatacat gggggaacct   6000
ctggaaaatg atgaagactg tgcacactgg aaagaagcta aaatgctcct agataacatc   6060
aacacgccag aaggaatcat tcctagcatg ttcgaaccag agcgtgaaaa ggtggatgcc   6120
```

```
attgatggcg aataccgctt gagaggagaa gcaaggaaaa cctttgtaga cttaatgaga   6180
agaggagacc taccagtctg gttggcctac agagtggcag ctgaaggcat caactacgca   6240
gacagaaggt ggtgttttga tggagtcaag aacaaccaaa tcctagaaga aaacgtggaa   6300
gttgaaatct ggacaaaaga aggggaaagg aagaaattga aacccagatg gttggatgct   6360
aggatctatt ctgacccact ggcgctaaaa gaatttaagg aatttgcagc cggaagaaag   6420
tctctgaccc tgaacctaat cacagaaatg ggtaggctcc caaccttcat gactcagaag   6480
gcaagagacg cactggacaa cttagcagtg ctgcacacgg ctgaggcagg tggaagggcg   6540
tacaaccatg ctctcagtga actgccggag accctggaga cattgctttt actgacactt   6600
ctggctacag tcacgggagg gatcttttta ttcttgatga gcgcaagggg catagggaag   6660
atgaccctgg gaatgtgctg cataatcacg gctagcatcc tcctatggta cgcacaaata   6720
cagccacact ggatagcagc ttcaataata ctggagtttt ttctcatagt tttgcttatt   6780
ccagaacctg aaaaacagag aacaccccaa gacaaccaac tgacctacgt tgtcatagcc   6840
atcctcacag tggtggccgc aaccatggca aacgagatgg gtttcctaga aaaaacgaag   6900
aaagatctcg gattgggaag cattgcaacc cagcaacccg agagcaacat cctggacata   6960
gatctacgtc ctgcatcagc atggacgctg tatgccgtgg ccacaacatt tgttacacca   7020
atgttgagac atagcattga aaattcctca gtgaatgtgt ccctaacagc tatagccaac   7080
caagccacag tgttaatggg tctcgggaaa ggatggccat tgtcaaagat ggacatcgga   7140
gttccccttc tcgccattgg atgctactca caagtcaacc ccataactct cacagcagct   7200
cttttcttat tggtagcaca ttatgccatc atagggccag gactccaagc aaaagcaacc   7260
agagaagctc agaaaagagc agcggcgggc atcatgaaaa acccaactgt cgatggaata   7320
acagtgattg acctagatcc aataccttat gatccaaagt ttgaaaagca gttgggacaa   7380
gtaatgctcc tagtcctctg cgtgactcaa gtattgatga tgaggactac atgggctctg   7440
tgtgaggctt taaccttagc taccgggccc atctccacat tgtgggaagg aaatccaggg   7500
aggttttgga acactaccat tgcggtgtca atggctaaca tttttagagg gagttacttg   7560
gccggagctg gacttctctt ttctattatg aagaacacaa ccaacacaag aaggggaact   7620
ggcaacatag gagagacgct tggagagaaa tggaaaagcc gattgaacgc attgggaaaa   7680
agtgaattcc agatctacaa gaaaagtgga atccaggaag tggatagaac cttagcaaaa   7740
gaaggcatta aaagaggaga aacggaccat cacgctgtgt cgcgaggctc agcaaaactg   7800
agatggttcg ttgagagaaa catggtcaca ccagaaggga aagtagtgga cctcggttgt   7860
ggcagaggag gctggtcata ctattgtgga ggactaaaga atgtaagaga agtcaaaggc   7920
ctaacaaaag gaggaccagg acacgaagaa cccatcccca tgtcaacata tgggtggaat   7980
ctagtgcgtc ttcaaagtgg agttgacgtt ttcttcatcc cgccagaaaa gtgtgacaca   8040
ttattgtgtg acatagggga gtcatcacca aatcccacag tggaagcagg acgaacactc   8100
agagtcctta acttagtaga aaattggttg aacaacaaca ctcaattttg cataaaggtt   8160
ctcaacccat atatgccctc agtcatagaa aaaatggaag cactacaaag gaaatatgga   8220
ggagccttag tgaggaatcc actctcacga aactccacac atgagatgta ctgggtatcc   8280
aatgcttccg ggaacatagt gtcatcagtg aacatgattt caaggatgtt gatcaacaga   8340
tttacaatga gatacaagaa agccacttac gagccggatg ttgacctcgg aagcggaacc   8400
cgtaacatcg ggattgaaag tgagatacca aacctagata taattgggaa aagaatagaa   8460
```

-continued

```
aaaataaagc aagagcatga aacatcatgg cactatgacc aagaccaccc atacaaaacg   8520
tgggcatacc atggtagcta tgaaacaaaa cagactggat cagcatcatc catggtcaac   8580
ggagtggtca ggctgctgac aaaaccttgg gacgtcgtcc ccatggtgac acagatggca   8640
atgacagaca cgactccatt tggacaacag cgcgttttta aagagaaagt ggacacgaga   8700
acccaagaac cgaaagaagg cacgaagaaa ctaatgaaaa taacagcaga gtggctttgg   8760
aaagaattag ggaagaaaaa gacacccagg atgtgcacca gagaagaatt cacaagaaag   8820
gtgagaagca atgcagcctt gggggccata ttcactgatg agaacaagtg gaagtcggca   8880
cgtgaggctg ttgaagatag taggttttgg gagctggttg acaaggaaag gaatctccat   8940
cttgaaggaa agtgtgaaac atgtgtgtac aacatgatgg gaaaaagaga gaagaagcta   9000
ggggaattcg gcaaggcaaa aggcagcaga gccatatggt acatgtggct tggagcacgc   9060
ttcttagagt ttgaagccct aggattctta aatgaagatc actggttctc cagagagaac   9120
tccctgagtg gagtggaagg agaagggctg cacaagctag gttacattct aagagacgtg   9180
agcaagaaag agggaggagc aatgtatgcc gatgacaccg caggatggga tacaagaatc   9240
acactagaag acctaaaaaa tgaagaaatg gtaacaaacc acatggaagg agaacacaag   9300
aaactagccg aggccatttt caaactaacg taccaaaaca aggtggtgcg tgtgcaaaga   9360
ccaacaccaa gaggcacagt aatggacatc atatcgagaa gagaccaaag aggtagtgga   9420
caagttggca cctatggact caatactttc accaatatgg aagcccaact aatcagacag   9480
atggagggag aaggagtctt taaaagcatt cagcacctaa caatcacaga agaaatcgct   9540
gtgcaaaact ggttagcaag agtggggcgc gaaaggttat caagaatggc catcagtgga   9600
gatgattgtg ttgtgaaacc tttagatgac aggttcgcaa gcgctttaac agctctaaat   9660
gacatgggaa agattaggaa agacatacaa caatgggaac cttcaagagg atggaatgat   9720
tggacacaag tgcccttctg ttcacaccat ttccatgagt taatcatgaa agacggtcgc   9780
gtactcgttg ttccatgtag aaaccaagat gaactgattg gcagagcccg aatctcccaa   9840
ggagcagggt ggtctttgcg ggagacggcc tgtttgggga agtcttacgc ccaaatgtgg   9900
agcttgatgt acttccacag acgcgacctc aggctggcgg caaatgctat ttgctcggca   9960
gtaccatcac attgggttcc aacaagtcga acaacctggt ccatacatgc taaacatgaa  10020
tggatgacaa cggaagacat gctgacagtc tggaacaggg tgtggattca agaaaaccca  10080
tggatggaag acaaaactcc agtggaatca tgggaggaaa tcccatactt ggggaaaaga  10140
gaagaccaat ggtgcggctc attgattggg ttaacaagca gggccacctg ggcaaagaac  10200
atccaagcag caataaatca agttagatcc cttataggca atgaagaata cacagattac  10260
atgccatcca tgaaaagatt cagaagagaa gaggaagaag caggagttct gtggtagaaa  10320
gcaaaactaa catgaaacaa ggctagaagt caggtcggat taagccatag tacggaaaaa  10380
actatgctac ctgtgagccc cgtccaagga cgttaaaaga agtcaggcca tcataaatgc  10440
catagcttga gtaaactatg cagcctgtag ctccacctga gaaggtgtaa aaaatccggg  10500
aggccacaaa ccatggaagc tgtacgcatg gcgtagtgga ctagcggtta gaggagaccc  10560
ctcccttaca aatcgcagca acaatggggg cccaaggcga gatgaagctg tagtctcgct  10620
ggaaggacta gaggttagag gagacccccc cgaaacaaaa aacagcatat tgacgctggg  10680
aaagaccaga gatcctgctg tctcctcagc atcattccag gcacagaacg ccagaaaatg  10740
gaatggtgct gttgaatcaa caggttct                                     10768
```

<210> SEQ ID NO 4
<211> LENGTH: 3406
<212> TYPE: PRT
<213> ORGANISM: Artificial Sequence
<220> FEATURE:
<223> OTHER INFORMATION: Synthetic polypeptide

<400> SEQUENCE: 4

Met Asn Asn Gln Arg Lys Lys Ala Lys Asn Thr Pro Phe Asn Met Leu
1 5 10 15

Lys Arg Glu Arg Asn Arg Val Ser Thr Val Gln Gln Leu Thr Lys Arg
20 25 30

Phe Ser Leu Gly Met Leu Gln Gly Arg Gly Pro Leu Lys Leu Phe Met
35 40 45

Ala Leu Val Ala Phe Leu Arg Phe Leu Thr Ile Pro Pro Thr Ala Gly
50 55 60

Ile Leu Lys Arg Trp Gly Thr Ile Lys Lys Ser Lys Ala Ile Asn Val
65 70 75 80

Leu Arg Gly Phe Arg Lys Glu Ile Gly Arg Met Leu Asn Ile Leu Asn
85 90 95

Arg Arg Arg Arg Ser Ala Gly Met Ile Val Gly Ile Val Gly Leu Leu
100 105 110

Leu Thr Thr Ala Met Ala Ala Glu Val Thr Arg Arg Gly Ser Ala Tyr
115 120 125

Tyr Met Tyr Leu Asp Arg Asn Asp Ala Gly Glu Ala Ile Ser Phe Pro
130 135 140

Thr Thr Leu Gly Met Asn Lys Cys Tyr Ile Gln Ile Met Asp Leu Gly
145 150 155 160

His Met Cys Asp Ala Thr Met Ser Tyr Glu Cys Pro Met Leu Asp Glu
165 170 175

Gly Val Glu Pro Asp Asp Val Asp Cys Trp Cys Asn Thr Thr Ser Thr
180 185 190

Trp Val Val Tyr Gly Thr Cys His His Lys Lys Gly Glu Ala Arg Arg
195 200 205

Ser Arg Arg Ala Val Thr Leu Pro Ser His Ser Thr Arg Lys Leu Gln
210 215 220

Thr Arg Ser Gln Thr Trp Leu Glu Ser Arg Glu Tyr Thr Lys His Leu
225 230 235 240

Ile Arg Val Glu Asn Trp Ile Phe Arg Asn Pro Gly Phe Ala Leu Ala
245 250 255

Ala Ala Ala Ile Ala Trp Leu Leu Gly Ser Ser Thr Ser Gln Lys Val
260 265 270

Ile Tyr Leu Val Met Ile Leu Leu Ile Ala Pro Ala Tyr Ser Ile Arg
275 280 285

Cys Ile Gly Val Ser Asn Arg Asp Phe Val Glu Gly Met Ser Gly Gly
290 295 300

Thr Trp Val Asp Ile Val Leu Glu His Gly Gly Cys Val Thr Val Met
305 310 315 320

Ala Gln Asp Lys Pro Thr Val Asp Ile Glu Leu Val Thr Thr Thr Val
325 330 335

Ser Asn Met Ala Glu Val Arg Ser Tyr Cys Tyr Glu Ala Ser Ile Ser
340 345 350

Asp Met Ala Ser Asp Ser Arg Cys Pro Thr Gln Gly Glu Ala Tyr Leu
355 360 365

Asp Lys Gln Ser Asp Thr Gln Tyr Val Cys Lys Arg Thr Leu Val Asp

```
    370                 375                 380

Arg Gly Trp Gly Asn Gly Cys Gly Leu Phe Gly Lys Gly Ser Leu Val
385                 390                 395                 400

Thr Cys Ala Lys Phe Ala Cys Ser Lys Lys Met Thr Gly Lys Ser Ile
                405                 410                 415

Gln Pro Glu Asn Leu Glu Tyr Arg Ile Met Leu Ser Val His Gly Ser
            420                 425                 430

Gln His Ser Gly Met Ile Val Asn Asp Thr Gly His Glu Thr Asp Glu
        435                 440                 445

Asn Arg Ala Lys Val Glu Ile Thr Pro Asn Ser Pro Arg Ala Glu Ala
    450                 455                 460

Thr Leu Gly Gly Phe Gly Ser Leu Gly Leu Asp Cys Ala Pro Arg Thr
465                 470                 475                 480

Gly Leu Asp Phe Ser Asp Leu Tyr Tyr Leu Thr Met Asn Asn Lys His
                485                 490                 495

Trp Leu Val His Lys Glu Trp Phe His Asp Ile Pro Leu Pro Trp His
            500                 505                 510

Ala Gly Ala Asp Thr Gly Thr Pro His Trp Asn Asn Lys Glu Ala Leu
        515                 520                 525

Val Glu Phe Lys Asp Ala His Ala Lys Arg Gln Thr Val Val Val Leu
    530                 535                 540

Gly Ser Gln Glu Gly Ala Val His Thr Ala Leu Ala Gly Ala Leu Glu
545                 550                 555                 560

Ala Glu Met Asp Gly Ala Lys Gly Arg Leu Ser Ser Gly His Leu Lys
                565                 570                 575

Cys Arg Leu Lys Met Asp Lys Leu Arg Leu Lys Gly Val Ser Tyr Ser
            580                 585                 590

Leu Cys Thr Ala Ala Phe Thr Phe Thr Lys Ile Pro Ala Glu Thr Leu
        595                 600                 605

His Gly Thr Val Thr Val Glu Val Gln Tyr Ala Gly Thr Asp Gly Pro
    610                 615                 620

Cys Lys Val Pro Ala Gln Met Ala Val Asp Met Gln Thr Leu Thr Pro
625                 630                 635                 640

Val Gly Arg Leu Ile Thr Ala Asn Pro Val Ile Thr Glu Ser Thr Glu
                645                 650                 655

Asn Ser Lys Met Met Leu Glu Leu Asp Pro Pro Phe Gly Asp Ser Tyr
            660                 665                 670

Ile Val Ile Gly Val Gly Glu Lys Lys Ile Thr His His Trp His Arg
        675                 680                 685

Ser Gly Ser Thr Ile Gly Lys Ala Phe Glu Ala Thr Val Arg Gly Ala
    690                 695                 700

Lys Arg Met Ala Val Leu Gly Asp Thr Ala Trp Asp Phe Gly Ser Val
705                 710                 715                 720

Gly Gly Ala Leu Asn Ser Leu Gly Lys Gly Ile His Gln Ile Phe Gly
                725                 730                 735

Ala Ala Phe Lys Ser Leu Phe Gly Gly Met Ser Trp Phe Ser Gln Ile
            740                 745                 750

Leu Ile Gly Thr Leu Leu Met Trp Leu Gly Leu Asn Thr Lys Asn Gly
        755                 760                 765

Ser Ile Ser Leu Met Cys Leu Ala Ala Gly Ile Val Thr Leu Tyr Leu
    770                 775                 780

Gly Val Met Val Gln Ala Asp Ser Gly Cys Val Val Ser Trp Lys Asn
785                 790                 795                 800
```

```
Lys Glu Leu Lys Cys Gly Ser Gly Ile Phe Ile Thr Asp Asn Val His
                805                 810                 815

Thr Trp Thr Glu Gln Tyr Lys Phe Gln Pro Glu Ser Pro Ser Lys Leu
            820                 825                 830

Ala Ser Ala Ile Gln Lys Ala His Glu Glu Asp Ile Cys Gly Ile Arg
        835                 840                 845

Ser Val Thr Arg Leu Glu Asn Leu Met Trp Lys Gln Ile Thr Pro Glu
    850                 855                 860

Leu Asn His Ile Leu Ser Glu Asn Glu Val Lys Leu Thr Ile Met Thr
865                 870                 875                 880

Gly Asp Ile Lys Gly Ile Met Gln Ala Gly Lys Arg Ser Leu Arg Pro
                885                 890                 895

Gln Pro Thr Glu Leu Lys Tyr Ser Trp Lys Thr Trp Gly Lys Ala Lys
            900                 905                 910

Met Leu Ser Thr Glu Ser His Asn Gln Thr Phe Leu Ile Asp Gly Pro
        915                 920                 925

Glu Thr Ala Glu Cys Pro Asn Thr Asn Arg Ala Trp Asn Ser Leu Glu
    930                 935                 940

Val Glu Asp Tyr Gly Phe Gly Val Phe Thr Thr Asn Ile Trp Leu Lys
945                 950                 955                 960

Leu Lys Glu Lys Gln Asp Val Phe Cys Asp Ser Lys Leu Met Ser Ala
                965                 970                 975

Ala Ile Lys Asp Asn Arg Ala Val His Ala Asp Met Gly Tyr Trp Ile
            980                 985                 990

Glu Ser Ala Leu Asn Asp Thr Trp  Lys Ile Glu Lys Ala  Ser Phe Ile
        995                 1000                 1005

Glu Val  Lys Asn Cys His Trp  Pro Lys Ser His Thr  Leu Trp Ser
    1010                 1015                 1020

Asn Gly  Val Leu Glu Ser Glu  Met Ile Ile Pro Lys  Asn Leu Ala
    1025                 1030                 1035

Gly Pro  Val Ser Gln His Asn  Tyr Arg Pro Gly Tyr  His Thr Gln
    1040                 1045                 1050

Ile Thr  Gly Pro Trp His Leu  Gly Lys Leu Glu Met  Asp Phe Asp
    1055                 1060                 1065

Phe Cys  Asp Gly Thr Thr Val  Val Val Thr Glu Asp  Cys Gly Asn
    1070                 1075                 1080

Arg Gly  Pro Ser Leu Arg Thr  Thr Thr Ala Ser Gly  Lys Leu Ile
    1085                 1090                 1095

Thr Glu  Trp Cys Cys Arg Ser  Cys Thr Leu Pro Pro  Leu Arg Tyr
    1100                 1105                 1110

Arg Gly  Glu Asp Gly Cys Trp  Tyr Gly Met Glu Ile  Arg Pro Leu
    1115                 1120                 1125

Lys Glu  Lys Glu Glu Asn Leu  Val Asn Ser Leu Val  Thr Ala Gly
    1130                 1135                 1140

His Gly  Gln Val Asp Asn Phe  Ser Leu Gly Val Leu  Gly Met Ala
    1145                 1150                 1155

Leu Phe  Leu Glu Glu Val Leu  Arg Thr Arg Val Gly  Thr Lys His
    1160                 1165                 1170

Ala Ile  Leu Leu Val Ala Val  Ser Phe Val Thr Leu  Ile Thr Gly
    1175                 1180                 1185

Asn Met  Ser Phe Arg Asp Leu  Gly Arg Val Met Val  Met Val Gly
    1190                 1195                 1200
```

```
Ala Thr Met Thr Asp Asp Ile Gly Met Gly Val Thr Tyr Leu Ala
    1205                1210                1215

Leu Leu Ala Ala Phe Lys Val Arg Pro Thr Phe Ala Ala Gly Leu
    1220                1225                1230

Leu Leu Arg Lys Leu Thr Ser Lys Glu Leu Met Met Thr Thr Ile
    1235                1240                1245

Gly Ile Val Leu Leu Ser Gln Ser Thr Ile Pro Glu Thr Ile Leu
    1250                1255                1260

Glu Leu Thr Asp Ala Leu Ala Leu Gly Met Met Val Leu Lys Met
    1265                1270                1275

Val Arg Asn Met Glu Lys Tyr Gln Leu Ala Val Thr Ile Met Ala
    1280                1285                1290

Ile Leu Cys Val Pro Asn Ala Val Ile Leu Gln Asn Ala Trp Lys
    1295                1300                1305

Val Ser Cys Thr Ile Leu Ala Val Val Ser Val Ser Pro Leu Phe
    1310                1315                1320

Leu Thr Ser Ser Gln Gln Lys Thr Asp Trp Ile Pro Leu Ala Leu
    1325                1330                1335

Thr Ile Lys Gly Leu Asn Pro Thr Ala Ile Phe Leu Thr Thr Leu
    1340                1345                1350

Ser Arg Thr Ser Lys Lys Arg Ser Trp Pro Leu Asn Glu Ala Ile
    1355                1360                1365

Met Ala Val Gly Met Val Ser Ile Leu Ala Ser Ser Leu Leu Lys
    1370                1375                1380

Asn Asp Ile Pro Met Thr Gly Pro Leu Val Ala Gly Gly Leu Leu
    1385                1390                1395

Thr Val Cys Tyr Val Leu Thr Gly Arg Ser Ala Asp Leu Glu Leu
    1400                1405                1410

Glu Arg Ala Ala Asp Val Lys Trp Glu Asp Gln Ala Glu Ile Ser
    1415                1420                1425

Gly Ser Ser Pro Ile Leu Ser Ile Thr Ile Ser Glu Asp Gly Ser
    1430                1435                1440

Met Ser Ile Lys Asn Glu Glu Glu Glu Gln Thr Leu Thr Ile Leu
    1445                1450                1455

Ile Arg Thr Gly Leu Leu Val Ile Ser Gly Leu Phe Pro Val Ser
    1460                1465                1470

Ile Pro Ile Thr Ala Ala Ala Trp Tyr Leu Trp Glu Val Lys Lys
    1475                1480                1485

Gln Arg Ala Gly Val Leu Trp Asp Val Pro Ser Pro Pro Pro Met
    1490                1495                1500

Gly Lys Ala Glu Leu Glu Asp Gly Ala Tyr Arg Ile Lys Gln Lys
    1505                1510                1515

Gly Ile Leu Gly Tyr Ser Gln Ile Gly Ala Gly Val Tyr Lys Glu
    1520                1525                1530

Gly Thr Phe His Thr Met Trp His Val Thr Arg Gly Ala Val Leu
    1535                1540                1545

Met His Lys Gly Lys Arg Ile Glu Pro Ser Trp Ala Asp Val Lys
    1550                1555                1560

Lys Asp Leu Ile Ser Tyr Gly Gly Gly Trp Lys Leu Glu Gly Glu
    1565                1570                1575

Trp Lys Glu Gly Glu Glu Val Gln Val Leu Ala Leu Glu Pro Gly
    1580                1585                1590

Lys Asn Pro Arg Ala Val Gln Thr Lys Pro Gly Leu Phe Lys Thr
```

```
    1595                1600                1605

Asn Ala  Gly Thr Ile Gly Ala  Val Ser Leu Asp Phe  Ser Pro Gly
    1610                1615                1620

Thr Ser  Gly Ser Pro Ile Ile  Asp Lys Lys Gly Lys  Val Val Gly
    1625                1630                1635

Leu Tyr  Gly Asn Gly Val Val  Thr Arg Ser Gly Ala  Tyr Val Ser
    1640                1645                1650

Ala Ile  Ala Gln Thr Glu Lys  Ser Ile Glu Asp Asn  Pro Glu Ile
    1655                1660                1665

Glu Asp  Asp Ile Phe Arg Lys  Arg Arg Leu Thr Ile  Met Asp Leu
    1670                1675                1680

His Pro  Gly Ala Gly Lys Thr  Lys Arg Tyr Leu Pro  Ala Ile Val
    1685                1690                1695

Arg Glu  Ala Ile Lys Arg Gly  Leu Arg Thr Leu Ile  Leu Ala Pro
    1700                1705                1710

Thr Arg  Val Val Ala Ala Glu  Met Glu Glu Ala Leu  Arg Gly Leu
    1715                1720                1725

Pro Ile  Arg Tyr Gln Thr Pro  Ala Ile Arg Ala Val  His Thr Gly
    1730                1735                1740

Arg Glu  Ile Val Asp Leu Met  Cys His Ala Thr Phe  Thr Met Arg
    1745                1750                1755

Leu Leu  Ser Pro Val Arg Val  Pro Asn Tyr Asn Leu  Ile Ile Met
    1760                1765                1770

Asp Glu  Ala His Phe Thr Asp  Pro Ala Ser Ile Ala  Ala Arg Gly
    1775                1780                1785

Tyr Ile  Ser Thr Arg Val Glu  Met Gly Glu Ala Ala  Gly Ile Phe
    1790                1795                1800

Met Thr  Ala Thr Pro Pro Gly  Ser Arg Asp Pro Phe  Pro Gln Ser
    1805                1810                1815

Asn Ala  Pro Ile Ile Asp Glu  Glu Arg Glu Ile Pro  Glu Arg Ser
    1820                1825                1830

Trp Asn  Ser Gly His Glu Trp  Val Thr Asp Phe Lys  Gly Lys Thr
    1835                1840                1845

Val Trp  Phe Val Pro Ser Ile  Lys Ala Gly Asn Asp  Ile Ala Ala
    1850                1855                1860

Cys Leu  Arg Lys Asn Gly Lys  Lys Val Ile Gln Leu  Ser Arg Lys
    1865                1870                1875

Thr Phe  Asp Ser Glu Tyr Val  Lys Thr Arg Thr Asn  Asp Trp Asp
    1880                1885                1890

Phe Val  Val Thr Thr Asp Ile  Ser Glu Met Gly Ala  Asn Phe Lys
    1895                1900                1905

Ala Glu  Arg Val Ile Asp Pro  Arg Arg Cys Met Lys  Pro Val Ile
    1910                1915                1920

Leu Thr  Asp Gly Glu Glu Arg  Val Ile Leu Ala Gly  Pro Met Pro
    1925                1930                1935

Val Thr  His Ser Ser Ala Ala  Gln Arg Arg Gly Arg  Ile Gly Arg
    1940                1945                1950

Asn Pro  Lys Asn Glu Asn Asp  Gln Tyr Ile Tyr Met  Gly Glu Pro
    1955                1960                1965

Leu Glu  Asn Asp Glu Asp Cys  Ala His Trp Lys Glu  Ala Lys Met
    1970                1975                1980

Leu Leu  Asp Asn Ile Asn Thr  Pro Glu Gly Ile Ile  Pro Ser Met
    1985                1990                1995
```

```
Phe Glu  Pro Glu Arg Glu Lys  Val Asp Ala Ile Asp  Gly Glu Tyr
    2000                 2005                 2010

Arg Leu  Arg Gly Glu Ala Arg  Lys Thr Phe Val Asp  Leu Met Arg
    2015                 2020                 2025

Arg Gly  Asp Leu Pro Val Trp  Leu Ala Tyr Arg Val  Ala Ala Glu
    2030                 2035                 2040

Gly Ile  Asn Tyr Ala Asp Arg  Arg Trp Cys Phe Asp  Gly Val Lys
    2045                 2050                 2055

Asn Asn  Gln Ile Leu Glu Glu  Asn Val Glu Val Glu  Ile Trp Thr
    2060                 2065                 2070

Lys Glu  Gly Glu Arg Lys Lys  Leu Lys Pro Arg Trp  Leu Asp Ala
    2075                 2080                 2085

Arg Ile  Tyr Ser Asp Pro Leu  Ala Leu Lys Glu Phe  Lys Glu Phe
    2090                 2095                 2100

Ala Ala  Gly Arg Lys Ser Leu  Thr Leu Asn Leu Ile  Thr Glu Met
    2105                 2110                 2115

Gly Arg  Leu Pro Thr Phe Met  Thr Gln Lys Ala Arg  Asp Ala Leu
    2120                 2125                 2130

Asp Asn  Leu Ala Val Leu His  Thr Ala Glu Ala Gly  Gly Arg Ala
    2135                 2140                 2145

Tyr Asn  His Ala Leu Ser Glu  Leu Pro Glu Thr Leu  Glu Thr Leu
    2150                 2155                 2160

Leu Leu  Leu Thr Leu Leu Ala  Thr Val Thr Gly Gly  Ile Phe Leu
    2165                 2170                 2175

Phe Leu  Met Ser Ala Arg Gly  Ile Gly Lys Met Thr  Leu Gly Met
    2180                 2185                 2190

Cys Cys  Ile Ile Thr Ala Ser  Ile Leu Leu Trp Tyr  Ala Gln Ile
    2195                 2200                 2205

Gln Pro  His Trp Ile Ala Ala  Ser Ile Ile Leu Glu  Phe Phe Leu
    2210                 2215                 2220

Ile Val  Leu Leu Ile Pro Glu  Pro Glu Lys Gln Arg  Thr Pro Gln
    2225                 2230                 2235

Asp Asn  Gln Leu Thr Tyr Val  Val Ile Ala Ile Leu  Thr Val Val
    2240                 2245                 2250

Ala Ala  Thr Met Ala Asn Glu  Met Gly Phe Leu Glu  Lys Thr Lys
    2255                 2260                 2265

Lys Asp  Leu Gly Leu Gly Ser  Ile Ala Thr Gln Gln  Pro Glu Ser
    2270                 2275                 2280

Asn Ile  Leu Asp Ile Asp Leu  Arg Pro Ala Ser Ala  Trp Thr Leu
    2285                 2290                 2295

Tyr Ala  Val Ala Thr Thr Phe  Val Thr Pro Met Leu  Arg His Ser
    2300                 2305                 2310

Ile Glu  Asn Ser Ser Val Asn  Val Ser Leu Thr Ala  Ile Ala Asn
    2315                 2320                 2325

Gln Ala  Thr Val Leu Met Gly  Leu Gly Lys Gly Trp  Pro Leu Ser
    2330                 2335                 2340

Lys Met  Asp Ile Gly Val Pro  Leu Leu Ala Ile Gly  Cys Tyr Ser
    2345                 2350                 2355

Gln Val  Asn Pro Ile Thr Leu  Thr Ala Ala Leu Phe  Leu Leu Val
    2360                 2365                 2370

Ala His  Tyr Ala Ile Ile Gly  Pro Gly Leu Gln Ala  Lys Ala Thr
    2375                 2380                 2385
```

```
Arg Glu  Ala Gln Lys Arg Ala  Ala Ala Gly Ile Met  Lys Asn Pro
    2390                 2395                 2400

Thr Val  Asp Gly Ile Thr Val  Ile Asp Leu Asp Pro  Ile Pro Tyr
    2405                 2410                 2415

Asp Pro  Lys Phe Glu Lys Gln  Leu Gly Gln Val Met  Leu Leu Val
    2420                 2425                 2430

Leu Cys  Val Thr Gln Val Leu  Met Met Arg Thr Thr  Trp Ala Leu
    2435                 2440                 2445

Cys Glu  Ala Leu Thr Leu Ala  Thr Gly Pro Ile Ser  Thr Leu Trp
    2450                 2455                 2460

Glu Gly  Asn Pro Gly Arg Phe  Trp Asn Thr Thr Ile  Ala Val Ser
    2465                 2470                 2475

Met Ala  Asn Ile Phe Arg Gly  Ser Tyr Leu Ala Gly  Ala Gly Leu
    2480                 2485                 2490

Leu Phe  Ser Ile Met Lys Asn  Thr Thr Asn Thr Arg  Arg Gly Thr
    2495                 2500                 2505

Gly Asn  Ile Gly Glu Thr Leu  Gly Glu Lys Trp Lys  Ser Arg Leu
    2510                 2515                 2520

Asn Ala  Leu Gly Lys Ser Glu  Phe Gln Ile Tyr Lys  Lys Ser Gly
    2525                 2530                 2535

Ile Gln  Glu Val Asp Arg Thr  Leu Ala Lys Glu Gly  Ile Lys Arg
    2540                 2545                 2550

Gly Glu  Thr Asp His His Ala  Val Ser Arg Gly Ser  Ala Lys Leu
    2555                 2560                 2565

Arg Trp  Phe Val Glu Arg Asn  Met Val Thr Pro Glu  Gly Lys Val
    2570                 2575                 2580

Val Asp  Leu Gly Cys Gly Arg  Gly Gly Trp Ser Tyr  Tyr Cys Gly
    2585                 2590                 2595

Gly Leu  Lys Asn Val Arg Glu  Val Lys Gly Leu Thr  Lys Gly Gly
    2600                 2605                 2610

Pro Gly  His Glu Glu Pro Ile  Pro Met Ser Thr Tyr  Gly Trp Asn
    2615                 2620                 2625

Leu Val  Arg Leu Gln Ser Gly  Val Asp Val Phe Phe  Ile Pro Pro
    2630                 2635                 2640

Glu Lys  Cys Asp Thr Leu Leu  Cys Asp Ile Gly Glu  Ser Ser Pro
    2645                 2650                 2655

Asn Pro  Thr Val Glu Ala Gly  Arg Thr Leu Arg Val  Leu Asn Leu
    2660                 2665                 2670

Val Glu  Asn Trp Leu Asn Asn  Asn Thr Gln Phe Cys  Ile Lys Val
    2675                 2680                 2685

Leu Asn  Pro Tyr Met Pro Ser  Val Ile Glu Lys Met  Glu Ala Leu
    2690                 2695                 2700

Gln Arg  Lys Tyr Gly Gly Ala  Leu Val Arg Asn Pro  Leu Ser Arg
    2705                 2710                 2715

Asn Ser  Thr His Glu Met Tyr  Trp Val Ser Asn Ala  Ser Gly Asn
    2720                 2725                 2730

Ile Val  Ser Ser Val Asn Met  Ile Ser Arg Met Leu  Ile Asn Arg
    2735                 2740                 2745

Phe Thr  Met Arg Tyr Lys Lys  Ala Thr Tyr Glu Pro  Asp Val Asp
    2750                 2755                 2760

Leu Gly  Ser Gly Thr Arg Asn  Ile Gly Ile Glu Ser  Glu Ile Pro
    2765                 2770                 2775

Asn Leu  Asp Ile Ile Gly Lys  Arg Ile Glu Lys Ile  Lys Gln Glu
```

```
    2780                2785                2790

His Glu  Thr Ser Trp His Tyr  Asp Gln Asp His Pro  Tyr Lys Thr
    2795                2800                2805

Trp Ala  Tyr His Gly Ser Tyr  Glu Thr Lys Gln Thr  Gly Ser Ala
    2810                2815                2820

Ser Ser  Met Val Asn Gly Val  Val Arg Leu Leu Thr  Lys Pro Trp
    2825                2830                2835

Asp Val  Val Pro Met Val Thr  Gln Met Ala Met Thr  Asp Thr Thr
    2840                2845                2850

Pro Phe  Gly Gln Gln Arg Val  Phe Lys Glu Lys Val  Asp Thr Arg
    2855                2860                2865

Thr Gln  Glu Pro Lys Glu Gly  Thr Lys Lys Leu Met  Lys Ile Thr
    2870                2875                2880

Ala Glu  Trp Leu Trp Lys Glu  Leu Gly Lys Lys Lys  Thr Pro Arg
    2885                2890                2895

Met Cys  Thr Arg Glu Glu Phe  Thr Arg Lys Val Arg  Ser Asn Ala
    2900                2905                2910

Ala Leu  Gly Ala Ile Phe Thr  Asp Glu Asn Lys Trp  Lys Ser Ala
    2915                2920                2925

Arg Glu  Ala Val Glu Asp Ser  Arg Phe Trp Glu Leu  Val Asp Lys
    2930                2935                2940

Glu Arg  Asn Leu His Leu Glu  Gly Lys Cys Glu Thr  Cys Val Tyr
    2945                2950                2955

Asn Met  Met Gly Lys Arg Glu  Lys Lys Leu Gly Glu  Phe Gly Lys
    2960                2965                2970

Ala Lys  Gly Ser Arg Ala Ile  Trp Tyr Met Trp Leu  Gly Ala Arg
    2975                2980                2985

Phe Leu  Glu Phe Glu Ala Leu  Gly Phe Leu Asn Glu  Asp His Trp
    2990                2995                3000

Phe Ser  Arg Glu Asn Ser Leu  Ser Gly Val Glu Gly  Glu Gly Leu
    3005                3010                3015

His Lys  Leu Gly Tyr Ile Leu  Arg Asp Val Ser Lys  Lys Glu Gly
    3020                3025                3030

Gly Ala  Met Tyr Ala Asp Asp  Thr Ala Gly Trp Asp  Thr Arg Ile
    3035                3040                3045

Thr Leu  Glu Asp Leu Lys Asn  Glu Glu Met Val Thr  Asn His Met
    3050                3055                3060

Glu Gly  Glu His Lys Lys Leu  Ala Glu Ala Ile Phe  Lys Leu Thr
    3065                3070                3075

Tyr Gln  Asn Lys Val Val Arg  Val Gln Arg Pro Thr  Pro Arg Gly
    3080                3085                3090

Thr Val  Met Asp Ile Ile Ser  Arg Arg Asp Gln Arg  Gly Ser Gly
    3095                3100                3105

Gln Val  Gly Thr Tyr Gly Leu  Asn Thr Phe Thr Asn  Met Glu Ala
    3110                3115                3120

Gln Leu  Ile Arg Gln Met Glu  Gly Glu Gly Val Phe  Lys Ser Ile
    3125                3130                3135

Gln His  Leu Thr Ile Thr Glu  Glu Ile Ala Val Gln  Asn Trp Leu
    3140                3145                3150

Ala Arg  Val Gly Arg Glu Arg  Leu Ser Arg Met Ala  Ile Ser Gly
    3155                3160                3165

Asp Asp  Cys Val Val Lys Pro  Leu Asp Asp Arg Phe  Ala Ser Ala
    3170                3175                3180
```

```
Leu Thr Ala Leu Asn Asp Met Gly Lys Ile Arg Lys Asp Ile Gln
    3185                3190                3195

Gln Trp Glu Pro Ser Arg Gly Trp Asn Asp Trp Thr Gln Val Pro
    3200                3205                3210

Phe Cys Ser His His Phe His Glu Leu Ile Met Lys Asp Gly Arg
    3215                3220                3225

Val Leu Val Val Pro Cys Arg Asn Gln Asp Glu Leu Ile Gly Arg
    3230                3235                3240

Ala Arg Ile Ser Gln Gly Ala Gly Trp Ser Leu Arg Glu Thr Ala
    3245                3250                3255

Cys Leu Gly Lys Ser Tyr Ala Gln Met Trp Ser Leu Met Tyr Phe
    3260                3265                3270

His Arg Arg Asp Leu Arg Leu Ala Ala Asn Ala Ile Cys Ser Ala
    3275                3280                3285

Val Pro Ser His Trp Val Pro Thr Ser Arg Thr Thr Trp Ser Ile
    3290                3295                3300

His Ala Lys His Glu Trp Met Thr Thr Glu Asp Met Leu Thr Val
    3305                3310                3315

Trp Asn Arg Val Trp Ile Gln Glu Asn Pro Trp Met Glu Asp Lys
    3320                3325                3330

Thr Pro Val Glu Ser Trp Glu Glu Ile Pro Tyr Leu Gly Lys Arg
    3335                3340                3345

Glu Asp Gln Trp Cys Gly Ser Leu Ile Gly Leu Thr Ser Arg Ala
    3350                3355                3360

Thr Trp Ala Lys Asn Ile Gln Ala Ala Ile Asn Gln Val Arg Ser
    3365                3370                3375

Leu Ile Gly Asn Glu Glu Tyr Thr Asp Tyr Met Pro Ser Met Lys
    3380                3385                3390

Arg Phe Arg Arg Glu Glu Glu Glu Ala Gly Val Leu Trp
    3395                3400                3405
```

<210> SEQ ID NO 5
<211> LENGTH: 10768
<212> TYPE: DNA
<213> ORGANISM: Artificial Sequence
<220> FEATURE:
<223> OTHER INFORMATION: Synthetic construct

<400> SEQUENCE: 5

```
agttgttagt ctacgtggac cgacaaagac agattctttg agggagctaa gctcaatgta     60

gttctaacag tttttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatccg cgggtactag tgtcggaatt    420

gttggcctcc tgctgaccac agctatggca gcggaggtca ctagacgtgg gagtgcatac    480

tatatgtact tggacagaaa cgatgctggg gaggccatat cttttccaac cacattgggg    540

atgaataagt gttatataca gatcatggat cttggacaca tgtgtgatgc caccatgagc    600

tatgaatgcc ctatgctgga tgagggggtg gaaccagatg acgtcgattg ttggtgcaac    660

acgacgtcaa cttgggttgt gtacggaacc tgccatcaca aaaaaggtga agcacggaga    720
```

-continued

```
agtagaagag ctgtgacgct cccctcccat tccactagga agctgcaaac gcggtcgcaa    780
acctggttgg aatcaagaga atacacaaag cacttgatta gagtcgaaaa ttggatattc    840
aggaaccctg gcttcgcgtt agcagcagct gccatcgctt ggcttttggg aagctcaacg    900
agccaaaaag tcatatactt ggtcatgata ctgctgattg ccccggcata cagcatcagg    960
tgcataggag tcagcaatag ggactttgtg gaaggtatgt caggtgggac ttgggttgat   1020
attgtcttgg aacatggagg ttgtgtcacc gtaatggcac aggacaaacc gactgtcgac   1080
atagagctgg ttacaacaac agtcagcaac atggcggagg taagatccta ctgctatgag   1140
gcatcaatat cagacatggc ttcggacagc cgctgcccaa cacaaggtga agcctacctt   1200
gacaagcaat cagacactca atatgtctgc aaaagaacgt tagtggacag aggctgggga   1260
aatggatgtg gactttttgg caaagggagt ctggtgacat gcgctaagtt tgcatgctcc   1320
aagaaaatga ccgggaagag catccagcca gagaatctgg agtaccggat aatgctgtca   1380
gttcatggct cccagcacag tgggatgatc gttaatgaca caggacatga aactgatgag   1440
aatagagcga aggttgagat aacgcccaat tcaccaagag ccgaagccac cctgggggt    1500
tttggaagcc taggacttga ttgtgaaccg aggacaggcc ttgacttttc agatttgtat   1560
tacttgacta tgaataacaa gcactggttg gttcacaagg agtggttcca cgacattcca   1620
ttaccttggc acgctggggc agacaccgga actccacact ggaacaacaa agaagcactg   1680
gtagagttca aggacgcaca tgccaaaagg caaactgtcg tggttctagg gagtcaagaa   1740
ggagcagttc acacggccct tgctggagct ctggaggctg agatggatgg tgcaaaggga   1800
aggctgtcct ctggccactt gaaatgtcgc ctgaaaatgg ataaacttag attgaagggc   1860
gtgtcatact ccttgtgtac cgcagcgttc acattcacca agatcccggc tgaaacactg   1920
cacgggacag tcacagtgga ggtacagtac gcagggacag atggaccttg caaggttcca   1980
gctcagatgg cggtggacat gcaaactctg accccagttg ggaggttgat aaccgctaac   2040
cccgtaatca ctgaaagcac tgagaactct aagatgatgc tggaacttga tccaccattt   2100
ggggactctt acattgtcat aggagtcggg gagaagaaga tcacccacca ctggcacagg   2160
agtggcagca ccattggaaa agcatttgaa gccactgtga gaggtgccaa gagaatggca   2220
gtcttgggag acacagcctg ggactttgga tcagttggag gcgctctcaa ctcattgggc   2280
aagggcatcc atcaaatttt tggagcagct ttcaaatcat tgtttggagg aatgtcctgg   2340
ttctcacaaa ttctcattgg aacgttgctg atgtggttgg gtctgaacac aaagaatgga   2400
tctatttccc ttatgtgctt ggccgccggc attgtgacac tgtatttggg agtcatggtg   2460
caggccgata gtggttgcgt tgtgagctgg aaaaacaaag aactgaaatg tggcagtggg   2520
attttcatca cagacaacgt gcacacatgg acagaacaat acaagttcca accagaatcc   2580
ccttcaaaac tagcttcagc tatccagaaa gcccatgaag aggacatttg tggaatccgc   2640
tcagtaacaa gactggagaa tctgatgtgg aaacaaataa caccagaatt gaatcacatt   2700
ctatcagaaa atgaggtgaa gttaactatt atgacaggag acatcaaagg aatcatgcag   2760
gcaggaaaac gatctctgcg gcctcagccc actgagctga agtattcatg gaaaacatgg   2820
ggcaaagcaa aaatgctctc tacagagtct cataaccaga cctttctcat tgatggcccc   2880
gaaacagcag aatgccccaa cacaaataga gcttggaatt cgttggaagt tgaagactat   2940
ggctttggag tattcaccac caatatatgg ctaaaattga aagaaaaaca ggatgtattc   3000
tgcgactcaa aactcatgtc agcggccata aaagacaaca gagccgtcca tgccgatatg   3060
```

-continued

```
ggttattgga tagaaagtgc actcaatgac acatggaaga tagagaaagc ctctttcatt   3120
gaagttaaaa actgccactg gccaaaatca cacaccctct ggagcaatgg agtgctagaa   3180
agtgagatga taattccaaa gaatctcgct ggaccagtgt ctcaacacaa ctatagacca   3240
ggctaccata cacaaataac aggaccatgg catctaggta agcttgagat ggactttgat   3300
ttctgtgatg gaacaacagt ggtagtgact gaggactgcg gaaatagagg accctctttg   3360
agaacaacca ctgcctctgg aaaactcata acagaatggt gctgccgatc ttgcacatta   3420
ccaccgctaa gatacagagg tgaggatggg tgctggtacg ggatggaaat cagaccattg   3480
aaggagaaag aagagaattt ggtcaactcc ttggtcacag ctggacatgg gcaggtcgac   3540
aacttttcac taggagtctt gggaatggca ttgttcctgg aggaagtgct taggacccga   3600
gtaggaacga aacatgcaat actactagtt gcagtttctt ttgtgacatt gatcacaggg   3660
aacatgtcct ttagagacct gggaagagtg atggttatgg taggcgccac tatgacggat   3720
gacataggta tgggcgtgac ttatcttgcc ctactagcag ccttcaaagt cagaccaact   3780
tttgcagctg gactactctt gagaaagctg acctccaagg aattgatgat gactactata   3840
ggaattgtac tcctctccca gagcaccata ccagagacca ttcttgagtt gactgatgcg   3900
ttagccttag gcatgatggt cctcaaaatg gtgagaaata tggaaaagta tcaattggca   3960
gtgactatca tggctatctt gtgcgtccca aacgcagtga tattacaaaa cgcatggaaa   4020
gtgagttgca caatattggc agtggtgtcc gtttccccac tgttcttaac atcctcacag   4080
caaaaaacag attggatacc attagcattg acgatcaaag gtctcaatcc aacagctatt   4140
tttctaacaa ccctctcaag aaccagcaag aaaaggagct ggccattaaa tgaggctatc   4200
atggcagtcg ggatggtgag cattttagcc agttctctcc taaaaaatga tattcccatg   4260
acaggaccat tagtggctgg agggctcctc actgtgtgct acgtgctcac tggacgatcg   4320
gccgatttgg aactggagag agcagccgat gtcaaatggg aagaccaggc agagatatca   4380
ggaagcagtc caatcctgtc aataacaata tcagaagatg gtagcatgtc gataaaaaat   4440
gaagaggaag aacaaacact gaccatactc attagaacag gattgctggt gatctcagga   4500
ctttttcctg tatcaatacc aatcacggca gcagcatggt acctgtggga agtgaagaaa   4560
caacgggccg gagtattgtg ggatgttcct tcacccccac ccatgggaaa ggctgaactg   4620
gaagatggag cctatagaat taagcaaaaa gggattcttg gatattccca gatcggagcc   4680
ggagtttaca aagaaggaac attccataca atgtggcatg tcacacgtgg cgctgttcta   4740
atgcataaag gaaagaggat tgaaccatca tgggcggacg tcaagaaaga cctaatatca   4800
tatggaggag gctggaagtt agaaggagaa tggaaggaag gagaagaagt ccaggtattg   4860
gcactggagc ctggaaaaaa tccaagagcc gtccaaacga aacctggtct tttcaaaacc   4920
aacgccggaa caataggtgc tgtatctctg gacttttctc ctggaacgtc aggatctcca   4980
attatcgaca aaaaaggaaa agttgtgggt ctttatggta atggtgttgt tacaaggagt   5040
ggagcatatg tgagtgctat agcccagact gaaaaaagca ttgaagacaa cccagagatc   5100
gaagatgaca ttttccgaaa gagaagactg accatcatgg acctccaccc aggagcggga   5160
aagacgaaga gataccttcc ggccatagtc agagaagcta taaaacgggg tttgagaaca   5220
ttaatcttgg cccccactag agttgtggca gctgaaatgg aggaagccct tagaggactt   5280
ccaataagat accagacccc agccatcaga gctgtgcaca ccgggcggga gattgtggac   5340
ctaatgtgtc atgccacatt taccatgagg ctgctatcac cagttagagt gccaaactac   5400
aacctgatta tcatggacga agcccatttc acagacccag caagtatagc agctagagga   5460
```

```
tacatctcaa ctcgagtgga gatgggtgag gcagctggga tttttatgac agccactccc   5520
ccgggaagca gagacccatt tcctcagagc aatgcaccaa tcatagatga agaaagagaa   5580
atccctgaac gctcgtggaa ttccggacat gaatgggtca cggattttaa agggaagact   5640
gtttggttcg ttccaagtat aaaagcagga aatgatatag cagcttgcct gaggaaaaat   5700
ggaaagaaag tgatacaact cagtaggaag acctttgatt ctgagtatgt caagactaga   5760
accaatgatt gggacttcgt ggttacaact gacatttcag aaatgggtgc caatttcaag   5820
gctgagaggg ttatagaccc cagacgctgc atgaaaccag tcatactaac agatggtgaa   5880
gagcgggtga ttctggcagg acctatgcca gtgacccact ctagtgcagc acaaagaaga   5940
gggagaatag gaagaaatcc aaaaaatgag aatgaccagt acatatacat gggggaacct   6000
ctggaaaatg atgaagactg tgcacactgg aaagaagcta aaatgctcct agataacatc   6060
aacacgccag aaggaatcat tcctagcatg ttcgaaccag agcgtgaaaa ggtggatgcc   6120
attgatggcg aataccgctt gagaggagaa gcaaggaaaa cctttgtaga cttaatgaga   6180
agaggagacc taccagtctg gttggcctac agagtggcag ctgaaggcat caactacgca   6240
gacagaaggt ggtgttttga tggagtcaag aacaaccaaa tcctagaaga aaacgtggaa   6300
gttgaaatct ggacaaaaga aggggaaagg aagaaattga aacccagatg gttggatgct   6360
aggatctatt ctgacccact ggcgctaaaa gaatttaagg aatttgcagc cggaagaaag   6420
tctctgaccc tgaacctaat cacagaaatg ggtaggctcc caaccttcat gactcagaag   6480
gcaagagacg cactggacaa cttagcagtg ctgcacacgg ctgaggcagg tggaagggcg   6540
tacaaccatg ctctcagtga actgccggag accctggaga cattgctttt actgacactt   6600
ctggctacag tcacgggagg gatcttttta ttcttgatga gcgcaagggg catagggaag   6660
atgaccctgg gaatgtgctg cataatcacg gctagcatcc tcctatggta cgcacaaata   6720
cagccacact ggatagcagc ttcaataata ctggagtttt ttctcatagt tttgcttatt   6780
ccagaacctg aaaaacagag aacacccaa gacaaccaac tgacctacgt tgtcatagcc   6840
atcctcacag tggtggccgc aaccatggca aacgagatgg gtttcctaga aaaaacgaag   6900
aaagatctcg gattgggaag cattgcaacc cagcaacccg agagcaacat cctggacata   6960
gatctacgtc ctgcatcagc atggacgctg tatgccgtgg ccacaacatt tgttacacca   7020
atgttgagac atagcattga aaattcctca gtgaatgtgt ccctaacagc tatagccaac   7080
caagccacag tgttaatggg tctcgggaaa ggatggccat tgtcaaagat ggacatcgga   7140
gttccccttc tcgccattgg atgctactca caagtcaacc ccataactct cacagcagct   7200
cttttcttat tggtagcaca ttatgccatc atagggccag gactccaagc aaaagcaacc   7260
agagaagctc agaaaagagc agcggcgggc atcatgaaaa acccaactgt cgatggaata   7320
acagtgattg acctagatcc aataccttat gatccaaagt ttgaaaagca gttgggacaa   7380
gtaatgctcc tagtcctctg cgtgactcaa gtattgatga tgaggactac atgggctctg   7440
tgtgaggctt taaccttagc taccgggccc atctccacat tgtgggaagg aaatccaggg   7500
aggttttgga acactaccat tgcggtgtca atggctaaca tttttagagg gagttacttg   7560
gccggagctg gacttctctt ttctattatg aagaacacaa ccaacacaag aaggggaact   7620
ggcaacatag gagagacgct tggagagaaa tggaaaagcc gattgaacgc attgggaaaa   7680
agtgaattcc agatctacaa gaaaagtgga atccaggaag tggatagaac cttagcaaaa   7740
gaaggcatta aaagaggaga aacggaccat cacgctgtgt cgcgaggctc agcaaaactg   7800
```

```
agatggttcg ttgagagaaa catggtcaca ccagaaggga aagtagtgga cctcggttgt   7860
ggcagaggag gctggtcata ctattgtgga ggactaaaga atgtaagaga agtcaaaggc   7920
ctaacaaaag gaggaccagg acacgaagaa cccatcccca tgtcaacata tgggtggaat   7980
ctagtgcgtc ttcaaagtgg agttgacgtt ttcttcatcc cgccagaaaa gtgtgacaca   8040
ttattgtgtg acatagggga gtcatcacca aatcccacag tggaagcagg acgaacactc   8100
agagtcctta acttagtaga aaattggttg aacaacaaca ctcaattttg cataaaggtt   8160
ctcaacccat atatgccctc agtcatagaa aaaatggaag cactacaaag gaaatatgga   8220
ggagccttag tgaggaatcc actctcacga aactccacac atgagatgta ctgggtatcc   8280
aatgcttccg ggaacatagt gtcatcagtg aacatgattt caaggatgtt gatcaacaga   8340
tttacaatga gatacaagaa agccacttac gagccggatg ttgacctcgg aagcggaacc   8400
cgtaacatcg ggattgaaag tgagatacca aacctagata taattgggaa aagaatagaa   8460
aaaataaagc aagagcatga aacatcatgg cactatgacc aagaccaccc atacaaaacg   8520
tgggcatacc atggtagcta tgaaacaaaa cagactggat cagcatcatc catggtcaac   8580
ggagtggtca ggctgctgac aaaaccttgg gacgtcgtcc ccatggtgac acagatggca   8640
atgacagaca cgactccatt tggacaacag cgcgttttta aagagaaagt ggacacgaga   8700
acccaagaac cgaaagaagg cacgaagaaa ctaatgaaaa taacagcaga gtggctttgg   8760
aaagaattag ggaagaaaaa gacacccagg atgtgcacca gagaagaatt cacaagaaag   8820
gtgagaagca atgcagcctt gggggccata ttcactgatg agaacaagtg gaagtcggca   8880
cgtgaggctg ttgaagatag taggttttgg gagctggttg acaaggaaag gaatctccat   8940
cttgaaggaa agtgtgaaac atgtgtgtac aacatgatgg gaaaaagaga gaagaagcta   9000
ggggaattcg gcaaggcaaa aggcagcaga gccatatggt acatgtggct tggagcacgc   9060
ttcttagagt ttgaagccct aggattctta aatgaagatc actggttctc cagagagaac   9120
tccctgagtg gagtggaagg agaagggctg cacaagctag gttacattct aagagacgtg   9180
agcaagaaag agggaggagc aatgtatgcc gatgacaccg caggatggga tacaagaatc   9240
acactagaag acctaaaaaa tgaagaaatg gtaacaaacc acatggaagg agaacacaag   9300
aaactagccg aggccatttt caaactaacg taccaaaaca aggtggtgcg tgtgcaaaga   9360
ccaacaccaa gaggcacagt aatggacatc atatcgagaa gagaccaaag aggtagtgga   9420
caagttggca cctatggact caatactttc accaatatgg aagcccaact aatcagacag   9480
atggagggag aaggagtctt taaaagcatt cagcacctaa caatcacaga agaaatcgct   9540
gtgcaaaact ggttagcaag agtggggcgc gaaaggttat caagaatggc catcagtgga   9600
gatgattgtg ttgtgaaacc tttagatgac aggttcgcaa gcgctttaac agctctaaat   9660
gacatgggaa agattaggaa agacatacaa caatgggaac cttcaagagg atggaatgat   9720
tggacacaag tgcccttctg ttcacaccat ttccatgagt taatcatgaa agacggtcgc   9780
gtactcgttg ttccatgtag aaaccaagat gaactgattg gcagagcccg aatctcccaa   9840
ggagcagggt ggtctttgcg ggagacggcc tgtttgggga agtcttacgc ccaaatgtgg   9900
agcttgatgt acttccacag acgcgacctc aggctggcgg caaatgctat ttgctcggca   9960
gtaccatcac attgggttcc aacaagtcga acaacctggt ccatacatgc taaacatgaa  10020
tggatgacaa cggaagacat gctgacagtc tggaacaggg tgtggattca agaaaaccca  10080
tggatggaag acaaaactcc agtggaatca tgggaggaaa tcccatactt ggggaaaaga  10140
gaagaccaat ggtgcggctc attgattggg ttaacaagca gggccacctg ggcaaagaac  10200
```

atccaagcag caataaatca agttagatcc cttataggca atgaagaata cacagattac 10260
atgccatcca tgaaaagatt cagaagagaa gaggaagaag caggagttct gtggtagaaa 10320
gcaaaactaa catgaaacaa ggctagaagt caggtcggat taagccatag tacggaaaaa 10380
actatgctac ctgtgagccc cgtccaagga cgttaaaaga agtcaggcca tcataaatgc 10440
catagcttga gtaaactatg cagcctgtag ctccacctga gaaggtgtaa aaaatccggg 10500
aggccacaaa ccatggaagc tgtacgcatg gcgtagtgga ctagcggtta gaggagaccc 10560
ctcccttaca aatcgcagca acaatggggg cccaaggcga gatgaagctg tagtctcgct 10620
ggaaggacta gaggttagag gagacccccc cgaaacaaaa aacagcatat tgacgctggg 10680
aaagaccaga gatcctgctg tctcctcagc atcattccag gcacagaacg ccagaaaatg 10740
gaatggtgct gttgaatcaa caggttct 10768

<210> SEQ ID NO 6
<211> LENGTH: 3406
<212> TYPE: PRT
<213> ORGANISM: Artificial Sequence
<220> FEATURE:
<223> OTHER INFORMATION: Synthetic polypeptide

<400> SEQUENCE: 6

Met Asn Asn Gln Arg Lys Lys Ala Lys Asn Thr Pro Phe Asn Met Leu
1 5 10 15

Lys Arg Glu Arg Asn Arg Val Ser Thr Val Gln Gln Leu Thr Lys Arg
20 25 30

Phe Ser Leu Gly Met Leu Gln Gly Arg Gly Pro Leu Lys Leu Phe Met
35 40 45

Ala Leu Val Ala Phe Leu Arg Phe Leu Thr Ile Pro Pro Thr Ala Gly
50 55 60

Ile Leu Lys Arg Trp Gly Thr Ile Lys Lys Ser Lys Ala Ile Asn Val
65 70 75 80

Leu Arg Gly Phe Arg Lys Glu Ile Gly Arg Met Leu Asn Ile Leu Asn
85 90 95

Arg Arg Arg Arg Ser Ala Gly Thr Ser Val Gly Ile Val Gly Leu Leu
100 105 110

Leu Thr Thr Ala Met Ala Ala Glu Val Thr Arg Arg Gly Ser Ala Tyr
115 120 125

Tyr Met Tyr Leu Asp Arg Asn Asp Ala Gly Glu Ala Ile Ser Phe Pro
130 135 140

Thr Thr Leu Gly Met Asn Lys Cys Tyr Ile Gln Ile Met Asp Leu Gly
145 150 155 160

His Met Cys Asp Ala Thr Met Ser Tyr Glu Cys Pro Met Leu Asp Glu
165 170 175

Gly Val Glu Pro Asp Asp Val Asp Cys Trp Cys Asn Thr Thr Ser Thr
180 185 190

Trp Val Val Tyr Gly Thr Cys His His Lys Lys Gly Glu Ala Arg Arg
195 200 205

Ser Arg Arg Ala Val Thr Leu Pro Ser His Ser Thr Arg Lys Leu Gln
210 215 220

Thr Arg Ser Gln Thr Trp Leu Glu Ser Arg Glu Tyr Thr Lys His Leu
225 230 235 240

Ile Arg Val Glu Asn Trp Ile Phe Arg Asn Pro Gly Phe Ala Leu Ala
245 250 255

-continued

```
Ala Ala Ala Ile Ala Trp Leu Leu Gly Ser Ser Thr Ser Gln Lys Val
            260                 265                 270

Ile Tyr Leu Val Met Ile Leu Leu Ile Ala Pro Ala Tyr Ser Ile Arg
        275                 280                 285

Cys Ile Gly Val Ser Asn Arg Asp Phe Val Glu Gly Met Ser Gly Gly
    290                 295                 300

Thr Trp Val Asp Ile Val Leu Glu His Gly Gly Cys Val Thr Val Met
305                 310                 315                 320

Ala Gln Asp Lys Pro Thr Val Asp Ile Glu Leu Val Thr Thr Thr Val
                325                 330                 335

Ser Asn Met Ala Glu Val Arg Ser Tyr Cys Tyr Glu Ala Ser Ile Ser
            340                 345                 350

Asp Met Ala Ser Asp Ser Arg Cys Pro Thr Gln Gly Glu Ala Tyr Leu
        355                 360                 365

Asp Lys Gln Ser Asp Thr Gln Tyr Val Cys Lys Arg Thr Leu Val Asp
    370                 375                 380

Arg Gly Trp Gly Asn Gly Cys Gly Leu Phe Gly Lys Gly Ser Leu Val
385                 390                 395                 400

Thr Cys Ala Lys Phe Ala Cys Ser Lys Lys Met Thr Gly Lys Ser Ile
                405                 410                 415

Gln Pro Glu Asn Leu Glu Tyr Arg Ile Met Leu Ser Val His Gly Ser
            420                 425                 430

Gln His Ser Gly Met Ile Val Asn Asp Thr Gly His Glu Thr Asp Glu
        435                 440                 445

Asn Arg Ala Lys Val Glu Ile Thr Pro Asn Ser Pro Arg Ala Glu Ala
    450                 455                 460

Thr Leu Gly Gly Phe Gly Ser Leu Gly Leu Asp Cys Glu Pro Arg Thr
465                 470                 475                 480

Gly Leu Asp Phe Ser Asp Leu Tyr Tyr Leu Thr Met Asn Asn Lys His
                485                 490                 495

Trp Leu Val His Lys Glu Trp Phe His Asp Ile Pro Leu Pro Trp His
            500                 505                 510

Ala Gly Ala Asp Thr Gly Thr Pro His Trp Asn Asn Lys Glu Ala Leu
        515                 520                 525

Val Glu Phe Lys Asp Ala His Ala Lys Arg Gln Thr Val Val Val Leu
    530                 535                 540

Gly Ser Gln Glu Gly Ala Val His Thr Ala Leu Ala Gly Ala Leu Glu
545                 550                 555                 560

Ala Glu Met Asp Gly Ala Lys Gly Arg Leu Ser Ser Gly His Leu Lys
                565                 570                 575

Cys Arg Leu Lys Met Asp Lys Leu Arg Leu Lys Gly Val Ser Tyr Ser
            580                 585                 590

Leu Cys Thr Ala Ala Phe Thr Phe Thr Lys Ile Pro Ala Glu Thr Leu
        595                 600                 605

His Gly Thr Val Thr Val Glu Val Gln Tyr Ala Gly Thr Asp Gly Pro
    610                 615                 620

Cys Lys Val Pro Ala Gln Met Ala Val Asp Met Gln Thr Leu Thr Pro
625                 630                 635                 640

Val Gly Arg Leu Ile Thr Ala Asn Pro Val Ile Thr Glu Ser Thr Glu
                645                 650                 655

Asn Ser Lys Met Met Leu Glu Leu Asp Pro Pro Phe Gly Asp Ser Tyr
            660                 665                 670

Ile Val Ile Gly Val Gly Glu Lys Lys Ile Thr His His Trp His Arg
```

```
        675                 680                 685

Ser Gly Ser Thr Ile Gly Lys Ala Phe Glu Ala Thr Val Arg Gly Ala
    690                 695                 700

Lys Arg Met Ala Val Leu Gly Asp Thr Ala Trp Asp Phe Gly Ser Val
705                 710                 715                 720

Gly Gly Ala Leu Asn Ser Leu Gly Lys Gly Ile His Gln Ile Phe Gly
                725                 730                 735

Ala Ala Phe Lys Ser Leu Phe Gly Gly Met Ser Trp Phe Ser Gln Ile
            740                 745                 750

Leu Ile Gly Thr Leu Leu Met Trp Leu Gly Leu Asn Thr Lys Asn Gly
        755                 760                 765

Ser Ile Ser Leu Met Cys Leu Ala Ala Gly Ile Val Thr Leu Tyr Leu
    770                 775                 780

Gly Val Met Val Gln Ala Asp Ser Gly Cys Val Val Ser Trp Lys Asn
785                 790                 795                 800

Lys Glu Leu Lys Cys Gly Ser Gly Ile Phe Ile Thr Asp Asn Val His
                805                 810                 815

Thr Trp Thr Glu Gln Tyr Lys Phe Gln Pro Glu Ser Pro Ser Lys Leu
            820                 825                 830

Ala Ser Ala Ile Gln Lys Ala His Glu Glu Asp Ile Cys Gly Ile Arg
        835                 840                 845

Ser Val Thr Arg Leu Glu Asn Leu Met Trp Lys Gln Ile Thr Pro Glu
    850                 855                 860

Leu Asn His Ile Leu Ser Glu Asn Glu Val Lys Leu Thr Ile Met Thr
865                 870                 875                 880

Gly Asp Ile Lys Gly Ile Met Gln Ala Gly Lys Arg Ser Leu Arg Pro
                885                 890                 895

Gln Pro Thr Glu Leu Lys Tyr Ser Trp Lys Thr Trp Gly Lys Ala Lys
            900                 905                 910

Met Leu Ser Thr Glu Ser His Asn Gln Thr Phe Leu Ile Asp Gly Pro
        915                 920                 925

Glu Thr Ala Glu Cys Pro Asn Thr Asn Arg Ala Trp Asn Ser Leu Glu
    930                 935                 940

Val Glu Asp Tyr Gly Phe Gly Val Phe Thr Thr Asn Ile Trp Leu Lys
945                 950                 955                 960

Leu Lys Glu Lys Gln Asp Val Phe Cys Asp Ser Lys Leu Met Ser Ala
                965                 970                 975

Ala Ile Lys Asp Asn Arg Ala Val His Ala Asp Met Gly Tyr Trp Ile
            980                 985                 990

Glu Ser Ala Leu Asn Asp Thr Trp  Lys Ile Glu Lys Ala  Ser Phe Ile
        995                 1000                1005

Glu Val  Lys Asn Cys His Trp  Pro Lys Ser His Thr  Leu Trp Ser
    1010                1015                1020

Asn Gly  Val Leu Glu Ser Glu  Met Ile Ile Pro Lys  Asn Leu Ala
    1025                1030                1035

Gly Pro  Val Ser Gln His Asn  Tyr Arg Pro Gly Tyr  His Thr Gln
    1040                1045                1050

Ile Thr  Gly Pro Trp His Leu  Gly Lys Leu Glu Met  Asp Phe Asp
    1055                1060                1065

Phe Cys  Asp Gly Thr Thr Val  Val Val Thr Glu Asp  Cys Gly Asn
    1070                1075                1080

Arg Gly  Pro Ser Leu Arg Thr  Thr Thr Ala Ser Gly  Lys Leu Ile
    1085                1090                1095
```

```
Thr Glu  Trp Cys Cys Arg Ser  Cys Thr Leu Pro Pro  Leu Arg Tyr
    1100                 1105                 1110

Arg Gly  Glu Asp Gly Cys Trp  Tyr Gly Met Glu Ile  Arg Pro Leu
    1115                 1120                 1125

Lys Glu  Lys Glu Glu Asn Leu  Val Asn Ser Leu Val  Thr Ala Gly
    1130                 1135                 1140

His Gly  Gln Val Asp Asn Phe  Ser Leu Gly Val Leu  Gly Met Ala
    1145                 1150                 1155

Leu Phe  Leu Glu Glu Val Leu  Arg Thr Arg Val Gly  Thr Lys His
    1160                 1165                 1170

Ala Ile  Leu Leu Val Ala Val  Ser Phe Val Thr Leu  Ile Thr Gly
    1175                 1180                 1185

Asn Met  Ser Phe Arg Asp Leu  Gly Arg Val Met Val  Met Val Gly
    1190                 1195                 1200

Ala Thr  Met Thr Asp Asp Ile  Gly Met Gly Val Thr  Tyr Leu Ala
    1205                 1210                 1215

Leu Leu  Ala Ala Phe Lys Val  Arg Pro Thr Phe Ala  Ala Gly Leu
    1220                 1225                 1230

Leu Leu  Arg Lys Leu Thr Ser  Lys Glu Leu Met Met  Thr Thr Ile
    1235                 1240                 1245

Gly Ile  Val Leu Leu Ser Gln  Ser Thr Ile Pro Glu  Thr Ile Leu
    1250                 1255                 1260

Glu Leu  Thr Asp Ala Leu Ala  Leu Gly Met Met Val  Leu Lys Met
    1265                 1270                 1275

Val Arg  Asn Met Glu Lys Tyr  Gln Leu Ala Val Thr  Ile Met Ala
    1280                 1285                 1290

Ile Leu  Cys Val Pro Asn Ala  Val Ile Leu Gln Asn  Ala Trp Lys
    1295                 1300                 1305

Val Ser  Cys Thr Ile Leu Ala  Val Val Ser Val Ser  Pro Leu Phe
    1310                 1315                 1320

Leu Thr  Ser Ser Gln Gln Lys  Thr Asp Trp Ile Pro  Leu Ala Leu
    1325                 1330                 1335

Thr Ile  Lys Gly Leu Asn Pro  Thr Ala Ile Phe Leu  Thr Thr Leu
    1340                 1345                 1350

Ser Arg  Thr Ser Lys Lys Arg  Ser Trp Pro Leu Asn  Glu Ala Ile
    1355                 1360                 1365

Met Ala  Val Gly Met Val Ser  Ile Leu Ala Ser Ser  Leu Leu Lys
    1370                 1375                 1380

Asn Asp  Ile Pro Met Thr Gly  Pro Leu Val Ala Gly  Gly Leu Leu
    1385                 1390                 1395

Thr Val  Cys Tyr Val Leu Thr  Gly Arg Ser Ala Asp  Leu Glu Leu
    1400                 1405                 1410

Glu Arg  Ala Ala Asp Val Lys  Trp Glu Asp Gln Ala  Glu Ile Ser
    1415                 1420                 1425

Gly Ser  Ser Pro Ile Leu Ser  Ile Thr Ile Ser Glu  Asp Gly Ser
    1430                 1435                 1440

Met Ser  Ile Lys Asn Glu Glu  Glu Glu Gln Thr Leu  Thr Ile Leu
    1445                 1450                 1455

Ile Arg  Thr Gly Leu Leu Val  Ile Ser Gly Leu Phe  Pro Val Ser
    1460                 1465                 1470

Ile Pro  Ile Thr Ala Ala Ala  Trp Tyr Leu Trp Glu  Val Lys Lys
    1475                 1480                 1485
```

```
Gln Arg  Ala Gly Val Leu Trp  Asp Val Pro Ser Pro  Pro Pro Met
    1490                 1495                 1500

Gly Lys  Ala Glu Leu Glu Asp  Gly Ala Tyr Arg Ile  Lys Gln Lys
    1505                 1510                 1515

Gly Ile  Leu Gly Tyr Ser Gln  Ile Gly Ala Gly Val  Tyr Lys Glu
    1520                 1525                 1530

Gly Thr  Phe His Thr Met Trp  His Val Thr Arg Gly  Ala Val Leu
    1535                 1540                 1545

Met His  Lys Gly Lys Arg Ile  Glu Pro Ser Trp Ala  Asp Val Lys
    1550                 1555                 1560

Lys Asp  Leu Ile Ser Tyr Gly  Gly Gly Trp Lys Leu  Glu Gly Glu
    1565                 1570                 1575

Trp Lys  Glu Gly Glu Glu Val  Gln Val Leu Ala Leu  Glu Pro Gly
    1580                 1585                 1590

Lys Asn  Pro Arg Ala Val Gln  Thr Lys Pro Gly Leu  Phe Lys Thr
    1595                 1600                 1605

Asn Ala  Gly Thr Ile Gly Ala  Val Ser Leu Asp Phe  Ser Pro Gly
    1610                 1615                 1620

Thr Ser  Gly Ser Pro Ile Ile  Asp Lys Lys Gly Lys  Val Val Gly
    1625                 1630                 1635

Leu Tyr  Gly Asn Gly Val Val  Thr Arg Ser Gly Ala  Tyr Val Ser
    1640                 1645                 1650

Ala Ile  Ala Gln Thr Glu Lys  Ser Ile Glu Asp Asn  Pro Glu Ile
    1655                 1660                 1665

Glu Asp  Asp Ile Phe Arg Lys  Arg Arg Leu Thr Ile  Met Asp Leu
    1670                 1675                 1680

His Pro  Gly Ala Gly Lys Thr  Lys Arg Tyr Leu Pro  Ala Ile Val
    1685                 1690                 1695

Arg Glu  Ala Ile Lys Arg Gly  Leu Arg Thr Leu Ile  Leu Ala Pro
    1700                 1705                 1710

Thr Arg  Val Val Ala Ala Glu  Met Glu Glu Ala Leu  Arg Gly Leu
    1715                 1720                 1725

Pro Ile  Arg Tyr Gln Thr Pro  Ala Ile Arg Ala Val  His Thr Gly
    1730                 1735                 1740

Arg Glu  Ile Val Asp Leu Met  Cys His Ala Thr Phe  Thr Met Arg
    1745                 1750                 1755

Leu Leu  Ser Pro Val Arg Val  Pro Asn Tyr Asn Leu  Ile Ile Met
    1760                 1765                 1770

Asp Glu  Ala His Phe Thr Asp  Pro Ala Ser Ile Ala  Ala Arg Gly
    1775                 1780                 1785

Tyr Ile  Ser Thr Arg Val Glu  Met Gly Glu Ala Ala  Gly Ile Phe
    1790                 1795                 1800

Met Thr  Ala Thr Pro Pro Gly  Ser Arg Asp Pro Phe  Pro Gln Ser
    1805                 1810                 1815

Asn Ala  Pro Ile Ile Asp Glu  Glu Arg Glu Ile Pro  Glu Arg Ser
    1820                 1825                 1830

Trp Asn  Ser Gly His Glu Trp  Val Thr Asp Phe Lys  Gly Lys Thr
    1835                 1840                 1845

Val Trp  Phe Val Pro Ser Ile  Lys Ala Gly Asn Asp  Ile Ala Ala
    1850                 1855                 1860

Cys Leu  Arg Lys Asn Gly Lys  Lys Val Ile Gln Leu  Ser Arg Lys
    1865                 1870                 1875

Thr Phe  Asp Ser Glu Tyr Val  Lys Thr Arg Thr Asn  Asp Trp Asp
```

```
    1880                1885                1890

Phe Val  Val Thr Thr Asp Ile  Ser Glu Met Gly Ala  Asn Phe Lys
    1895                1900                1905

Ala Glu  Arg Val Ile Asp Pro  Arg Arg Cys Met Lys  Pro Val Ile
    1910                1915                1920

Leu Thr  Asp Gly Glu Glu Arg  Val Ile Leu Ala Gly  Pro Met Pro
    1925                1930                1935

Val Thr  His Ser Ser Ala Ala  Gln Arg Arg Gly Arg  Ile Gly Arg
    1940                1945                1950

Asn Pro  Lys Asn Glu Asn Asp  Gln Tyr Ile Tyr Met  Gly Glu Pro
    1955                1960                1965

Leu Glu  Asn Asp Glu Asp Cys  Ala His Trp Lys Glu  Ala Lys Met
    1970                1975                1980

Leu Leu  Asp Asn Ile Asn Thr  Pro Glu Gly Ile Ile  Pro Ser Met
    1985                1990                1995

Phe Glu  Pro Glu Arg Glu Lys  Val Asp Ala Ile Asp  Gly Glu Tyr
    2000                2005                2010

Arg Leu  Arg Gly Glu Ala Arg  Lys Thr Phe Val Asp  Leu Met Arg
    2015                2020                2025

Arg Gly  Asp Leu Pro Val Trp  Leu Ala Tyr Arg Val  Ala Ala Glu
    2030                2035                2040

Gly Ile  Asn Tyr Ala Asp Arg  Arg Trp Cys Phe Asp  Gly Val Lys
    2045                2050                2055

Asn Asn  Gln Ile Leu Glu Glu  Asn Val Glu Val Glu  Ile Trp Thr
    2060                2065                2070

Lys Glu  Gly Glu Arg Lys Lys  Leu Lys Pro Arg Trp  Leu Asp Ala
    2075                2080                2085

Arg Ile  Tyr Ser Asp Pro Leu  Ala Leu Lys Glu Phe  Lys Glu Phe
    2090                2095                2100

Ala Ala  Gly Arg Lys Ser Leu  Thr Leu Asn Leu Ile  Thr Glu Met
    2105                2110                2115

Gly Arg  Leu Pro Thr Phe Met  Thr Gln Lys Ala Arg  Asp Ala Leu
    2120                2125                2130

Asp Asn  Leu Ala Val Leu His  Thr Ala Glu Ala Gly  Gly Arg Ala
    2135                2140                2145

Tyr Asn  His Ala Leu Ser Glu  Leu Pro Glu Thr Leu  Glu Thr Leu
    2150                2155                2160

Leu Leu  Leu Thr Leu Leu Ala  Thr Val Thr Gly Gly  Ile Phe Leu
    2165                2170                2175

Phe Leu  Met Ser Ala Arg Gly  Ile Gly Lys Met Thr  Leu Gly Met
    2180                2185                2190

Cys Cys  Ile Ile Thr Ala Ser  Ile Leu Leu Trp Tyr  Ala Gln Ile
    2195                2200                2205

Gln Pro  His Trp Ile Ala Ala  Ser Ile Ile Leu Glu  Phe Phe Leu
    2210                2215                2220

Ile Val  Leu Leu Ile Pro Glu  Pro Glu Lys Gln Arg  Thr Pro Gln
    2225                2230                2235

Asp Asn  Gln Leu Thr Tyr Val  Val Ile Ala Ile Leu  Thr Val Val
    2240                2245                2250

Ala Ala  Thr Met Ala Asn Glu  Met Gly Phe Leu Glu  Lys Thr Lys
    2255                2260                2265

Lys Asp  Leu Gly Leu Gly Ser  Ile Ala Thr Gln Gln  Pro Glu Ser
    2270                2275                2280
```

```
Asn Ile  Leu Asp Ile Asp Leu  Arg Pro Ala Ser Ala  Trp Thr Leu
    2285                 2290                 2295

Tyr Ala  Val Ala Thr Thr Phe  Val Thr Pro Met Leu  Arg His Ser
    2300                 2305                 2310

Ile Glu  Asn Ser Ser Val Asn  Val Ser Leu Thr Ala  Ile Ala Asn
    2315                 2320                 2325

Gln Ala  Thr Val Leu Met Gly  Leu Gly Lys Gly Trp  Pro Leu Ser
    2330                 2335                 2340

Lys Met  Asp Ile Gly Val Pro  Leu Leu Ala Ile Gly  Cys Tyr Ser
    2345                 2350                 2355

Gln Val  Asn Pro Ile Thr Leu  Thr Ala Ala Leu Phe  Leu Leu Val
    2360                 2365                 2370

Ala His  Tyr Ala Ile Ile Gly  Pro Gly Leu Gln Ala  Lys Ala Thr
    2375                 2380                 2385

Arg Glu  Ala Gln Lys Arg Ala  Ala Ala Gly Ile Met  Lys Asn Pro
    2390                 2395                 2400

Thr Val  Asp Gly Ile Thr Val  Ile Asp Leu Asp Pro  Ile Pro Tyr
    2405                 2410                 2415

Asp Pro  Lys Phe Glu Lys Gln  Leu Gly Gln Val Met  Leu Leu Val
    2420                 2425                 2430

Leu Cys  Val Thr Gln Val Leu  Met Met Arg Thr Thr  Trp Ala Leu
    2435                 2440                 2445

Cys Glu  Ala Leu Thr Leu Ala  Thr Gly Pro Ile Ser  Thr Leu Trp
    2450                 2455                 2460

Glu Gly  Asn Pro Gly Arg Phe  Trp Asn Thr Thr Ile  Ala Val Ser
    2465                 2470                 2475

Met Ala  Asn Ile Phe Arg Gly  Ser Tyr Leu Ala Gly  Ala Gly Leu
    2480                 2485                 2490

Leu Phe  Ser Ile Met Lys Asn  Thr Thr Asn Thr Arg  Arg Gly Thr
    2495                 2500                 2505

Gly Asn  Ile Gly Glu Thr Leu  Gly Glu Lys Trp Lys  Ser Arg Leu
    2510                 2515                 2520

Asn Ala  Leu Gly Lys Ser Glu  Phe Gln Ile Tyr Lys  Lys Ser Gly
    2525                 2530                 2535

Ile Gln  Glu Val Asp Arg Thr  Leu Ala Lys Glu Gly  Ile Lys Arg
    2540                 2545                 2550

Gly Glu  Thr Asp His His Ala  Val Ser Arg Gly Ser  Ala Lys Leu
    2555                 2560                 2565

Arg Trp  Phe Val Glu Arg Asn  Met Val Thr Pro Glu  Gly Lys Val
    2570                 2575                 2580

Val Asp  Leu Gly Cys Gly Arg  Gly Gly Trp Ser Tyr  Tyr Cys Gly
    2585                 2590                 2595

Gly Leu  Lys Asn Val Arg Glu  Val Lys Gly Leu Thr  Lys Gly Gly
    2600                 2605                 2610

Pro Gly  His Glu Glu Pro Ile  Pro Met Ser Thr Tyr  Gly Trp Asn
    2615                 2620                 2625

Leu Val  Arg Leu Gln Ser Gly  Val Asp Val Phe Phe  Ile Pro Pro
    2630                 2635                 2640

Glu Lys  Cys Asp Thr Leu Leu  Cys Asp Ile Gly Glu  Ser Ser Pro
    2645                 2650                 2655

Asn Pro  Thr Val Glu Ala Gly  Arg Thr Leu Arg Val  Leu Asn Leu
    2660                 2665                 2670
```

```
Val Glu Asn Trp Leu Asn Asn Asn Thr Gln Phe Cys Ile Lys Val
    2675                2680                2685

Leu Asn Pro Tyr Met Pro Ser Val Ile Glu Lys Met Glu Ala Leu
    2690                2695                2700

Gln Arg Lys Tyr Gly Gly Ala Leu Val Arg Asn Pro Leu Ser Arg
    2705                2710                2715

Asn Ser Thr His Glu Met Tyr Trp Val Ser Asn Ala Ser Gly Asn
    2720                2725                2730

Ile Val Ser Ser Val Asn Met Ile Ser Arg Met Leu Ile Asn Arg
    2735                2740                2745

Phe Thr Met Arg Tyr Lys Lys Ala Thr Tyr Glu Pro Asp Val Asp
    2750                2755                2760

Leu Gly Ser Gly Thr Arg Asn Ile Gly Ile Glu Ser Glu Ile Pro
    2765                2770                2775

Asn Leu Asp Ile Ile Gly Lys Arg Ile Glu Lys Ile Lys Gln Glu
    2780                2785                2790

His Glu Thr Ser Trp His Tyr Asp Gln Asp His Pro Tyr Lys Thr
    2795                2800                2805

Trp Ala Tyr His Gly Ser Tyr Glu Thr Lys Gln Thr Gly Ser Ala
    2810                2815                2820

Ser Ser Met Val Asn Gly Val Val Arg Leu Leu Thr Lys Pro Trp
    2825                2830                2835

Asp Val Val Pro Met Val Thr Gln Met Ala Met Thr Asp Thr Thr
    2840                2845                2850

Pro Phe Gly Gln Gln Arg Val Phe Lys Glu Lys Val Asp Thr Arg
    2855                2860                2865

Thr Gln Glu Pro Lys Glu Gly Thr Lys Lys Leu Met Lys Ile Thr
    2870                2875                2880

Ala Glu Trp Leu Trp Lys Glu Leu Gly Lys Lys Lys Thr Pro Arg
    2885                2890                2895

Met Cys Thr Arg Glu Glu Phe Thr Arg Lys Val Arg Ser Asn Ala
    2900                2905                2910

Ala Leu Gly Ala Ile Phe Thr Asp Glu Asn Lys Trp Lys Ser Ala
    2915                2920                2925

Arg Glu Ala Val Glu Asp Ser Arg Phe Trp Glu Leu Val Asp Lys
    2930                2935                2940

Glu Arg Asn Leu His Leu Glu Gly Lys Cys Glu Thr Cys Val Tyr
    2945                2950                2955

Asn Met Met Gly Lys Arg Glu Lys Lys Leu Gly Glu Phe Gly Lys
    2960                2965                2970

Ala Lys Gly Ser Arg Ala Ile Trp Tyr Met Trp Leu Gly Ala Arg
    2975                2980                2985

Phe Leu Glu Phe Glu Ala Leu Gly Phe Leu Asn Glu Asp His Trp
    2990                2995                3000

Phe Ser Arg Glu Asn Ser Leu Ser Gly Val Glu Gly Glu Gly Leu
    3005                3010                3015

His Lys Leu Gly Tyr Ile Leu Arg Asp Val Ser Lys Lys Glu Gly
    3020                3025                3030

Gly Ala Met Tyr Ala Asp Asp Thr Ala Gly Trp Asp Thr Arg Ile
    3035                3040                3045

Thr Leu Glu Asp Leu Lys Asn Glu Glu Met Val Thr Asn His Met
    3050                3055                3060

Glu Gly Glu His Lys Lys Leu Ala Glu Ala Ile Phe Lys Leu Thr
```

```
    3065                3070                3075

Tyr Gln  Asn Lys Val Val Arg  Val Gln Arg Pro Thr  Pro Arg Gly
    3080                3085                3090

Thr Val  Met Asp Ile Ile Ser  Arg Arg Asp Gln Arg  Gly Ser Gly
    3095                3100                3105

Gln Val  Gly Thr Tyr Gly Leu  Asn Thr Phe Thr Asn  Met Glu Ala
    3110                3115                3120

Gln Leu  Ile Arg Gln Met Glu  Gly Glu Gly Val Phe  Lys Ser Ile
    3125                3130                3135

Gln His  Leu Thr Ile Thr Glu  Glu Ile Ala Val Gln  Asn Trp Leu
    3140                3145                3150

Ala Arg  Val Gly Arg Glu Arg  Leu Ser Arg Met Ala  Ile Ser Gly
    3155                3160                3165

Asp Asp  Cys Val Val Lys Pro  Leu Asp Asp Arg Phe  Ala Ser Ala
    3170                3175                3180

Leu Thr  Ala Leu Asn Asp Met  Gly Lys Ile Arg Lys  Asp Ile Gln
    3185                3190                3195

Gln Trp  Glu Pro Ser Arg Gly  Trp Asn Asp Trp Thr  Gln Val Pro
    3200                3205                3210

Phe Cys  Ser His His Phe His  Glu Leu Ile Met Lys  Asp Gly Arg
    3215                3220                3225

Val Leu  Val Val Pro Cys Arg  Asn Gln Asp Glu Leu  Ile Gly Arg
    3230                3235                3240

Ala Arg  Ile Ser Gln Gly Ala  Gly Trp Ser Leu Arg  Glu Thr Ala
    3245                3250                3255

Cys Leu  Gly Lys Ser Tyr Ala  Gln Met Trp Ser Leu  Met Tyr Phe
    3260                3265                3270

His Arg  Arg Asp Leu Arg Leu  Ala Ala Asn Ala Ile  Cys Ser Ala
    3275                3280                3285

Val Pro  Ser His Trp Val Pro  Thr Ser Arg Thr Thr  Trp Ser Ile
    3290                3295                3300

His Ala  Lys His Glu Trp Met  Thr Thr Glu Asp Met  Leu Thr Val
    3305                3310                3315

Trp Asn  Arg Val Trp Ile Gln  Glu Asn Pro Trp Met  Glu Asp Lys
    3320                3325                3330

Thr Pro  Val Glu Ser Trp Glu  Glu Ile Pro Tyr Leu  Gly Lys Arg
    3335                3340                3345

Glu Asp  Gln Trp Cys Gly Ser  Leu Ile Gly Leu Thr  Ser Arg Ala
    3350                3355                3360

Thr Trp  Ala Lys Asn Ile Gln  Ala Ala Ile Asn Gln  Val Arg Ser
    3365                3370                3375

Leu Ile  Gly Asn Glu Glu Tyr  Thr Asp Tyr Met Pro  Ser Met Lys
    3380                3385                3390

Arg Phe  Arg Arg Glu Glu Glu  Glu Ala Gly Val Leu  Trp
    3395                3400                3405
```

<210> SEQ ID NO 7
<211> LENGTH: 10807
<212> TYPE: DNA
<213> ORGANISM: Zika virus strain R103451

<400> SEQUENCE: 7

```
agttgttgat ctgtgtgaat cagactgcga cagttcgagt ttgaagcgaa agctagcaac      60

agtatcaaca ggttttattt tggatttgga aacgagagtt tctggtcatg aaaaacccaa     120
```

```
aaaagaaatc cggaggattc cggattgtca atatgctaaa acgcggagta gcccgtgtga    180
gccccctttgg gggcttgaag aggctgccag ccggacttct gctgggtcat gggcccatca    240
ggatggtctt ggcgattcta gcctttttga gattcacggc aatcaagcca tcactgggtc    300
tcatcaatag atggggttca gtggggaaaa aagaggctat ggaaataata aagaagttca    360
agaaagatct ggctgccatg ctgagaataa tcaatgctag gaaggagaag aagagacgag    420
gcgcagatac tagtgtcgga attgttggcc tcctgctgac cacagctatg gcagcggagg    480
tcactagacg tgggagtgca tactatatgt acttggacag aaacgatgct ggggaggcca    540
tatcttttcc aaccacattg ggatgaata agtgttatat acagatcatg gatcttggac    600
acatgtgtga tgccaccatg agctatgaat gccctatgct ggatgagggg gtggaaccag    660
atgacgtcga ttgttggtgc aacacgacgt caacttgggt tgtgtacgga acctgccatc    720
acaaaaaagg tgaagcacgg agatctagaa gagctgtgac gctcccctcc cattccacta    780
ggaagctgca aacgcggtcg caaacctggt tggaatcaag agaatacaca aagcacttga    840
ttagagtcga aaattggata ttcaggaacc ctggcttcgc gttagcagca gctgccatcg    900
cttggctttt gggaagctca acgagccaaa aagtcatata cttggtcatg atactgctga    960
ttgccccggc atacagcatc aggtgcatag gagtcagcaa tagggacttt gtggaaggta   1020
tgtcaggtgg gacttgggtt gatgttgtct tggaacatgg aggttgtgtc accgtaatgg   1080
cacaggacaa accgactgtc gacatagagc tggttacaac aacagtcagc aacatggcgg   1140
aggtaagatc ctactgctat gaggcatcaa tatcagacat ggcttcggac agccgctgcc   1200
caacacaagg tgaagcctac cttgacaagc aatcagacac tcaatatgtc tgcaaaagaa   1260
cgttagtgga cagaggctgg ggaaatggat gtggactttt tggcaaaggg agcctggtga   1320
catgcgctaa gtttgcatgc tccaagaaaa tgaccgggaa gagcatccag ccagagaatc   1380
tggagtaccg gataatgctg tcagttcatg gctcccagca cagtgggatg atcgttaatg   1440
acacaggaca tgaaactgat gagaatagag cgaaggttga gataacgccc aattcaccaa   1500
gagccgaagc caccctgggg ggttttggaa gcctaggact tgattgtgaa ccgaggacag   1560
gccttgactt ttcagatttg tattacttga ctatgaataa caagcactgg ttggttcaca   1620
aggagtggtt ccacgacatt ccattacctt ggcacgctgg ggcagacacc ggaactccac   1680
actggaacaa caaagaagca ctggtagagt tcaaggacgc acatgccaaa aggcaaactg   1740
tcgtggttct agggagtcaa gaaggagcag ttcacacggc ccttgctgga gctctggagg   1800
ctgagatgga tggtgcaaag ggaaggctgt cctctggcca cttgaaatgt cgcctgaaaa   1860
tggataaact tagattgaag ggcgtgtcat actccttgtg taccgcagcg ttcacattca   1920
ccaagatccc ggctgaaaca ctgcacggga cagtcacagt ggaggtacag tacgcaggga   1980
cagatggacc ttgcaaggtt ccagctcaga tggcggtgga catgcaaact ctgaccccag   2040
ttgggaggtt gataaccgct aaccccgtaa tcactgaaag cactgagaac tctaagatga   2100
tgctggaact tgatccacca tttggggact cttacattgt cataggagtc ggggagaaga   2160
agatcaccca ccactggcac aggagtggca gcaccattgg aaaagcattt gaagccactg   2220
tgagaggtgc caagagaatg gcagtcttgg gagacacagc ctgggacttt ggatcagttg   2280
gaggcgctct caactcattg ggcaagggca tccatcaaat ttttggagca gctttcaaat   2340
cattgtttgg aggaatgtcc tggttctcac aaattctcat tggaacgttg ctgatgtggt   2400
tgggtctgaa cacaaagaat ggatctattt ccccttatgtg cttggcctta gggggagtgt   2460
```

-continued

```
tgatcttctt atccacagcc gtctctgctg atgtggggtg ctcggtggac ttctcaaaga   2520

aggagacgag atgcggtaca ggggtgttcg tctataacga cgttgaagcc tggagggaca   2580

ggtacaagta ccatcctgac tccccccgta gattggcagc agcagtcaag caagcctggg   2640

aagatggtat ctgcgggatc tcctctgttt caagaatgga aaacatcatg tggagatcag   2700

tagaagggga gctcaacgca atcctggaag agaatggagt tcaactgacg gtcgttgtgg   2760

gatctgtaaa aaaccccatg tggagagctc cacagagatt gcccgtgcct gtgaacgagc   2820

tgccccacgg ctggaaggct tgggggaaat cgtacttcgt cagagcagca aagacaaata   2880

acagctttgt cgtggatggt gacacactga aggaatgccc actcaaacat agagcatgga   2940

acagctttct tgtggaggat catgggttcg ggtatttca cactagtgtc tggctcaagg   3000

ttagagaaga ttattcatta gagtgtgatc cagccgttat tggaacagct gttaagggaa   3060

aggaggctgt acacagtgat ctaggctact ggattgagag tgagaagaat gacacatgga   3120

ggctgaagag ggcccatctg atcgagatga aaacatgtga atggccaaag tcccacacat   3180

tgtggacaga tggaatagaa gagagtgatc tgatcatacc caagtcttta gctgggccac   3240

tcagccatca caataccaga gagggctaca ggacccaaat gaaagggcca tggcacagtg   3300

aagagcttga aattcggttt gaggaatgcc caggcactaa ggtccacgtg gaggaaacat   3360

gtggaacaag aggaccatct ctgagatcaa ccactgcaag cggaagggtg atcgaggaat   3420

ggtgctgcag ggagtgcaca atgcccccac tgtcgttccg ggctaaagat ggctgttggt   3480

atggaatgga gataaggccc aggaaagaac cagaaagcaa cttagtaagg tcaatggtga   3540

ctgcaggatc aactgatcac atggatcact tctcccttgg agtgcttgtg attctgctca   3600

tggtgcagga agggctaaag aagagaatga ccacaaagat catcataagc acatcaatgg   3660

cagtgctggt agctatgatc ctgggaggat tttcaatgag tgacctggct aagcttgcaa   3720

ttttgatggg tgccaccttc gcggaaatga acactggagg agatgtagct catctggcgc   3780

tgatagcggc attcaaagtc agaccagcgt tgctggtatc tttcatcttc agagctaatt   3840

ggacaccccg tgaaagcatg ctactggcct tggcctcgtg tcttttgcaa actgcgatct   3900

ccgccttgga aggcgacctg atggttctca tcaatggttt tgctttggcc tggttggcaa   3960

tacgagcgat ggttgttcca cgcactgata acatcacctt ggcaatcctg gctgctctga   4020

caccactggc ccggggcaca ctgcttgtgg cgtggagagc aggccttgct acttgcgggg   4080

ggtttatgct cctctctctg aagggaaaag gcagtgtgaa gaagaactta ccatttgtca   4140

tggccctggg actaaccgct gtgaggctgg tcgaccccat caacgtggtg ggactgctgt   4200

tgctcacaag gagtgggaag cggagctggc cccctagcga agtactcaca gctgttggcc   4260

tgatatgcgc attggctgga gggttcgcca aggcagatat agagatggct gggcccatgg   4320

ccgcggtcgg tctgctaatt gtcagttacg tggtctcagg aaagagtgtg gacatgtaca   4380

ttgaaagagc aggtgacatc acatgggaaa aagatgcgga agtcactgga aacagtcccc   4440

ggctcgatgt ggcgctagat gagagtggtg atttctccct ggtggaggat gacggtcccc   4500

ccatgagaga gatcatactc aaggtggtcc tgatgaccat ctgtggcatg aacccaatag   4560

ccataccctt cgcagctgga gcgtggtacg tatacgtgaa gactggaaaa aggagtggtg   4620

ctctatggga tgtgcctgct cccaaggaag taaaaaaggg ggagaccaca gatggagtgt   4680

acagagtaat gactcgtaga ctgctaggtt caacacaagt tggagtggga gttatgcaag   4740

agggggtctt tcacactatg tggcacgtca caaaaggatc cgcactgaga agcggtgaag   4800

ggagacttga tccatactgg ggagatgtca agcaggatct ggtgtcatac tgtggtccat   4860
```

```
ggaagctaga tgccgcctgg gacgggcaca gcgaggtgca gctcttggcc gtgccccccg   4920
gagagagagc gaggaacatc cagactctgc ccggaatatt taagacaaag gatggggaca   4980
ttggagcggt tgcgctggat tacccagcag gaacttcagg atctccaatc ctagacaagt   5040
gtgggagagt gataggactt tatggcaatg gggtcgtgat caaaaatggg agttatgtta   5100
gtgccatcac ccaagggagg agggaggaag agactcctgt tgagtgcttc gagccttcga   5160
tgctgaagaa gaagcagcta actgtcttag acttacatcc tggagctggg aaaaccagga   5220
gagttcttcc tgaaatagtc cgtgaagcca taaaaacaag actccgtact gtgatcttag   5280
ctccaaccag ggttgtcgct gctgaaatgg aggaggccct tagagggctt ccagtgcgtt   5340
atatgacaac agcagtcaat gtcacccact ctggaacaga aatcgtcgac ttaatgtgcc   5400
atgccacctt cacttcacgt ctactacagc caatcagagt ccccaactat aatctgtata   5460
ttatggatga ggcccacttc acagatccct caagtatagc agcaagagga tacatttcaa   5520
caagggttga gatgggcgag gcggctgcca tcttcatgac cgccacgcca ccaggaaccc   5580
gtgacgcatt tccggactcc aactcaccaa ttatggacac cgaagtggaa gtcccagaga   5640
gagcctggag ctcaggcttt gattgggtga cggatcattc tggaaaaaca gtttggtttg   5700
ttccaagcgt gaggaacggc aatgagatcg cagcttgtct gacaaaggct ggaaaacggg   5760
tcatacagct cagcagaaag acttttgaga cagagttcca gaaaacaaaa catcaagagt   5820
gggactttgt cgtgacaact gacatttcag agatgggcgc caactttaaa gctgaccgtg   5880
tcatagattc caggagatgc ctaaagccgg tcatacttga tggcgagaga gtcattctgg   5940
ctggacccat gcctgtcaca catgccagcg ctgcccagag gagggggcgc ataggcagga   6000
atcccaacaa acctggagat gagtatctgt atggaggtgg gtgcgcagag actgacgaag   6060
accatgcaca ctggcttgaa gcaagaatgc tccttgacaa tatttacctc caagatggcc   6120
tcatagcctc gctctatcga cctgaggccg acaaagtagc agccattgag ggagagttca   6180
agcttaggac ggagcaaagg aagacctttg tggaactcat gaaaagagga gatcttcctg   6240
tttggctggc ctatcaggtt gcatctgccg gaataaccta cacagataga agatggtgct   6300
ttgatggcac gaccaacaac accatactgg aagacagcgt gccggcagag gtgtggacca   6360
gacacggaga gaaaagagtg ctcaaaccga ggtggatgga cgccagagtt tgttcagatc   6420
atgcggccct gaagtcattc aaggagtttg ccgctgggaa aagaggagcg gcttttggag   6480
tgatggaagc cctgggaaca ctgccaggac acatgacaga gagattccag gaagccattg   6540
acaacctcgc tgtgctcatg cgggcagaga ctggaagcag gccttacaaa gccgcggcgg   6600
cccaattgcc ggagacccta gagaccatta tgcttttggg gttgctggga acagtctcgc   6660
tgggaatctt tttcgtcttg atgaggaaca agggcatagg gaagatgggc tttggaatgg   6720
tgacccttgg ggccagtgca tggctcatgt ggctctcgga aattgagcca gccagaattg   6780
catgcgtcct cattgttgtg ttcctattgc tggtggtgct catacctgag ccagaaaagc   6840
aaagatctcc ccaggacaac caaatggcaa tcatcatcat ggtagcagta ggtcttctgg   6900
gcttgattac cgccaatgaa ctcggatggt tggagagaac aaagagtgac ctaagccatc   6960
taatgggaag gagagaggag gggggcaacca taggattctc aatggacatt gacctgcggc   7020
cagcctcagc ttgggccatc tatgctgcct tgacaacttt cattacccca gccgtccaac   7080
atgcagtgac cacttcatac aacaactact ccttaatggc gatggccacg caagctggag   7140
tgttgtttgg tatgggcaaa gggatgccat tctacgcatg ggactttgga gtcccgctgc   7200
```

```
taatgatagg ttgctactca caattaacac ccctgaccct aatagtggcc atcattttgc   7260
tcgtggcgca ctacatgtac ttgatcccag ggctgcaggc agcagctgcg cgtgctgccc   7320
agaagagaac ggcagctggc atcatgaaga accctgttgt ggatggaata gtggtgactg   7380
acattgacac aatgacaatt gacccccaag tggagaaaaa gatgggacag gtgctactca   7440
tagcagtagc cgtctccagc gccatactgt cgcggaccgc ctgggggtgg ggggaggctg   7500
gggccctgat cacagccgca acttccactt tgtgggaagg ctctccgaac aagtactgga   7560
actcctctac agccacttca ctgtgtaaca tttttagggg aagttacttg gctggagcct   7620
ctctaatcta cacagtaaca agaaacgctg gcttggtcaa gagacgtggg ggtggaacag   7680
gagagaccct gggagagaaa tggaaggccc gcttgaacca gatgtcggcc ctggagttct   7740
actcctacaa aaagtcaggc atcaccgagg tgtgcagaga agaggcccgc cgcgccctca   7800
aggacggtgt ggcaacggga ggccatgctg tgtcccgagg aagtgcaaag ctgagatggt   7860
tggtggagcg gggatacctg cagccctatg gaaaggtcat tgatcttgga tgtggcagag   7920
gggctggag ttactacgcc gccaccatcc gcaaagttca agaagtgaaa ggatacacaa   7980
aaggaggccc tggtcatgaa gaacccgtgt tggtgcaaag ctatgggtgg aacattgtcc   8040
gtcttaagag tggggtggac gtctttcata tggcggctga gccgtgtgac acgttgctgt   8100
gtgacatagg tgagtcatca tctagtcctg aagtggaaga agcacggacg ctcagagtcc   8160
tctccatggt gggggattgg cttgaaaaaa gaccaggagc cttttgtata aaagtgttgt   8220
gcccatacac cagcactatg atggaaaccc tggagcgact gcagcgtagg tatgggggag   8280
gactggtcag agtgccactc tcccgcaact ctacacatga gatgtactgg gtctctggag   8340
cgaaaagcaa caccataaaa agtgtgtcca ccacgagcca gctcctcttg ggcgcatgg   8400
acgggcctag gaggccagtg aaatatgagg aggatgtgaa tctcggctct ggcacgcggg   8460
ctgtggtaag ctgcgctgaa gctcccaaca tgaagatcat tggtaaccgc attgaaagga   8520
tccgcagtga gcacgcggaa acgtggttct ttgacgagaa ccacccatat aggacatggg   8580
cttaccatgg aagctatgag gcccccacac aagggtcagc gtcctctcta ataaacgggg   8640
ttgtcaggct cctgtcaaaa ccctgggatg tggtgactgg agtcacagga atagccatga   8700
ccgacaccac accgtatggt cagcaaagag ttttcaagga aaaagtggac actagggtgc   8760
cagaccccca agaaggcact cgtcaggtta tgagcatggt ctcttcctgg ttgtggaaag   8820
agctaggcaa acacaaacgg ccacgagtct gtaccaaaga agagttcatc aacaaggttc   8880
gtagcaatgc agcattaggg gcaatatttg aagaggaaaa agagtggaag actgcagtgg   8940
aagctgtgaa cgatccaagg ttctgggctc tagtggacaa ggaaagagag caccacctga   9000
gaggagagtg ccagagttgt gtgtacaaca tgatgggaaa aagagaaaag aaacaagggg   9060
aatttggaaa ggccaagggc agccgcgcca tctggtatat gtggctaggg gctagatttc   9120
tagagttcga agcccttgga ttcttgaacg aggatcactg gatggggaga gagaactcag   9180
gaggtggtgt tgaagggctg ggattacaaa gactcggata tgtcctagaa gagatgagtt   9240
gcataccagg aggaaggatg tatgcagatg acactgctgg ctgggacacc cgcatcagca   9300
ggtttgatct ggagaatgaa gctctaatca ccaaccaaat ggagaaaggg cacagggcct   9360
tggcattggc cataatcaag tacacatacc aaaacaaagt ggtaaaggtc cttagaccag   9420
ctgaaaaagg gaaaacagtt atggacatta tttcgagaca agaccaaagg gggagcggac   9480
aagttgtcac ttacgctctt aacacattta ccaacctagt ggtgcaactc attcggaata   9540
tggaggctga ggaagttcta gagatgcaag acttgtggct gctgcggagg tcagagaaag   9600
```

```
tgaccaactg gttgcagagc aacggatggg ataggctcaa acgaatggca gtcagtggag    9660
atgattgcgt tgtgaagcca attgatgata ggtttgcaca tgccctcagg ttcttgaatg    9720
atatgggaaa agttaggaag gacacacaag agtggaaacc ctcaactgga tgggacaact    9780
gggaagaagt tccgttttgc tcccaccact tcaacaagct ccatctcaag gacgggaggt    9840
ccattgtggt tccctgccgc caccaagatg aactgattgg ccgggcccgc gtctctccag    9900
gggcgggatg gagcatccgg gagactgctt gcctagcaaa atcatatgcg caaatgtggc    9960
agctccttta tttccacaga agggacctcc gactgatggc caatgccatt tgttcatctg   10020
tgccagttga ctgggttcca actgggagaa ctacctggtc aatccatgga aagggagaat   10080
ggatgaccac tgaagacatg cttgtggtgt ggaacagagt gtggattgag gagaacgacc   10140
acatggaaga caagacccca gttacgaaat ggacagacat tccctatttg ggaaaaaggg   10200
aagacttgtg gtgtggatct ctcatagggc acagaccgcg caccacctgg gctgagaaca   10260
ttaaaaacac agtcaacatg gtgcgcagga tcataggtga tgaagaaaag tacatggact   10320
acctatccac ccaagttcgc tacttgggtg aagaagggtc tacacctgga gtgctgtaag   10380
caccaatctt aacgttgtca ggcctgctag tcagccacag cttggggaaa gctgtgcagc   10440
ctgtgacccc cccaggagaa gctgggaaac caagcctata gtcaggccga gaacgccatg   10500
gcacggaaga agccatgctg cctgtgagcc cctcagagga cactgagtca aaaaacccca   10560
cgcgcttgga ggcgcaggat gggaaaagaa ggtggcgacc ttccccaccc ttcaatctgg   10620
ggcctgaact ggagatcagc tgtggatctc cagaagaggg actagtggtt agaggagacc   10680
ccccggaaaa cgcaaaacag catattgacg ctgggaaaga ccagagactc catgagtttc   10740
caccacgctg gccgccaggc acagatcgcc gaatagcggc ggccggtgtg gggaaatcca   10800
tgggtct                                                             10807
```

<210> SEQ ID NO 8
<211> LENGTH: 3423
<212> TYPE: PRT
<213> ORGANISM: Zika virus strain R103451

<400> SEQUENCE: 8

```
Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
```

```
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575
```

```
Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Asp Gly Ile
        835                 840                 845

Cys Gly Ile Ser Ser Val Ser Arg Met Glu Asn Ile Met Trp Arg Ser
    850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Ala Pro Gln
                885                 890                 895

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
        915                 920                 925

Val Asp Gly Asp Thr Leu Lys Glu Cys Pro Leu Lys His Arg Ala Trp
    930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
            980                 985                 990
```

```
Gly Tyr Trp Ile Glu Ser Glu Lys  Asn Asp Thr Trp Arg  Leu Lys Arg
        995                 1000                 1005

Ala His  Leu Ile Glu Met Lys  Thr Cys Glu Trp Pro  Lys Ser His
    1010                 1015                 1020

Thr Leu  Trp Thr Asp Gly Ile  Glu Glu Ser Asp Leu  Ile Ile Pro
    1025                 1030                 1035

Lys Ser  Leu Ala Gly Pro Leu  Ser His His Asn Thr  Arg Glu Gly
    1040                 1045                 1050

Tyr Arg  Thr Gln Met Lys Gly  Pro Trp His Ser Glu  Glu Leu Glu
    1055                 1060                 1065

Ile Arg  Phe Glu Glu Cys Pro  Gly Thr Lys Val His  Val Glu Glu
    1070                 1075                 1080

Thr Cys  Gly Thr Arg Gly Pro  Ser Leu Arg Ser Thr  Thr Ala Ser
    1085                 1090                 1095

Gly Arg  Val Ile Glu Glu Trp  Cys Cys Arg Glu Cys  Thr Met Pro
    1100                 1105                 1110

Pro Leu  Ser Phe Arg Ala Lys  Asp Gly Cys Trp Tyr  Gly Met Glu
    1115                 1120                 1125

Ile Arg  Pro Arg Lys Glu Pro  Glu Ser Asn Leu Val  Arg Ser Met
    1130                 1135                 1140

Val Thr  Ala Gly Ser Thr Asp  His Met Asp His Phe  Ser Leu Gly
    1145                 1150                 1155

Val Leu  Val Ile Leu Leu Met  Val Gln Glu Gly Leu  Lys Lys Arg
    1160                 1165                 1170

Met Thr  Thr Lys Ile Ile Ile  Ser Thr Ser Met Ala  Val Leu Val
    1175                 1180                 1185

Ala Met  Ile Leu Gly Gly Phe  Ser Met Ser Asp Leu  Ala Lys Leu
    1190                 1195                 1200

Ala Ile  Leu Met Gly Ala Thr  Phe Ala Glu Met Asn  Thr Gly Gly
    1205                 1210                 1215

Asp Val  Ala His Leu Ala Leu  Ile Ala Ala Phe Lys  Val Arg Pro
    1220                 1225                 1230

Ala Leu  Leu Val Ser Phe Ile  Phe Arg Ala Asn Trp  Thr Pro Arg
    1235                 1240                 1245

Glu Ser  Met Leu Leu Ala Leu  Ala Ser Cys Leu Leu  Gln Thr Ala
    1250                 1255                 1260

Ile Ser  Ala Leu Glu Gly Asp  Leu Met Val Leu Ile  Asn Gly Phe
    1265                 1270                 1275

Ala Leu  Ala Trp Leu Ala Ile  Arg Ala Met Val Val  Pro Arg Thr
    1280                 1285                 1290

Asp Asn  Ile Thr Leu Ala Ile  Leu Ala Ala Leu Thr  Pro Leu Ala
    1295                 1300                 1305

Arg Gly  Thr Leu Leu Val Ala  Trp Arg Ala Gly Leu  Ala Thr Cys
    1310                 1315                 1320

Gly Gly  Phe Met Leu Leu Ser  Leu Lys Gly Lys Gly  Ser Val Lys
    1325                 1330                 1335

Lys Asn  Leu Pro Phe Val Met  Ala Leu Gly Leu Thr  Ala Val Arg
    1340                 1345                 1350

Leu Val  Asp Pro Ile Asn Val  Val Gly Leu Leu Leu  Leu Thr Arg
    1355                 1360                 1365

Ser Gly  Lys Arg Ser Trp Pro  Pro Ser Glu Val Leu  Thr Ala Val
    1370                 1375                 1380

Gly Leu  Ile Cys Ala Leu Ala  Gly Gly Phe Ala Lys  Ala Asp Ile
```

```
    1385                1390                1395

Glu Met  Ala Gly Pro Met Ala  Ala Val Gly Leu Leu  Ile Val Ser
    1400                1405                1410

Tyr Val  Val Ser Gly Lys Ser  Val Asp Met Tyr Ile  Glu Arg Ala
    1415                1420                1425

Gly Asp  Ile Thr Trp Glu Lys  Asp Ala Glu Val Thr  Gly Asn Ser
    1430                1435                1440

Pro Arg  Leu Asp Val Ala Leu  Asp Glu Ser Gly Asp  Phe Ser Leu
    1445                1450                1455

Val Glu  Asp Asp Gly Pro Pro  Met Arg Glu Ile Ile  Leu Lys Val
    1460                1465                1470

Val Leu  Met Thr Ile Cys Gly  Met Asn Pro Ile Ala  Ile Pro Phe
    1475                1480                1485

Ala Ala  Gly Ala Trp Tyr Val  Tyr Val Lys Thr Gly  Lys Arg Ser
    1490                1495                1500

Gly Ala  Leu Trp Asp Val Pro  Ala Pro Lys Glu Val  Lys Lys Gly
    1505                1510                1515

Glu Thr  Thr Asp Gly Val Tyr  Arg Val Met Thr Arg  Arg Leu Leu
    1520                1525                1530

Gly Ser  Thr Gln Val Gly Val  Gly Val Met Gln Glu  Gly Val Phe
    1535                1540                1545

His Thr  Met Trp His Val Thr  Lys Gly Ser Ala Leu  Arg Ser Gly
    1550                1555                1560

Glu Gly  Arg Leu Asp Pro Tyr  Trp Gly Asp Val Lys  Gln Asp Leu
    1565                1570                1575

Val Ser  Tyr Cys Gly Pro Trp  Lys Leu Asp Ala Ala  Trp Asp Gly
    1580                1585                1590

His Ser  Glu Val Gln Leu Leu  Ala Val Pro Pro Gly  Glu Arg Ala
    1595                1600                1605

Arg Asn  Ile Gln Thr Leu Pro  Gly Ile Phe Lys Thr  Lys Asp Gly
    1610                1615                1620

Asp Ile  Gly Ala Val Ala Leu  Asp Tyr Pro Ala Gly  Thr Ser Gly
    1625                1630                1635

Ser Pro  Ile Leu Asp Lys Cys  Gly Arg Val Ile Gly  Leu Tyr Gly
    1640                1645                1650

Asn Gly  Val Val Ile Lys Asn  Gly Ser Tyr Val Ser  Ala Ile Thr
    1655                1660                1665

Gln Gly  Arg Arg Glu Glu Glu  Thr Pro Val Glu Cys  Phe Glu Pro
    1670                1675                1680

Ser Met  Leu Lys Lys Lys Gln  Leu Thr Val Leu Asp  Leu His Pro
    1685                1690                1695

Gly Ala  Gly Lys Thr Arg Arg  Val Leu Pro Glu Ile  Val Arg Glu
    1700                1705                1710

Ala Ile  Lys Thr Arg Leu Arg  Thr Val Ile Leu Ala  Pro Thr Arg
    1715                1720                1725

Val Val  Ala Ala Glu Met Glu  Glu Ala Leu Arg Gly  Leu Pro Val
    1730                1735                1740

Arg Tyr  Met Thr Thr Ala Val  Asn Val Thr His Ser  Gly Thr Glu
    1745                1750                1755

Ile Val  Asp Leu Met Cys His  Ala Thr Phe Thr Ser  Arg Leu Leu
    1760                1765                1770

Gln Pro  Ile Arg Val Pro Asn  Tyr Asn Leu Tyr Ile  Met Asp Glu
    1775                1780                1785
```

```
Ala His  Phe Thr Asp Pro Ser  Ser Ile Ala Ala Arg  Gly Tyr Ile
    1790                 1795                 1800

Ser Thr  Arg Val Glu Met Gly  Glu Ala Ala Ala Ile  Phe Met Thr
    1805                 1810                 1815

Ala Thr  Pro Pro Gly Thr Arg  Asp Ala Phe Pro Asp  Ser Asn Ser
    1820                 1825                 1830

Pro Ile  Met Asp Thr Glu Val  Glu Val Pro Glu Arg  Ala Trp Ser
    1835                 1840                 1845

Ser Gly  Phe Asp Trp Val Thr  Asp His Ser Gly Lys  Thr Val Trp
    1850                 1855                 1860

Phe Val  Pro Ser Val Arg Asn  Gly Asn Glu Ile Ala  Ala Cys Leu
    1865                 1870                 1875

Thr Lys  Ala Gly Lys Arg Val  Ile Gln Leu Ser Arg  Lys Thr Phe
    1880                 1885                 1890

Glu Thr  Glu Phe Gln Lys Thr  Lys His Gln Glu Trp  Asp Phe Val
    1895                 1900                 1905

Val Thr  Thr Asp Ile Ser Glu  Met Gly Ala Asn Phe  Lys Ala Asp
    1910                 1915                 1920

Arg Val  Ile Asp Ser Arg Arg  Cys Leu Lys Pro Val  Ile Leu Asp
    1925                 1930                 1935

Gly Glu  Arg Val Ile Leu Ala  Gly Pro Met Pro Val  Thr His Ala
    1940                 1945                 1950

Ser Ala  Ala Gln Arg Arg Gly  Arg Ile Gly Arg Asn  Pro Asn Lys
    1955                 1960                 1965

Pro Gly  Asp Glu Tyr Leu Tyr  Gly Gly Gly Cys Ala  Glu Thr Asp
    1970                 1975                 1980

Glu Asp  His Ala His Trp Leu  Glu Ala Arg Met Leu  Leu Asp Asn
    1985                 1990                 1995

Ile Tyr  Leu Gln Asp Gly Leu  Ile Ala Ser Leu Tyr  Arg Pro Glu
    2000                 2005                 2010

Ala Asp  Lys Val Ala Ala Ile  Glu Gly Glu Phe Lys  Leu Arg Thr
    2015                 2020                 2025

Glu Gln  Arg Lys Thr Phe Val  Glu Leu Met Lys Arg  Gly Asp Leu
    2030                 2035                 2040

Pro Val  Trp Leu Ala Tyr Gln  Val Ala Ser Ala Gly  Ile Thr Tyr
    2045                 2050                 2055

Thr Asp  Arg Arg Trp Cys Phe  Asp Gly Thr Thr Asn  Asn Thr Ile
    2060                 2065                 2070

Leu Glu  Asp Ser Val Pro Ala  Glu Val Trp Thr Arg  His Gly Glu
    2075                 2080                 2085

Lys Arg  Val Leu Lys Pro Arg  Trp Met Asp Ala Arg  Val Cys Ser
    2090                 2095                 2100

Asp His  Ala Ala Leu Lys Ser  Phe Lys Glu Phe Ala  Ala Gly Lys
    2105                 2110                 2115

Arg Gly  Ala Ala Phe Gly Val  Met Glu Ala Leu Gly  Thr Leu Pro
    2120                 2125                 2130

Gly His  Met Thr Glu Arg Phe  Gln Glu Ala Ile Asp  Asn Leu Ala
    2135                 2140                 2145

Val Leu  Met Arg Ala Glu Thr  Gly Ser Arg Pro Tyr  Lys Ala Ala
    2150                 2155                 2160

Ala Ala  Gln Leu Pro Glu Thr  Leu Glu Thr Ile Met  Leu Leu Gly
    2165                 2170                 2175
```

```
Leu Leu  Gly Thr Val Ser Leu  Gly Ile Phe Phe Val  Leu Met Arg
    2180                 2185                 2190

Asn Lys  Gly Ile Gly Lys Met  Gly Phe Gly Met Val  Thr Leu Gly
    2195                 2200                 2205

Ala Ser  Ala Trp Leu Met Trp  Leu Ser Glu Ile Glu  Pro Ala Arg
    2210                 2215                 2220

Ile Ala  Cys Val Leu Ile Val  Val Phe Leu Leu Leu  Val Val Leu
    2225                 2230                 2235

Ile Pro  Glu Pro Glu Lys Gln  Arg Ser Pro Gln Asp  Asn Gln Met
    2240                 2245                 2250

Ala Ile  Ile Ile Met Val Ala  Val Gly Leu Leu Gly  Leu Ile Thr
    2255                 2260                 2265

Ala Asn  Glu Leu Gly Trp Leu  Glu Arg Thr Lys Ser  Asp Leu Ser
    2270                 2275                 2280

His Leu  Met Gly Arg Arg Glu  Glu Gly Ala Thr Ile  Gly Phe Ser
    2285                 2290                 2295

Met Asp  Ile Asp Leu Arg Pro  Ala Ser Ala Trp Ala  Ile Tyr Ala
    2300                 2305                 2310

Ala Leu  Thr Thr Phe Ile Thr  Pro Ala Val Gln His  Ala Val Thr
    2315                 2320                 2325

Thr Ser  Tyr Asn Asn Tyr Ser  Leu Met Ala Met Ala  Thr Gln Ala
    2330                 2335                 2340

Gly Val  Leu Phe Gly Met Gly  Lys Gly Met Pro Phe  Tyr Ala Trp
    2345                 2350                 2355

Asp Phe  Gly Val Pro Leu Leu  Met Ile Gly Cys Tyr  Ser Gln Leu
    2360                 2365                 2370

Thr Pro  Leu Thr Leu Ile Val  Ala Ile Ile Leu Leu  Val Ala His
    2375                 2380                 2385

Tyr Met  Tyr Leu Ile Pro Gly  Leu Gln Ala Ala Ala  Ala Arg Ala
    2390                 2395                 2400

Ala Gln  Lys Arg Thr Ala Ala  Gly Ile Met Lys Asn  Pro Val Val
    2405                 2410                 2415

Asp Gly  Ile Val Val Thr Asp  Ile Asp Thr Met Thr  Ile Asp Pro
    2420                 2425                 2430

Gln Val  Glu Lys Lys Met Gly  Gln Val Leu Leu Ile  Ala Val Ala
    2435                 2440                 2445

Val Ser  Ser Ala Ile Leu Ser  Arg Thr Ala Trp Gly  Trp Gly Glu
    2450                 2455                 2460

Ala Gly  Ala Leu Ile Thr Ala  Ala Thr Ser Thr Leu  Trp Glu Gly
    2465                 2470                 2475

Ser Pro  Asn Lys Tyr Trp Asn  Ser Ser Thr Ala Thr  Ser Leu Cys
    2480                 2485                 2490

Asn Ile  Phe Arg Gly Ser Tyr  Leu Ala Gly Ala Ser  Leu Ile Tyr
    2495                 2500                 2505

Thr Val  Thr Arg Asn Ala Gly  Leu Val Lys Arg Arg  Gly Gly Gly
    2510                 2515                 2520

Thr Gly  Glu Thr Leu Gly Glu  Lys Trp Lys Ala Arg  Leu Asn Gln
    2525                 2530                 2535

Met Ser  Ala Leu Glu Phe Tyr  Ser Tyr Lys Lys Ser  Gly Ile Thr
    2540                 2545                 2550

Glu Val  Cys Arg Glu Glu Ala  Arg Arg Ala Leu Lys  Asp Gly Val
    2555                 2560                 2565

Ala Thr  Gly Gly His Ala Val  Ser Arg Gly Ser Ala  Lys Leu Arg
```

```
    2570                2575                2580

Trp Leu Val Glu Arg Gly Tyr Leu Gln Pro Tyr Gly Lys Val Ile
    2585                2590                2595

Asp Leu Gly Cys Gly Arg Gly Gly Trp Ser Tyr Tyr Ala Ala Thr
    2600                2605                2610

Ile Arg Lys Val Gln Glu Val Lys Gly Tyr Thr Lys Gly Gly Pro
    2615                2620                2625

Gly His Glu Glu Pro Val Leu Val Gln Ser Tyr Gly Trp Asn Ile
    2630                2635                2640

Val Arg Leu Lys Ser Gly Val Asp Val Phe His Met Ala Ala Glu
    2645                2650                2655

Pro Cys Asp Thr Leu Leu Cys Asp Ile Gly Glu Ser Ser Ser Ser
    2660                2665                2670

Pro Glu Val Glu Glu Ala Arg Thr Leu Arg Val Leu Ser Met Val
    2675                2680                2685

Gly Asp Trp Leu Glu Lys Arg Pro Gly Ala Phe Cys Ile Lys Val
    2690                2695                2700

Leu Cys Pro Tyr Thr Ser Thr Met Met Glu Thr Leu Glu Arg Leu
    2705                2710                2715

Gln Arg Arg Tyr Gly Gly Gly Leu Val Arg Val Pro Leu Ser Arg
    2720                2725                2730

Asn Ser Thr His Glu Met Tyr Trp Val Ser Gly Ala Lys Ser Asn
    2735                2740                2745

Thr Ile Lys Ser Val Ser Thr Thr Ser Gln Leu Leu Leu Gly Arg
    2750                2755                2760

Met Asp Gly Pro Arg Arg Pro Val Lys Tyr Glu Glu Asp Val Asn
    2765                2770                2775

Leu Gly Ser Gly Thr Arg Ala Val Val Ser Cys Ala Glu Ala Pro
    2780                2785                2790

Asn Met Lys Ile Ile Gly Asn Arg Ile Glu Arg Ile Arg Ser Glu
    2795                2800                2805

His Ala Glu Thr Trp Phe Phe Asp Glu Asn His Pro Tyr Arg Thr
    2810                2815                2820

Trp Ala Tyr His Gly Ser Tyr Glu Ala Pro Thr Gln Gly Ser Ala
    2825                2830                2835

Ser Ser Leu Ile Asn Gly Val Val Arg Leu Leu Ser Lys Pro Trp
    2840                2845                2850

Asp Val Val Thr Gly Val Thr Gly Ile Ala Met Thr Asp Thr Thr
    2855                2860                2865

Pro Tyr Gly Gln Gln Arg Val Phe Lys Glu Lys Val Asp Thr Arg
    2870                2875                2880

Val Pro Asp Pro Gln Glu Gly Thr Arg Gln Val Met Ser Met Val
    2885                2890                2895

Ser Ser Trp Leu Trp Lys Glu Leu Gly Lys His Lys Arg Pro Arg
    2900                2905                2910

Val Cys Thr Lys Glu Glu Phe Ile Asn Lys Val Arg Ser Asn Ala
    2915                2920                2925

Ala Leu Gly Ala Ile Phe Glu Glu Glu Lys Glu Trp Lys Thr Ala
    2930                2935                2940

Val Glu Ala Val Asn Asp Pro Arg Phe Trp Ala Leu Val Asp Lys
    2945                2950                2955

Glu Arg Glu His His Leu Arg Gly Glu Cys Gln Ser Cys Val Tyr
    2960                2965                2970
```

```
Asn Met  Met Gly Lys Arg Glu  Lys Lys Gln Gly Glu  Phe Gly Lys
    2975                 2980                 2985

Ala Lys  Gly Ser Arg Ala Ile  Trp Tyr Met Trp Leu  Gly Ala Arg
    2990                 2995                 3000

Phe Leu  Glu Phe Glu Ala Leu  Gly Phe Leu Asn Glu  Asp His Trp
    3005                 3010                 3015

Met Gly  Arg Glu Asn Ser Gly  Gly Gly Val Glu Gly  Leu Gly Leu
    3020                 3025                 3030

Gln Arg  Leu Gly Tyr Val Leu  Glu Glu Met Ser Cys  Ile Pro Gly
    3035                 3040                 3045

Gly Arg  Met Tyr Ala Asp Asp  Thr Ala Gly Trp Asp  Thr Arg Ile
    3050                 3055                 3060

Ser Arg  Phe Asp Leu Glu Asn  Glu Ala Leu Ile Thr  Asn Gln Met
    3065                 3070                 3075

Glu Lys  Gly His Arg Ala Leu  Ala Leu Ala Ile Ile  Lys Tyr Thr
    3080                 3085                 3090

Tyr Gln  Asn Lys Val Val Lys  Val Leu Arg Pro Ala  Glu Lys Gly
    3095                 3100                 3105

Lys Thr  Val Met Asp Ile Ile  Ser Arg Gln Asp Gln  Arg Gly Ser
    3110                 3115                 3120

Gly Gln  Val Val Thr Tyr Ala  Leu Asn Thr Phe Thr  Asn Leu Val
    3125                 3130                 3135

Val Gln  Leu Ile Arg Asn Met  Glu Ala Glu Glu Val  Leu Glu Met
    3140                 3145                 3150

Gln Asp  Leu Trp Leu Leu Arg  Arg Ser Glu Lys Val  Thr Asn Trp
    3155                 3160                 3165

Leu Gln  Ser Asn Gly Trp Asp  Arg Leu Lys Arg Met  Ala Val Ser
    3170                 3175                 3180

Gly Asp  Asp Cys Val Val Lys  Pro Ile Asp Asp Arg  Phe Ala His
    3185                 3190                 3195

Ala Leu  Arg Phe Leu Asn Asp  Met Gly Lys Val Arg  Lys Asp Thr
    3200                 3205                 3210

Gln Glu  Trp Lys Pro Ser Thr  Gly Trp Asp Asn Trp  Glu Glu Val
    3215                 3220                 3225

Pro Phe  Cys Ser His His Phe  Asn Lys Leu His Leu  Lys Asp Gly
    3230                 3235                 3240

Arg Ser  Ile Val Val Pro Cys  Arg His Gln Asp Glu  Leu Ile Gly
    3245                 3250                 3255

Arg Ala  Arg Val Ser Pro Gly  Ala Gly Trp Ser Ile  Arg Glu Thr
    3260                 3265                 3270

Ala Cys  Leu Ala Lys Ser Tyr  Ala Gln Met Trp Gln  Leu Leu Tyr
    3275                 3280                 3285

Phe His  Arg Arg Asp Leu Arg  Leu Met Ala Asn Ala  Ile Cys Ser
    3290                 3295                 3300

Ser Val  Pro Val Asp Trp Val  Pro Thr Gly Arg Thr  Thr Trp Ser
    3305                 3310                 3315

Ile His  Gly Lys Gly Glu Trp  Met Thr Thr Glu Asp  Met Leu Val
    3320                 3325                 3330

Val Trp  Asn Arg Val Trp Ile  Glu Glu Asn Asp His  Met Glu Asp
    3335                 3340                 3345

Lys Thr  Pro Val Thr Lys Trp  Thr Asp Ile Pro Tyr  Leu Gly Lys
    3350                 3355                 3360
```

```
Arg Glu  Asp Leu Trp Cys Gly  Ser Leu Ile Gly His  Arg Pro Arg
    3365                 3370                 3375

Thr Thr  Trp Ala Glu Asn Ile  Lys Asn Thr Val Asn  Met Val Arg
    3380                 3385                 3390

Arg Ile  Ile Gly Asp Glu Glu  Lys Tyr Met Asp Tyr  Leu Ser Thr
    3395                 3400                 3405

Gln Val  Arg Tyr Leu Gly Glu  Glu Gly Ser Thr Pro  Gly Val Leu
    3410                 3415                 3420
```

<210> SEQ ID NO 9
<211> LENGTH: 10723
<212> TYPE: DNA
<213> ORGANISM: Dengue virus type 2 strain 16681

<400> SEQUENCE: 9

```
agttgttagt ctacgtggac cgacaaagac agattctttg agggagctaa gctcaacgta     60

gttctaacag tttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatctg caggcatgat cattatgctg    420

attccaacag tgatggcgtt ccatttaacc acacgtaacg gagaaccaca catgatcgtc    480

agcagacaag agaaagggaa aagtcttctg tttaaaacag aggatggcgt gaacatgtgt    540

accctcatgg ccatggacct tggtgaattg tgtgaagaca caatcacgta caagtgtccc    600

cttctcaggc agaatgagcc agaagacata gactgttggt gcaactctac gtccacgtgg    660

gtaacttatg ggacgtgtac caccatggga gaacatagaa gagaaaaaag atcagtggca    720

ctcgttccac atgtgggaat gggactggag acacgaactg aaacatggat gtcatcagaa    780

ggggcctgga aacatgtcca gagaattgaa acttggatct tgagacatcc aggcttcacc    840

atgatggcag caatcctggc atacaccata ggaacgacac atttccaaag agccctgatt    900

ttcatcttac tgacagctgt cactccttca atgacaatgc gttgcatagg aatgtcaaat    960

agagactttg tggaaggggt ttcaggagga agctgggttg acatagtctt agaacatgga   1020

agctgtgtga cgacgatggc aaaaaacaaa ccaacattgg attttgaact gataaaaaca   1080

gaagccaaac agcctgccac cctaaggaag tactgtatag aggcaaagct aaccaacaca   1140

acaacagaat ctcgctgccc aacacaaggg gaacccagcc taaatgaaga gcaggacaaa   1200

aggttcgtct gcaaacactc catggtagac agaggatggg gaaatggatg tggactattt   1260

ggaaagggag gcattgtgac ctgtgctatg ttcagatgca aaaagaacat ggaaggaaaa   1320

gttgtgcaac cagaaaactt ggaatacacc attgtgataa cacctcactc aggggaagag   1380

catgcagtcg gaaatgacac aggaaaacat ggcaaggaaa tcaaaataac accacagagt   1440

tccatcacag aagcagaatt gacaggttat ggcactgtca caatggagtg ctctccaaga   1500

acgggcctcg acttcaatga gatggtgttg ctgcagatgg aaaataaagc ttggctggtg   1560

cacaggcaat ggttcctaga cctgccgtta ccatggttgc ccggagcgga cacacaaggg   1620

tcaaattgga tacagaaaga gacattggtc actttcaaaa atccccatgc gaagaaacag   1680

gatgttgttg ttttaggatc ccaagaaggg gccatgcaca cagcacttac aggggccaca   1740

gaaatccaaa tgtcatcagg aaacttactc ttcacaggac atctcaagtg caggctgaga   1800
```

-continued

```
atggacaagc tacagctcaa aggaatgtca tactctatgt gcacaggaaa gtttaaagtt   1860
gtgaaggaaa tagcagaaac acaacatgga acaatagtta tcagagtgca atatgaaggg   1920
gacggctctc catgcaagat cccttttgag ataatggatt tggaaaaaag acatgtctta   1980
ggtcgcctga ttacagtcaa cccaattgtg acagaaaaag atagcccagt caacatagaa   2040
gcagaacctc cattcggaga cagctacatc atcataggag tagagccggg acaactgaag   2100
ctcaactggt ttaagaaagg aagttctatc ggccaaatgt ttgagacaac aatgaggggg   2160
gcgaagagaa tggccatttt aggtgacaca gcctgggatt ttggatcctt gggaggagtg   2220
tttacatcta taggaaaggc tctccaccaa gtctttggag caatctatgg agctgccttc   2280
agtggggttt catggactat gaaaatcctc ataggagtca ttatcacatg gataggaatg   2340
aattcacgca gcacctcact gtctgtgaca ctagtattgg tgggaattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagagggc   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgctc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
```

-continued

```
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctga gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgttcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
```

```
cttttactga cacttctggc tacagtcacg ggagggatct ttttattctt gatgagcgga   6600
aggggcatag ggaagatgac cctgggaatg tgctgcataa tcacggctag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
```

```
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
agctgtagtc tcgctggaag gactagaggt tagaggagac ccccccgaaa caaaaaacag  10620
catattgacg ctgggaaaga ccagagatcc tgctgtctcc tcagcatcat tccaggcaca  10680
gaacgccaga aaatggaatg gtgctgttga atcaacaggt tct                    10723
```

<210> SEQ ID NO 10
<211> LENGTH: 3391
<212> TYPE: PRT
<213> ORGANISM: Dengue virus type 2 strain 16681

<400> SEQUENCE: 10

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45
```

```
Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Ala Gly Met Ile Ile Met Leu Ile Pro Thr Val
            100                 105                 110

Met Ala Phe His Leu Thr Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220

Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
            260                 265                 270

Met Leu Val Ala Pro Ser Tyr Gly Met Arg Cys Val Gly Val Gly Asn
        275                 280                 285

Arg Asp Phe Val Glu Gly Val Ser Gly Gly Ala Trp Val Asp Leu Val
    290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
            420                 425                 430

Asn Asp Thr Ser Asn His Gly Val Thr Ala Thr Ile Thr Pro Arg Ser
        435                 440                 445

Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
```

```
465                 470                 475                 480

Met Lys Lys Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
        515                 520                 525

Asp Val Thr Val Leu Gly Ser Gln Glu Gly Ala Met His Ser Ala Leu
    530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
            580                 585                 590

Ala Glu Thr Gln His Gly Thr Thr Val Val Lys Val Lys Tyr Glu Gly
        595                 600                 605

Ala Gly Ala Pro Cys Lys Val Pro Ile Glu Ile Arg Asp Val Asn Lys
    610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
                645                 650                 655

Tyr Ile Val Ile Gly Val Gly Asn Ser Ala Leu Thr Leu His Trp Phe
            660                 665                 670

Arg Lys Gly Ser Ser Ile Gly Lys Met Phe Glu Ser Thr Tyr Arg Gly
        675                 680                 685

Ala Lys Arg Met Ala Ile Leu Gly Glu Thr Ala Trp Asp Phe Gly Ser
    690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
                725                 730                 735

Ile Leu Ile Gly Phe Leu Val Leu Trp Ile Gly Thr Asn Ser Arg Asn
            740                 745                 750

Thr Ser Met Ala Met Thr Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895
```

```
Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                 1005

Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Asp Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Lys Glu Leu Met Met  Thr Thr Ile
    1220                 1225                 1230

Gly Ile  Val Leu Leu Ser Gln  Ser Thr Ile Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290
```

```
Val Ser  Cys Thr Ile Leu Ala  Val Val Ser Val Ser  Pro Leu Phe
    1295                 1300                 1305

Leu Thr  Ser Ser Gln Gln Lys  Thr Asp Trp Ile Pro  Leu Ala Leu
    1310                 1315                 1320

Thr Ile  Lys Gly Leu Asn Pro  Thr Ala Ile Phe Leu  Thr Thr Leu
    1325                 1330                 1335

Ser Arg  Thr Ser Lys Lys Arg  Ser Trp Pro Leu Asn  Glu Ala Ile
    1340                 1345                 1350

Met Ala  Val Gly Met Val Ser  Ile Leu Ala Ser Ser  Leu Leu Lys
    1355                 1360                 1365

Asn Asp  Ile Pro Met Thr Gly  Pro Leu Val Ala Gly  Gly Leu Leu
    1370                 1375                 1380

Thr Val  Cys Tyr Val Leu Thr  Gly Arg Ser Ala Asp  Leu Glu Leu
    1385                 1390                 1395

Glu Arg  Ala Ala Asp Val Lys  Trp Glu Asp Gln Ala  Glu Ile Ser
    1400                 1405                 1410

Gly Ser  Ser Pro Ile Leu Ser  Ile Thr Ile Ser Glu  Asp Gly Ser
    1415                 1420                 1425

Met Ser  Ile Lys Asn Glu Glu  Glu Glu Gln Thr Leu  Thr Ile Leu
    1430                 1435                 1440

Ile Arg  Thr Gly Leu Leu Val  Ile Ser Gly Leu Phe  Pro Val Ser
    1445                 1450                 1455

Ile Pro  Ile Thr Ala Ala Ala  Trp Tyr Leu Trp Glu  Val Lys Lys
    1460                 1465                 1470

Gln Arg  Ala Gly Val Leu Trp  Asp Val Pro Ser Pro  Pro Pro Met
    1475                 1480                 1485

Gly Lys  Ala Glu Leu Glu Asp  Gly Ala Tyr Arg Ile  Lys Gln Lys
    1490                 1495                 1500

Gly Ile  Leu Gly Tyr Ser Gln  Ile Gly Ala Gly Val  Tyr Lys Glu
    1505                 1510                 1515

Gly Thr  Phe His Thr Met Trp  His Val Thr Arg Gly  Ala Val Leu
    1520                 1525                 1530

Met His  Lys Gly Lys Arg Ile  Glu Pro Ser Trp Ala  Asp Val Lys
    1535                 1540                 1545

Lys Asp  Leu Ile Ser Tyr Gly  Gly Gly Trp Lys Leu  Glu Gly Glu
    1550                 1555                 1560

Trp Lys  Glu Gly Glu Glu Val  Gln Val Leu Ala Leu  Glu Pro Gly
    1565                 1570                 1575

Lys Asn  Pro Arg Ala Val Gln  Thr Lys Pro Gly Leu  Phe Lys Thr
    1580                 1585                 1590

Asn Ala  Gly Thr Ile Gly Ala  Val Ser Leu Asp Phe  Ser Pro Gly
    1595                 1600                 1605

Thr Ser  Gly Ser Pro Ile Ile  Asp Lys Lys Gly Lys  Val Val Gly
    1610                 1615                 1620

Leu Tyr  Gly Asn Gly Val Val  Thr Arg Ser Gly Ala  Tyr Val Ser
    1625                 1630                 1635

Ala Ile  Ala Gln Thr Glu Lys  Ser Ile Glu Asp Asn  Pro Glu Ile
    1640                 1645                 1650

Glu Asp  Asp Ile Phe Arg Lys  Arg Arg Leu Thr Ile  Met Asp Leu
    1655                 1660                 1665

His Pro  Gly Ala Gly Lys Thr  Lys Arg Tyr Leu Pro  Ala Ile Val
    1670                 1675                 1680

Arg Glu  Ala Ile Lys Arg Gly  Leu Arg Thr Leu Ile  Leu Ala Pro
```

```
    1685                1690                1695

Thr Arg  Val Val Ala Ala Glu  Met Glu Glu Ala Leu  Arg Gly Leu
    1700                1705                1710

Pro Ile  Arg Tyr Gln Thr Pro  Ala Ile Arg Ala Val  His Thr Gly
    1715                1720                1725

Arg Glu  Ile Val Asp Leu Met  Cys His Ala Thr Phe  Thr Met Arg
    1730                1735                1740

Leu Leu  Ser Pro Val Arg Val  Pro Asn Tyr Asn Leu  Ile Ile Met
    1745                1750                1755

Asp Glu  Ala His Phe Thr Asp  Pro Ala Ser Ile Ala  Ala Arg Gly
    1760                1765                1770

Tyr Ile  Ser Thr Arg Val Glu  Met Gly Glu Ala Ala  Gly Ile Phe
    1775                1780                1785

Met Thr  Ala Thr Pro Pro Gly  Ser Arg Asp Pro Phe  Pro Gln Ser
    1790                1795                1800

Asn Ala  Pro Ile Ile Asp Glu  Glu Arg Glu Ile Pro  Glu Arg Ser
    1805                1810                1815

Trp Asn  Ser Gly His Glu Trp  Val Thr Asp Phe Lys  Gly Lys Thr
    1820                1825                1830

Val Trp  Phe Val Pro Ser Ile  Lys Ala Gly Asn Asp  Ile Ala Ala
    1835                1840                1845

Cys Leu  Arg Lys Asn Gly Lys  Lys Val Ile Gln Leu  Ser Arg Lys
    1850                1855                1860

Thr Phe  Asp Ser Glu Tyr Val  Lys Thr Arg Thr Asn  Asp Trp Asp
    1865                1870                1875

Phe Val  Val Thr Thr Asp Ile  Ser Glu Met Gly Ala  Asn Phe Lys
    1880                1885                1890

Ala Glu  Arg Val Ile Asp Pro  Arg Arg Cys Met Lys  Pro Val Ile
    1895                1900                1905

Leu Thr  Asp Gly Glu Glu Arg  Val Ile Leu Ala Gly  Pro Met Pro
    1910                1915                1920

Val Thr  His Ser Ser Ala Ala  Gln Arg Arg Gly Arg  Ile Gly Arg
    1925                1930                1935

Asn Pro  Lys Asn Glu Asn Asp  Gln Tyr Ile Tyr Met  Gly Glu Pro
    1940                1945                1950

Leu Glu  Asn Asp Glu Asp Cys  Ala His Trp Lys Glu  Ala Lys Met
    1955                1960                1965

Leu Leu  Asp Asn Ile Asn Thr  Pro Glu Gly Ile Ile  Pro Ser Met
    1970                1975                1980

Phe Glu  Pro Glu Arg Glu Lys  Val Asp Ala Ile Asp  Gly Glu Tyr
    1985                1990                1995

Arg Leu  Arg Gly Glu Ala Arg  Lys Thr Phe Val Asp  Leu Met Arg
    2000                2005                2010

Arg Gly  Asp Leu Pro Val Trp  Leu Ala Tyr Arg Val  Ala Ala Glu
    2015                2020                2025

Gly Ile  Asn Tyr Ala Asp Arg  Arg Trp Cys Phe Asp  Gly Val Lys
    2030                2035                2040

Asn Asn  Gln Ile Leu Glu Glu  Asn Val Glu Val Glu  Ile Trp Thr
    2045                2050                2055

Lys Glu  Gly Glu Arg Lys Lys  Leu Lys Pro Arg Trp  Leu Asp Ala
    2060                2065                2070

Arg Ile  Tyr Ser Asp Pro Leu  Ala Leu Lys Glu Phe  Lys Glu Phe
    2075                2080                2085
```

```
Ala Ala  Gly Arg Lys Ser Leu  Thr Leu Asn Leu Ile  Thr Glu Met
    2090                 2095                 2100

Gly Arg  Leu Pro Thr Phe Met  Thr Gln Lys Ala Arg  Asp Ala Leu
    2105                 2110                 2115

Asp Asn  Leu Ala Val Leu His  Thr Ala Glu Ala Gly  Gly Arg Ala
    2120                 2125                 2130

Tyr Asn  His Ala Leu Ser Glu  Leu Pro Glu Thr Leu  Glu Thr Leu
    2135                 2140                 2145

Leu Leu  Leu Thr Leu Leu Ala  Thr Val Thr Gly Gly  Ile Phe Leu
    2150                 2155                 2160

Phe Leu  Met Ser Ala Arg Gly  Ile Gly Lys Met Thr  Leu Gly Met
    2165                 2170                 2175

Cys Cys  Ile Ile Thr Ala Ser  Ile Leu Leu Trp Tyr  Ala Gln Ile
    2180                 2185                 2190

Gln Pro  His Trp Ile Ala Ala  Ser Ile Ile Leu Glu  Phe Phe Leu
    2195                 2200                 2205

Ile Val  Leu Leu Ile Pro Glu  Pro Glu Lys Gln Arg  Thr Pro Gln
    2210                 2215                 2220

Asp Asn  Gln Leu Thr Tyr Val  Val Ile Ala Ile Leu  Thr Val Val
    2225                 2230                 2235

Ala Ala  Thr Met Ala Asn Glu  Met Gly Phe Leu Glu  Lys Thr Lys
    2240                 2245                 2250

Lys Asp  Leu Gly Leu Gly Ser  Ile Ala Thr Gln Gln  Pro Glu Ser
    2255                 2260                 2265

Asn Ile  Leu Asp Ile Asp Leu  Arg Pro Ala Ser Ala  Trp Thr Leu
    2270                 2275                 2280

Tyr Ala  Val Ala Thr Thr Phe  Val Thr Pro Met Leu  Arg His Ser
    2285                 2290                 2295

Ile Glu  Asn Ser Ser Val Asn  Val Ser Leu Thr Ala  Ile Ala Asn
    2300                 2305                 2310

Gln Ala  Thr Val Leu Met Gly  Leu Gly Lys Gly Trp  Pro Leu Ser
    2315                 2320                 2325

Lys Met  Asp Ile Gly Val Pro  Leu Leu Ala Ile Gly  Cys Tyr Ser
    2330                 2335                 2340

Gln Val  Asn Pro Ile Thr Leu  Thr Ala Ala Leu Phe  Leu Leu Val
    2345                 2350                 2355

Ala His  Tyr Ala Ile Ile Gly  Pro Gly Leu Gln Ala  Lys Ala Thr
    2360                 2365                 2370

Arg Glu  Ala Gln Lys Arg Ala  Ala Ala Gly Ile Met  Lys Asn Pro
    2375                 2380                 2385

Thr Val  Asp Gly Ile Thr Val  Ile Asp Leu Asp Pro  Ile Pro Tyr
    2390                 2395                 2400

Asp Pro  Lys Phe Glu Lys Gln  Leu Gly Gln Val Met  Leu Leu Val
    2405                 2410                 2415

Leu Cys  Val Thr Gln Val Leu  Met Met Arg Thr Thr  Trp Ala Leu
    2420                 2425                 2430

Cys Glu  Ala Leu Thr Leu Ala  Thr Gly Pro Ile Ser  Thr Leu Trp
    2435                 2440                 2445

Glu Gly  Asn Pro Gly Arg Phe  Trp Asn Thr Thr Ile  Ala Val Ser
    2450                 2455                 2460

Met Ala  Asn Ile Phe Arg Gly  Ser Tyr Leu Ala Gly  Ala Gly Leu
    2465                 2470                 2475
```

```
Leu Phe  Ser Ile Met Lys Asn  Thr Thr Asn Thr Arg  Arg Gly Thr
    2480                 2485                 2490

Gly Asn  Ile Gly Glu Thr Leu  Gly Glu Lys Trp Lys  Ser Arg Leu
    2495                 2500                 2505

Asn Ala  Leu Gly Lys Ser Glu  Phe Gln Ile Tyr Lys  Lys Ser Gly
    2510                 2515                 2520

Ile Gln  Glu Val Asp Arg Thr  Leu Ala Lys Glu Gly  Ile Lys Arg
    2525                 2530                 2535

Gly Glu  Thr Asp His His Ala  Val Ser Arg Gly Ser  Ala Lys Leu
    2540                 2545                 2550

Arg Trp  Phe Val Glu Arg Asn  Met Val Thr Pro Glu  Gly Lys Val
    2555                 2560                 2565

Val Asp  Leu Gly Cys Gly Arg  Gly Gly Trp Ser Tyr  Tyr Cys Gly
    2570                 2575                 2580

Gly Leu  Lys Asn Val Arg Glu  Val Lys Gly Leu Thr  Lys Gly Gly
    2585                 2590                 2595

Pro Gly  His Glu Glu Pro Ile  Pro Met Ser Thr Tyr  Gly Trp Asn
    2600                 2605                 2610

Leu Val  Arg Leu Gln Ser Gly  Val Asp Val Phe Phe  Ile Pro Pro
    2615                 2620                 2625

Glu Lys  Cys Asp Thr Leu Leu  Cys Asp Ile Gly Glu  Ser Ser Pro
    2630                 2635                 2640

Asn Pro  Thr Val Glu Ala Gly  Arg Thr Leu Arg Val  Leu Asn Leu
    2645                 2650                 2655

Val Glu  Asn Trp Leu Asn Asn  Asn Thr Gln Phe Cys  Ile Lys Val
    2660                 2665                 2670

Leu Asn  Pro Tyr Met Pro Ser  Val Ile Glu Lys Met  Glu Ala Leu
    2675                 2680                 2685

Gln Arg  Lys Tyr Gly Gly Ala  Leu Val Arg Asn Pro  Leu Ser Arg
    2690                 2695                 2700

Asn Ser  Thr His Glu Met Tyr  Trp Val Ser Asn Ala  Ser Gly Asn
    2705                 2710                 2715

Ile Val  Ser Ser Val Asn Met  Ile Ser Arg Met Leu  Ile Asn Arg
    2720                 2725                 2730

Phe Thr  Met Arg Tyr Lys Lys  Ala Thr Tyr Glu Pro  Asp Val Asp
    2735                 2740                 2745

Leu Gly  Ser Gly Thr Arg Asn  Ile Gly Ile Glu Ser  Glu Ile Pro
    2750                 2755                 2760

Asn Leu  Asp Ile Ile Gly Lys  Arg Ile Glu Lys Ile  Lys Gln Glu
    2765                 2770                 2775

His Glu  Thr Ser Trp His Tyr  Asp Gln Asp His Pro  Tyr Lys Thr
    2780                 2785                 2790

Trp Ala  Tyr His Gly Ser Tyr  Glu Thr Lys Gln Thr  Gly Ser Ala
    2795                 2800                 2805

Ser Ser  Met Val Asn Gly Val  Val Arg Leu Leu Thr  Lys Pro Trp
    2810                 2815                 2820

Asp Val  Val Pro Met Val Thr  Gln Met Ala Met Thr  Asp Thr Thr
    2825                 2830                 2835

Pro Phe  Gly Gln Gln Arg Val  Phe Lys Glu Lys Val  Asp Thr Arg
    2840                 2845                 2850

Thr Gln  Glu Pro Lys Glu Gly  Thr Lys Lys Leu Met  Lys Ile Thr
    2855                 2860                 2865

Ala Glu  Trp Leu Trp Lys Glu  Leu Gly Lys Lys Lys  Thr Pro Arg
```

```
    2870                2875                2880

Met Cys Thr Arg Glu Glu Phe Thr Arg Lys Val Arg Ser Asn Ala
    2885                2890                2895

Ala Leu Gly Ala Ile Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925

Glu Arg Asn Leu His Leu Glu Gly Lys Cys Glu Thr Cys Val Tyr
    2930                2935                2940

Asn Met Met Gly Lys Arg Glu Lys Lys Leu Gly Glu Phe Gly Lys
    2945                2950                2955

Ala Lys Gly Ser Arg Ala Ile Trp Tyr Met Trp Leu Gly Ala Arg
    2960                2965                2970

Phe Leu Glu Phe Glu Ala Leu Gly Phe Leu Asn Glu Asp His Trp
    2975                2980                2985

Phe Ser Arg Glu Asn Ser Leu Ser Gly Val Glu Gly Glu Gly Leu
    2990                2995                3000

His Lys Leu Gly Tyr Ile Leu Arg Asp Val Ser Lys Lys Glu Gly
    3005                3010                3015

Gly Ala Met Tyr Ala Asp Asp Thr Ala Gly Trp Asp Thr Arg Ile
    3020                3025                3030

Thr Leu Glu Asp Leu Lys Asn Glu Glu Met Val Thr Asn His Met
    3035                3040                3045

Glu Gly Glu His Lys Lys Leu Ala Glu Ala Ile Phe Lys Leu Thr
    3050                3055                3060

Tyr Gln Asn Lys Val Val Arg Val Gln Arg Pro Thr Pro Arg Gly
    3065                3070                3075

Thr Val Met Asp Ile Ile Ser Arg Arg Asp Gln Arg Gly Ser Gly
    3080                3085                3090

Gln Val Gly Thr Tyr Gly Leu Asn Thr Phe Thr Asn Met Glu Ala
    3095                3100                3105

Gln Leu Ile Arg Gln Met Glu Gly Glu Gly Val Phe Lys Ser Ile
    3110                3115                3120

Gln His Leu Thr Ile Thr Glu Glu Ile Ala Val Gln Asn Trp Leu
    3125                3130                3135

Ala Arg Val Gly Arg Glu Arg Leu Ser Arg Met Ala Ile Ser Gly
    3140                3145                3150

Asp Asp Cys Val Val Lys Pro Leu Asp Asp Arg Phe Ala Ser Ala
    3155                3160                3165

Leu Thr Ala Leu Asn Asp Met Gly Lys Ile Arg Lys Asp Ile Gln
    3170                3175                3180

Gln Trp Glu Pro Ser Arg Gly Trp Asn Asp Trp Thr Gln Val Pro
    3185                3190                3195

Phe Cys Ser His His Phe His Glu Leu Ile Met Lys Asp Gly Arg
    3200                3205                3210

Val Leu Val Val Pro Cys Arg Asn Gln Asp Glu Leu Ile Gly Arg
    3215                3220                3225

Ala Arg Ile Ser Gln Gly Ala Gly Trp Ser Leu Arg Glu Thr Ala
    3230                3235                3240

Cys Leu Gly Lys Ser Tyr Ala Gln Met Trp Ser Leu Met Tyr Phe
    3245                3250                3255

His Arg Arg Asp Leu Arg Leu Ala Ala Asn Ala Ile Cys Ser Ala
    3260                3265                3270
```

```
Val Pro  Ser His Trp Val Pro  Thr Ser Arg Thr Thr  Trp Ser Ile
    3275                 3280                 3285

His Ala  Lys His Glu Trp Met  Thr Thr Glu Asp Met  Leu Thr Val
    3290                 3295                 3300

Trp Asn  Arg Val Trp Ile Gln  Glu Asn Pro Trp Met  Glu Asp Lys
    3305                 3310                 3315

Thr Pro  Val Glu Ser Trp Glu  Glu Ile Pro Tyr Leu  Gly Lys Arg
    3320                 3325                 3330

Glu Asp  Gln Trp Cys Gly Ser  Leu Ile Gly Leu Thr  Ser Arg Ala
    3335                 3340                 3345

Thr Trp  Ala Lys Asn Ile Gln  Ala Ala Ile Asn Gln  Val Arg Ser
    3350                 3355                 3360

Leu Ile  Gly Asn Glu Glu Tyr  Thr Asp Tyr Met Pro  Ser Met Lys
    3365                 3370                 3375

Arg Phe  Arg Arg Glu Glu Glu  Glu Ala Gly Val Leu  Trp
    3380                 3385                 3390


<210> SEQ ID NO 11
<211> LENGTH: 10723
<212> TYPE: DNA
<213> ORGANISM: Dengue virus type 2 strain PDK-53

<400> SEQUENCE: 11

agttgttagt ctacgtggac cgacaaagac agattctttg agggagctaa gctcaatgta     60

gttctaacag tttttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatctg caggcatgat cattatgctg    420

attccaacag tgatggcgtt ccatttaacc acacgtaacg gagaaccaca catgatcgtc    480

agcagacaag agaaagggaa aagtcttctg tttaaaacag aggttggcgt gaacatgtgt    540

accctcatgg ccatggacct tggtgaattg tgtgaagaca caatcacgta caagtgtccc    600

cttctcaggc agaatgagcc agaagacata gactgttggt gcaactctac gtccacgtgg    660

gtaacttatg ggacgtgtac caccatggga gaacatagaa gagaaaaaag atcagtggca    720

ctcgttccac atgtgggaat gggactggag acacgaactg aaacatggat gtcatcagaa    780

ggggcctgga aacatgtcca gagaattgaa acttggatct tgagacatcc aggcttcacc    840

atgatggcag caatcctggc atacaccata ggaacgacac atttccaaag agccctgatt    900

ttcatcttac tgacagctgt cactccttca atgacaatgc gttgcatagg aatgtcaaat    960

agagactttg tggaaggggt ttcaggagga agctgggttg acatagtctt agaacatgga   1020

agctgtgtga cgacgatggc aaaaaacaaa ccaacattgg attttgaact gataaaaaca   1080

gaagccaaac agcctgccac cctaaggaag tactgtatag aggcaaagct aaccaacaca   1140

acaacagaat ctcgctgccc aacacaaggg gaacccagcc taaatgaaga gcaggacaaa   1200

aggttcgtct gcaaacactc catggtagac agaggatggg gaaatggatg tggactattt   1260

ggaaagggag gcattgtgac ctgtgctatg ttcagatgca aaaagaacat ggaaggaaaa   1320

gttgtgcaac cagaaaactt ggaatacacc attgtgataa cacctcactc aggggaagag   1380
```

```
catgcagtcg gaaatgacac aggaaaacat ggcaaggaaa tcaaaataac accacagagt   1440
tccatcacag aagcagaatt gacaggttat ggcactgtca caatggagtg ctctccaaga   1500
acgggcctcg acttcaatga gatggtgttg ctgcagatgg aaaataaagc ttggctggtg   1560
cacaggcaat ggttcctaga cctgccgtta ccatggttgc ccggagcgga cacacaaggg   1620
tcaaattgga tacagaaaga gacattggtc actttcaaaa atccccatgc gaagaaacag   1680
gatgttgttg ttttaggatc ccaagaaggg gccatgcaca cagcacttac aggggccaca   1740
gaaatccaaa tgtcatcagg aaacttactc ttcacaggac atctcaagtg caggctgaga   1800
atggacaagc tacagctcaa aggaatgtca tactctatgt gcacaggaaa gtttaaagtt   1860
gtgaaggaaa tagcagaaac acaacatgga acaatagtta tcagagtgca atatgaaggg   1920
gacggctctc catgcaagat ccctttgag ataatggatt tggaaaaaag acatgtctta   1980
ggtcgcctga ttacagtcaa cccaattgtg acagaaaaag atagcccagt caacatagaa   2040
gcagaacctc catttggaga cagctacatc atcataggag tagagccggg acaactgaag   2100
ctcaactggt ttaagaaagg aagttctatc ggccaaatgt ttgagacaac aatgaggggg   2160
gcgaagagaa tggccatttt aggtgacaca gcctgggatt ttggatcctt gggaggagtg   2220
tttacatcta taggaaaggc tctccaccaa gtctttggag caatctatgg agctgccttc   2280
agtggggttt catggactat gaaaatcctc ataggagtca ttatcacatg gataggaatg   2340
aattcacgca gcacctcact gtctgtgaca ctagtattgg tgggaattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
```

```
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
```

```
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattcttt gatgagcgca   6600
aggggcatag ggaagatgac cctgggaatg tgctgcataa tcacggctag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
```

```
tcatccatgg tcaacggagt ggtcaggctg ctgacaaaac cttgggacgt tgtccccatg   8580
gtgacacaga tggcaatgac agacacgact ccatttggac aacagcgcgt tttaaagag    8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
agctgtagtc tcgctggaag gactagaggt tagaggagac ccccccgaaa caaaaaacag  10620
catattgacg ctgggaaaga ccagagatcc tgctgtctcc tcagcatcat tccaggcaca  10680
gaacgccaga aaatggaatg gtgctgttga atcaacaggt tct                    10723
```

<210> SEQ ID NO 12
<211> LENGTH: 3391
<212> TYPE: PRT

```
<213> ORGANISM: Dengue virus type 2 strain PDK-53

<400> SEQUENCE: 12

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Val Gly
    130                 135                 140

Val Asn Met Cys Thr Leu Met Ala Met Asp Leu Gly Glu Leu Cys Glu
145                 150                 155                 160

Asp Thr Ile Thr Tyr Lys Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Met Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Val Gln Arg Ile Glu Thr Trp
225                 230                 235                 240

Ile Leu Arg His Pro Gly Phe Thr Met Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Thr Pro Ser Met Thr Met Arg Cys Ile Gly Met Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Gly Ile Val Thr Cys Ala Met Phe Arg
385                 390                 395                 400
```

```
Cys Lys Lys Asn Met Glu Gly Lys Val Val Gln Pro Glu Asn Leu Glu
                405                 410                 415

Tyr Thr Ile Val Ile Thr Pro His Ser Gly Glu Glu His Ala Val Gly
            420                 425                 430

Asn Asp Thr Gly Lys His Gly Lys Glu Ile Lys Ile Thr Pro Gln Ser
        435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525

Asp Val Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
        595                 600                 605

Asp Gly Ser Pro Cys Lys Ile Pro Phe Glu Ile Met Asp Leu Glu Lys
    610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asn Trp Phe
            660                 665                 670

Lys Lys Gly Ser Ser Ile Gly Gln Met Phe Glu Thr Thr Met Arg Gly
        675                 680                 685

Ala Lys Arg Met Ala Ile Leu Gly Asp Thr Ala Trp Asp Phe Gly Ser
    690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
            740                 745                 750

Thr Ser Leu Ser Val Thr Leu Val Leu Val Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
```

```
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                1015                1020

Gly Pro  Val Ser Gln His Asn  Tyr Arg Pro Gly Tyr  His Thr Gln
    1025                1030                1035

Ile Thr  Gly Pro Trp His Leu  Gly Lys Leu Glu Met  Asp Phe Asp
    1040                1045                1050

Phe Cys  Asp Gly Thr Thr Val  Val Val Thr Glu Asp  Cys Gly Asn
    1055                1060                1065

Arg Gly  Pro Ser Leu Arg Thr  Thr Thr Ala Ser Gly  Lys Leu Ile
    1070                1075                1080

Thr Glu  Trp Cys Cys Arg Ser  Cys Thr Leu Pro Pro  Leu Arg Tyr
    1085                1090                1095

Arg Gly  Glu Asp Gly Cys Trp  Tyr Gly Met Glu Ile  Arg Pro Leu
    1100                1105                1110

Lys Glu  Lys Glu Glu Asn Leu  Val Asn Ser Leu Val  Thr Ala Gly
    1115                1120                1125

His Gly  Gln Val Asp Asn Phe  Ser Leu Gly Val Leu  Gly Met Ala
    1130                1135                1140

Leu Phe  Leu Glu Glu Met Leu  Arg Thr Arg Val Gly  Thr Lys His
    1145                1150                1155

Ala Ile  Leu Leu Val Ala Val  Ser Phe Val Thr Leu  Ile Thr Gly
    1160                1165                1170

Asn Met  Ser Phe Arg Asp Leu  Gly Arg Val Met Val  Met Val Gly
    1175                1180                1185

Ala Thr  Met Thr Asp Asp Ile  Gly Met Gly Val Thr  Tyr Leu Ala
    1190                1195                1200

Leu Leu  Ala Ala Phe Lys Val  Arg Pro Thr Phe Ala  Ala Gly Leu
    1205                1210                1215

Leu Leu  Arg Lys Leu Thr Ser  Lys Glu Leu Met Met  Thr Thr Ile
    1220                1225                1230
```

```
Gly Ile  Val Leu Leu Ser Gln  Ser Thr Ile Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290

Val Ser  Cys Thr Ile Leu Ala  Val Val Ser Val Ser  Pro Leu Phe
    1295                 1300                 1305

Leu Thr  Ser Ser Gln Gln Lys  Thr Asp Trp Ile Pro  Leu Ala Leu
    1310                 1315                 1320

Thr Ile  Lys Gly Leu Asn Pro  Thr Ala Ile Phe Leu  Thr Thr Leu
    1325                 1330                 1335

Ser Arg  Thr Ser Lys Lys Arg  Ser Trp Pro Leu Asn  Glu Ala Ile
    1340                 1345                 1350

Met Ala  Val Gly Met Val Ser  Ile Leu Ala Ser Ser  Leu Leu Lys
    1355                 1360                 1365

Asn Asp  Ile Pro Met Thr Gly  Pro Leu Val Ala Gly  Gly Leu Leu
    1370                 1375                 1380

Thr Val  Cys Tyr Val Leu Thr  Gly Arg Ser Ala Asp  Leu Glu Leu
    1385                 1390                 1395

Glu Arg  Ala Ala Asp Val Lys  Trp Glu Asp Gln Ala  Glu Ile Ser
    1400                 1405                 1410

Gly Ser  Ser Pro Ile Leu Ser  Ile Thr Ile Ser Glu  Asp Gly Ser
    1415                 1420                 1425

Met Ser  Ile Lys Asn Glu Glu  Glu Glu Gln Thr Leu  Thr Ile Leu
    1430                 1435                 1440

Ile Arg  Thr Gly Leu Leu Val  Ile Ser Gly Leu Phe  Pro Val Ser
    1445                 1450                 1455

Ile Pro  Ile Thr Ala Ala Ala  Trp Tyr Leu Trp Glu  Val Lys Lys
    1460                 1465                 1470

Gln Arg  Ala Gly Val Leu Trp  Asp Val Pro Ser Pro  Pro Pro Met
    1475                 1480                 1485

Gly Lys  Ala Glu Leu Glu Asp  Gly Ala Tyr Arg Ile  Lys Gln Lys
    1490                 1495                 1500

Gly Ile  Leu Gly Tyr Ser Gln  Ile Gly Ala Gly Val  Tyr Lys Glu
    1505                 1510                 1515

Gly Thr  Phe His Thr Met Trp  His Val Thr Arg Gly  Ala Val Leu
    1520                 1525                 1530

Met His  Lys Gly Lys Arg Ile  Glu Pro Ser Trp Ala  Asp Val Lys
    1535                 1540                 1545

Lys Asp  Leu Ile Ser Tyr Gly  Gly Gly Trp Lys Leu  Glu Gly Glu
    1550                 1555                 1560

Trp Lys  Glu Gly Glu Glu Val  Gln Val Leu Ala Leu  Glu Pro Gly
    1565                 1570                 1575

Lys Asn  Pro Arg Ala Val Gln  Thr Lys Pro Gly Leu  Phe Lys Thr
    1580                 1585                 1590

Asn Ala  Gly Thr Ile Gly Ala  Val Ser Leu Asp Phe  Ser Pro Gly
    1595                 1600                 1605

Thr Ser  Gly Ser Pro Ile Ile  Asp Lys Lys Gly Lys  Val Val Gly
    1610                 1615                 1620
```

```
Leu Tyr  Gly Asn Gly Val Val  Thr Arg Ser Gly Ala  Tyr Val Ser
    1625                 1630                 1635

Ala Ile  Ala Gln Thr Glu Lys  Ser Ile Glu Asp Asn  Pro Glu Ile
    1640                 1645                 1650

Glu Asp  Asp Ile Phe Arg Lys  Arg Arg Leu Thr Ile  Met Asp Leu
    1655                 1660                 1665

His Pro  Gly Ala Gly Lys Thr  Lys Arg Tyr Leu Pro  Ala Ile Val
    1670                 1675                 1680

Arg Glu  Ala Ile Lys Arg Gly  Leu Arg Thr Leu Ile  Leu Ala Pro
    1685                 1690                 1695

Thr Arg  Val Val Ala Ala Glu  Met Glu Glu Ala Leu  Arg Gly Leu
    1700                 1705                 1710

Pro Ile  Arg Tyr Gln Thr Pro  Ala Ile Arg Ala Val  His Thr Gly
    1715                 1720                 1725

Arg Glu  Ile Val Asp Leu Met  Cys His Ala Thr Phe  Thr Met Arg
    1730                 1735                 1740

Leu Leu  Ser Pro Val Arg Val  Pro Asn Tyr Asn Leu  Ile Ile Met
    1745                 1750                 1755

Asp Glu  Ala His Phe Thr Asp  Pro Ala Ser Ile Ala  Ala Arg Gly
    1760                 1765                 1770

Tyr Ile  Ser Thr Arg Val Glu  Met Gly Glu Ala Ala  Gly Ile Phe
    1775                 1780                 1785

Met Thr  Ala Thr Pro Pro Gly  Ser Arg Asp Pro Phe  Pro Gln Ser
    1790                 1795                 1800

Asn Ala  Pro Ile Ile Asp Glu  Glu Arg Glu Ile Pro  Glu Arg Ser
    1805                 1810                 1815

Trp Asn  Ser Gly His Glu Trp  Val Thr Asp Phe Lys  Gly Lys Thr
    1820                 1825                 1830

Val Trp  Phe Val Pro Ser Ile  Lys Ala Gly Asn Asp  Ile Ala Ala
    1835                 1840                 1845

Cys Leu  Arg Lys Asn Gly Lys  Lys Val Ile Gln Leu  Ser Arg Lys
    1850                 1855                 1860

Thr Phe  Asp Ser Glu Tyr Val  Lys Thr Arg Thr Asn  Asp Trp Asp
    1865                 1870                 1875

Phe Val  Val Thr Thr Asp Ile  Ser Glu Met Gly Ala  Asn Phe Lys
    1880                 1885                 1890

Ala Glu  Arg Val Ile Asp Pro  Arg Arg Cys Met Lys  Pro Val Ile
    1895                 1900                 1905

Leu Thr  Asp Gly Glu Glu Arg  Val Ile Leu Ala Gly  Pro Met Pro
    1910                 1915                 1920

Val Thr  His Ser Ser Ala Ala  Gln Arg Arg Gly Arg  Ile Gly Arg
    1925                 1930                 1935

Asn Pro  Lys Asn Glu Asn Asp  Gln Tyr Ile Tyr Met  Gly Glu Pro
    1940                 1945                 1950

Leu Glu  Asn Asp Glu Asp Cys  Ala His Trp Lys Glu  Ala Lys Met
    1955                 1960                 1965

Leu Leu  Asp Asn Ile Asn Thr  Pro Glu Gly Ile Ile  Pro Ser Met
    1970                 1975                 1980

Phe Glu  Pro Glu Arg Glu Lys  Val Asp Ala Ile Asp  Gly Glu Tyr
    1985                 1990                 1995

Arg Leu  Arg Gly Glu Ala Arg  Lys Thr Phe Val Asp  Leu Met Arg
    2000                 2005                 2010

Arg Gly  Asp Leu Pro Val Trp  Leu Ala Tyr Arg Val  Ala Ala Glu
```

-continued

```
    2015                2020                2025

Gly Ile  Asn Tyr Ala Asp Arg  Arg Trp Cys Phe Asp  Gly Val Lys
    2030                2035                2040

Asn Asn  Gln Ile Leu Glu Glu  Asn Val Glu Val Glu  Ile Trp Thr
    2045                2050                2055

Lys Glu  Gly Glu Arg Lys Lys  Leu Lys Pro Arg Trp  Leu Asp Ala
    2060                2065                2070

Arg Ile  Tyr Ser Asp Pro Leu  Ala Leu Lys Glu Phe  Lys Glu Phe
    2075                2080                2085

Ala Ala  Gly Arg Lys Ser Leu  Thr Leu Asn Leu Ile  Thr Glu Met
    2090                2095                2100

Gly Arg  Leu Pro Thr Phe Met  Thr Gln Lys Ala Arg  Asp Ala Leu
    2105                2110                2115

Asp Asn  Leu Ala Val Leu His  Thr Ala Glu Ala Gly  Gly Arg Ala
    2120                2125                2130

Tyr Asn  His Ala Leu Ser Glu  Leu Pro Glu Thr Leu  Glu Thr Leu
    2135                2140                2145

Leu Leu  Leu Thr Leu Leu Ala  Thr Val Thr Gly Gly  Ile Phe Leu
    2150                2155                2160

Phe Leu  Met Ser Ala Arg Gly  Ile Gly Lys Met Thr  Leu Gly Met
    2165                2170                2175

Cys Cys  Ile Ile Thr Ala Ser  Ile Leu Leu Trp Tyr  Ala Gln Ile
    2180                2185                2190

Gln Pro  His Trp Ile Ala Ala  Ser Ile Ile Leu Glu  Phe Phe Leu
    2195                2200                2205

Ile Val  Leu Leu Ile Pro Glu  Pro Glu Lys Gln Arg  Thr Pro Gln
    2210                2215                2220

Asp Asn  Gln Leu Thr Tyr Val  Val Ile Ala Ile Leu  Thr Val Val
    2225                2230                2235

Ala Ala  Thr Met Ala Asn Glu  Met Gly Phe Leu Glu  Lys Thr Lys
    2240                2245                2250

Lys Asp  Leu Gly Leu Gly Ser  Ile Ala Thr Gln Gln  Pro Glu Ser
    2255                2260                2265

Asn Ile  Leu Asp Ile Asp Leu  Arg Pro Ala Ser Ala  Trp Thr Leu
    2270                2275                2280

Tyr Ala  Val Ala Thr Thr Phe  Val Thr Pro Met Leu  Arg His Ser
    2285                2290                2295

Ile Glu  Asn Ser Ser Val Asn  Val Ser Leu Thr Ala  Ile Ala Asn
    2300                2305                2310

Gln Ala  Thr Val Leu Met Gly  Leu Gly Lys Gly Trp  Pro Leu Ser
    2315                2320                2325

Lys Met  Asp Ile Gly Val Pro  Leu Leu Ala Ile Gly  Cys Tyr Ser
    2330                2335                2340

Gln Val  Asn Pro Ile Thr Leu  Thr Ala Ala Leu Phe  Leu Leu Val
    2345                2350                2355

Ala His  Tyr Ala Ile Ile Gly  Pro Gly Leu Gln Ala  Lys Ala Thr
    2360                2365                2370

Arg Glu  Ala Gln Lys Arg Ala  Ala Ala Gly Ile Met  Lys Asn Pro
    2375                2380                2385

Thr Val  Asp Gly Ile Thr Val  Ile Asp Leu Asp Pro  Ile Pro Tyr
    2390                2395                2400

Asp Pro  Lys Phe Glu Lys Gln  Leu Gly Gln Val Met  Leu Leu Val
    2405                2410                2415
```

```
Leu Cys  Val Thr Gln Val Leu  Met Met Arg Thr Thr  Trp Ala Leu
    2420                 2425                 2430

Cys Glu  Ala Leu Thr Leu Ala  Thr Gly Pro Ile Ser  Thr Leu Trp
    2435                 2440                 2445

Glu Gly  Asn Pro Gly Arg Phe  Trp Asn Thr Thr Ile  Ala Val Ser
    2450                 2455                 2460

Met Ala  Asn Ile Phe Arg Gly  Ser Tyr Leu Ala Gly  Ala Gly Leu
    2465                 2470                 2475

Leu Phe  Ser Ile Met Lys Asn  Thr Thr Asn Thr Arg  Arg Gly Thr
    2480                 2485                 2490

Gly Asn  Ile Gly Glu Thr Leu  Gly Glu Lys Trp Lys  Ser Arg Leu
    2495                 2500                 2505

Asn Ala  Leu Gly Lys Ser Glu  Phe Gln Ile Tyr Lys  Lys Ser Gly
    2510                 2515                 2520

Ile Gln  Glu Val Asp Arg Thr  Leu Ala Lys Glu Gly  Ile Lys Arg
    2525                 2530                 2535

Gly Glu  Thr Asp His His Ala  Val Ser Arg Gly Ser  Ala Lys Leu
    2540                 2545                 2550

Arg Trp  Phe Val Glu Arg Asn  Met Val Thr Pro Glu  Gly Lys Val
    2555                 2560                 2565

Val Asp  Leu Gly Cys Gly Arg  Gly Gly Trp Ser Tyr  Tyr Cys Gly
    2570                 2575                 2580

Gly Leu  Lys Asn Val Arg Glu  Val Lys Gly Leu Thr  Lys Gly Gly
    2585                 2590                 2595

Pro Gly  His Glu Glu Pro Ile  Pro Met Ser Thr Tyr  Gly Trp Asn
    2600                 2605                 2610

Leu Val  Arg Leu Gln Ser Gly  Val Asp Val Phe Phe  Ile Pro Pro
    2615                 2620                 2625

Glu Lys  Cys Asp Thr Leu Leu  Cys Asp Ile Gly Glu  Ser Ser Pro
    2630                 2635                 2640

Asn Pro  Thr Val Glu Ala Gly  Arg Thr Leu Arg Val  Leu Asn Leu
    2645                 2650                 2655

Val Glu  Asn Trp Leu Asn Asn  Asn Thr Gln Phe Cys  Ile Lys Val
    2660                 2665                 2670

Leu Asn  Pro Tyr Met Pro Ser  Val Ile Glu Lys Met  Glu Ala Leu
    2675                 2680                 2685

Gln Arg  Lys Tyr Gly Gly Ala  Leu Val Arg Asn Pro  Leu Ser Arg
    2690                 2695                 2700

Asn Ser  Thr His Glu Met Tyr  Trp Val Ser Asn Ala  Ser Gly Asn
    2705                 2710                 2715

Ile Val  Ser Ser Val Asn Met  Ile Ser Arg Met Leu  Ile Asn Arg
    2720                 2725                 2730

Phe Thr  Met Arg Tyr Lys Lys  Ala Thr Tyr Glu Pro  Asp Val Asp
    2735                 2740                 2745

Leu Gly  Ser Gly Thr Arg Asn  Ile Gly Ile Glu Ser  Glu Ile Pro
    2750                 2755                 2760

Asn Leu  Asp Ile Ile Gly Lys  Arg Ile Glu Lys Ile  Lys Gln Glu
    2765                 2770                 2775

His Glu  Thr Ser Trp His Tyr  Asp Gln Asp His Pro  Tyr Lys Thr
    2780                 2785                 2790

Trp Ala  Tyr His Gly Ser Tyr  Glu Thr Lys Gln Thr  Gly Ser Ala
    2795                 2800                 2805
```

```
Ser Ser  Met Val Asn Gly Val  Val Arg Leu Leu Thr  Lys Pro Trp
    2810                 2815                 2820

Asp Val  Val Pro Met Val Thr  Gln Met Ala Met Thr  Asp Thr Thr
    2825                 2830                 2835

Pro Phe  Gly Gln Gln Arg Val  Phe Lys Glu Lys Val  Asp Thr Arg
    2840                 2845                 2850

Thr Gln  Glu Pro Lys Glu Gly  Thr Lys Lys Leu Met  Lys Ile Thr
    2855                 2860                 2865

Ala Glu  Trp Leu Trp Lys Glu  Leu Gly Lys Lys Lys  Thr Pro Arg
    2870                 2875                 2880

Met Cys  Thr Arg Glu Glu Phe  Thr Arg Lys Val Arg  Ser Asn Ala
    2885                 2890                 2895

Ala Leu  Gly Ala Ile Phe Thr  Asp Glu Asn Lys Trp  Lys Ser Ala
    2900                 2905                 2910

Arg Glu  Ala Val Glu Asp Ser  Arg Phe Trp Glu Leu  Val Asp Lys
    2915                 2920                 2925

Glu Arg  Asn Leu His Leu Glu  Gly Lys Cys Glu Thr  Cys Val Tyr
    2930                 2935                 2940

Asn Met  Met Gly Lys Arg Glu  Lys Lys Leu Gly Glu  Phe Gly Lys
    2945                 2950                 2955

Ala Lys  Gly Ser Arg Ala Ile  Trp Tyr Met Trp Leu  Gly Ala Arg
    2960                 2965                 2970

Phe Leu  Glu Phe Glu Ala Leu  Gly Phe Leu Asn Glu  Asp His Trp
    2975                 2980                 2985

Phe Ser  Arg Glu Asn Ser Leu  Ser Gly Val Glu Gly  Glu Gly Leu
    2990                 2995                 3000

His Lys  Leu Gly Tyr Ile Leu  Arg Asp Val Ser Lys  Lys Glu Gly
    3005                 3010                 3015

Gly Ala  Met Tyr Ala Asp Asp  Thr Ala Gly Trp Asp  Thr Arg Ile
    3020                 3025                 3030

Thr Leu  Glu Asp Leu Lys Asn  Glu Glu Met Val Thr  Asn His Met
    3035                 3040                 3045

Glu Gly  Glu His Lys Lys Leu  Ala Glu Ala Ile Phe  Lys Leu Thr
    3050                 3055                 3060

Tyr Gln  Asn Lys Val Val Arg  Val Gln Arg Pro Thr  Pro Arg Gly
    3065                 3070                 3075

Thr Val  Met Asp Ile Ile Ser  Arg Arg Asp Gln Arg  Gly Ser Gly
    3080                 3085                 3090

Gln Val  Gly Thr Tyr Gly Leu  Asn Thr Phe Thr Asn  Met Glu Ala
    3095                 3100                 3105

Gln Leu  Ile Arg Gln Met Glu  Gly Glu Gly Val Phe  Lys Ser Ile
    3110                 3115                 3120

Gln His  Leu Thr Ile Thr Glu  Glu Ile Ala Val Gln  Asn Trp Leu
    3125                 3130                 3135

Ala Arg  Val Gly Arg Glu Arg  Leu Ser Arg Met Ala  Ile Ser Gly
    3140                 3145                 3150

Asp Asp  Cys Val Val Lys Pro  Leu Asp Asp Arg Phe  Ala Ser Ala
    3155                 3160                 3165

Leu Thr  Ala Leu Asn Asp Met  Gly Lys Ile Arg Lys  Asp Ile Gln
    3170                 3175                 3180

Gln Trp  Glu Pro Ser Arg Gly  Trp Asn Asp Trp Thr  Gln Val Pro
    3185                 3190                 3195

Phe Cys  Ser His His Phe His  Glu Leu Ile Met Lys  Asp Gly Arg
```

```
    3200                3205                3210

Val Leu  Val Val Pro Cys Arg  Asn Gln Asp Glu Leu  Ile Gly Arg
    3215                3220                3225

Ala Arg  Ile Ser Gln Gly Ala  Gly Trp Ser Leu Arg  Glu Thr Ala
    3230                3235                3240

Cys Leu  Gly Lys Ser Tyr Ala  Gln Met Trp Ser Leu  Met Tyr Phe
    3245                3250                3255

His Arg  Arg Asp Leu Arg Leu  Ala Ala Asn Ala Ile  Cys Ser Ala
    3260                3265                3270

Val Pro  Ser His Trp Val Pro  Thr Ser Arg Thr Thr  Trp Ser Ile
    3275                3280                3285

His Ala  Lys His Glu Trp Met  Thr Thr Glu Asp Met  Leu Thr Val
    3290                3295                3300

Trp Asn  Arg Val Trp Ile Gln  Glu Asn Pro Trp Met  Glu Asp Lys
    3305                3310                3315

Thr Pro  Val Glu Ser Trp Glu  Glu Ile Pro Tyr Leu  Gly Lys Arg
    3320                3325                3330

Glu Asp  Gln Trp Cys Gly Ser  Leu Ile Gly Leu Thr  Ser Arg Ala
    3335                3340                3345

Thr Trp  Ala Lys Asn Ile Gln  Ala Ala Ile Asn Gln  Val Arg Ser
    3350                3355                3360

Leu Ile  Gly Asn Glu Glu Tyr  Thr Asp Tyr Met Pro  Ser Met Lys
    3365                3370                3375

Arg Phe  Arg Arg Glu Glu Glu  Glu Ala Gly Val Leu  Trp
    3380                3385                3390
```

<210> SEQ ID NO 13
<211> LENGTH: 10807
<212> TYPE: DNA
<213> ORGANISM: Zika virus strain PRVABC59

<400> SEQUENCE: 13

```
agttgttgat ctgtgtgaat cagactgcga cagttcgagt ttgaagcgaa agctagcaac     60

agtatcaaca ggttttattt tggatttgga aacgagagtt tctggtcatg aaaaacccaa    120

aaaagaaatc cggaggattc cggattgtca atatgctaaa acgcggagta gcccgtgtga    180

gcccctttgg gggcttgaag aggctgccag ccggacttct gctgggtcat gggcccatca    240

ggatggtctt ggcgattcta gcctttttga gattcacggc aatcaagcca tcactgggtc    300

tcatcaatag atggggttca gtggggaaaa aagaggctat ggaaacaata aagaagttca    360

agaaagatct ggctgccatg ctgagaataa tcaatgctag gaaggagaag aagagacgag    420

gcgcagatac tagtgtcgga attgttggcc tcctgctgac cacagctatg gcagcggagg    480

tcactagacg tgggagtgca tactatatgt acttggacag aaacgatgct ggggaggcca    540

tatcttttcc aaccacattg gggatgaata agtgttatat acagatcatg gatcttggac    600

acatgtgtga tgccaccatg agctatgaat gccctatgct ggatgagggg gtggaaccag    660

atgacgtcga ttgttggtgc aacacgacgt caacttgggt tgtgtacgga acctgccatc    720

acaaaaaagg tgaagcacgg agatctagaa gagctgtgac gctcccctcc cattccacca    780

ggaagctgca aacgcggtcg caaacctggt tggaatcaag agaatacaca aagcacttga    840

ttagagtcga aaattggata ttcaggaacc ctggcttcgc gttagcagca gctgccatcg    900

cttggctttt gggaagctca acgagccaaa aagtcatata cttggtcatg atactgctga    960

ttgccccggc atacagcatc aggtgcatag gagtcagcaa tagggacttt gtggaaggta   1020
```

```
tgtcaggtgg gacttgggtt gatgttgtct tggaacatgg aggttgtgtc accgtaatgg   1080
cacaggacaa accgactgtc gacatagagc tggttacaac aacagtcagc aacatggcgg   1140
aggtaagatc ctactgctat gaggcatcaa tatcagacat ggcttctgac agccgctgcc   1200
caacacaagg tgaagcctac cttgacaagc aatcagacac tcaatatgtc tgcaaaagaa   1260
cgttagtgga cagaggctgg ggaaatggat gtggactttt tggcaaaggg agcctggtga   1320
catgcgctaa gtttgcatgc tccaagaaaa tgaccgggaa gagcatccag ccagagaatc   1380
tggagtaccg gataatgctg tcagttcatg gctcccagca cagtgggatg atcgttaatg   1440
acacaggaca tgaaactgat gagaatagag cgaaagttga gataacgccc aattcaccga   1500
gagccgaagc caccctgggg ggttttggaa gcctaggact tgattgtgaa ccgaggacag   1560
gccttgactt ttcagatttg tattacttga ctatgaataa caagcactgg ttggttcaca   1620
aggagtggtt ccacgacatt ccattacctt ggcacgctgg ggcagacacc ggaactccac   1680
actggaacaa caaagaagca ctggtagagt tcaaggacgc acatgccaaa aggcaaactg   1740
tcgtggttct agggagtcaa gaaggagcag ttcacacggc ccttgctgga gctctggagg   1800
ctgagatgga tggtgcaaag ggaaggctgt cctctggcca cttgaaatgt cgcctgaaaa   1860
tggataaact tagattgaag ggcgtgtcat actccttgtg tactgcagcg ttcacattca   1920
ccaagatccc ggctgaaaca ctgcacggga cagtcacagt ggaggtacag tacgcaggga   1980
cagatggacc ttgcaaggtt ccagctcaga tggcggtgga catgcaaact ctgaccccag   2040
ttgggaggtt gataaccgct aaccccgtaa tcactgaaag cactgagaac tctaagatga   2100
tgctggaact tgatccacca tttggggact cttacattgt cataggagtc ggggagaaga   2160
agatcaccca ccactggcac aggagtggca gcaccattgg aaaagcattt gaagccactg   2220
tgagaggtgc caagagaatg gcagtcttgg gagacacagc ctgggacttt ggatcagttg   2280
gaggcgctct caactcattg ggcaagggca tccatcaaat ttttggagca gctttcaaat   2340
cattgtttgg aggaatgtcc tggttctcac aaattctcat tggaacgttg ctgatgtggt   2400
tgggtctgaa cacaaagaat ggatctattt cccttatgtg cttggcctta gggggagtgt   2460
tgatcttctt atccacagcc gtctctgctg atgtggggtg ctcggtggac ttctcaaaga   2520
aggagacgag atgcggtaca ggggtgttcg tctataacga cgttgaagcc tggagggaca   2580
ggtacaagta ccatcctgac tccccccgta gattggcagc agcagtcaag caagcctggg   2640
aagatggtat ctgcgggatc tcctctgttt caagaatgga aaacatcatg tggagatcag   2700
tagaagggga gctcaacgca atcctggaag agaatggagt tcaactgacg gtcgttgtgg   2760
gatctgtaaa aaaccccatg tggagaggtc cacagagatt gcccgtgcct gtgaacgagc   2820
tgccccacgg ctggaaggct tgggggaaat cgtatttcgt cagagcagca aagacaaata   2880
acagctttgt cgtggatggt gacacactga aggaatgccc actcaaacat agagcatgga   2940
acagctttct tgtggaggat catgggttcg ggggtatttca cactagtgtc tggctcaagg   3000
ttagagaaga ttattcatta gagtgtgatc cagccgttat tggaacagct gttaagggaa   3060
aggaggctgt acacagtgat ctaggctact ggattgagag tgagaagaat gacacatgga   3120
ggctgaagag ggcccatctg atcgagatga aaacatgtga atggccaaag tcccacacat   3180
tgtggacaga tggaatagaa gagagtgatc tgatcatacc caagtcttta gctgggccac   3240
tcagccatca caataccaga gagggctaca ggacccaaat gaaagggcca tggcacagtg   3300
aagagcttga aattcggttt gaggaatgcc caggcactaa ggtccacgtg gaggaaacat   3360
```

```
gtggaacaag aggaccatct ctgagatcaa ccactgcaag cggaagggtg atcgaggaat   3420
ggtgctgcag ggagtgcaca atgcccccac tgtcgttccg ggctaaagat ggctgttggt   3480
atggaatgga gataaggccc aggaaagaac cagaaagcaa cttagtaagg tcaatggtga   3540
ctgcaggatc aactgatcac atggaccact tctcccttgg agtgcttgtg atcctgctca   3600
tggtgcagga agggctgaag aagagaatga ccacaaagat catcataagc acatcaatgg   3660
cagtgctggt agctatgatc ctgggaggat tttcaatgag tgacctggct aagcttgcaa   3720
ttttgatggg tgccaccttc gcggaaatga acactggagg agatgtagct catctggcgc   3780
tgatagcggc attcaaagtc agaccagcgt tgctggtatc tttcatcttc agagctaatt   3840
ggacaccccg tgaaagcatg ctgctggcct tggcctcgtg tcttttgcaa actgcgatct   3900
ccgccttgga aggcgacctg atggttctca tcaatggttt tgctttggcc tggttggcaa   3960
tacgagcgat ggttgttcca cgcactgata acatcacctt ggcaatcctg gctgctctga   4020
caccactggc ccggggcaca ctgcttgtgg cgtggagagc aggccttgct acttgcgggg   4080
ggtttatgct cctctctctg aagggaaaag gcagtgtgaa gaagaactta ccatttgtca   4140
tggccctggg actaaccgct gtgaggctgg tcgaccccat caacgtggtg ggactgctgt   4200
tgctcacaag gagtgggaag cggagctggc cccctagcga agtactcaca gctgttggcc   4260
tgatatgcgc attggctgga gggttcgcca aggcagatat agagatggct gggcccatgg   4320
ccgcggtcgg tctgctaatt gtcagttacg tggtctcagg aaagagtgtg gacatgtaca   4380
ttgaaagagc aggtgacatc acatgggaaa aagatgcgga agtcactgga aacagtcccc   4440
ggctcgatgt ggcgctagat gagagtggtg atttctccct ggtggaggat gacggtcccc   4500
ccatgagaga gatcatactc aaggtggtcc tgatgaccat ctgtggcatg aacccaatag   4560
ccataccctt tgcagctgga gcgtggtacg tatacgtgaa gactggaaaa aggagtggtg   4620
ctctatggga tgtgcctgct cccaaggaag taaaaaaggg ggagaccaca gatggagtgt   4680
acagagtaat gactcgtaga ctgctaggtt caacacaagt tggagtggga gttatgcaag   4740
agggggtctt tcacactatg tggcacgtca caaaaggatc cgcgctgaga agcggtgaag   4800
ggagacttga tccatactgg ggagatgtca agcaggatct ggtgtcatac tgtggtccat   4860
ggaagctaga tgccgcctgg gatgggcaca gcgaggtgca gctcttggcc gtgccccccg   4920
gagagagagc gaggaacatc cagactctgc ccggaatatt taagacaaag gatggggaca   4980
ttggagcggt tgcgctggat tacccagcag gaacttcagg atctccaatc ctagacaagt   5040
gtgggagagt gataggactt tatggcaatg gggtcgtgat caaaaacggg agttatgtta   5100
gtgccatcac ccaagggagg agggaggaag agactcctgt tgagtgcttc gagccctcga   5160
tgctgaagaa gaagcagcta actgtcttag acttgcatcc tggagctggg aaaaccagga   5220
gagttcttcc tgaaatagtc cgtgaagcca taaaaacaag actccgtact gtgatcttag   5280
ctccaaccag ggttgtcgct gctgaaatgg aggaggccct tagagggctt ccagtgcgtt   5340
atatgacaac agcagtcaat gtcacccact ctggaacaga aatcgtcgac ttaatgtgcc   5400
atgccacctt cacttcacgt ctactacagc caatcagagt ccccaactat aatctgtata   5460
ttatggatga ggcccacttc acagatccct caagtatagc agcaagagga tacatttcaa   5520
caagggttga gatgggcgag gcggctgcca tcttcatgac cgccacgcca ccaggaaccc   5580
gtgacgcatt tccggactcc aactcaccaa ttatggacac cgaagtggaa gtcccagaga   5640
gagcctggag ctcaggcttt gattgggtga cggatcattc tggaaaaaca gtttggtttg   5700
ttccaagcgt gaggaacggc aatgagatcg cagcttgtct gacaaaggct ggaaaacggg   5760
```

```
tcatacagct cagcagaaag acttttgaga cagagttcca gaaaacaaaa catcaagagt   5820

gggactttgt cgtgacaact gacatttcag agatgggcgc caactttaaa gctgaccgtg   5880

tcatagattc caggagatgc ctaaagccgg tcatacttga tggcgagaga gtcattctgg   5940

ctggacccat gcctgtcaca catgccagcg ctgcccagag gaggggggcgc ataggcagga   6000

atcccaacaa acctggagat gagtatctgt atggaggtgg gtgcgcagag actgacgaag   6060

accatgcaca ctggcttgaa gcaagaatgc tccttgacaa tatttacctc caagatggcc   6120

tcatagcctc gctctatcga cctgaggccg acaaagtagc agccattgag ggagagttca   6180

agcttaggac ggagcaaagg aagacctttg tggaactcat gaaaagagga gatcttcctg   6240

tttggctggc ctatcaggtt gcatctgccg gaataaccta cacagataga agatggtgct   6300

ttgatggcac gaccaacaac accataatgg aagacagtgt gccggcagag gtgtggacca   6360

gacacggaga gaaaagagtg ctcaaaccga ggtggatgga cgccagagtt tgttcagatc   6420

atgcggccct gaagtcattc aaggagtttg ccgctgggaa aagaggagcg gcttttggag   6480

tgatggaagc cctgggaaca ctgccaggac acatgacaga gagattccag gaagccattg   6540

acaacctcgc tgtgctcatg cgggcagaga ctggaagcag gccttacaaa gccgcggcgg   6600

cccaattgcc ggagacccta gagaccataa tgcttttggg gttgctggga acagtctcgc   6660

tgggaatctt cttcgtcttg atgaggaaca agggcatagg gaagatgggc tttggaatgg   6720

tgactcttgg ggccagcgca tggctcatgt ggctctcgga aattgagcca gccagaattg   6780

catgtgtcct cattgttgtg ttcctattgc tggtggtgct catacctgag ccagaaaagc   6840

aaagatctcc ccaggacaac caaatggcaa tcatcatcat ggtagcagta ggtcttctgg   6900

gcttgattac cgccaatgaa ctcggatggt tggagagaac aaagagtgac ctaagccatc   6960

taatgggaag gagagaggag ggggcaacca taggattctc aatggacatt gacctgcggc   7020

cagcctcagc ttgggccatc tatgctgcct tgacaacttt cattacccca gccgtccaac   7080

atgcagtgac cacctcatac aacaactact ccttaatggc gatggccacg caagctggag   7140

tgttgtttgg catgggcaaa gggatgccat tctacgcatg ggactttgga gtcccgctgc   7200

taatgatagg ttgctactca caattaacac ccctgaccct aatagtggcc atcattttgc   7260

tcgtggcgca ctacatgtac ttgatcccag ggctgcaggc agcagctgcg cgtgctgccc   7320

agaagagaac ggcagctggc atcatgaaga accctgttgt ggatggaata gtggtgactg   7380

acattgacac aatgacaatt gacccccaag tggagaaaaa gatgggacag gtgctactca   7440

tagcagtagc cgtctccagc gccatactgt cgcggaccgc ctgggggtgg ggggaggctg   7500

gggctctgat cacagccgca acttccactt tgtgggaagg ctctccgaac aagtactgga   7560

actcctctac agccacttca ctgtgtaaca tttttagggg aagttacttg gctggagctt   7620

ctctaatcta cacagtaaca agaaacgctg gcttggtcaa gagacgtggg ggtggaacag   7680

gagagaccct gggagagaaa tggaaggccc gcttgaacca gatgtcggcc ctggagttct   7740

actcctacaa aaagtcaggc atcaccgagg tgtgcagaga agaggcccgc cgcgccctca   7800

aggacggtgt ggcaacggga ggccatgctg tgtcccgagg aagtgcaaag ctgagatggt   7860

tggtggagcg gggatacctg cagccctatg gaaaggtcat tgatcttgga tgtggcagag   7920

ggggctggag ttactacgtc gccaccatcc gcaaagttca agaagtgaaa ggatacacaa   7980

aaggaggccc tggtcatgaa gaacccgtgt tggtgcaaag ctatgggtgg aacatagtcc   8040

gtcttaagag tggggtggac gtctttcata tggcggctga gccgtgtgac acgttgctgt   8100
```

```
gtgacatagg tgagtcatca tctagtcctg aagtggaaga agcacggacg ctcagagtcc   8160
tctccatggt gggggattgg cttgaaaaaa gaccaggagc cttttgtata aaagtgttgt   8220
gcccatacac cagcactatg atggaaaccc tggagcgact gcagcgtagg tatgggggag   8280
gactggtcag agtgccactc tcccgcaact ctacacatga gatgtactgg gtctctggag   8340
cgaaaagcaa caccataaaa agtgtgtcca ccacgagcca gctcctcttg ggcgcatgg    8400
acgggcctag gaggccagtg aaatatgagg aggatgtgaa tctcggctct ggcacgcggg   8460
ctgtggtaag ctgcgctgaa gctcccaaca tgaagatcat tggtaaccgc attgaaagga   8520
tccgcagtga gcacgcggaa acgtggttct ttgacgagaa ccacccatat aggacatggg   8580
cttaccatgg aagctatgag gcccccacac aagggtcagc gtcctctcta ataaacgggg   8640
ttgtcaggct cctgtcaaaa ccctgggatg tggtgactgg agtcacagga atagccatga   8700
ccgacaccac accgtatggt cagcaaagag ttttcaagga aaaagtggac actagggtgc   8760
cagaccccca agaaggcact cgtcaggtta tgagcatggt ctcttcctgg ttgtggaaag   8820
agctaggcaa acacaaacgg ccacgagtct gcaccaaaga agagttcatc aacaaggttc   8880
gtagcaatgc agcattaggg gcaatatttg aagaggaaaa agagtggaag actgcagtgg   8940
aagctgtgaa cgatccaagg ttctgggctc tagtggacaa ggaaagagag caccacctga   9000
gaggagagtg ccagagctgt gtgtacaaca tgatgggaaa aagagaaaag aaacaagggg   9060
aatttggaaa ggccaagggc agccgcgcca tctggtatat gtggctaggg gctagatttc   9120
tagagttcga agcccttgga ttcttgaacg aggatcactg gatgggggaga gagaactcag   9180
gaggtggtgt tgaagggctg ggattacaaa gactcggata tgtcctagaa gagatgagtc   9240
gtataccagg aggaaggatg tatgcagatg acactgctgg ctgggacacc cgcattagca   9300
ggtttgatct ggagaatgaa gctctaatca ccaaccaaat ggagaaaggg cacagggcct   9360
tggcattggc cataatcaag tacacatacc aaaacaaagt ggtaaaggtc cttagaccag   9420
ctgaaaaagg gaaaacagtt atggacatta tttcgagaca agaccaaagg gggagcggac   9480
aagttgtcac ttacgctctt aacacattta ccaacctagt ggtgcaactc attcggaata   9540
tggaggctga ggaagttcta gagatgcaag acttgtggct gctgcggagg tcagagaaag   9600
tgaccaactg gttgcagagc aacggatggg ataggctcaa acgaatggca gtcagtggag   9660
atgattgcgt tgtgaagcca attgatgata ggtttgcaca tgccctcagg ttcttgaatg   9720
atatgggaaa agttaggaag gacacacaag agtggaaacc ctcaactgga tgggacaact   9780
gggaagaagt tccgttttgc tcccaccact tcaacaagct ccatctcaag gacgggaggt   9840
ccattgtggt tccctgccgc caccaagatg aactgattgg ccgggcccgc gtctctccag   9900
ggcgggatg gagcatccgg gagactgctt gcctagcaaa atcatatgcg caaatgtggc    9960
agctccttta tttccacaga agggacctcc gactgatggc caatgccatt tgttcatctg  10020
tgccagttga ctgggttcca actgggagaa ctacctggtc aatccatgga aagggagaat  10080
ggatgaccac tgaagacatg cttgtggtgt ggaacagagt gtggattgag gagaacgacc  10140
acatggaaga caagacccca gttacgaaat ggacagacat tccctatttg ggaaaaaggg  10200
aagacttgtg gtgtggatct ctcatagggc acagaccgcg caccacctgg gctgagaaca  10260
ttaaaaacac agtcaacatg gtgcgcagga tcataggtga tgaagaaaag tacatggact  10320
acctatccac ccaagttcgc tacttgggtg aagaagggtc tacacctgga gtgctgtaag  10380
caccaatctt aatgttgtca ggcctgctag tcagccacag cttggggaaa gctgtgcagc  10440
ctgtgacccc cccaggagaa gctgggaaac caagcctata gtcaggccga gaacgccatg  10500
```

```
gcacggaaga agccatgctg cctgtgagcc cctcagagga cactgagtca aaaaacccca  10560

cgcgcttgga ggcgcaggat gggaaaagaa ggtggcgacc ttccccaccc ttcaatctgg  10620

ggcctgaact ggagatcagc tgtggatctc cagaagaggg actagtggtt agaggagacc  10680

ccccggaaaa cgcaaaacag catattgacg ctgggaaaga ccagagactc catgagtttc  10740

caccacgctg gccgccaggc acagatcgcc gaatagcggc ggccggtgtg gggaaatcca  10800

tgggtct                                                            10807
```

<210> SEQ ID NO 14
<211> LENGTH: 3423
<212> TYPE: PRT
<213> ORGANISM: Zika virus strain PRVABC59

<400> SEQUENCE: 14

```
Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Thr
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
```

-continued

```
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735
```

```
Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Asp Gly Ile
        835                 840                 845

Cys Gly Ile Ser Ser Val Ser Arg Met Glu Asn Ile Met Trp Arg Ser
    850                 855                 860

Val Glu Gly Glu Leu Asn Ala Ile Leu Glu Glu Asn Gly Val Gln Leu
865                 870                 875                 880

Thr Val Val Val Gly Ser Val Lys Asn Pro Met Trp Arg Gly Pro Gln
                885                 890                 895

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
        915                 920                 925

Val Asp Gly Asp Thr Leu Lys Glu Cys Pro Leu Lys His Arg Ala Trp
    930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
                965                 970                 975

Val Ile Gly Thr Ala Val Lys Gly Lys Glu Ala Val His Ser Asp Leu
            980                 985                 990

Gly Tyr Trp Ile Glu Ser Glu Lys  Asn Asp Thr Trp Arg  Leu Lys Arg
        995                 1000                 1005

Ala His  Leu Ile Glu Met Lys  Thr Cys Glu Trp Pro  Lys Ser His
    1010                 1015                 1020

Thr Leu  Trp Thr Asp Gly Ile  Glu Glu Ser Asp Leu  Ile Ile Pro
    1025                 1030                 1035

Lys Ser  Leu Ala Gly Pro Leu  Ser His His Asn Thr  Arg Glu Gly
    1040                 1045                 1050

Tyr Arg  Thr Gln Met Lys Gly  Pro Trp His Ser Glu  Glu Leu Glu
    1055                 1060                 1065

Ile Arg  Phe Glu Glu Cys Pro  Gly Thr Lys Val His  Val Glu Glu
    1070                 1075                 1080

Thr Cys  Gly Thr Arg Gly Pro  Ser Leu Arg Ser Thr  Thr Ala Ser
    1085                 1090                 1095

Gly Arg  Val Ile Glu Glu Trp  Cys Cys Arg Glu Cys  Thr Met Pro
    1100                 1105                 1110

Pro Leu  Ser Phe Arg Ala Lys  Asp Gly Cys Trp Tyr  Gly Met Glu
    1115                 1120                 1125

Ile Arg  Pro Arg Lys Glu Pro  Glu Ser Asn Leu Val  Arg Ser Met
    1130                 1135                 1140
```

```
Val Thr  Ala Gly Ser Thr Asp  His Met Asp His Phe  Ser Leu Gly
    1145                 1150                 1155

Val Leu  Val Ile Leu Leu Met  Val Gln Glu Gly Leu  Lys Lys Arg
    1160                 1165                 1170

Met Thr  Thr Lys Ile Ile Ile  Ser Thr Ser Met Ala  Val Leu Val
    1175                 1180                 1185

Ala Met  Ile Leu Gly Gly Phe  Ser Met Ser Asp Leu  Ala Lys Leu
    1190                 1195                 1200

Ala Ile  Leu Met Gly Ala Thr  Phe Ala Glu Met Asn  Thr Gly Gly
    1205                 1210                 1215

Asp Val  Ala His Leu Ala Leu  Ile Ala Ala Phe Lys  Val Arg Pro
    1220                 1225                 1230

Ala Leu  Leu Val Ser Phe Ile  Phe Arg Ala Asn Trp  Thr Pro Arg
    1235                 1240                 1245

Glu Ser  Met Leu Leu Ala Leu  Ala Ser Cys Leu Leu  Gln Thr Ala
    1250                 1255                 1260

Ile Ser  Ala Leu Glu Gly Asp  Leu Met Val Leu Ile  Asn Gly Phe
    1265                 1270                 1275

Ala Leu  Ala Trp Leu Ala Ile  Arg Ala Met Val Val  Pro Arg Thr
    1280                 1285                 1290

Asp Asn  Ile Thr Leu Ala Ile  Leu Ala Ala Leu Thr  Pro Leu Ala
    1295                 1300                 1305

Arg Gly  Thr Leu Leu Val Ala  Trp Arg Ala Gly Leu  Ala Thr Cys
    1310                 1315                 1320

Gly Gly  Phe Met Leu Leu Ser  Leu Lys Gly Lys Gly  Ser Val Lys
    1325                 1330                 1335

Lys Asn  Leu Pro Phe Val Met  Ala Leu Gly Leu Thr  Ala Val Arg
    1340                 1345                 1350

Leu Val  Asp Pro Ile Asn Val  Val Gly Leu Leu Leu  Leu Thr Arg
    1355                 1360                 1365

Ser Gly  Lys Arg Ser Trp Pro  Pro Ser Glu Val Leu  Thr Ala Val
    1370                 1375                 1380

Gly Leu  Ile Cys Ala Leu Ala  Gly Gly Phe Ala Lys  Ala Asp Ile
    1385                 1390                 1395

Glu Met  Ala Gly Pro Met Ala  Ala Val Gly Leu Leu  Ile Val Ser
    1400                 1405                 1410

Tyr Val  Val Ser Gly Lys Ser  Val Asp Met Tyr Ile  Glu Arg Ala
    1415                 1420                 1425

Gly Asp  Ile Thr Trp Glu Lys  Asp Ala Glu Val Thr  Gly Asn Ser
    1430                 1435                 1440

Pro Arg  Leu Asp Val Ala Leu  Asp Glu Ser Gly Asp  Phe Ser Leu
    1445                 1450                 1455

Val Glu  Asp Asp Gly Pro Pro  Met Arg Glu Ile Ile  Leu Lys Val
    1460                 1465                 1470

Val Leu  Met Thr Ile Cys Gly  Met Asn Pro Ile Ala  Ile Pro Phe
    1475                 1480                 1485

Ala Ala  Gly Ala Trp Tyr Val  Tyr Val Lys Thr Gly  Lys Arg Ser
    1490                 1495                 1500

Gly Ala  Leu Trp Asp Val Pro  Ala Pro Lys Glu Val  Lys Lys Gly
    1505                 1510                 1515

Glu Thr  Thr Asp Gly Val Tyr  Arg Val Met Thr Arg  Arg Leu Leu
    1520                 1525                 1530

Gly Ser  Thr Gln Val Gly Val  Gly Val Met Gln Glu  Gly Val Phe
```

```
    1535                1540                1545

His Thr  Met Trp His Val Thr  Lys Gly Ser Ala Leu  Arg Ser Gly
    1550                1555                1560

Glu Gly  Arg Leu Asp Pro Tyr  Trp Gly Asp Val Lys  Gln Asp Leu
    1565                1570                1575

Val Ser  Tyr Cys Gly Pro Trp  Lys Leu Asp Ala Ala  Trp Asp Gly
    1580                1585                1590

His Ser  Glu Val Gln Leu Leu  Ala Val Pro Pro Gly  Glu Arg Ala
    1595                1600                1605

Arg Asn  Ile Gln Thr Leu Pro  Gly Ile Phe Lys Thr  Lys Asp Gly
    1610                1615                1620

Asp Ile  Gly Ala Val Ala Leu  Asp Tyr Pro Ala Gly  Thr Ser Gly
    1625                1630                1635

Ser Pro  Ile Leu Asp Lys Cys  Gly Arg Val Ile Gly  Leu Tyr Gly
    1640                1645                1650

Asn Gly  Val Val Ile Lys Asn  Gly Ser Tyr Val Ser  Ala Ile Thr
    1655                1660                1665

Gln Gly  Arg Arg Glu Glu Glu  Thr Pro Val Glu Cys  Phe Glu Pro
    1670                1675                1680

Ser Met  Leu Lys Lys Lys Gln  Leu Thr Val Leu Asp  Leu His Pro
    1685                1690                1695

Gly Ala  Gly Lys Thr Arg Arg  Val Leu Pro Glu Ile  Val Arg Glu
    1700                1705                1710

Ala Ile  Lys Thr Arg Leu Arg  Thr Val Ile Leu Ala  Pro Thr Arg
    1715                1720                1725

Val Val  Ala Ala Glu Met Glu  Glu Ala Leu Arg Gly  Leu Pro Val
    1730                1735                1740

Arg Tyr  Met Thr Thr Ala Val  Asn Val Thr His Ser  Gly Thr Glu
    1745                1750                1755

Ile Val  Asp Leu Met Cys His  Ala Thr Phe Thr Ser  Arg Leu Leu
    1760                1765                1770

Gln Pro  Ile Arg Val Pro Asn  Tyr Asn Leu Tyr Ile  Met Asp Glu
    1775                1780                1785

Ala His  Phe Thr Asp Pro Ser  Ser Ile Ala Ala Arg  Gly Tyr Ile
    1790                1795                1800

Ser Thr  Arg Val Glu Met Gly  Glu Ala Ala Ala Ile  Phe Met Thr
    1805                1810                1815

Ala Thr  Pro Pro Gly Thr Arg  Asp Ala Phe Pro Asp  Ser Asn Ser
    1820                1825                1830

Pro Ile  Met Asp Thr Glu Val  Glu Val Pro Glu Arg  Ala Trp Ser
    1835                1840                1845

Ser Gly  Phe Asp Trp Val Thr  Asp His Ser Gly Lys  Thr Val Trp
    1850                1855                1860

Phe Val  Pro Ser Val Arg Asn  Gly Asn Glu Ile Ala  Ala Cys Leu
    1865                1870                1875

Thr Lys  Ala Gly Lys Arg Val  Ile Gln Leu Ser Arg  Lys Thr Phe
    1880                1885                1890

Glu Thr  Glu Phe Gln Lys Thr  Lys His Gln Glu Trp  Asp Phe Val
    1895                1900                1905

Val Thr  Thr Asp Ile Ser Glu  Met Gly Ala Asn Phe  Lys Ala Asp
    1910                1915                1920

Arg Val  Ile Asp Ser Arg Arg  Cys Leu Lys Pro Val  Ile Leu Asp
    1925                1930                1935
```

```
Gly Glu  Arg Val Ile Leu Ala  Gly Pro Met Pro Val  Thr His Ala
    1940                 1945                 1950

Ser Ala  Ala Gln Arg Arg Gly  Arg Ile Gly Arg Asn  Pro Asn Lys
    1955                 1960                 1965

Pro Gly  Asp Glu Tyr Leu Tyr  Gly Gly Gly Cys Ala  Glu Thr Asp
    1970                 1975                 1980

Glu Asp  His Ala His Trp Leu  Glu Ala Arg Met Leu  Leu Asp Asn
    1985                 1990                 1995

Ile Tyr  Leu Gln Asp Gly Leu  Ile Ala Ser Leu Tyr  Arg Pro Glu
    2000                 2005                 2010

Ala Asp  Lys Val Ala Ala Ile  Glu Gly Glu Phe Lys  Leu Arg Thr
    2015                 2020                 2025

Glu Gln  Arg Lys Thr Phe Val  Glu Leu Met Lys Arg  Gly Asp Leu
    2030                 2035                 2040

Pro Val  Trp Leu Ala Tyr Gln  Val Ala Ser Ala Gly  Ile Thr Tyr
    2045                 2050                 2055

Thr Asp  Arg Arg Trp Cys Phe  Asp Gly Thr Thr Asn  Asn Thr Ile
    2060                 2065                 2070

Met Glu  Asp Ser Val Pro Ala  Glu Val Trp Thr Arg  His Gly Glu
    2075                 2080                 2085

Lys Arg  Val Leu Lys Pro Arg  Trp Met Asp Ala Arg  Val Cys Ser
    2090                 2095                 2100

Asp His  Ala Ala Leu Lys Ser  Phe Lys Glu Phe Ala  Ala Gly Lys
    2105                 2110                 2115

Arg Gly  Ala Ala Phe Gly Val  Met Glu Ala Leu Gly  Thr Leu Pro
    2120                 2125                 2130

Gly His  Met Thr Glu Arg Phe  Gln Glu Ala Ile Asp  Asn Leu Ala
    2135                 2140                 2145

Val Leu  Met Arg Ala Glu Thr  Gly Ser Arg Pro Tyr  Lys Ala Ala
    2150                 2155                 2160

Ala Ala  Gln Leu Pro Glu Thr  Leu Glu Thr Ile Met  Leu Leu Gly
    2165                 2170                 2175

Leu Leu  Gly Thr Val Ser Leu  Gly Ile Phe Phe Val  Leu Met Arg
    2180                 2185                 2190

Asn Lys  Gly Ile Gly Lys Met  Gly Phe Gly Met Val  Thr Leu Gly
    2195                 2200                 2205

Ala Ser  Ala Trp Leu Met Trp  Leu Ser Glu Ile Glu  Pro Ala Arg
    2210                 2215                 2220

Ile Ala  Cys Val Leu Ile Val  Val Phe Leu Leu Leu  Val Val Leu
    2225                 2230                 2235

Ile Pro  Glu Pro Glu Lys Gln  Arg Ser Pro Gln Asp  Asn Gln Met
    2240                 2245                 2250

Ala Ile  Ile Ile Met Val Ala  Val Gly Leu Leu Gly  Leu Ile Thr
    2255                 2260                 2265

Ala Asn  Glu Leu Gly Trp Leu  Glu Arg Thr Lys Ser  Asp Leu Ser
    2270                 2275                 2280

His Leu  Met Gly Arg Arg Glu  Glu Gly Ala Thr Ile  Gly Phe Ser
    2285                 2290                 2295

Met Asp  Ile Asp Leu Arg Pro  Ala Ser Ala Trp Ala  Ile Tyr Ala
    2300                 2305                 2310

Ala Leu  Thr Thr Phe Ile Thr  Pro Ala Val Gln His  Ala Val Thr
    2315                 2320                 2325
```

```
Thr Ser  Tyr Asn Asn Tyr Ser  Leu Met Ala Met Ala  Thr Gln Ala
    2330                 2335                 2340

Gly Val  Leu Phe Gly Met Gly  Lys Gly Met Pro Phe  Tyr Ala Trp
    2345                 2350                 2355

Asp Phe  Gly Val Pro Leu Leu  Met Ile Gly Cys Tyr  Ser Gln Leu
    2360                 2365                 2370

Thr Pro  Leu Thr Leu Ile Val  Ala Ile Ile Leu Leu  Val Ala His
    2375                 2380                 2385

Tyr Met  Tyr Leu Ile Pro Gly  Leu Gln Ala Ala Ala  Ala Arg Ala
    2390                 2395                 2400

Ala Gln  Lys Arg Thr Ala Ala  Gly Ile Met Lys Asn  Pro Val Val
    2405                 2410                 2415

Asp Gly  Ile Val Val Thr Asp  Ile Asp Thr Met Thr  Ile Asp Pro
    2420                 2425                 2430

Gln Val  Glu Lys Lys Met Gly  Gln Val Leu Leu Ile  Ala Val Ala
    2435                 2440                 2445

Val Ser  Ser Ala Ile Leu Ser  Arg Thr Ala Trp Gly  Trp Gly Glu
    2450                 2455                 2460

Ala Gly  Ala Leu Ile Thr Ala  Ala Thr Ser Thr Leu  Trp Glu Gly
    2465                 2470                 2475

Ser Pro  Asn Lys Tyr Trp Asn  Ser Ser Thr Ala Thr  Ser Leu Cys
    2480                 2485                 2490

Asn Ile  Phe Arg Gly Ser Tyr  Leu Ala Gly Ala Ser  Leu Ile Tyr
    2495                 2500                 2505

Thr Val  Thr Arg Asn Ala Gly  Leu Val Lys Arg Arg  Gly Gly Gly
    2510                 2515                 2520

Thr Gly  Glu Thr Leu Gly Glu  Lys Trp Lys Ala Arg  Leu Asn Gln
    2525                 2530                 2535

Met Ser  Ala Leu Glu Phe Tyr  Ser Tyr Lys Lys Ser  Gly Ile Thr
    2540                 2545                 2550

Glu Val  Cys Arg Glu Glu Ala  Arg Arg Ala Leu Lys  Asp Gly Val
    2555                 2560                 2565

Ala Thr  Gly Gly His Ala Val  Ser Arg Gly Ser Ala  Lys Leu Arg
    2570                 2575                 2580

Trp Leu  Val Glu Arg Gly Tyr  Leu Gln Pro Tyr Gly  Lys Val Ile
    2585                 2590                 2595

Asp Leu  Gly Cys Gly Arg Gly  Gly Trp Ser Tyr Tyr  Val Ala Thr
    2600                 2605                 2610

Ile Arg  Lys Val Gln Glu Val  Lys Gly Tyr Thr Lys  Gly Gly Pro
    2615                 2620                 2625

Gly His  Glu Glu Pro Val Leu  Val Gln Ser Tyr Gly  Trp Asn Ile
    2630                 2635                 2640

Val Arg  Leu Lys Ser Gly Val  Asp Val Phe His Met  Ala Ala Glu
    2645                 2650                 2655

Pro Cys  Asp Thr Leu Leu Cys  Asp Ile Gly Glu Ser  Ser Ser Ser
    2660                 2665                 2670

Pro Glu  Val Glu Glu Ala Arg  Thr Leu Arg Val Leu  Ser Met Val
    2675                 2680                 2685

Gly Asp  Trp Leu Glu Lys Arg  Pro Gly Ala Phe Cys  Ile Lys Val
    2690                 2695                 2700

Leu Cys  Pro Tyr Thr Ser Thr  Met Met Glu Thr Leu  Glu Arg Leu
    2705                 2710                 2715

Gln Arg  Arg Tyr Gly Gly Gly  Leu Val Arg Val Pro  Leu Ser Arg
```

```
    2720                2725                2730

Asn Ser  Thr His Glu Met Tyr  Trp Val Ser Gly Ala  Lys Ser Asn
    2735                2740                2745

Thr Ile  Lys Ser Val Ser Thr  Thr Ser Gln Leu Leu  Leu Gly Arg
    2750                2755                2760

Met Asp  Gly Pro Arg Arg Pro  Val Lys Tyr Glu Glu  Asp Val Asn
    2765                2770                2775

Leu Gly  Ser Gly Thr Arg Ala  Val Val Ser Cys Ala  Glu Ala Pro
    2780                2785                2790

Asn Met  Lys Ile Ile Gly Asn  Arg Ile Glu Arg Ile  Arg Ser Glu
    2795                2800                2805

His Ala  Glu Thr Trp Phe Phe  Asp Glu Asn His Pro  Tyr Arg Thr
    2810                2815                2820

Trp Ala  Tyr His Gly Ser Tyr  Glu Ala Pro Thr Gln  Gly Ser Ala
    2825                2830                2835

Ser Ser  Leu Ile Asn Gly Val  Val Arg Leu Leu Ser  Lys Pro Trp
    2840                2845                2850

Asp Val  Val Thr Gly Val Thr  Gly Ile Ala Met Thr  Asp Thr Thr
    2855                2860                2865

Pro Tyr  Gly Gln Gln Arg Val  Phe Lys Glu Lys Val  Asp Thr Arg
    2870                2875                2880

Val Pro  Asp Pro Gln Glu Gly  Thr Arg Gln Val Met  Ser Met Val
    2885                2890                2895

Ser Ser  Trp Leu Trp Lys Glu  Leu Gly Lys His Lys  Arg Pro Arg
    2900                2905                2910

Val Cys  Thr Lys Glu Glu Phe  Ile Asn Lys Val Arg  Ser Asn Ala
    2915                2920                2925

Ala Leu  Gly Ala Ile Phe Glu  Glu Glu Lys Glu Trp  Lys Thr Ala
    2930                2935                2940

Val Glu  Ala Val Asn Asp Pro  Arg Phe Trp Ala Leu  Val Asp Lys
    2945                2950                2955

Glu Arg  Glu His His Leu Arg  Gly Glu Cys Gln Ser  Cys Val Tyr
    2960                2965                2970

Asn Met  Met Gly Lys Arg Glu  Lys Lys Gln Gly Glu  Phe Gly Lys
    2975                2980                2985

Ala Lys  Gly Ser Arg Ala Ile  Trp Tyr Met Trp Leu  Gly Ala Arg
    2990                2995                3000

Phe Leu  Glu Phe Glu Ala Leu  Gly Phe Leu Asn Glu  Asp His Trp
    3005                3010                3015

Met Gly  Arg Glu Asn Ser Gly  Gly Gly Val Glu Gly  Leu Gly Leu
    3020                3025                3030

Gln Arg  Leu Gly Tyr Val Leu  Glu Glu Met Ser Arg  Ile Pro Gly
    3035                3040                3045

Gly Arg  Met Tyr Ala Asp Asp  Thr Ala Gly Trp Asp  Thr Arg Ile
    3050                3055                3060

Ser Arg  Phe Asp Leu Glu Asn  Glu Ala Leu Ile Thr  Asn Gln Met
    3065                3070                3075

Glu Lys  Gly His Arg Ala Leu  Ala Leu Ala Ile Ile  Lys Tyr Thr
    3080                3085                3090

Tyr Gln  Asn Lys Val Val Lys  Val Leu Arg Pro Ala  Glu Lys Gly
    3095                3100                3105

Lys Thr  Val Met Asp Ile Ile  Ser Arg Gln Asp Gln  Arg Gly Ser
    3110                3115                3120
```

Gly Gln Val Val Thr Tyr Ala Leu Asn Thr Phe Thr Asn Leu Val
3125 3130 3135

Val Gln Leu Ile Arg Asn Met Glu Ala Glu Glu Val Leu Glu Met
3140 3145 3150

Gln Asp Leu Trp Leu Leu Arg Arg Ser Glu Lys Val Thr Asn Trp
3155 3160 3165

Leu Gln Ser Asn Gly Trp Asp Arg Leu Lys Arg Met Ala Val Ser
3170 3175 3180

Gly Asp Asp Cys Val Val Lys Pro Ile Asp Asp Arg Phe Ala His
3185 3190 3195

Ala Leu Arg Phe Leu Asn Asp Met Gly Lys Val Arg Lys Asp Thr
3200 3205 3210

Gln Glu Trp Lys Pro Ser Thr Gly Trp Asp Asn Trp Glu Glu Val
3215 3220 3225

Pro Phe Cys Ser His His Phe Asn Lys Leu His Leu Lys Asp Gly
3230 3235 3240

Arg Ser Ile Val Val Pro Cys Arg His Gln Asp Glu Leu Ile Gly
3245 3250 3255

Arg Ala Arg Val Ser Pro Gly Ala Gly Trp Ser Ile Arg Glu Thr
3260 3265 3270

Ala Cys Leu Ala Lys Ser Tyr Ala Gln Met Trp Gln Leu Leu Tyr
3275 3280 3285

Phe His Arg Arg Asp Leu Arg Leu Met Ala Asn Ala Ile Cys Ser
3290 3295 3300

Ser Val Pro Val Asp Trp Val Pro Thr Gly Arg Thr Thr Trp Ser
3305 3310 3315

Ile His Gly Lys Gly Glu Trp Met Thr Thr Glu Asp Met Leu Val
3320 3325 3330

Val Trp Asn Arg Val Trp Ile Glu Glu Asn Asp His Met Glu Asp
3335 3340 3345

Lys Thr Pro Val Thr Lys Trp Thr Asp Ile Pro Tyr Leu Gly Lys
3350 3355 3360

Arg Glu Asp Leu Trp Cys Gly Ser Leu Ile Gly His Arg Pro Arg
3365 3370 3375

Thr Thr Trp Ala Glu Asn Ile Lys Asn Thr Val Asn Met Val Arg
3380 3385 3390

Arg Ile Ile Gly Asp Glu Glu Lys Tyr Met Asp Tyr Leu Ser Thr
3395 3400 3405

Gln Val Arg Tyr Leu Gly Glu Glu Gly Ser Thr Pro Gly Val Leu
3410 3415 3420

<210> SEQ ID NO 15
<211> LENGTH: 10768
<212> TYPE: DNA
<213> ORGANISM: Artificial Sequence
<220> FEATURE:
<223> OTHER INFORMATION: Synthetic construct

<400> SEQUENCE: 15
agttgttagt ctacgtggac cgacaaagac agattctttg agggagctaa gctcaacgta 60
gttctaacag tttttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gaccattaaa actgttcatg 240

-continued

```
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagatccg cgggtactag tgtcggaatt    420
gttggcctcc tgctgaccac agctatggca gcggaggtca ctagacgtgg gagtgcatac    480
tatatgtact tggacagaaa cgatgctggg gaggccatat cttttccaac cacattgggg    540
atgaataagt gttatataca gatcatggat cttggacaca tgtgtgatgc caccatgagc    600
tatgaatgcc ctatgctgga tgagggggtg gaaccagatg acgtcgattg ttggtgcaac    660
acgacgtcaa cttgggttgt gtacggaacc tgccatcaca aaaaaggtga agcacggaga    720
agtagaagag ctgtgacgct cccctcccat tccactagga agctgcaaac gcggtcgcaa    780
acctggttgg aatcaagaga atacacaaag cacttgatta gagtcgaaaa ttggatattc    840
aggaaccctg gcttcgcgtt agcagcagct gccatcgctt ggcttttggg aagctcaacg    900
agccaaaaag tcatatactt ggtcatgata ctgctgattg ccccggcata cagcatcagg    960
tgcataggag tcagcaatag ggactttgtg gaaggtatgt caggtgggac ttgggttgat   1020
attgtcttgg aacatggagg ttgtgtcacc gtaatggcac aggacaaacc gactgtcgac   1080
atagagctgg ttacaacaac agtcagcaac atggcggagg taagatccta ctgctatgag   1140
gcatcaatat cagacatggc ttcggacagc cgctgcccaa cacaaggtga agcctacctt   1200
gacaagcaat cagacactca atatgtctgc aaaagaacgt tagtggacag aggctgggga   1260
aatggatgtg gactttttgg caaagggagt ctggtgacat gcgctaagtt tgcatgctcc   1320
aagaaaatga ccgggaagag catccagcca gagaatctgg agtaccggat aatgctgtca   1380
gttcatggct cccagcacag tgggatgatc gttaatgaca caggacatga aactgatgag   1440
aatagagcga aggttgagat aacgcccaat tcaccaagag ccgaagccac cctggggggt   1500
tttggaagcc taggacttga ttgtgaaccg aggacaggcc ttgacttttc agatttgtat   1560
tacttgacta tgaataacaa gcactggttg gttcacaagg agtggttcca cgacattcca   1620
ttaccttggc acgctggggc agacaccgga actccacact ggaacaacaa agaagcactg   1680
gtagagttca aggacgcaca tgccaaaagg caaactgtcg tggttctagg gagtcaagaa   1740
ggagcagttc acacggccct tgctggagct ctggaggctg agatggatgg tgcaaaggga   1800
aggctgtcct ctggccactt gaaatgtcgc ctgaaaatgg ataaacttag attgaagggc   1860
gtgtcatact ccttgtgtac cgcagcgttc acattcacca agatcccggc tgaaacactg   1920
cacgggacag tcacagtgga ggtacagtac gcagggacag atggaccttg caaggttcca   1980
gctcagatgg cggtggacat gcaaactctg accccagttg ggaggttgat aaccgctaac   2040
cccgtaatca ctgaaagcac tgagaactct aagatgatgc tggaacttga tccaccattt   2100
ggggactctt acattgtcat aggagtcggg gagaagaaga tcacccacca ctggcacagg   2160
agtggcagca ccattggaaa agcatttgaa gccactgtga gaggtgccaa gagaatggca   2220
gtcttgggag acacagcctg ggactttgga tcagttggag gcgctctcaa ctcattgggc   2280
aagggcatcc atcaaatttt tggagcagct ttcaaatcat tgtttggagg aatgtcctgg   2340
ttctcaagaa ttctcattgg aacgttgctg atgtggttgg gtctgaacac aaagaatgga   2400
tctatttccc ttatgtgctt ggccgccggc tttgtgacac tgtatttggg ggtcatggtg   2460
caggccgata gtggttgcgt tgtgagctgg aaaaacaaag aactgaaatg tggcagtggg   2520
attttcatca cagacaacgt gcacacatgg acagaacaat acaagttcca accagaatcc   2580
ccttcaaaac tagcttcagc tatccagaaa gcccatgaag agggcatttg tggaatccgc   2640
```

```
tcagtaacaa gactggagaa tctgatgtgg aaacaaataa caccagaatt gaatcacatt   2700
ctatcagaaa atgaggtgaa gttaactatt atgacaggag acatcaaagg aatcatgcag   2760
gcaggaaaac gatctctgcg gcctcagccc actgagctga agtattcatg gaaaacatgg   2820
ggcaaagcaa aaatgctctc tacagagtct cataaccaga cctttctcat tgatggcccc   2880
gaaacagcag aatgccccaa cacaaataga gcttggaatt cgttggaagt tgaagactat   2940
ggctttggag tattcaccac caatatatgg ctaaaattga aagaaaaaca ggatgtattc   3000
tgcgactcaa aactcatgtc agcggccata aaagacaaca gagccgtcca tgccgatatg   3060
ggttattgga tagaaagtgc actcaatgac acatggaaga tagagaaagc ctctttcatt   3120
gaagttaaaa actgccactg gccaaaatca cacaccctct ggagcaatgg agtgctagaa   3180
agtgagatga taattccaaa gaatctcgct ggaccagtgt ctcaacacaa ctatagacca   3240
ggctaccata cacaaataac aggaccatgg catctaggta agcttgagat ggactttgat   3300
ttctgtgatg gaacaacagt ggtagtgact gaggactgcg gaaatagagg accctctttg   3360
agaacaacca ctgcctctgg aaaactcata acagaatggt gctgccgatc ttgcacatta   3420
ccaccgctaa gatacagagg tgaggatggg tgctggtacg ggatggaaat cagaccattg   3480
aaggagaaag aagagaattt ggtcaactcc ttggtcacag ctggacatgg gcaggtcgac   3540
aacttttcac taggagtctt gggaatggca ttgttcctgg aggaaatgct taggacccga   3600
gtaggaacga aacatgcaat actactagtt gcagtttctt ttgtgacatt gatcacaggg   3660
aacatgtcct ttagagacct gggaagagtg atggttatgg taggcgccac tatgacggat   3720
gacataggta tgggcgtgac ttatcttgcc ctactagcag ccttcaaagt cagaccaact   3780
tttgcagctg gactactctt gagaaagctg acctccaatg aattgatgat gactactata   3840
ggaattgtac tcctctccca gagcaccata ccagagacca ttcttgagtt gactgatgcg   3900
ttagccttag gcatgatggt cctcaaaatg gtgagaaata tggaaaagta tcaattggca   3960
gtgactatca tggctatctt gtgcgtccca aacgcagtga tattacaaaa cgcatggaaa   4020
gtgagttgca caatattggc agtggtgtcc gtttccccac tgctcttaac atcctcacag   4080
caaaaaacag attggatacc attagcattg acgatcaaag gtctcaatcc aacagctatt   4140
tttctaacaa ccctctcaag aaccagcaag aaaaggagct ggccattaaa tgaggctatc   4200
atggcagtcg ggatggtgag cattttagcc agttctctcc taaaaaatga tattcccatg   4260
acaggaccat tagtggctgg agggctcctc actgtgtgct acgtgctcac tggacgatcg   4320
gccgatttgg aactggagag agcagccgat gtcaaatggg aagaccaggc agagatatca   4380
ggaagcagtc caatcctgtc aataacaata tcagaagatg gtagcatgtc gataaaaaat   4440
gaagaggaag aacaaacact gaccatactc attagaacag gattgctggt gatctcagga   4500
ctttttcctg tatcaatacc aatcacggca gcagcatggt acctgtggga agtgaagaaa   4560
caacgggccg gagtattgtg ggatgttcct tcacccccac ccatgggaaa ggctgaactg   4620
gaagatggag cctatagaat taagcaaaaa gggattcttg gatattccca gatcggagcc   4680
ggagtttaca aagaaggaac attccataca atgtggcatg tcacacgtgg cgctgttcta   4740
atgcataaag gaaagaggat tgaaccatca tgggcggacg tcaagaaaga cctaatatca   4800
tatggaggag gctggaagtt agaaggagaa tggaaggaag gagaagaagt ccaggtattg   4860
gcactggagc ctggaaaaaa tccaagagcc gtccaaacga aacctggtct tttcaaaacc   4920
aacgccggaa caataggtgc tgtatctctg gacttttctc ctggaacgtc aggatctcca   4980
```

```
attatcgaca aaaaaggaaa agttgtgggt ctttatggta atggtgttgt tacaaggagt   5040
ggagcatatg tgagtgctat agcccagact gaaaaaagca ttgaagacaa cccagagatc   5100
gaagatgaca ttttccgaaa gagaagactg accatcatgg acctccaccc aggagcggga   5160
aagacgaaga gataccttcc ggccatagtc agagaagcta taaaacgggg tttgagaaca   5220
ttaatcttgg cccccactag agttgtggca gctgaaatgg aggaagccct tagaggactt   5280
ccaataagat accagacccc agccatcaga gctgagcaca ccgggcggga gattgtggac   5340
ctaatgtgtc atgccacatt taccatgagg ctgctatcac cagttagagt gccaaactac   5400
aacctgatta tcatggacga agcccatttc acagacccag caagtatagc agctagagga   5460
tacatctcaa ctcgagtgga gatgggtgag gcagctggga tttttatgac agccactccc   5520
ccgggaagca gagacccatt tcctcagagc aatgcaccaa tcatagatga agaaagagaa   5580
atccctgaac gttcgtggaa ttccggacat gaatgggtca cggattttaa agggaagact   5640
gtttggttcg ttccaagtat aaaagcagga aatgatatag cagcttgcct gaggaaaaat   5700
ggaaagaaag tgatacaact cagtaggaag acctttgatt ctgagtatgt caagactaga   5760
accaatgatt gggacttcgt ggttacaact gacatttcag aaatgggtgc caatttcaag   5820
gctgagaggg ttatagaccc cagacgctgc atgaaaccag tcatactaac agatggtgaa   5880
gagcgggtga ttctggcagg acctatgcca gtgacccact ctagtgcagc acaaagaaga   5940
gggagaatag gaagaaatcc aaaaaatgag aatgaccagt acatatacat gggggaacct   6000
ctggaaaatg atgaagactg tgcacactgg aaagaagcta aaatgctcct agataacatc   6060
aacacgccag aaggaatcat tcctagcatg ttcgaaccag agcgtgaaaa ggtggatgcc   6120
attgatggcg aataccgctt gagaggagaa gcaaggaaaa cctttgtaga cttaatgaga   6180
agaggagacc taccagtctg gttggcctac agagtggcag ctgaaggcat caactacgca   6240
gacagaaggt ggtgttttga tggagtcaag aacaaccaaa tcctagaaga aaacgtggaa   6300
gttgaaatct ggacaaaaga aggggaaagg aagaaattga aacccagatg gttggatgct   6360
aggatctatt ctgacccact ggcgctaaaa gaatttaagg aatttgcagc cggaagaaag   6420
tctctgaccc tgaacctaat cacagaaatg ggtaggctcc caaccttcat gactcagaag   6480
gcaagaaacg cactggacaa cttagcagtg ctgcacacgg ctgaggcagg tggaagggcg   6540
tacaaccatg ctctcagtga actgccggag accctggaga cattgctttt actgacactt   6600
ctggctacag tcacgggagg gatcttttta ttcttgatga gcggaagggg catagggaag   6660
atgaccctgg gaatgtgctg cataatcacg gctagcatcc tcctatggta cgcacaaata   6720
cagccacact ggatagcagc ttcaataata ctggagtttt ttctcatagt tttgcttatt   6780
ccagaacctg aaaaacagag aacaccccaa gacaaccaac tgacctacgt tgtcatagcc   6840
atcctcacag tggtggccgc aaccatggca aacgagatgg gtttcctaga aaaaacgaag   6900
aaagatctcg gattgggaag cattgcaacc cagcaacccg agagcaacat cctggacata   6960
gatctacgtc ctgcatcagc atggacgctg tatgccgtgg ccacaacatt tgttacacca   7020
atgttgagac atagcattga aaattcctca gtgaatgtgt ccctaacagc tatagccaac   7080
caagccacag tgttaatggg tctcgggaaa ggatggccat tgtcaaagat ggacatcgga   7140
gttccccttc tcgccattgg atgctactca caagtcaacc ccataactct cacagcagct   7200
cttttcttat tggtagcaca ttatgccatc atagggccag gactccaagc aaaagcaacc   7260
agagaagctc agaaaagagc agcggcgggc atcatgaaaa acccaactgt cgatggaata   7320
acagtgattg acctagatcc aataccttat gatccaaagt ttgaaaagca gttgggacaa   7380
```

```
gtaatgctcc tagtcctctg cgtgactcaa gtattgatga tgaggactac atgggctctg   7440
tgtgaggctt taaccttagc taccgggccc atctccacat tgtgggaagg aaatccaggg   7500
aggttttgga acactaccat tgcggtgtca atggctaaca tttttagagg gagttacttg   7560
gccggagctg gacttctctt ttctattatg aagaacacaa ccaacacaag aaggggaact   7620
ggcaacatag gagagacgct tggagagaaa tggaaaagcc gattgaacgc attgggaaaa   7680
agtgaattcc agatctacaa gaaaagtgga atccaggaag tggatagaac cttagcaaaa   7740
gaaggcatta aaagaggaga aacggaccat cacgctgtgt cgcgaggctc agcaaaactg   7800
agatggttcg ttgagagaaa catggtcaca ccagaaggga aagtagtgga cctcggttgt   7860
ggcagaggag gctggtcata ctattgtgga ggactaaaga atgtaagaga agtcaaaggc   7920
ctaacaaaag gaggaccagg acacgaagaa cccatcccca tgtcaacata tgggtggaat   7980
ctagtgcgtc ttcaaagtgg agttgacgtt ttcttcatcc cgccagaaaa gtgtgacaca   8040
ttattgtgtg acatagggga gtcatcacca aatcccacag tggaagcagg acgaacactc   8100
agagtcctta acttagtaga aaattggttg aacaacaaca ctcaattttg cataaaggtt   8160
ctcaacccat atatgccctc agtcatagaa aaaatggaag cactacaaag gaaatatgga   8220
ggagccttag tgaggaatcc actctcacga aactccacac atgagatgta ctgggtatcc   8280
aatgcttccg ggaacatagt gtcatcagtg aacatgattt caaggatgtt gatcaacaga   8340
tttacaatga gatacaagaa agccacttac gagccggatg ttgacctcgg aagcggaacc   8400
cgtaacatcg ggattgaaag tgagatacca aacctagata taattgggaa aagaatagaa   8460
aaaataaagc aagagcatga aacatcatgg cactatgacc aagaccaccc atacaaaacg   8520
tgggcatacc atggtagcta tgaaacaaaa cagactggat cagcatcatc catggtcaac   8580
ggagtggtca ggctgctgac aaaaccttgg gacgtcgtcc ccatggtgac acagatggca   8640
atgacagaca cgactccatt tggacaacag cgcgttttta aagagaaagt ggacacgaga   8700
acccaagaac cgaaagaagg cacgaagaaa ctaatgaaaa taacagcaga gtggctttgg   8760
aaagaattag ggaagaaaaa gacacccagg atgtgcacca gagaagaatt cacaagaaag   8820
gtgagaagca atgcagcctt gggggccata ttcactgatg agaacaagtg gaagtcggca   8880
cgtgaggctg ttgaagatag taggttttgg gagctggttg acaaggaaag gaatctccat   8940
cttgaaggaa agtgtgaaac atgtgtgtac aacatgatgg gaaaaagaga gaagaagcta   9000
ggggaattcg gcaaggcaaa aggcagcaga gccatatggt acatgtggct tggagcacgc   9060
ttcttagagt ttgaagccct aggattctta aatgaagatc actggttctc cagagagaac   9120
tccctgagtg gagtggaagg agaagggctg cacaagctag gttacattct aagagacgtg   9180
agcaagaaag agggaggagc aatgtatgcc gatgacaccg caggatggga tacaagaatc   9240
acactagaag acctaaaaaa tgaagaaatg gtaacaaacc acatggaagg agaacacaag   9300
aaactagccg aggccatttt caaactaacg taccaaaaca aggtggtgcg tgtgcaaaga   9360
ccaacaccaa gaggcacagt aatggacatc atatcgagaa gagaccaaag aggtagtgga   9420
caagttggca cctatggact caatactttc accaatatgg aagcccaact aatcagacag   9480
atggagggag aaggagtctt taaaagcatt cagcacctaa caatcacaga agaaatcgct   9540
gtgcaaaact ggttagcaag agtggggcgc gaaaggttat caagaatggc catcagtgga   9600
gatgattgtg ttgtgaaacc tttagatgac aggttcgcaa gcgctttaac agctctaaat   9660
gacatgggaa agattaggaa agacatacaa caatgggaac cttcaagagg atggaatgat   9720
```

```
tggacacaag tgcccttctg ttcacaccat ttccatgagt taatcatgaa agacggtcgc   9780

gtactcgttg ttccatgtag aaaccaagat gaactgattg gcagagcccg aatctcccaa   9840

ggagcagggt ggtctttgcg ggagacggcc tgtttgggga agtcttacgc ccaaatgtgg   9900

agcttgatgt acttccacag acgcgacctc aggctggcgg caaatgctat ttgctcggca   9960

gtaccatcac attgggttcc aacaagtcga acaacctggt ccatacatgc taaacatgaa  10020

tggatgacaa cggaagacat gctgacagtc tggaacaggg tgtggattca agaaaaccca  10080

tggatggaag acaaaactcc agtggaatca tgggaggaaa tcccatactt ggggaaaaga  10140

gaagaccaat ggtgcggctc attgattggg ttaacaagca gggccacctg ggcaaagaac  10200

atccaagcag caataaatca agttagatcc cttataggca atgaagaata cacagattac  10260

atgccatcca tgaaaagatt cagaagagaa gaggaagaag caggagttct gtggtagaaa  10320

gcaaaactaa catgaaacaa ggctagaagt caggtcggat taagccatag tacggaaaaa  10380

actatgctac ctgtgagccc cgtccaagga cgttaaaaga agtcaggcca tcataaatgc  10440

catagcttga gtaaactatg cagcctgtag ctccacctga gaaggtgtaa aaaatccggg  10500

aggccacaaa ccatggaagc tgtacgcatg gcgtagtgga ctagcggtta gaggagaccc  10560

ctcccttaca aatcgcagca acaatggggg cccaaggcga gatgaagctg tagtctcgct  10620

ggaaggacta gaggttagag gagacccccc cgaaacaaaa aacagcatat tgacgctggg  10680

aaagaccaga gatcctgctg tctcctcagc atcattccag gcacagaacg ccagaaaatg  10740

gaatggtgct gttgaatcaa caggttct                                     10768
```

<210> SEQ ID NO 16
<211> LENGTH: 3406
<212> TYPE: PRT
<213> ORGANISM: Artificial Sequence
<220> FEATURE:
<223> OTHER INFORMATION: Synthetic polypeptide

<400> SEQUENCE: 16

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Thr Ser Val Gly Ile Val Gly Leu Leu
            100                 105                 110

Leu Thr Thr Ala Met Ala Ala Glu Val Thr Arg Arg Gly Ser Ala Tyr
        115                 120                 125

Tyr Met Tyr Leu Asp Arg Asn Asp Ala Gly Glu Ala Ile Ser Phe Pro
    130                 135                 140

Thr Thr Leu Gly Met Asn Lys Cys Tyr Ile Gln Ile Met Asp Leu Gly
145                 150                 155                 160

His Met Cys Asp Ala Thr Met Ser Tyr Glu Cys Pro Met Leu Asp Glu
                165                 170                 175
```

```
Gly Val Glu Pro Asp Asp Val Asp Cys Trp Cys Asn Thr Thr Ser Thr
            180                 185                 190

Trp Val Val Tyr Gly Thr Cys His His Lys Lys Gly Glu Ala Arg Arg
        195                 200                 205

Ser Arg Arg Ala Val Thr Leu Pro Ser His Ser Thr Arg Lys Leu Gln
    210                 215                 220

Thr Arg Ser Gln Thr Trp Leu Glu Ser Arg Glu Tyr Thr Lys His Leu
225                 230                 235                 240

Ile Arg Val Glu Asn Trp Ile Phe Arg Asn Pro Gly Phe Ala Leu Ala
                245                 250                 255

Ala Ala Ala Ile Ala Trp Leu Leu Gly Ser Ser Thr Ser Gln Lys Val
            260                 265                 270

Ile Tyr Leu Val Met Ile Leu Leu Ile Ala Pro Ala Tyr Ser Ile Arg
        275                 280                 285

Cys Ile Gly Val Ser Asn Arg Asp Phe Val Glu Gly Met Ser Gly Gly
    290                 295                 300

Thr Trp Val Asp Ile Val Leu Glu His Gly Gly Cys Val Thr Val Met
305                 310                 315                 320

Ala Gln Asp Lys Pro Thr Val Asp Ile Glu Leu Val Thr Thr Thr Val
                325                 330                 335

Ser Asn Met Ala Glu Val Arg Ser Tyr Cys Tyr Glu Ala Ser Ile Ser
            340                 345                 350

Asp Met Ala Ser Asp Ser Arg Cys Pro Thr Gln Gly Glu Ala Tyr Leu
        355                 360                 365

Asp Lys Gln Ser Asp Thr Gln Tyr Val Cys Lys Arg Thr Leu Val Asp
    370                 375                 380

Arg Gly Trp Gly Asn Gly Cys Gly Leu Phe Gly Lys Gly Ser Leu Val
385                 390                 395                 400

Thr Cys Ala Lys Phe Ala Cys Ser Lys Lys Met Thr Gly Lys Ser Ile
                405                 410                 415

Gln Pro Glu Asn Leu Glu Tyr Arg Ile Met Leu Ser Val His Gly Ser
            420                 425                 430

Gln His Ser Gly Met Ile Val Asn Asp Thr Gly His Glu Thr Asp Glu
        435                 440                 445

Asn Arg Ala Lys Val Glu Ile Thr Pro Asn Ser Pro Arg Ala Glu Ala
    450                 455                 460

Thr Leu Gly Gly Phe Gly Ser Leu Gly Leu Asp Cys Glu Pro Arg Thr
465                 470                 475                 480

Gly Leu Asp Phe Ser Asp Leu Tyr Tyr Leu Thr Met Asn Asn Lys His
                485                 490                 495

Trp Leu Val His Lys Glu Trp Phe His Asp Ile Pro Leu Pro Trp His
            500                 505                 510

Ala Gly Ala Asp Thr Gly Thr Pro His Trp Asn Asn Lys Glu Ala Leu
        515                 520                 525

Val Glu Phe Lys Asp Ala His Ala Lys Arg Gln Thr Val Val Val Leu
    530                 535                 540

Gly Ser Gln Glu Gly Ala Val His Thr Ala Leu Ala Gly Ala Leu Glu
545                 550                 555                 560

Ala Glu Met Asp Gly Ala Lys Gly Arg Leu Ser Ser Gly His Leu Lys
                565                 570                 575

Cys Arg Leu Lys Met Asp Lys Leu Arg Leu Lys Gly Val Ser Tyr Ser
            580                 585                 590

Leu Cys Thr Ala Ala Phe Thr Phe Thr Lys Ile Pro Ala Glu Thr Leu
```

```
        595                 600                 605

His Gly Thr Val Thr Val Glu Val Gln Tyr Ala Gly Thr Asp Gly Pro
    610                 615                 620

Cys Lys Val Pro Ala Gln Met Ala Val Asp Met Gln Thr Leu Thr Pro
625                 630                 635                 640

Val Gly Arg Leu Ile Thr Ala Asn Pro Val Ile Thr Glu Ser Thr Glu
                645                 650                 655

Asn Ser Lys Met Met Leu Glu Leu Asp Pro Pro Phe Gly Asp Ser Tyr
            660                 665                 670

Ile Val Ile Gly Val Gly Glu Lys Lys Ile Thr His His Trp His Arg
        675                 680                 685

Ser Gly Ser Thr Ile Gly Lys Ala Phe Glu Ala Thr Val Arg Gly Ala
    690                 695                 700

Lys Arg Met Ala Val Leu Gly Asp Thr Ala Trp Asp Phe Gly Ser Val
705                 710                 715                 720

Gly Gly Ala Leu Asn Ser Leu Gly Lys Gly Ile His Gln Ile Phe Gly
                725                 730                 735

Ala Ala Phe Lys Ser Leu Phe Gly Gly Met Ser Trp Phe Ser Arg Ile
            740                 745                 750

Leu Ile Gly Thr Leu Leu Met Trp Leu Gly Leu Asn Thr Lys Asn Gly
        755                 760                 765

Ser Ile Ser Leu Met Cys Leu Ala Ala Gly Phe Val Thr Leu Tyr Leu
    770                 775                 780

Gly Val Met Val Gln Ala Asp Ser Gly Cys Val Val Ser Trp Lys Asn
785                 790                 795                 800

Lys Glu Leu Lys Cys Gly Ser Gly Ile Phe Ile Thr Asp Asn Val His
                805                 810                 815

Thr Trp Thr Glu Gln Tyr Lys Phe Gln Pro Glu Ser Pro Ser Lys Leu
            820                 825                 830

Ala Ser Ala Ile Gln Lys Ala His Glu Glu Gly Ile Cys Gly Ile Arg
        835                 840                 845

Ser Val Thr Arg Leu Glu Asn Leu Met Trp Lys Gln Ile Thr Pro Glu
    850                 855                 860

Leu Asn His Ile Leu Ser Glu Asn Glu Val Lys Leu Thr Ile Met Thr
865                 870                 875                 880

Gly Asp Ile Lys Gly Ile Met Gln Ala Gly Lys Arg Ser Leu Arg Pro
                885                 890                 895

Gln Pro Thr Glu Leu Lys Tyr Ser Trp Lys Thr Trp Gly Lys Ala Lys
            900                 905                 910

Met Leu Ser Thr Glu Ser His Asn Gln Thr Phe Leu Ile Asp Gly Pro
        915                 920                 925

Glu Thr Ala Glu Cys Pro Asn Thr Asn Arg Ala Trp Asn Ser Leu Glu
    930                 935                 940

Val Glu Asp Tyr Gly Phe Gly Val Phe Thr Thr Asn Ile Trp Leu Lys
945                 950                 955                 960

Leu Lys Glu Lys Gln Asp Val Phe Cys Asp Ser Lys Leu Met Ser Ala
                965                 970                 975

Ala Ile Lys Asp Asn Arg Ala Val His Ala Asp Met Gly Tyr Trp Ile
            980                 985                 990

Glu Ser Ala Leu Asn Asp Thr Trp  Lys Ile Glu Lys Ala  Ser Phe Ile
        995                 1000                1005

Glu Val  Lys Asn Cys His Trp  Pro Lys Ser His Thr  Leu Trp Ser
    1010                1015                1020
```

```
Asn Gly  Val Leu Glu Ser Glu  Met Ile Ile Pro Lys  Asn Leu Ala
    1025                 1030                 1035

Gly Pro  Val Ser Gln His Asn  Tyr Arg Pro Gly Tyr  His Thr Gln
    1040                 1045                 1050

Ile Thr  Gly Pro Trp His Leu  Gly Lys Leu Glu Met  Asp Phe Asp
    1055                 1060                 1065

Phe Cys  Asp Gly Thr Thr Val  Val Val Thr Glu Asp  Cys Gly Asn
    1070                 1075                 1080

Arg Gly  Pro Ser Leu Arg Thr  Thr Thr Ala Ser Gly  Lys Leu Ile
    1085                 1090                 1095

Thr Glu  Trp Cys Cys Arg Ser  Cys Thr Leu Pro Pro  Leu Arg Tyr
    1100                 1105                 1110

Arg Gly  Glu Asp Gly Cys Trp  Tyr Gly Met Glu Ile  Arg Pro Leu
    1115                 1120                 1125

Lys Glu  Lys Glu Glu Asn Leu  Val Asn Ser Leu Val  Thr Ala Gly
    1130                 1135                 1140

His Gly  Gln Val Asp Asn Phe  Ser Leu Gly Val Leu  Gly Met Ala
    1145                 1150                 1155

Leu Phe  Leu Glu Glu Met Leu  Arg Thr Arg Val Gly  Thr Lys His
    1160                 1165                 1170

Ala Ile  Leu Leu Val Ala Val  Ser Phe Val Thr Leu  Ile Thr Gly
    1175                 1180                 1185

Asn Met  Ser Phe Arg Asp Leu  Gly Arg Val Met Val  Met Val Gly
    1190                 1195                 1200

Ala Thr  Met Thr Asp Asp Ile  Gly Met Gly Val Thr  Tyr Leu Ala
    1205                 1210                 1215

Leu Leu  Ala Ala Phe Lys Val  Arg Pro Thr Phe Ala  Ala Gly Leu
    1220                 1225                 1230

Leu Leu  Arg Lys Leu Thr Ser  Asn Glu Leu Met Met  Thr Thr Ile
    1235                 1240                 1245

Gly Ile  Val Leu Leu Ser Gln  Ser Thr Ile Pro Glu  Thr Ile Leu
    1250                 1255                 1260

Glu Leu  Thr Asp Ala Leu Ala  Leu Gly Met Met Val  Leu Lys Met
    1265                 1270                 1275

Val Arg  Asn Met Glu Lys Tyr  Gln Leu Ala Val Thr  Ile Met Ala
    1280                 1285                 1290

Ile Leu  Cys Val Pro Asn Ala  Val Ile Leu Gln Asn  Ala Trp Lys
    1295                 1300                 1305

Val Ser  Cys Thr Ile Leu Ala  Val Val Ser Val Ser  Pro Leu Leu
    1310                 1315                 1320

Leu Thr  Ser Ser Gln Gln Lys  Thr Asp Trp Ile Pro  Leu Ala Leu
    1325                 1330                 1335

Thr Ile  Lys Gly Leu Asn Pro  Thr Ala Ile Phe Leu  Thr Thr Leu
    1340                 1345                 1350

Ser Arg  Thr Ser Lys Lys Arg  Ser Trp Pro Leu Asn  Glu Ala Ile
    1355                 1360                 1365

Met Ala  Val Gly Met Val Ser  Ile Leu Ala Ser Ser  Leu Leu Lys
    1370                 1375                 1380

Asn Asp  Ile Pro Met Thr Gly  Pro Leu Val Ala Gly  Gly Leu Leu
    1385                 1390                 1395

Thr Val  Cys Tyr Val Leu Thr  Gly Arg Ser Ala Asp  Leu Glu Leu
    1400                 1405                 1410
```

```
Glu Arg  Ala Ala Asp Val Lys  Trp Glu Asp Gln Ala  Glu Ile Ser
    1415                 1420                 1425

Gly Ser  Ser Pro Ile Leu Ser  Ile Thr Ile Ser Glu  Asp Gly Ser
    1430                 1435                 1440

Met Ser  Ile Lys Asn Glu Glu  Glu Glu Gln Thr Leu  Thr Ile Leu
    1445                 1450                 1455

Ile Arg  Thr Gly Leu Leu Val  Ile Ser Gly Leu Phe  Pro Val Ser
    1460                 1465                 1470

Ile Pro  Ile Thr Ala Ala Ala  Trp Tyr Leu Trp Glu  Val Lys Lys
    1475                 1480                 1485

Gln Arg  Ala Gly Val Leu Trp  Asp Val Pro Ser Pro  Pro Pro Met
    1490                 1495                 1500

Gly Lys  Ala Glu Leu Glu Asp  Gly Ala Tyr Arg Ile  Lys Gln Lys
    1505                 1510                 1515

Gly Ile  Leu Gly Tyr Ser Gln  Ile Gly Ala Gly Val  Tyr Lys Glu
    1520                 1525                 1530

Gly Thr  Phe His Thr Met Trp  His Val Thr Arg Gly  Ala Val Leu
    1535                 1540                 1545

Met His  Lys Gly Lys Arg Ile  Glu Pro Ser Trp Ala  Asp Val Lys
    1550                 1555                 1560

Lys Asp  Leu Ile Ser Tyr Gly  Gly Gly Trp Lys Leu  Glu Gly Glu
    1565                 1570                 1575

Trp Lys  Glu Gly Glu Glu Val  Gln Val Leu Ala Leu  Glu Pro Gly
    1580                 1585                 1590

Lys Asn  Pro Arg Ala Val Gln  Thr Lys Pro Gly Leu  Phe Lys Thr
    1595                 1600                 1605

Asn Ala  Gly Thr Ile Gly Ala  Val Ser Leu Asp Phe  Ser Pro Gly
    1610                 1615                 1620

Thr Ser  Gly Ser Pro Ile Ile  Asp Lys Lys Gly Lys  Val Val Gly
    1625                 1630                 1635

Leu Tyr  Gly Asn Gly Val Val  Thr Arg Ser Gly Ala  Tyr Val Ser
    1640                 1645                 1650

Ala Ile  Ala Gln Thr Glu Lys  Ser Ile Glu Asp Asn  Pro Glu Ile
    1655                 1660                 1665

Glu Asp  Asp Ile Phe Arg Lys  Arg Arg Leu Thr Ile  Met Asp Leu
    1670                 1675                 1680

His Pro  Gly Ala Gly Lys Thr  Lys Arg Tyr Leu Pro  Ala Ile Val
    1685                 1690                 1695

Arg Glu  Ala Ile Lys Arg Gly  Leu Arg Thr Leu Ile  Leu Ala Pro
    1700                 1705                 1710

Thr Arg  Val Val Ala Ala Glu  Met Glu Glu Ala Leu  Arg Gly Leu
    1715                 1720                 1725

Pro Ile  Arg Tyr Gln Thr Pro  Ala Ile Arg Ala Glu  His Thr Gly
    1730                 1735                 1740

Arg Glu  Ile Val Asp Leu Met  Cys His Ala Thr Phe  Thr Met Arg
    1745                 1750                 1755

Leu Leu  Ser Pro Val Arg Val  Pro Asn Tyr Asn Leu  Ile Ile Met
    1760                 1765                 1770

Asp Glu  Ala His Phe Thr Asp  Pro Ala Ser Ile Ala  Ala Arg Gly
    1775                 1780                 1785

Tyr Ile  Ser Thr Arg Val Glu  Met Gly Glu Ala Ala  Gly Ile Phe
    1790                 1795                 1800

Met Thr  Ala Thr Pro Pro Gly  Ser Arg Asp Pro Phe  Pro Gln Ser
```

```
    1805                1810                1815

Asn Ala Pro Ile Ile Asp Glu Glu Arg Glu Ile Pro Glu Arg Ser
    1820                1825                1830

Trp Asn Ser Gly His Glu Trp Val Thr Asp Phe Lys Gly Lys Thr
    1835                1840                1845

Val Trp Phe Val Pro Ser Ile Lys Ala Gly Asn Asp Ile Ala Ala
    1850                1855                1860

Cys Leu Arg Lys Asn Gly Lys Lys Val Ile Gln Leu Ser Arg Lys
    1865                1870                1875

Thr Phe Asp Ser Glu Tyr Val Lys Thr Arg Thr Asn Asp Trp Asp
    1880                1885                1890

Phe Val Val Thr Thr Asp Ile Ser Glu Met Gly Ala Asn Phe Lys
    1895                1900                1905

Ala Glu Arg Val Ile Asp Pro Arg Arg Cys Met Lys Pro Val Ile
    1910                1915                1920

Leu Thr Asp Gly Glu Glu Arg Val Ile Leu Ala Gly Pro Met Pro
    1925                1930                1935

Val Thr His Ser Ser Ala Ala Gln Arg Arg Gly Arg Ile Gly Arg
    1940                1945                1950

Asn Pro Lys Asn Glu Asn Asp Gln Tyr Ile Tyr Met Gly Glu Pro
    1955                1960                1965

Leu Glu Asn Asp Glu Asp Cys Ala His Trp Lys Glu Ala Lys Met
    1970                1975                1980

Leu Leu Asp Asn Ile Asn Thr Pro Glu Gly Ile Ile Pro Ser Met
    1985                1990                1995

Phe Glu Pro Glu Arg Glu Lys Val Asp Ala Ile Asp Gly Glu Tyr
    2000                2005                2010

Arg Leu Arg Gly Glu Ala Arg Lys Thr Phe Val Asp Leu Met Arg
    2015                2020                2025

Arg Gly Asp Leu Pro Val Trp Leu Ala Tyr Arg Val Ala Ala Glu
    2030                2035                2040

Gly Ile Asn Tyr Ala Asp Arg Arg Trp Cys Phe Asp Gly Val Lys
    2045                2050                2055

Asn Asn Gln Ile Leu Glu Glu Asn Val Glu Val Glu Ile Trp Thr
    2060                2065                2070

Lys Glu Gly Glu Arg Lys Lys Leu Lys Pro Arg Trp Leu Asp Ala
    2075                2080                2085

Arg Ile Tyr Ser Asp Pro Leu Ala Leu Lys Glu Phe Lys Glu Phe
    2090                2095                2100

Ala Ala Gly Arg Lys Ser Leu Thr Leu Asn Leu Ile Thr Glu Met
    2105                2110                2115

Gly Arg Leu Pro Thr Phe Met Thr Gln Lys Ala Arg Asp Ala Leu
    2120                2125                2130

Asp Asn Leu Ala Val Leu His Thr Ala Glu Ala Gly Gly Arg Ala
    2135                2140                2145

Tyr Asn His Ala Leu Ser Glu Leu Pro Glu Thr Leu Glu Thr Leu
    2150                2155                2160

Leu Leu Leu Thr Leu Leu Ala Thr Val Thr Gly Gly Ile Phe Leu
    2165                2170                2175

Phe Leu Met Ser Gly Arg Gly Ile Gly Lys Met Thr Leu Gly Met
    2180                2185                2190

Cys Cys Ile Ile Thr Ala Ser Ile Leu Leu Trp Tyr Ala Gln Ile
    2195                2200                2205
```

```
Gln Pro  His Trp Ile Ala Ala  Ser Ile Ile Leu Glu  Phe Phe Leu
    2210                 2215                 2220

Ile Val  Leu Leu Ile Pro Glu  Pro Glu Lys Gln Arg  Thr Pro Gln
    2225                 2230                 2235

Asp Asn  Gln Leu Thr Tyr Val  Val Ile Ala Ile Leu  Thr Val Val
    2240                 2245                 2250

Ala Ala  Thr Met Ala Asn Glu  Met Gly Phe Leu Glu  Lys Thr Lys
    2255                 2260                 2265

Lys Asp  Leu Gly Leu Gly Ser  Ile Ala Thr Gln Gln  Pro Glu Ser
    2270                 2275                 2280

Asn Ile  Leu Asp Ile Asp Leu  Arg Pro Ala Ser Ala  Trp Thr Leu
    2285                 2290                 2295

Tyr Ala  Val Ala Thr Thr Phe  Val Thr Pro Met Leu  Arg His Ser
    2300                 2305                 2310

Ile Glu  Asn Ser Ser Val Asn  Val Ser Leu Thr Ala  Ile Ala Asn
    2315                 2320                 2325

Gln Ala  Thr Val Leu Met Gly  Leu Gly Lys Gly Trp  Pro Leu Ser
    2330                 2335                 2340

Lys Met  Asp Ile Gly Val Pro  Leu Leu Ala Ile Gly  Cys Tyr Ser
    2345                 2350                 2355

Gln Val  Asn Pro Ile Thr Leu  Thr Ala Ala Leu Phe  Leu Leu Val
    2360                 2365                 2370

Ala His  Tyr Ala Ile Ile Gly  Pro Gly Leu Gln Ala  Lys Ala Thr
    2375                 2380                 2385

Arg Glu  Ala Gln Lys Arg Ala  Ala Ala Gly Ile Met  Lys Asn Pro
    2390                 2395                 2400

Thr Val  Asp Gly Ile Thr Val  Ile Asp Leu Asp Pro  Ile Pro Tyr
    2405                 2410                 2415

Asp Pro  Lys Phe Glu Lys Gln  Leu Gly Gln Val Met  Leu Leu Val
    2420                 2425                 2430

Leu Cys  Val Thr Gln Val Leu  Met Met Arg Thr Thr  Trp Ala Leu
    2435                 2440                 2445

Cys Glu  Ala Leu Thr Leu Ala  Thr Gly Pro Ile Ser  Thr Leu Trp
    2450                 2455                 2460

Glu Gly  Asn Pro Gly Arg Phe  Trp Asn Thr Thr Ile  Ala Val Ser
    2465                 2470                 2475

Met Ala  Asn Ile Phe Arg Gly  Ser Tyr Leu Ala Gly  Ala Gly Leu
    2480                 2485                 2490

Leu Phe  Ser Ile Met Lys Asn  Thr Thr Asn Thr Arg  Arg Gly Thr
    2495                 2500                 2505

Gly Asn  Ile Gly Glu Thr Leu  Gly Glu Lys Trp Lys  Ser Arg Leu
    2510                 2515                 2520

Asn Ala  Leu Gly Lys Ser Glu  Phe Gln Ile Tyr Lys  Lys Ser Gly
    2525                 2530                 2535

Ile Gln  Glu Val Asp Arg Thr  Leu Ala Lys Glu Gly  Ile Lys Arg
    2540                 2545                 2550

Gly Glu  Thr Asp His His Ala  Val Ser Arg Gly Ser  Ala Lys Leu
    2555                 2560                 2565

Arg Trp  Phe Val Glu Arg Asn  Met Val Thr Pro Glu  Gly Lys Val
    2570                 2575                 2580

Val Asp  Leu Gly Cys Gly Arg  Gly Gly Trp Ser Tyr  Tyr Cys Gly
    2585                 2590                 2595
```

```
Gly Leu  Lys Asn Val Arg Glu  Val Lys Gly Leu Thr  Lys Gly Gly
    2600                 2605                 2610

Pro Gly  His Glu Glu Pro Ile  Pro Met Ser Thr Tyr  Gly Trp Asn
    2615                 2620                 2625

Leu Val  Arg Leu Gln Ser Gly  Val Asp Val Phe Phe  Ile Pro Pro
    2630                 2635                 2640

Glu Lys  Cys Asp Thr Leu Leu  Cys Asp Ile Gly Glu  Ser Ser Pro
    2645                 2650                 2655

Asn Pro  Thr Val Glu Ala Gly  Arg Thr Leu Arg Val  Leu Asn Leu
    2660                 2665                 2670

Val Glu  Asn Trp Leu Asn Asn  Asn Thr Gln Phe Cys  Ile Lys Val
    2675                 2680                 2685

Leu Asn  Pro Tyr Met Pro Ser  Val Ile Glu Lys Met  Glu Ala Leu
    2690                 2695                 2700

Gln Arg  Lys Tyr Gly Gly Ala  Leu Val Arg Asn Pro  Leu Ser Arg
    2705                 2710                 2715

Asn Ser  Thr His Glu Met Tyr  Trp Val Ser Asn Ala  Ser Gly Asn
    2720                 2725                 2730

Ile Val  Ser Ser Val Asn Met  Ile Ser Arg Met Leu  Ile Asn Arg
    2735                 2740                 2745

Phe Thr  Met Arg Tyr Lys Lys  Ala Thr Tyr Glu Pro  Asp Val Asp
    2750                 2755                 2760

Leu Gly  Ser Gly Thr Arg Asn  Ile Gly Ile Glu Ser  Glu Ile Pro
    2765                 2770                 2775

Asn Leu  Asp Ile Ile Gly Lys  Arg Ile Glu Lys Ile  Lys Gln Glu
    2780                 2785                 2790

His Glu  Thr Ser Trp His Tyr  Asp Gln Asp His Pro  Tyr Lys Thr
    2795                 2800                 2805

Trp Ala  Tyr His Gly Ser Tyr  Glu Thr Lys Gln Thr  Gly Ser Ala
    2810                 2815                 2820

Ser Ser  Met Val Asn Gly Val  Val Arg Leu Leu Thr  Lys Pro Trp
    2825                 2830                 2835

Asp Val  Val Pro Met Val Thr  Gln Met Ala Met Thr  Asp Thr Thr
    2840                 2845                 2850

Pro Phe  Gly Gln Gln Arg Val  Phe Lys Glu Lys Val  Asp Thr Arg
    2855                 2860                 2865

Thr Gln  Glu Pro Lys Glu Gly  Thr Lys Lys Leu Met  Lys Ile Thr
    2870                 2875                 2880

Ala Glu  Trp Leu Trp Lys Glu  Leu Gly Lys Lys Lys  Thr Pro Arg
    2885                 2890                 2895

Met Cys  Thr Arg Glu Glu Phe  Thr Arg Lys Val Arg  Ser Asn Ala
    2900                 2905                 2910

Ala Leu  Gly Ala Ile Phe Thr  Asp Glu Asn Lys Trp  Lys Ser Ala
    2915                 2920                 2925

Arg Glu  Ala Val Glu Asp Ser  Arg Phe Trp Glu Leu  Val Asp Lys
    2930                 2935                 2940

Glu Arg  Asn Leu His Leu Glu  Gly Lys Cys Glu Thr  Cys Val Tyr
    2945                 2950                 2955

Asn Met  Met Gly Lys Arg Glu  Lys Lys Leu Gly Glu  Phe Gly Lys
    2960                 2965                 2970

Ala Lys  Gly Ser Arg Ala Ile  Trp Tyr Met Trp Leu  Gly Ala Arg
    2975                 2980                 2985

Phe Leu  Glu Phe Glu Ala Leu  Gly Phe Leu Asn Glu  Asp His Trp
```

```
    2990                2995                3000

Phe Ser  Arg Glu Asn Ser Leu  Ser Gly Val Glu Gly  Glu Gly Leu
    3005                3010                3015

His Lys  Leu Gly Tyr Ile Leu  Arg Asp Val Ser Lys  Lys Glu Gly
    3020                3025                3030

Gly Ala  Met Tyr Ala Asp Asp  Thr Ala Gly Trp Asp  Thr Arg Ile
    3035                3040                3045

Thr Leu  Glu Asp Leu Lys Asn  Glu Glu Met Val Thr  Asn His Met
    3050                3055                3060

Glu Gly  Glu His Lys Lys Leu  Ala Glu Ala Ile Phe  Lys Leu Thr
    3065                3070                3075

Tyr Gln  Asn Lys Val Val Arg  Val Gln Arg Pro Thr  Pro Arg Gly
    3080                3085                3090

Thr Val  Met Asp Ile Ile Ser  Arg Arg Asp Gln Arg  Gly Ser Gly
    3095                3100                3105

Gln Val  Gly Thr Tyr Gly Leu  Asn Thr Phe Thr Asn  Met Glu Ala
    3110                3115                3120

Gln Leu  Ile Arg Gln Met Glu  Gly Glu Gly Val Phe  Lys Ser Ile
    3125                3130                3135

Gln His  Leu Thr Ile Thr Glu  Glu Ile Ala Val Gln  Asn Trp Leu
    3140                3145                3150

Ala Arg  Val Gly Arg Glu Arg  Leu Ser Arg Met Ala  Ile Ser Gly
    3155                3160                3165

Asp Asp  Cys Val Val Lys Pro  Leu Asp Asp Arg Phe  Ala Ser Ala
    3170                3175                3180

Leu Thr  Ala Leu Asn Asp Met  Gly Lys Ile Arg Lys  Asp Ile Gln
    3185                3190                3195

Gln Trp  Glu Pro Ser Arg Gly  Trp Asn Asp Trp Thr  Gln Val Pro
    3200                3205                3210

Phe Cys  Ser His His Phe His  Glu Leu Ile Met Lys  Asp Gly Arg
    3215                3220                3225

Val Leu  Val Val Pro Cys Arg  Asn Gln Asp Glu Leu  Ile Gly Arg
    3230                3235                3240

Ala Arg  Ile Ser Gln Gly Ala  Gly Trp Ser Leu Arg  Glu Thr Ala
    3245                3250                3255

Cys Leu  Gly Lys Ser Tyr Ala  Gln Met Trp Ser Leu  Met Tyr Phe
    3260                3265                3270

His Arg  Arg Asp Leu Arg Leu  Ala Ala Asn Ala Ile  Cys Ser Ala
    3275                3280                3285

Val Pro  Ser His Trp Val Pro  Thr Ser Arg Thr Thr  Trp Ser Ile
    3290                3295                3300

His Ala  Lys His Glu Trp Met  Thr Thr Glu Asp Met  Leu Thr Val
    3305                3310                3315

Trp Asn  Arg Val Trp Ile Gln  Glu Asn Pro Trp Met  Glu Asp Lys
    3320                3325                3330

Thr Pro  Val Glu Ser Trp Glu  Glu Ile Pro Tyr Leu  Gly Lys Arg
    3335                3340                3345

Glu Asp  Gln Trp Cys Gly Ser  Leu Ile Gly Leu Thr  Ser Arg Ala
    3350                3355                3360

Thr Trp  Ala Lys Asn Ile Gln  Ala Ala Ile Asn Gln  Val Arg Ser
    3365                3370                3375

Leu Ile  Gly Asn Glu Glu Tyr  Thr Asp Tyr Met Pro  Ser Met Lys
    3380                3385                3390
```

```
Arg Phe  Arg Arg Glu Glu Glu  Glu Ala Gly Val Leu  Trp
    3395                 3400                 3405
```

<210> SEQ ID NO 17
<211> LENGTH: 10768
<212> TYPE: DNA
<213> ORGANISM: Artificial Sequence
<220> FEATURE:
<223> OTHER INFORMATION: Synthetic construct

<400> SEQUENCE: 17

```
agttgttagt ctacgtggac cgacaaagac agattctttg agggagctaa gctcaatgta      60

gttctaacag tttttaatt agagagcaga tctctgatga ataaccaacg gaaaaaggcg      120

aaaaacacgc ctttcaatat gctgaaacgc gagagaaacc gcgtgtcgac tgtgcaacag     180

ctgacaaaga gattctcact tggaatgctg cagggacgag gaccattaaa actgttcatg     240

gccctggtgg cgttccttcg tttcctaaca atcccaccaa cagcagggat attgaagaga     300

tggggaacaa ttaaaaaatc aaaagctatt aatgttttga gagggttcag gaaagagatt     360

ggaaggatgc tgaacatctt gaataggaga cgcagatccg cgggtactag tgtcggaatt     420

gttggcctcc tgctgaccac agctatggca gcggaggtca ctagacgtgg gagtgcatac     480

tatatgtact tggacagaaa cgatgctggg gaggccatat cttttccaac cacattgggg     540

atgaataagt gttatataca gatcatggat cttggacaca tgtgtgatgc caccatgagc     600

tatgaatgcc ctatgctgga tgagggggtg gaaccagatg acgtcgattg ttggtgcaac     660

acgacgtcaa cttgggttgt gtacggaacc tgccatcaca aaaaaggtga agcacggaga     720

agtagaagag ctgtgacgct cccctcccat tccactagga agctgcaaac gcggtcgcaa     780

acctggttgg aatcaagaga atacacaaag cacttgatta gagtcgaaaa ttggatattc     840

aggaaccctg gcttcgcgtt agcagcagct gccatcgctt ggcttttggg aagctcaacg     900

agccaaaaag tcatatactt ggtcatgata ctgctgattg ccccggcata cagcatcagg     960

tgcataggag tcagcaatag ggactttgtg gaaggtatgt caggtgggac ttgggttgat    1020

attgtcttgg aacatggagg ttgtgtcacc gtaatggcac aggacaaacc gactgtcgac    1080

atagagctgg ttacaacaac agtcagcaac atggcggagg taagatccta ctgctatgag    1140

gcatcaatat cagacatggc ttcggacagc cgctgcccaa cacaaggtga agcctacctt    1200

gacaagcaat cagacactca atatgtctgc aaaagaacgt tagtggacag aggctgggga    1260

aatggatgtg gacttttttgg caaagggagt ctggtgacat gcgctaagtt tgcatgctcc   1320

aagaaaatga ccgggaagag catccagcca gagaatctgg agtaccggat aatgctgtca    1380

gttcatggct cccagcacag tgggatgatc gttaatgaca caggacatga aactgatgag    1440

aatagagcga aggttgagat aacgcccaat tcaccaagag ccgaagccac cctgggggt     1500

tttggaagcc taggacttga ttgtgaaccg aggacaggcc ttgacttttc agatttgtat    1560

tacttgacta tgaataacaa gcactggttg gttcacaagg agtggttcca cgacattcca    1620

ttaccttggc acgctggggc agacaccgga actccacact ggaacaacaa agaagcactg    1680

gtagagttca aggacgcaca tgccaaaagg caaactgtcg tggttctagg gagtcaagaa    1740

ggagcagttc acacggccct tgctggagct ctggaggctg agatggatgg tgcaaaggga    1800

aggctgtcct ctggccactt gaaatgtcgc ctgaaaatgg ataaacttag attgaagggc    1860

gtgtcatact ccttgtgtac cgcagcgttc acattcacca agatcccggc tgaaacactg    1920

cacgggacag tcacagtgga ggtacagtac gcagggacag atggaccttg caaggttcca    1980
```

```
gctcagatgg cggtggacat gcaaactctg accccagttg ggaggttgat aaccgctaac   2040
cccgtaatca ctgaaagcac tgagaactct aagatgatgc tggaacttga tccaccattt   2100
ggggactctt acattgtcat aggagtcggg gagaagaaga tcacccacca ctggcacagg   2160
agtggcagca ccattggaaa agcatttgaa gccactgtga gaggtgccaa gagaatggca   2220
gtcttgggag acacagcctg ggactttgga tcagttggag gcgctctcaa ctcattgggc   2280
aagggcatcc atcaaatttt tggagcagct ttcaaatcat tgtttggagg aatgtcctgg   2340
ttctcaagaa ttctcattgg aacgttgctg atgtggttgg gtctgaacac aaagaatgga   2400
tctatttccc ttatgtgctt ggccgccggc tttgtgacac tgtatttggg agtcatggtg   2460
caggccgata gtggttgcgt tgtgagctgg aaaaacaaag aactgaaatg tggcagtggg   2520
attttcatca cagacaacgt gcacacatgg acagaacaat acaagttcca accagaatcc   2580
ccttcaaaac tagcttcagc tatccagaaa gcccatgaag aggacatttg tggaatccgc   2640
tcagtaacaa gactggagaa tctgatgtgg aaacaaataa caccagaatt gaatcacatt   2700
ctatcagaaa atgaggtgaa gttaactatt atgacaggag acatcaaagg aatcatgcag   2760
gcaggaaaac gatctctgcg gcctcagccc actgagctga agtattcatg gaaaacatgg   2820
ggcaaagcaa aaatgctctc tacagagtct cataaccaga cctttctcat tgatggcccc   2880
gaaacagcag aatgccccaa cacaaataga gcttggaatt cgttggaagt tgaagactat   2940
ggctttggag tattcaccac caatatatgg ctaaaattga aagaaaaaca ggatgtattc   3000
tgcgactcaa aactcatgtc agcggccata aaagacaaca gagccgtcca tgccgatatg   3060
ggttattgga tagaaagtgc actcaatgac acatggaaga tagagaaagc ctctttcatt   3120
gaagttaaaa actgccactg gccaaaatca cacaccctct ggagcaatgg agtgctagaa   3180
agtgagatga taattccaaa gaatctcgct ggaccagtgt ctcaacacaa ctatagacca   3240
ggctaccata cacaaataac aggaccatgg catctaggta agcttgagat ggactttgat   3300
ttctgtgatg gaacaacagt ggtagtgact gaggactgcg gaaatagagg accctctttg   3360
agaacaacca ctgcctctgg aaaactcata acagaatggt gctgccgatc ttgcacatta   3420
ccaccgctaa gatacagagg tgaggatggg tgctggtacg ggatggaaat cagaccattg   3480
aaggagaaag aagagaattt ggtcaactcc ttggtcacag ctggacatgg gcaggtcgac   3540
aacttttcac taggagtctt gggaatggca ttgttcctgg aggaaatgct taggacccga   3600
gtaggaacga aacatgcaat actactagtt gcagtttctt ttgtgacatt gatcacaggg   3660
aacatgtcct ttagagacct gggaagagtg atggttatgg taggcgccac tatgacggat   3720
gacataggta tgggcgtgac ttatcttgcc ctactagcag ccttcaaagt cagaccaact   3780
tttgcagctg gactactctt gagaaagctg acctccaatg aattgatgat gactactata   3840
ggaattgtac tcctctccca gagcaccata ccagagacca ttcttgagtt gactgatgcg   3900
ttagccttag gcatgatggt cctcaaaatg gtgagaaata tggaaaagta tcaattggca   3960
gtgactatca tggctatctt gtgcgtccca aacgcagtga tattacaaaa cgcatggaaa   4020
gtgagttgca caatattggc agtggtgtcc gtttccccac tgttcttaac atcctcacag   4080
caaaaaacag attggatacc attagcattg acgatcaaag gtctcaatcc aacagctatt   4140
tttctaacaa ccctctcaag aaccagcaag aaaaggagct ggccattaaa tgaggctatc   4200
atggcagtcg ggatggtgag cattttagcc agttctctcc taaaaaatga tattcccatg   4260
acaggaccat tagtggctgg agggctcctc actgtgtgct acgtgctcac tggacgatcg   4320
```

```
gccgatttgg aactggagag agcagccgat gtcaaatggg aagaccaggc agagatatca   4380
ggaagcagtc caatcctgtc aataacaata tcagaagatg gtagcatgtc gataaaaaat   4440
gaagaggaag aacaaacact gaccatactc attagaacag gattgctggt gatctcagga   4500
ctttttcctg tatcaatacc aatcacggca gcagcatggt acctgtggga agtgaagaaa   4560
caacgggccg gagtattgtg ggatgttcct tcacccccac ccatgggaaa ggctgaactg   4620
gaagatggag cctatagaat taagcaaaaa gggattcttg gatattccca gatcggagcc   4680
ggagtttaca aagaaggaac attccataca atgtggcatg tcacacgtgg cgctgttcta   4740
atgcataaag gaaagaggat tgaaccatca tgggcggacg tcaagaaaga cctaatatca   4800
tatggaggag gctggaagtt agaaggagaa tggaaggaag gagaagaagt ccaggtattg   4860
gcactggagc ctggaaaaaa tccaagagcc gtccaaacga aacctggtct tttcaaaacc   4920
aacgccggaa caataggtgc tgtatctctg gacttttctc ctggaacgtc aggatctcca   4980
attatcgaca aaaaaggaaa agttgtgggt ctttatggta atggtgttgt tacaaggagt   5040
ggagcatatg tgagtgctat agcccagact gaaaaaagca ttgaagacaa cccagagatc   5100
gaagatgaca ttttccgaaa gagaagactg accatcatgg acctccaccc aggagcggga   5160
aagacgaaga gatacccttcc ggccatagtc agagaagcta taaaacgggg tttgagaaca   5220
ttaatcttgg cccccactag agttgtggca gctgaaatgg aggaagccct tagaggactt   5280
ccaataagat accagacccc agccatcaga gctgtgcaca ccgggcggga gattgtggac   5340
ctaatgtgtc atgccacatt taccatgagg ctgctatcac cagttagagt gccaaactac   5400
aacctgatta tcatggacga agcccatttc acagacccag caagtatagc agctagagga   5460
tacatctcaa ctcgagtgga gatgggtgag gcagctggga tttttatgac agccactccc   5520
ccgggaagca gagacccatt tcctcagagc aatgcaccaa tcatagatga agaaagagaa   5580
atccctgaac gctcgtggaa ttccggacat gaatgggtca cggattttaa agggaagact   5640
gtttggttcg ttccaagtat aaaagcagga aatgatatag cagcttgcct gaggaaaaat   5700
ggaaagaaag tgatacaact cagtaggaag acctttgatt ctgagtatgt caagactaga   5760
accaatgatt gggacttcgt ggttacaact gacatttcag aaatgggtgc caatttcaag   5820
gctgagaggg ttatagaccc cagacgctgc atgaaaccag tcatactaac agatggtgaa   5880
gagcgggtga ttctggcagg acctatgcca gtgacccact ctagtgcagc acaaagaaga   5940
gggagaatag gaagaaatcc aaaaaatgag aatgaccagt acatatacat gggggaacct   6000
ctggaaaatg atgaagactg tgcacactgg aaagaagcta aaatgctcct agataacatc   6060
aacacgccag aaggaatcat tcctagcatg ttcgaaccag agcgtgaaaa ggtggatgcc   6120
attgatggcg aataccgctt gagaggagaa gcaaggaaaa cctttgtaga cttaatgaga   6180
agaggagacc taccagtctg gttggcctac agagtggcag ctgaaggcat caactacgca   6240
gacagaaggt ggtgttttga tggagtcaag aacaaccaaa tcctagaaga aaacgtggaa   6300
gttgaaatct ggacaaaaga aggggaaagg aagaaattga aacccagatg gttggatgct   6360
aggatctatt ctgacccact ggcgctaaaa gaatttaagg aatttgcagc cggaagaaag   6420
tctctgaccc tgaacctaat cacagaaatg ggtaggctcc caaccttcat gactcagaag   6480
gcaagaaacg cactggacaa cttagcagtg ctgcacacgg ctgaggcagg tggaagggcg   6540
tacaaccatg ctctcagtga actgccggag accctggaga cattgctttt actgacactt   6600
ctggctacag tcacgggagg gatcttttta ttcttgatga gcgcaagggg catagggaag   6660
atgaccctgg gaatgtgctg cataatcacg gctagcatcc tcctatggta cgcacaaata   6720
```

-continued

```
cagccacact ggatagcagc ttcaataata ctggagtttt ttctcatagt tttgcttatt   6780
ccagaacctg aaaaacagag aacaccccaa gacaaccaac tgacctacgt tgtcatagcc   6840
atcctcacag tggtggccgc aaccatggca aacgagatgg gtttcctaga aaaaacgaag   6900
aaagatctcg gattgggaag cattgcaacc cagcaacccg agagcaacat cctggacata   6960
gatctacgtc ctgcatcagc atggacgctg tatgccgtgg ccacaacatt tgttacacca   7020
atgttgagac atagcattga aaattcctca gtgaatgtgt ccctaacagc tatagccaac   7080
caagccacag tgttaatggg tctcgggaaa ggatggccat tgtcaaagat ggacatcgga   7140
gttcccccttc tcgccattgg atgctactca caagtcaacc ccataactct cacagcagct   7200
cttttcttat tggtagcaca ttatgccatc atagggccag gactccaagc aaaagcaacc   7260
agagaagctc agaaaagagc agcggcgggc atcatgaaaa acccaactgt cgatggaata   7320
acagtgattg acctagatcc aataccttat gatccaaagt ttgaaaagca gttgggacaa   7380
gtaatgctcc tagtcctctg cgtgactcaa gtattgatga tgaggactac atgggctctg   7440
tgtgaggctt taaccttagc taccgggccc atctccacat tgtgggaagg aaatccaggg   7500
aggttttgga acactaccat tgcggtgtca atggctaaca tttttagagg gagttacttg   7560
gccggagctg gacttctctt ttctattatg aagaacacaa ccaacacaag aaggggaact   7620
ggcaacatag gagagacgct tggagagaaa tggaaaagcc gattgaacgc attgggaaaa   7680
agtgaattcc agatctacaa gaaaagtgga atccaggaag tggatagaac cttagcaaaa   7740
gaaggcatta aaagaggaga aacggaccat cacgctgtgt cgcgaggctc agcaaaactg   7800
agatggttcg ttgagagaaa catggtcaca ccagaaggga aagtagtgga cctcggttgt   7860
ggcagaggag gctggtcata ctattgtgga ggactaaaga atgtaagaga agtcaaaggc   7920
ctaacaaaag gaggaccagg acacgaagaa cccatcccca tgtcaacata tgggtggaat   7980
ctagtgcgtc ttcaaagtgg agttgacgtt ttcttcatcc cgccagaaaa gtgtgacaca   8040
ttattgtgtg acataggga gtcatcacca aatcccacag tggaagcagg acgaacactc   8100
agagtcctta acttagtaga aaattggttg aacaacaaca ctcaattttg cataaaggtt   8160
ctcaacccat atatgccctc agtcatagaa aaaatggaag cactacaaag gaaatatgga   8220
ggagccttag tgaggaatcc actctcacga aactccacac atgagatgta ctgggtatcc   8280
aatgcttccg ggaacatagt gtcatcagtg aacatgattt caaggatgtt gatcaacaga   8340
tttacaatga gatacaagaa agccacttac gagccggatg ttgacctcgg aagcggaacc   8400
cgtaacatcg ggattgaaag tgagatacca aacctagata taattgggaa aagaatagaa   8460
aaaataaagc aagagcatga aacatcatgg cactatgacc aagaccaccc atacaaaacg   8520
tgggcatacc atggtagcta tgaaacaaaa cagactggat cagcatcatc catggtcaac   8580
ggagtggtca ggctgctgac aaaaccttgg gacgtcgtcc ccatggtgac acagatggca   8640
atgacagaca cgactccatt tggacaacag cgcgttttta aagagaaagt ggacacgaga   8700
acccaagaac cgaaagaagg cacgaagaaa ctaatgaaaa taacagcaga gtggctttgg   8760
aaagaattag ggaagaaaaa gacacccagg atgtgcacca gagaagaatt cacaagaaag   8820
gtgagaagca atgcagcctt gggggccata ttcactgatg agaacaagtg gaagtcggca   8880
cgtgaggctg ttgaagatag taggttttgg gagctggttg acaaggaaag gaatctccat   8940
cttgaaggaa agtgtgaaac atgtgtgtac aacatgatgg gaaaaagaga gaagaagcta   9000
ggggaattcg gcaaggcaaa aggcagcaga gccatatggt acatgtggct tggagcacgc   9060
```

```
ttcttagagt ttgaagccct aggattctta aatgaagatc actggttctc cagagagaac   9120

tccctgagtg gagtggaagg agaagggctg cacaagctag gttacattct aagagacgtg   9180

agcaagaaag agggaggagc aatgtatgcc gatgacaccg caggatggga tacaagaatc   9240

acactagaag acctaaaaaa tgaagaaatg gtaacaaacc acatggaagg agaacacaag   9300

aaactagccg aggccatttt caaactaacg taccaaaaca aggtggtgcg tgtgcaaaga   9360

ccaacaccaa gaggcacagt aatggacatc atatcgagaa gagaccaaag aggtagtgga   9420

caagttggca cctatggact caatactttc accaatatgg aagcccaact aatcagacag   9480

atggagggag aaggagtctt taaaagcatt cagcacctaa caatcacaga agaaatcgct   9540

gtgcaaaact ggttagcaag agtggggcgc gaaaggttat caagaatggc catcagtgga   9600

gatgattgtg ttgtgaaacc tttagatgac aggttcgcaa gcgctttaac agctctaaat   9660

gacatgggaa agattaggaa agacatacaa caatgggaac cttcaagagg atggaatgat   9720

tggacacaag tgcccttctg ttcacaccat ttccatgagt taatcatgaa agacggtcgc   9780

gtactcgttg ttccatgtag aaaccaagat gaactgattg gcagagcccg aatctcccaa   9840

ggagcagggt ggtctttgcg ggagacggcc tgtttgggga agtcttacgc ccaaatgtgg   9900

agcttgatgt acttccacag acgcgacctc aggctggcgg caaatgctat ttgctcggca   9960

gtaccatcac attgggttcc aacaagtcga acaacctggt ccatacatgc taaacatgaa  10020

tggatgacaa cggaagacat gctgacagtc tggaacaggg tgtggattca agaaaaccca  10080

tggatggaag acaaaactcc agtggaatca tgggaggaaa tcccatactt ggggaaaaga  10140

gaagaccaat ggtgcggctc attgattggg ttaacaagca gggccacctg ggcaaagaac  10200

atccaagcag caataaatca agttagatcc cttataggca atgaagaata cacagattac  10260

atgccatcca tgaaaagatt cagaagagaa gaggaagaag caggagttct gtggtagaaa  10320

gcaaaactaa catgaaacaa ggctagaagt caggtcggat taagccatag tacggaaaaa  10380

actatgctac ctgtgagccc cgtccaagga cgttaaaaga agtcaggcca tcataaatgc  10440

catagcttga gtaaactatg cagcctgtag ctccacctga gaaggtgtaa aaaatccggg  10500

aggccacaaa ccatggaagc tgtacgcatg gcgtagtgga ctagcggtta gaggagaccc  10560

ctcccttaca aatcgcagca acaatggggg cccaaggcga gatgaagctg tagtctcgct  10620

ggaaggacta gaggttagag gagacccccc cgaaacaaaa aacagcatat tgacgctggg  10680

aaagaccaga gatcctgctg tctcctcagc atcattccag gcacagaacg ccagaaaatg  10740

gaatggtgct gttgaatcaa caggttct                                     10768
```

```
<210> SEQ ID NO 18
<211> LENGTH: 3406
<212> TYPE: PRT
<213> ORGANISM: Artificial Sequence
<220> FEATURE:
<223> OTHER INFORMATION: Synthetic polypeptide

<400> SEQUENCE: 18

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60
```

```
Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Thr Ser Val Gly Ile Val Gly Leu Leu
            100                 105                 110

Leu Thr Thr Ala Met Ala Ala Glu Val Thr Arg Arg Gly Ser Ala Tyr
        115                 120                 125

Tyr Met Tyr Leu Asp Arg Asn Asp Ala Gly Glu Ala Ile Ser Phe Pro
    130                 135                 140

Thr Thr Leu Gly Met Asn Lys Cys Tyr Ile Gln Ile Met Asp Leu Gly
145                 150                 155                 160

His Met Cys Asp Ala Thr Met Ser Tyr Glu Cys Pro Met Leu Asp Glu
                165                 170                 175

Gly Val Glu Pro Asp Asp Val Asp Cys Trp Cys Asn Thr Thr Ser Thr
            180                 185                 190

Trp Val Val Tyr Gly Thr Cys His His Lys Lys Gly Glu Ala Arg Arg
        195                 200                 205

Ser Arg Arg Ala Val Thr Leu Pro Ser His Ser Thr Arg Lys Leu Gln
    210                 215                 220

Thr Arg Ser Gln Thr Trp Leu Glu Ser Arg Glu Tyr Thr Lys His Leu
225                 230                 235                 240

Ile Arg Val Glu Asn Trp Ile Phe Arg Asn Pro Gly Phe Ala Leu Ala
                245                 250                 255

Ala Ala Ala Ile Ala Trp Leu Leu Gly Ser Ser Thr Ser Gln Lys Val
            260                 265                 270

Ile Tyr Leu Val Met Ile Leu Leu Ile Ala Pro Ala Tyr Ser Ile Arg
        275                 280                 285

Cys Ile Gly Val Ser Asn Arg Asp Phe Val Glu Gly Met Ser Gly Gly
    290                 295                 300

Thr Trp Val Asp Ile Val Leu Glu His Gly Gly Cys Val Thr Val Met
305                 310                 315                 320

Ala Gln Asp Lys Pro Thr Val Asp Ile Glu Leu Val Thr Thr Thr Val
                325                 330                 335

Ser Asn Met Ala Glu Val Arg Ser Tyr Cys Tyr Glu Ala Ser Ile Ser
            340                 345                 350

Asp Met Ala Ser Asp Ser Arg Cys Pro Thr Gln Gly Glu Ala Tyr Leu
        355                 360                 365

Asp Lys Gln Ser Asp Thr Gln Tyr Val Cys Lys Arg Thr Leu Val Asp
    370                 375                 380

Arg Gly Trp Gly Asn Gly Cys Gly Leu Phe Gly Lys Gly Ser Leu Val
385                 390                 395                 400

Thr Cys Ala Lys Phe Ala Cys Ser Lys Lys Met Thr Gly Lys Ser Ile
                405                 410                 415

Gln Pro Glu Asn Leu Glu Tyr Arg Ile Met Leu Ser Val His Gly Ser
            420                 425                 430

Gln His Ser Gly Met Ile Val Asn Asp Thr Gly His Glu Thr Asp Glu
        435                 440                 445

Asn Arg Ala Lys Val Glu Ile Thr Pro Asn Ser Pro Arg Ala Glu Ala
    450                 455                 460

Thr Leu Gly Gly Phe Gly Ser Leu Gly Leu Asp Cys Glu Pro Arg Thr
465                 470                 475                 480
```

```
Gly Leu Asp Phe Ser Asp Leu Tyr Tyr Leu Thr Met Asn Asn Lys His
                485                 490                 495

Trp Leu Val His Lys Glu Trp Phe His Asp Ile Pro Leu Pro Trp His
            500                 505                 510

Ala Gly Ala Asp Thr Gly Thr Pro His Trp Asn Asn Lys Glu Ala Leu
        515                 520                 525

Val Glu Phe Lys Asp Ala His Ala Lys Arg Gln Thr Val Val Val Leu
    530                 535                 540

Gly Ser Gln Glu Gly Ala Val His Thr Ala Leu Ala Gly Ala Leu Glu
545                 550                 555                 560

Ala Glu Met Asp Gly Ala Lys Gly Arg Leu Ser Ser Gly His Leu Lys
                565                 570                 575

Cys Arg Leu Lys Met Asp Lys Leu Arg Leu Lys Gly Val Ser Tyr Ser
            580                 585                 590

Leu Cys Thr Ala Ala Phe Thr Phe Thr Lys Ile Pro Ala Glu Thr Leu
        595                 600                 605

His Gly Thr Val Thr Val Glu Val Gln Tyr Ala Gly Thr Asp Gly Pro
    610                 615                 620

Cys Lys Val Pro Ala Gln Met Ala Val Asp Met Gln Thr Leu Thr Pro
625                 630                 635                 640

Val Gly Arg Leu Ile Thr Ala Asn Pro Val Ile Thr Glu Ser Thr Glu
                645                 650                 655

Asn Ser Lys Met Met Leu Glu Leu Asp Pro Pro Phe Gly Asp Ser Tyr
            660                 665                 670

Ile Val Ile Gly Val Gly Glu Lys Lys Ile Thr His His Trp His Arg
        675                 680                 685

Ser Gly Ser Thr Ile Gly Lys Ala Phe Glu Ala Thr Val Arg Gly Ala
    690                 695                 700

Lys Arg Met Ala Val Leu Gly Asp Thr Ala Trp Asp Phe Gly Ser Val
705                 710                 715                 720

Gly Gly Ala Leu Asn Ser Leu Gly Lys Gly Ile His Gln Ile Phe Gly
                725                 730                 735

Ala Ala Phe Lys Ser Leu Phe Gly Gly Met Ser Trp Phe Ser Arg Ile
            740                 745                 750

Leu Ile Gly Thr Leu Leu Met Trp Leu Gly Leu Asn Thr Lys Asn Gly
        755                 760                 765

Ser Ile Ser Leu Met Cys Leu Ala Ala Gly Phe Val Thr Leu Tyr Leu
    770                 775                 780

Gly Val Met Val Gln Ala Asp Ser Gly Cys Val Val Ser Trp Lys Asn
785                 790                 795                 800

Lys Glu Leu Lys Cys Gly Ser Gly Ile Phe Ile Thr Asp Asn Val His
                805                 810                 815

Thr Trp Thr Glu Gln Tyr Lys Phe Gln Pro Glu Ser Pro Ser Lys Leu
            820                 825                 830

Ala Ser Ala Ile Gln Lys Ala His Glu Glu Asp Ile Cys Gly Ile Arg
        835                 840                 845

Ser Val Thr Arg Leu Glu Asn Leu Met Trp Lys Gln Ile Thr Pro Glu
    850                 855                 860

Leu Asn His Ile Leu Ser Glu Asn Glu Val Lys Leu Thr Ile Met Thr
865                 870                 875                 880

Gly Asp Ile Lys Gly Ile Met Gln Ala Gly Lys Arg Ser Leu Arg Pro
                885                 890                 895

Gln Pro Thr Glu Leu Lys Tyr Ser Trp Lys Thr Trp Gly Lys Ala Lys
```

```
            900                 905                 910

Met Leu Ser Thr Glu Ser His Asn Gln Thr Phe Leu Ile Asp Gly Pro
        915                 920                 925

Glu Thr Ala Glu Cys Pro Asn Thr Asn Arg Ala Trp Asn Ser Leu Glu
    930                 935                 940

Val Glu Asp Tyr Gly Phe Gly Val Phe Thr Thr Asn Ile Trp Leu Lys
945                 950                 955                 960

Leu Lys Glu Lys Gln Asp Val Phe Cys Asp Ser Lys Leu Met Ser Ala
                965                 970                 975

Ala Ile Lys Asp Asn Arg Ala Val His Ala Asp Met Gly Tyr Trp Ile
            980                 985                 990

Glu Ser Ala Leu Asn Asp Thr Trp  Lys Ile Glu Lys Ala  Ser Phe Ile
        995                 1000                1005

Glu Val  Lys Asn Cys His Trp  Pro Lys Ser His Thr  Leu Trp Ser
    1010                 1015                 1020

Asn Gly  Val Leu Glu Ser Glu  Met Ile Ile Pro Lys  Asn Leu Ala
    1025                 1030                 1035

Gly Pro  Val Ser Gln His Asn  Tyr Arg Pro Gly Tyr  His Thr Gln
    1040                 1045                 1050

Ile Thr  Gly Pro Trp His Leu  Gly Lys Leu Glu Met  Asp Phe Asp
    1055                 1060                 1065

Phe Cys  Asp Gly Thr Thr Val  Val Val Thr Glu Asp  Cys Gly Asn
    1070                 1075                 1080

Arg Gly  Pro Ser Leu Arg Thr  Thr Thr Ala Ser Gly  Lys Leu Ile
    1085                 1090                 1095

Thr Glu  Trp Cys Cys Arg Ser  Cys Thr Leu Pro Pro  Leu Arg Tyr
    1100                 1105                 1110

Arg Gly  Glu Asp Gly Cys Trp  Tyr Gly Met Glu Ile  Arg Pro Leu
    1115                 1120                 1125

Lys Glu  Lys Glu Glu Asn Leu  Val Asn Ser Leu Val  Thr Ala Gly
    1130                 1135                 1140

His Gly  Gln Val Asp Asn Phe  Ser Leu Gly Val Leu  Gly Met Ala
    1145                 1150                 1155

Leu Phe  Leu Glu Glu Met Leu  Arg Thr Arg Val Gly  Thr Lys His
    1160                 1165                 1170

Ala Ile  Leu Leu Val Ala Val  Ser Phe Val Thr Leu  Ile Thr Gly
    1175                 1180                 1185

Asn Met  Ser Phe Arg Asp Leu  Gly Arg Val Met Val  Met Val Gly
    1190                 1195                 1200

Ala Thr  Met Thr Asp Asp Ile  Gly Met Gly Val Thr  Tyr Leu Ala
    1205                 1210                 1215

Leu Leu  Ala Ala Phe Lys Val  Arg Pro Thr Phe Ala  Ala Gly Leu
    1220                 1225                 1230

Leu Leu  Arg Lys Leu Thr Ser  Asn Glu Leu Met Met  Thr Thr Ile
    1235                 1240                 1245

Gly Ile  Val Leu Leu Ser Gln  Ser Thr Ile Pro Glu  Thr Ile Leu
    1250                 1255                 1260

Glu Leu  Thr Asp Ala Leu Ala  Leu Gly Met Met Val  Leu Lys Met
    1265                 1270                 1275

Val Arg  Asn Met Glu Lys Tyr  Gln Leu Ala Val Thr  Ile Met Ala
    1280                 1285                 1290

Ile Leu  Cys Val Pro Asn Ala  Val Ile Leu Gln Asn  Ala Trp Lys
    1295                 1300                 1305
```

```
Val Ser  Cys Thr Ile Leu Ala  Val Val Ser Val Ser  Pro Leu Phe
    1310                 1315                 1320

Leu Thr  Ser Ser Gln Gln Lys  Thr Asp Trp Ile Pro  Leu Ala Leu
    1325                 1330                 1335

Thr Ile  Lys Gly Leu Asn Pro  Thr Ala Ile Phe Leu  Thr Thr Leu
    1340                 1345                 1350

Ser Arg  Thr Ser Lys Lys Arg  Ser Trp Pro Leu Asn  Glu Ala Ile
    1355                 1360                 1365

Met Ala  Val Gly Met Val Ser  Ile Leu Ala Ser Ser  Leu Leu Lys
    1370                 1375                 1380

Asn Asp  Ile Pro Met Thr Gly  Pro Leu Val Ala Gly  Gly Leu Leu
    1385                 1390                 1395

Thr Val  Cys Tyr Val Leu Thr  Gly Arg Ser Ala Asp  Leu Glu Leu
    1400                 1405                 1410

Glu Arg  Ala Ala Asp Val Lys  Trp Glu Asp Gln Ala  Glu Ile Ser
    1415                 1420                 1425

Gly Ser  Ser Pro Ile Leu Ser  Ile Thr Ile Ser Glu  Asp Gly Ser
    1430                 1435                 1440

Met Ser  Ile Lys Asn Glu Glu  Glu Glu Gln Thr Leu  Thr Ile Leu
    1445                 1450                 1455

Ile Arg  Thr Gly Leu Leu Val  Ile Ser Gly Leu Phe  Pro Val Ser
    1460                 1465                 1470

Ile Pro  Ile Thr Ala Ala Ala  Trp Tyr Leu Trp Glu  Val Lys Lys
    1475                 1480                 1485

Gln Arg  Ala Gly Val Leu Trp  Asp Val Pro Ser Pro  Pro Pro Met
    1490                 1495                 1500

Gly Lys  Ala Glu Leu Glu Asp  Gly Ala Tyr Arg Ile  Lys Gln Lys
    1505                 1510                 1515

Gly Ile  Leu Gly Tyr Ser Gln  Ile Gly Ala Gly Val  Tyr Lys Glu
    1520                 1525                 1530

Gly Thr  Phe His Thr Met Trp  His Val Thr Arg Gly  Ala Val Leu
    1535                 1540                 1545

Met His  Lys Gly Lys Arg Ile  Glu Pro Ser Trp Ala  Asp Val Lys
    1550                 1555                 1560

Lys Asp  Leu Ile Ser Tyr Gly  Gly Gly Trp Lys Leu  Glu Gly Glu
    1565                 1570                 1575

Trp Lys  Glu Gly Glu Glu Val  Gln Val Leu Ala Leu  Glu Pro Gly
    1580                 1585                 1590

Lys Asn  Pro Arg Ala Val Gln  Thr Lys Pro Gly Leu  Phe Lys Thr
    1595                 1600                 1605

Asn Ala  Gly Thr Ile Gly Ala  Val Ser Leu Asp Phe  Ser Pro Gly
    1610                 1615                 1620

Thr Ser  Gly Ser Pro Ile Ile  Asp Lys Lys Gly Lys  Val Val Gly
    1625                 1630                 1635

Leu Tyr  Gly Asn Gly Val Val  Thr Arg Ser Gly Ala  Tyr Val Ser
    1640                 1645                 1650

Ala Ile  Ala Gln Thr Glu Lys  Ser Ile Glu Asp Asn  Pro Glu Ile
    1655                 1660                 1665

Glu Asp  Asp Ile Phe Arg Lys  Arg Arg Leu Thr Ile  Met Asp Leu
    1670                 1675                 1680

His Pro  Gly Ala Gly Lys Thr  Lys Arg Tyr Leu Pro  Ala Ile Val
    1685                 1690                 1695
```

```
Arg Glu  Ala Ile Lys Arg Gly  Leu Arg Thr Leu Ile  Leu Ala Pro
    1700                 1705                 1710

Thr Arg  Val Val Ala Ala Glu  Met Glu Glu Ala Leu  Arg Gly Leu
    1715                 1720                 1725

Pro Ile  Arg Tyr Gln Thr Pro  Ala Ile Arg Ala Val  His Thr Gly
    1730                 1735                 1740

Arg Glu  Ile Val Asp Leu Met  Cys His Ala Thr Phe  Thr Met Arg
    1745                 1750                 1755

Leu Leu  Ser Pro Val Arg Val  Pro Asn Tyr Asn Leu  Ile Ile Met
    1760                 1765                 1770

Asp Glu  Ala His Phe Thr Asp  Pro Ala Ser Ile Ala  Ala Arg Gly
    1775                 1780                 1785

Tyr Ile  Ser Thr Arg Val Glu  Met Gly Glu Ala Ala  Gly Ile Phe
    1790                 1795                 1800

Met Thr  Ala Thr Pro Pro Gly  Ser Arg Asp Pro Phe  Pro Gln Ser
    1805                 1810                 1815

Asn Ala  Pro Ile Ile Asp Glu  Glu Arg Glu Ile Pro  Glu Arg Ser
    1820                 1825                 1830

Trp Asn  Ser Gly His Glu Trp  Val Thr Asp Phe Lys  Gly Lys Thr
    1835                 1840                 1845

Val Trp  Phe Val Pro Ser Ile  Lys Ala Gly Asn Asp  Ile Ala Ala
    1850                 1855                 1860

Cys Leu  Arg Lys Asn Gly Lys  Lys Val Ile Gln Leu  Ser Arg Lys
    1865                 1870                 1875

Thr Phe  Asp Ser Glu Tyr Val  Lys Thr Arg Thr Asn  Asp Trp Asp
    1880                 1885                 1890

Phe Val  Val Thr Thr Asp Ile  Ser Glu Met Gly Ala  Asn Phe Lys
    1895                 1900                 1905

Ala Glu  Arg Val Ile Asp Pro  Arg Arg Cys Met Lys  Pro Val Ile
    1910                 1915                 1920

Leu Thr  Asp Gly Glu Glu Arg  Val Ile Leu Ala Gly  Pro Met Pro
    1925                 1930                 1935

Val Thr  His Ser Ser Ala Ala  Gln Arg Arg Gly Arg  Ile Gly Arg
    1940                 1945                 1950

Asn Pro  Lys Asn Glu Asn Asp  Gln Tyr Ile Tyr Met  Gly Glu Pro
    1955                 1960                 1965

Leu Glu  Asn Asp Glu Asp Cys  Ala His Trp Lys Glu  Ala Lys Met
    1970                 1975                 1980

Leu Leu  Asp Asn Ile Asn Thr  Pro Glu Gly Ile Ile  Pro Ser Met
    1985                 1990                 1995

Phe Glu  Pro Glu Arg Glu Lys  Val Asp Ala Ile Asp  Gly Glu Tyr
    2000                 2005                 2010

Arg Leu  Arg Gly Glu Ala Arg  Lys Thr Phe Val Asp  Leu Met Arg
    2015                 2020                 2025

Arg Gly  Asp Leu Pro Val Trp  Leu Ala Tyr Arg Val  Ala Ala Glu
    2030                 2035                 2040

Gly Ile  Asn Tyr Ala Asp Arg  Arg Trp Cys Phe Asp  Gly Val Lys
    2045                 2050                 2055

Asn Asn  Gln Ile Leu Glu Glu  Asn Val Glu Val Glu  Ile Trp Thr
    2060                 2065                 2070

Lys Glu  Gly Glu Arg Lys Lys  Leu Lys Pro Arg Trp  Leu Asp Ala
    2075                 2080                 2085

Arg Ile  Tyr Ser Asp Pro Leu  Ala Leu Lys Glu Phe  Lys Glu Phe
```

```
    2090                2095                2100

Ala Ala  Gly Arg Lys Ser Leu  Thr Leu Asn Leu Ile  Thr Glu Met
    2105                2110                2115

Gly Arg  Leu Pro Thr Phe Met  Thr Gln Lys Ala Arg  Asn Ala Leu
    2120                2125                2130

Asp Asn  Leu Ala Val Leu His  Thr Ala Glu Ala Gly  Gly Arg Ala
    2135                2140                2145

Tyr Asn  His Ala Leu Ser Glu  Leu Pro Glu Thr Leu  Glu Thr Leu
    2150                2155                2160

Leu Leu  Leu Thr Leu Leu Ala  Thr Val Thr Gly Gly  Ile Phe Leu
    2165                2170                2175

Phe Leu  Met Ser Ala Arg Gly  Ile Gly Lys Met Thr  Leu Gly Met
    2180                2185                2190

Cys Cys  Ile Ile Thr Ala Ser  Ile Leu Leu Trp Tyr  Ala Gln Ile
    2195                2200                2205

Gln Pro  His Trp Ile Ala Ala  Ser Ile Ile Leu Glu  Phe Phe Leu
    2210                2215                2220

Ile Val  Leu Leu Ile Pro Glu  Pro Glu Lys Gln Arg  Thr Pro Gln
    2225                2230                2235

Asp Asn  Gln Leu Thr Tyr Val  Val Ile Ala Ile Leu  Thr Val Val
    2240                2245                2250

Ala Ala  Thr Met Ala Asn Glu  Met Gly Phe Leu Glu  Lys Thr Lys
    2255                2260                2265

Lys Asp  Leu Gly Leu Gly Ser  Ile Ala Thr Gln Gln  Pro Glu Ser
    2270                2275                2280

Asn Ile  Leu Asp Ile Asp Leu  Arg Pro Ala Ser Ala  Trp Thr Leu
    2285                2290                2295

Tyr Ala  Val Ala Thr Thr Phe  Val Thr Pro Met Leu  Arg His Ser
    2300                2305                2310

Ile Glu  Asn Ser Ser Val Asn  Val Ser Leu Thr Ala  Ile Ala Asn
    2315                2320                2325

Gln Ala  Thr Val Leu Met Gly  Leu Gly Lys Gly Trp  Pro Leu Ser
    2330                2335                2340

Lys Met  Asp Ile Gly Val Pro  Leu Leu Ala Ile Gly  Cys Tyr Ser
    2345                2350                2355

Gln Val  Asn Pro Ile Thr Leu  Thr Ala Ala Leu Phe  Leu Leu Val
    2360                2365                2370

Ala His  Tyr Ala Ile Ile Gly  Pro Gly Leu Gln Ala  Lys Ala Thr
    2375                2380                2385

Arg Glu  Ala Gln Lys Arg Ala  Ala Ala Gly Ile Met  Lys Asn Pro
    2390                2395                2400

Thr Val  Asp Gly Ile Thr Val  Ile Asp Leu Asp Pro  Ile Pro Tyr
    2405                2410                2415

Asp Pro  Lys Phe Glu Lys Gln  Leu Gly Gln Val Met  Leu Leu Val
    2420                2425                2430

Leu Cys  Val Thr Gln Val Leu  Met Met Arg Thr Thr  Trp Ala Leu
    2435                2440                2445

Cys Glu  Ala Leu Thr Leu Ala  Thr Gly Pro Ile Ser  Thr Leu Trp
    2450                2455                2460

Glu Gly  Asn Pro Gly Arg Phe  Trp Asn Thr Thr Ile  Ala Val Ser
    2465                2470                2475

Met Ala  Asn Ile Phe Arg Gly  Ser Tyr Leu Ala Gly  Ala Gly Leu
    2480                2485                2490
```

```
Leu Phe  Ser Ile Met Lys Asn  Thr Thr Asn Thr Arg  Arg Gly Thr
    2495                 2500                 2505

Gly Asn  Ile Gly Glu Thr Leu  Gly Glu Lys Trp Lys  Ser Arg Leu
    2510                 2515                 2520

Asn Ala  Leu Gly Lys Ser Glu  Phe Gln Ile Tyr Lys  Lys Ser Gly
    2525                 2530                 2535

Ile Gln  Glu Val Asp Arg Thr  Leu Ala Lys Glu Gly  Ile Lys Arg
    2540                 2545                 2550

Gly Glu  Thr Asp His His Ala  Val Ser Arg Gly Ser  Ala Lys Leu
    2555                 2560                 2565

Arg Trp  Phe Val Glu Arg Asn  Met Val Thr Pro Glu  Gly Lys Val
    2570                 2575                 2580

Val Asp  Leu Gly Cys Gly Arg  Gly Gly Trp Ser Tyr  Tyr Cys Gly
    2585                 2590                 2595

Gly Leu  Lys Asn Val Arg Glu  Val Lys Gly Leu Thr  Lys Gly Gly
    2600                 2605                 2610

Pro Gly  His Glu Glu Pro Ile  Pro Met Ser Thr Tyr  Gly Trp Asn
    2615                 2620                 2625

Leu Val  Arg Leu Gln Ser Gly  Val Asp Val Phe Phe  Ile Pro Pro
    2630                 2635                 2640

Glu Lys  Cys Asp Thr Leu Leu  Cys Asp Ile Gly Glu  Ser Ser Pro
    2645                 2650                 2655

Asn Pro  Thr Val Glu Ala Gly  Arg Thr Leu Arg Val  Leu Asn Leu
    2660                 2665                 2670

Val Glu  Asn Trp Leu Asn Asn  Asn Thr Gln Phe Cys  Ile Lys Val
    2675                 2680                 2685

Leu Asn  Pro Tyr Met Pro Ser  Val Ile Glu Lys Met  Glu Ala Leu
    2690                 2695                 2700

Gln Arg  Lys Tyr Gly Gly Ala  Leu Val Arg Asn Pro  Leu Ser Arg
    2705                 2710                 2715

Asn Ser  Thr His Glu Met Tyr  Trp Val Ser Asn Ala  Ser Gly Asn
    2720                 2725                 2730

Ile Val  Ser Ser Val Asn Met  Ile Ser Arg Met Leu  Ile Asn Arg
    2735                 2740                 2745

Phe Thr  Met Arg Tyr Lys Lys  Ala Thr Tyr Glu Pro  Asp Val Asp
    2750                 2755                 2760

Leu Gly  Ser Gly Thr Arg Asn  Ile Gly Ile Glu Ser  Glu Ile Pro
    2765                 2770                 2775

Asn Leu  Asp Ile Ile Gly Lys  Arg Ile Glu Lys Ile  Lys Gln Glu
    2780                 2785                 2790

His Glu  Thr Ser Trp His Tyr  Asp Gln Asp His Pro  Tyr Lys Thr
    2795                 2800                 2805

Trp Ala  Tyr His Gly Ser Tyr  Glu Thr Lys Gln Thr  Gly Ser Ala
    2810                 2815                 2820

Ser Ser  Met Val Asn Gly Val  Val Arg Leu Leu Thr  Lys Pro Trp
    2825                 2830                 2835

Asp Val  Val Pro Met Val Thr  Gln Met Ala Met Thr  Asp Thr Thr
    2840                 2845                 2850

Pro Phe  Gly Gln Gln Arg Val  Phe Lys Glu Lys Val  Asp Thr Arg
    2855                 2860                 2865

Thr Gln  Glu Pro Lys Glu Gly  Thr Lys Lys Leu Met  Lys Ile Thr
    2870                 2875                 2880
```

```
Ala Glu  Trp Leu Trp Lys Glu  Leu Gly Lys Lys Lys  Thr Pro Arg
    2885                 2890                 2895

Met Cys  Thr Arg Glu Glu Phe  Thr Arg Lys Val Arg  Ser Asn Ala
    2900                 2905                 2910

Ala Leu  Gly Ala Ile Phe Thr  Asp Glu Asn Lys Trp  Lys Ser Ala
    2915                 2920                 2925

Arg Glu  Ala Val Glu Asp Ser  Arg Phe Trp Glu Leu  Val Asp Lys
    2930                 2935                 2940

Glu Arg  Asn Leu His Leu Glu  Gly Lys Cys Glu Thr  Cys Val Tyr
    2945                 2950                 2955

Asn Met  Met Gly Lys Arg Glu  Lys Lys Leu Gly Glu  Phe Gly Lys
    2960                 2965                 2970

Ala Lys  Gly Ser Arg Ala Ile  Trp Tyr Met Trp Leu  Gly Ala Arg
    2975                 2980                 2985

Phe Leu  Glu Phe Glu Ala Leu  Gly Phe Leu Asn Glu  Asp His Trp
    2990                 2995                 3000

Phe Ser  Arg Glu Asn Ser Leu  Ser Gly Val Glu Gly  Glu Gly Leu
    3005                 3010                 3015

His Lys  Leu Gly Tyr Ile Leu  Arg Asp Val Ser Lys  Lys Glu Gly
    3020                 3025                 3030

Gly Ala  Met Tyr Ala Asp Asp  Thr Ala Gly Trp Asp  Thr Arg Ile
    3035                 3040                 3045

Thr Leu  Glu Asp Leu Lys Asn  Glu Glu Met Val Thr  Asn His Met
    3050                 3055                 3060

Glu Gly  Glu His Lys Lys Leu  Ala Glu Ala Ile Phe  Lys Leu Thr
    3065                 3070                 3075

Tyr Gln  Asn Lys Val Val Arg  Val Gln Arg Pro Thr  Pro Arg Gly
    3080                 3085                 3090

Thr Val  Met Asp Ile Ile Ser  Arg Arg Asp Gln Arg  Gly Ser Gly
    3095                 3100                 3105

Gln Val  Gly Thr Tyr Gly Leu  Asn Thr Phe Thr Asn  Met Glu Ala
    3110                 3115                 3120

Gln Leu  Ile Arg Gln Met Glu  Gly Glu Gly Val Phe  Lys Ser Ile
    3125                 3130                 3135

Gln His  Leu Thr Ile Thr Glu  Glu Ile Ala Val Gln  Asn Trp Leu
    3140                 3145                 3150

Ala Arg  Val Gly Arg Glu Arg  Leu Ser Arg Met Ala  Ile Ser Gly
    3155                 3160                 3165

Asp Asp  Cys Val Val Lys Pro  Leu Asp Asp Arg Phe  Ala Ser Ala
    3170                 3175                 3180

Leu Thr  Ala Leu Asn Asp Met  Gly Lys Ile Arg Lys  Asp Ile Gln
    3185                 3190                 3195

Gln Trp  Glu Pro Ser Arg Gly  Trp Asn Asp Trp Thr  Gln Val Pro
    3200                 3205                 3210

Phe Cys  Ser His His Phe His  Glu Leu Ile Met Lys  Asp Gly Arg
    3215                 3220                 3225

Val Leu  Val Val Pro Cys Arg  Asn Gln Asp Glu Leu  Ile Gly Arg
    3230                 3235                 3240

Ala Arg  Ile Ser Gln Gly Ala  Gly Trp Ser Leu Arg  Glu Thr Ala
    3245                 3250                 3255

Cys Leu  Gly Lys Ser Tyr Ala  Gln Met Trp Ser Leu  Met Tyr Phe
    3260                 3265                 3270

His Arg  Arg Asp Leu Arg Leu  Ala Ala Asn Ala Ile  Cys Ser Ala
```

```
    3275                3280                3285

Val Pro  Ser His Trp Val Pro  Thr Ser Arg Thr Thr  Trp Ser Ile
    3290                3295                3300

His Ala  Lys His Glu Trp Met  Thr Thr Glu Asp Met  Leu Thr Val
    3305                3310                3315

Trp Asn  Arg Val Trp Ile Gln  Glu Asn Pro Trp Met  Glu Asp Lys
    3320                3325                3330

Thr Pro  Val Glu Ser Trp Glu  Glu Ile Pro Tyr Leu  Gly Lys Arg
    3335                3340                3345

Glu Asp  Gln Trp Cys Gly Ser  Leu Ile Gly Leu Thr  Ser Arg Ala
    3350                3355                3360

Thr Trp  Ala Lys Asn Ile Gln  Ala Ala Ile Asn Gln  Val Arg Ser
    3365                3370                3375

Leu Ile  Gly Asn Glu Glu Tyr  Thr Asp Tyr Met Pro  Ser Met Lys
    3380                3385                3390

Arg Phe  Arg Arg Glu Glu Glu  Glu Ala Gly Val Leu  Trp
    3395                3400                3405


<210> SEQ ID NO 19
<211> LENGTH: 10768
<212> TYPE: DNA
<213> ORGANISM: Artificial Sequence
<220> FEATURE:
<223> OTHER INFORMATION: Synthetic construct

<400> SEQUENCE: 19

agttgttagt ctacgtggac cgacaaagac agattctttg agggagctaa gctcaacgta     60

gttctaacag tttttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatccg cgggtactag tgtcggaatt    420

gttggcctcc tgctgaccac agctatggca gcggaggtca ctagacgtgg gagtgcatac    480

tatatgtact tggacagaaa cgatgctggg gaggccatat cttttccaac cacattgggg    540

atgaataagt gttatataca gatcatggat cttggacaca tgtgtgatgc caccatgagc    600

tatgaatgcc ctatgctgga tgagggggtg gaaccagatg acgtcgattg ttggtgcaac    660

acgacgtcaa cttgggttgt gtacggaacc tgccatcaca aaaaaggtga agcacggaga    720

agtagaagag ctgtgacgct cccctcccat tccactagga agctgcaaac gcggtcgcaa    780

acctggttgg aatcaagaga atacacaaag cacttgatta gagtcgaaaa ttggatattc    840

aggaaccctg gcttcgcgtt agcagcagct gccatcgctt ggcttttggg aagctcaacg    900

agccaaaaag tcatatactt ggtcatgata ctgctgattg ccccggcata cagcatcagg    960

tgcataggag tcagcaatag ggactttgtg gaaggtatgt caggtgggac ttgggttgat   1020

attgtcttgg aacatggagg ttgtgtcacc gtaatggcac aggacaaacc gactgtcgac   1080

atagagctgg ttacaacaac agtcagcaac atggcggagg taagatccta ctgctatgag   1140

gcatcaatat cagacatggc ttcggacagc cgctgcccaa cacaaggtga agcctacctt   1200

gacaagcaat cagacactca atatgtctgc aaaagaacgt tagtggacag aggctgggga   1260

aatggatgtg gactttttgg caaagggagt ctggtgacat gcgctaagtt tgcatgctcc   1320
```

```
aagaaaatga ccgggaagag catccagcca gagaatctgg agtaccggat aatgctgtca   1380
gttcatggct cccagcacag tgggatgatc gttaatgaca caggacatga aactgatgag   1440
aatagagcga aggttgagat aacgcccaat tcaccaagag ccgaagccac cctgggggt    1500
tttggaagcc taggacttga ttgtgaaccg aggacaggcc ttgacttttc agatttgtat   1560
tacttgacta tgaataacaa gcactggttg gttcacaagg agtggttcca cgacattcca   1620
ttaccttggc acgctggggc agacaccgga actccacact ggaacaacaa agaagcactg   1680
gtagagttca aggacgcaca tgccaaaagg caaactgtcg tggttctagg gagtcaagaa   1740
ggagcagttc acacggccct tgctggagct ctggaggctg agatggatgg tgcaaaggga   1800
aggctgtcct ctggccactt gaaatgtcgc ctgaaaatgg ataaacttag attgaagggc   1860
gtgtcatact ccttgtgtac cgcagcgttc acattcacca agatcccggc tgaaacactg   1920
cacgggacag tcacagtgga ggtacagtac gcagggacag atggaccttg caaggttcca   1980
gctcagatgg cggtggacat gcaaactctg accccagttg ggaggttgat aaccgctaac   2040
cccgtaatca ctgaaagcac tgagaactct aagatgatgc tggaacttga tccaccattt   2100
ggggactctt acattgtcat aggagtcggg gagaagaaga tcacccacca ctggcacagg   2160
agtggcagca ccattggaaa agcatttgaa gccactgtga gaggtgccaa gagaatggca   2220
gtcttgggag acacagcctg ggactttgga tcagttggag gcgctctcaa ctcattgggc   2280
aagggcatcc atcaaatttt tggagcagct ttcaaatcat tgtttggagg aatgtcctgg   2340
ttctcaagaa ttctcattgg aacgttgctg atgtggttgg gtctgaacac aaagaatgga   2400
tctacttccc ttatgtgctt ggccgccggc tttgtgacac tgtatttggg ggtcatggtg   2460
caggccgata gtggttgcgt tgtgagctgg aaaaacaaag aactgaaatg tggcagtggg   2520
attttcatca cagacaacgt gcacacatgg acagaacaat acaagttcca accagaatcc   2580
ccttcaaaac tagcttcagc tatccagaaa gcccatgaag agggcatttg tggaatccgc   2640
tcagtaacaa gactggagaa tctgatgtgg aaacaaataa caccagaatt gaatcacatt   2700
ctatcagaaa atgaggtgaa gttaactatt atgacaggag acatcaaagg aatcatgcag   2760
gcaggaaaac gatctctgcg gcctcagccc actgagctga agtattcatg gaaaacatgg   2820
ggcaaagcaa aaatgctctc tacagagtct cataaccaga cctttctcat tgatggcccc   2880
gaaacagcag aatgccccaa cacaaataga gcttggaatt cgttggaagt tgaagactat   2940
ggctttggag tattcaccac caatatatgg ctaaaattga aagaaaaaca ggatgtattc   3000
tgcgactcaa aactcatgtc agcggccata aaagacaaca gagccgtcca tgccgatatg   3060
ggttattgga tagaaagtgc actcaatgac acatggaaga tagagaaagc ctctttcatt   3120
gaagttaaaa actgccactg gccaaaatca cacaccctct ggagcaatgg agtgctagaa   3180
agtgagatga taattccaaa gaatctcgct ggaccagtgt ctcaacacaa ctatagacca   3240
ggctaccata cacaaataac aggaccatgg catctaggta agcttgagat ggactttgat   3300
ttctgtgatg gaacaacagt ggtagtgact gaggactgcg gaaatagagg accctctttg   3360
agaacaacca ctgcctctgg aaaactcata acagaatggt gctgccgatc ttgcacatta   3420
ccaccgctaa gatacagagg tgaggatggg tgctggtacg ggatggaaat cagaccattg   3480
aaggagaaag aagagaattt ggtcaactcc ttggtcacag ctggacatgg gcaggtcgac   3540
aacttttcac taggagtctt gggaatggca ttgttcctgg aggaaatgct taggacccga   3600
gtaggaacga aacatgcaat actactagtt gcagtttctt ttgtgacatt gatcacaggg   3660
```

```
aacatgtcct ttagagacct gggaagagtg atggttatgg taggcgccac tatgacggat   3720
gacataggta tgggcgtgac ttatcttgcc ctactagcag ccttcaaagt cagaccaact   3780
tttgcagctg gactactctt gagaaagctg acctccaatg aattgatgat gactactata   3840
ggaattgtac tcctctccca gagcaccata ccagagacca ttcttgagtt gactgatgcg   3900
ttagccttag gcatgatggt cctcaaaatg gtgagaaata tggaaaagta tcaattggca   3960
gtgactatca tggctatctt gtgcgtccca aacgcagtga tattacaaaa cgcatggaaa   4020
gtgagttgca caatattggc agtggtgtcc gtttccccac tgctcttaac atcctcacag   4080
caaaaaacag attggatacc attagcattg acgatcaaag gtctcaatcc aacagctatt   4140
tttctaacaa ccctctcaag aaccagcaag aaaaggagct ggccattaaa tgaggctatc   4200
atggcagtcg ggatggtgag cattttagcc agttctctcc taaaaaatga tattcccatg   4260
acaggaccat tagtggctgg agggctcctc actgtgtgct acgtgctcac tggacgatcg   4320
gccgatttgg aactggagag agcagccgat gtcaaatggg aagaccaggc agagatatca   4380
ggaagcagtc caatcctgtc aataacaata tcagaagatg gtagcatgtc gataaaaaat   4440
gaagaggaag aacaaacact gaccatactc attagaacag gattgctggt gatctcagga   4500
ctttttcctg tatcaatacc aatcacggca gcagcatggt acctgtggga agtgaagaaa   4560
caacgggccg gagtattgtg ggatgttcct tcacccccac ccatgggaaa ggctgaactg   4620
gaagatggag cctatagaat taagcaaaaa gggattcttg gatattccca gatcggagcc   4680
ggagtttaca aagaaggaac attccataca atgtggcatg tcacacgtgg cgctgttcta   4740
atgcataaag gaaagaggat tgaaccatca tgggcggacg tcaagaaaga cctaatatca   4800
tatggaggag gctggaagtt agaaggagaa tggaaggaag gagaagaagt ccaggtattg   4860
gcactggagc ctggaaaaaa tccaagagcc gtccaaacga aacctggtct tttcaaaacc   4920
aacgccggaa caataggtgc tgtatctctg gacttttctc ctggaacgtc aggatctcca   4980
attatcgaca aaaaaggaaa agttgtgggt ctttatggta atggtgttgt tacaaggagt   5040
ggagcatatg tgagtgctat agcccagact gaaaaaagca ttgaagacaa cccagagatc   5100
gaagatgaca ttttccgaaa gagaagactg accatcatgg acctccaccc aggagcggga   5160
aagacgaaga gataccttcc ggccatagtc agagaagcta taaaacgggg tttgagaaca   5220
ttaatcttgg cccccactag agttgtggca gctgaaatgg aggaagccct tagaggactt   5280
ccaataagat accagacccc agccatcaga gctgagcaca ccgggcggga gattgtggac   5340
ctaatgtgtc atgccacatt taccatgagg ctgctatcac cagttagagt gccaaactac   5400
aacctgatta tcatggacga agcccatttc acagacccag caagtatagc agctagagga   5460
tacatctcaa ctcgagtgga gatgggtgag gcagctggga tttttatgac agccactccc   5520
ccgggaagca gagacccatt tcctcagagc aatgcaccaa tcatagatga agaaagagaa   5580
atccctgaac gttcgtggaa ttccggacat gaatgggtca cggattttaa agggaagact   5640
gtttggttcg ttccaagtat aaaagcagga aatgatatag cagcttgcct gaggaaaaat   5700
ggaaagaaag tgatacaact cagtaggaag acctttgatt ctgagtatgt caagactaga   5760
accaatgatt gggacttcgt ggttacaact gacatttcag aaatgggtgc caatttcaag   5820
gctgagaggg ttatagaccc cagacgctgc atgaaaccag tcatactaac agatggtgaa   5880
gagcgggtga ttctggcagg acctatgcca gtgacccact ctagtgcagc acaaagaaga   5940
gggagaatag gaagaaatcc aaaaaatgag aatgaccagt acatatacat gggggaacct   6000
ctggaaaatg atgaagactg tgcacactgg aaagaagcta aaatgctcct agataacatc   6060
```

```
aacacgccag aaggaatcat tcctagcatg ttcgaaccag agcgtgaaaa ggtggatgcc   6120
attgatggcg aataccgctt gagaggagaa gcaaggaaaa cctttgtaga cttaatgaga   6180
agaggagacc taccagtctg gttggcctac agagtggcag ctgaaggcat caactacgca   6240
gacagaaggt ggtgttttga tggagtcaag aacaaccaaa tcctagaaga aaacgtggaa   6300
gttgaaatct ggacaaaaga aggggaaagg aagaaattga aacccagatg gttggatgct   6360
aggatctatt ctgacccact ggcgctaaaa gaatttaagg aatttgcagc cggaagaaag   6420
tctctgaccc tgaacctaat cacagaaatg ggtaggctcc caaccttcat gactcagaag   6480
gcaagagacg cactggacaa cttagcagtg ctgcacacgg ctgaggcagg tggaagggcg   6540
tacaaccatg ctctcagtga actgccggag accctggaga cattgctttt actgacactt   6600
ctggctacag tcacgggagg gatcttttta ttcttgatga gcggaagggg catagggaag   6660
atgaccctgg gaatgtgctg cataatcacg gctagcatcc tcctatggta cgcacaaata   6720
cagccacact ggatagcagc ttcaataata ctggagtttt ttctcatagt tttgcttatt   6780
ccagaacctg aaaaacagag aacaccccaa gacaaccaac tgacctacgt tgtcatagcc   6840
atcctcacag tggtggccgc aaccatggca aacgagatgg gtttcctaga aaaaacgaag   6900
aaagatctcg gattgggaag cattgcaacc cagcaacccg agagcaacat cctggacata   6960
gatctacgtc ctgcatcagc atggacgctg tatgccgtgg ccacaacatt tgttacacca   7020
atgttgagac atagcattga aaattcctca gtgaatgtgt ccctaacagc tatagccaac   7080
caagccacag tgttaatggg tctcgggaaa ggatggccat tgtcaaagat ggacatcgga   7140
gttccccttc tcgccattgg atgctactca caagtcaacc ccataactct cacagcagct   7200
cttttcttat tggtagcaca ttatgccatc atagggccag gactccaagc aaaagcaacc   7260
agagaagctc agaaaagagc agcggcgggc atcatgaaaa acccaactgt cgatggaata   7320
acagtgattg acctagatcc aataccttat gatccaaagt ttgaaaagca gttgggacaa   7380
gtaatgctcc tagtcctctg cgtgactcaa gtattgatga tgaggactac atgggctctg   7440
tgtgaggctt taaccttagc taccgggccc atctccacat tgtgggaagg aaatccaggg   7500
aggttttgga acactaccat tgcggtgtca atggctaaca tttttagagg gagttacttg   7560
gccggagctg gacttctctt ttctattatg aagaacacaa ccaacacaag aaggggaact   7620
ggcaacatag gagagacgct tggagagaaa tggaaaagcc gattgaacgc attgggaaaa   7680
agtgaattcc agatctacaa gaaaagtgga atccaggaag tggatagaac cttagcaaaa   7740
gaaggcatta aaagaggaga aacggaccat cacgctgtgt cgcgaggctc agcaaaactg   7800
agatggttcg ttgagagaaa catggtcaca ccagaaggga aagtagtgga cctcggttgt   7860
ggcagaggag gctggtcata ctattgtgga ggactaaaga atgtaagaga agtcaaaggc   7920
ctaacaaaag gaggaccagg acacgaagaa cccatcccca tgtcaacata tgggtggaat   7980
ctagtgcgtc ttcaaagtgg agttgacgtt ttcttcatcc cgccagaaaa gtgtgacaca   8040
ttattgtgtg acatagggga gtcatcacca aatcccacag tggaagcagg acgaacactc   8100
agagtcctta acttagtaga aaattggttg aacaacaaca ctcaattttg cataaaggtt   8160
ctcaacccat atatgccctc agtcatagaa aaaatggaag cactacaaag gaaatatgga   8220
ggagccttag tgaggaatcc actctcacga aactccacac atgagatgta ctgggtatcc   8280
aatgcttccg ggaacatagt gtcatcagtg aacatgattt caaggatgtt gatcaacaga   8340
tttacaatga gatacaagaa agccacttac gagccggatg ttgacctcgg aagcggaacc   8400
```

-continued

```
cgtaacatcg ggattgaaag tgagatacca aacctagata taattgggaa aagaatagaa   8460
aaaataaagc aagagcatga aacatcatgg cactatgacc aagaccaccc atacaaaacg   8520
tgggcatacc atggtagcta tgaaacaaaa cagactggat cagcatcatc catggtcaac   8580
ggagtggtca ggctgctgac aaaaccttgg gacgtcgtcc ccatggtgac acagatggca   8640
atgacagaca cgactccatt tggacaacag cgcgttttta aagagaaagt ggacacgaga   8700
acccaagaac cgaaagaagg cacgaagaaa ctaatgaaaa taacagcaga gtggctttgg   8760
aaagaattag ggaagaaaaa gacacccagg atgtgcacca gagaagaatt cacaagaaag   8820
gtgagaagca atgcagcctt gggggccata ttcactgatg agaacaagtg gaagtcggca   8880
cgtgaggctg ttgaagatag taggttttgg gagctggttg acaaggaaag gaatctccat   8940
cttgaaggaa agtgtgaaac atgtgtgtac aacatgatgg gaaaaagaga gaagaagcta   9000
ggggaattcg gcaaggcaaa aggcagcaga gccatatggt acatgtggct tggagcacgc   9060
ttcttagagt ttgaagccct aggattctta aatgaagatc actggttctc cagagagaac   9120
tccctgagtg gagtggaagg agaagggctg cacaagctag gttacattct aagagacgtg   9180
agcaagaaag agggaggagc aatgtatgcc gatgacaccg caggatggga tacaagaatc   9240
acactagaag acctaaaaaa tgaagaaatg gtaacaaacc acatggaagg agaacacaag   9300
aaactagccg aggccatttt caaactaacg taccaaaaca aggtggtgcg tgtgcaaaga   9360
ccaacaccaa gaggcacagt aatggacatc atatcgagaa gagaccaaag aggtagtgga   9420
caagttggca cctatggact caatactttc accaatatgg aagcccaact aatcagacag   9480
atggagggag aaggagtctt taaaagcatt cagcacctaa caatcacaga agaaatcgct   9540
gtgcaaaact ggttagcaag agtggggcgc gaaaggttat caagaatggc catcagtgga   9600
gatgattgtg ttgtgaaacc tttagatgac aggttcgcaa gcgctttaac agctctaaat   9660
gacatgggaa agattaggaa agacatacaa caatgggaac cttcaagagg atggaatgat   9720
tggacacaag tgcccttctg ttcacaccat ttccatgagt taatcatgaa agacggtcgc   9780
gtactcgttg ttccatgtag aaaccaagat gaactgattg gcagagcccg aatctcccaa   9840
ggagcagggt ggtctttgcg ggagacggcc tgtttgggga agtcttacgc ccaaatgtgg   9900
agcttgatgt acttccacag acgcgacctc aggctggcgg caaatgctat ttgctcggca   9960
gtaccatcac attgggttcc aacaagtcga acaacctggt ccatacatgc taaacatgaa  10020
tggatgacaa cggaagacat gctgacagtc tggaacaggg tgtggattca agaaaaccca  10080
tggatggaag acaaaactcc agtggaatca tgggaggaaa tcccatactt ggggaaaaga  10140
gaagaccaat ggtgcggctc attgattggg ttaacaagca gggccacctg ggcaaagaac  10200
atccaagcag caataaatca agttagatcc cttataggca atgaagaata cacagattac  10260
atgccatcca tgaaaagatt cagaagagaa gaggaagaag caggagttct gtggtagaaa  10320
gcaaaactaa catgaaacaa ggctagaagt caggtcggat taagccatag tacggaaaaa  10380
actatgctac ctgtgagccc cgtccaagga cgttaaaaga agtcaggcca tcataaatgc  10440
catagcttga gtaaactatg cagcctgtag ctccacctga gaaggtgtaa aaaatccggg  10500
aggccacaaa ccatggaagc tgtacgcatg gcgtagtgga ctagcggtta gaggagaccc  10560
ctcccttaca aatcgcagca acaatggggg cccaaggcga gatgaagctg tagtctcgct  10620
ggaaggacta gaggttagag gagacccccc cgaaacaaaa aacagcatat tgacgctggg  10680
aaagaccaga gatcctgctg tctcctcagc atcattccag gcacagaacg ccagaaaatg  10740
gaatggtgct gttgaatcaa caggttct                                     10768
```

<210> SEQ ID NO 20
<211> LENGTH: 3406
<212> TYPE: PRT
<213> ORGANISM: Artificial Sequence
<220> FEATURE:
<223> OTHER INFORMATION: Synthetic polypeptide

<400> SEQUENCE: 20

Met Asn Asn Gln Arg Lys Lys Ala Lys Asn Thr Pro Phe Asn Met Leu
1 5 10 15

Lys Arg Glu Arg Asn Arg Val Ser Thr Val Gln Gln Leu Thr Lys Arg
20 25 30

Phe Ser Leu Gly Met Leu Gln Gly Arg Gly Pro Leu Lys Leu Phe Met
35 40 45

Ala Leu Val Ala Phe Leu Arg Phe Leu Thr Ile Pro Pro Thr Ala Gly
50 55 60

Ile Leu Lys Arg Trp Gly Thr Ile Lys Lys Ser Lys Ala Ile Asn Val
65 70 75 80

Leu Arg Gly Phe Arg Lys Glu Ile Gly Arg Met Leu Asn Ile Leu Asn
85 90 95

Arg Arg Arg Arg Ser Ala Gly Thr Ser Val Gly Ile Val Gly Leu Leu
100 105 110

Leu Thr Thr Ala Met Ala Ala Glu Val Thr Arg Arg Gly Ser Ala Tyr
115 120 125

Tyr Met Tyr Leu Asp Arg Asn Asp Ala Gly Glu Ala Ile Ser Phe Pro
130 135 140

Thr Thr Leu Gly Met Asn Lys Cys Tyr Ile Gln Ile Met Asp Leu Gly
145 150 155 160

His Met Cys Asp Ala Thr Met Ser Tyr Glu Cys Pro Met Leu Asp Glu
165 170 175

Gly Val Glu Pro Asp Asp Val Asp Cys Trp Cys Asn Thr Thr Ser Thr
180 185 190

Trp Val Val Tyr Gly Thr Cys His His Lys Lys Gly Glu Ala Arg Arg
195 200 205

Ser Arg Arg Ala Val Thr Leu Pro Ser His Ser Thr Arg Lys Leu Gln
210 215 220

Thr Arg Ser Gln Thr Trp Leu Glu Ser Arg Glu Tyr Thr Lys His Leu
225 230 235 240

Ile Arg Val Glu Asn Trp Ile Phe Arg Asn Pro Gly Phe Ala Leu Ala
245 250 255

Ala Ala Ala Ile Ala Trp Leu Leu Gly Ser Ser Thr Ser Gln Lys Val
260 265 270

Ile Tyr Leu Val Met Ile Leu Leu Ile Ala Pro Ala Tyr Ser Ile Arg
275 280 285

Cys Ile Gly Val Ser Asn Arg Asp Phe Val Glu Gly Met Ser Gly Gly
290 295 300

Thr Trp Val Asp Ile Val Leu Glu His Gly Gly Cys Val Thr Val Met
305 310 315 320

Ala Gln Asp Lys Pro Thr Val Asp Ile Glu Leu Val Thr Thr Thr Val
325 330 335

Ser Asn Met Ala Glu Val Arg Ser Tyr Cys Tyr Glu Ala Ser Ile Ser
340 345 350

Asp Met Ala Ser Asp Ser Arg Cys Pro Thr Gln Gly Glu Ala Tyr Leu
355 360 365

```
Asp Lys Gln Ser Asp Thr Gln Tyr Val Cys Lys Arg Thr Leu Val Asp
    370                 375                 380

Arg Gly Trp Gly Asn Gly Cys Gly Leu Phe Gly Lys Gly Ser Leu Val
385                 390                 395                 400

Thr Cys Ala Lys Phe Ala Cys Ser Lys Lys Met Thr Gly Lys Ser Ile
                405                 410                 415

Gln Pro Glu Asn Leu Glu Tyr Arg Ile Met Leu Ser Val His Gly Ser
            420                 425                 430

Gln His Ser Gly Met Ile Val Asn Asp Thr Gly His Glu Thr Asp Glu
        435                 440                 445

Asn Arg Ala Lys Val Glu Ile Thr Pro Asn Ser Pro Arg Ala Glu Ala
    450                 455                 460

Thr Leu Gly Gly Phe Gly Ser Leu Gly Leu Asp Cys Glu Pro Arg Thr
465                 470                 475                 480

Gly Leu Asp Phe Ser Asp Leu Tyr Tyr Leu Thr Met Asn Asn Lys His
                485                 490                 495

Trp Leu Val His Lys Glu Trp Phe His Asp Ile Pro Leu Pro Trp His
            500                 505                 510

Ala Gly Ala Asp Thr Gly Thr Pro His Trp Asn Asn Lys Glu Ala Leu
        515                 520                 525

Val Glu Phe Lys Asp Ala His Ala Lys Arg Gln Thr Val Val Val Leu
    530                 535                 540

Gly Ser Gln Glu Gly Ala Val His Thr Ala Leu Ala Gly Ala Leu Glu
545                 550                 555                 560

Ala Glu Met Asp Gly Ala Lys Gly Arg Leu Ser Ser Gly His Leu Lys
                565                 570                 575

Cys Arg Leu Lys Met Asp Lys Leu Arg Leu Lys Gly Val Ser Tyr Ser
            580                 585                 590

Leu Cys Thr Ala Ala Phe Thr Phe Thr Lys Ile Pro Ala Glu Thr Leu
        595                 600                 605

His Gly Thr Val Thr Val Glu Val Gln Tyr Ala Gly Thr Asp Gly Pro
    610                 615                 620

Cys Lys Val Pro Ala Gln Met Ala Val Asp Met Gln Thr Leu Thr Pro
625                 630                 635                 640

Val Gly Arg Leu Ile Thr Ala Asn Pro Val Ile Thr Glu Ser Thr Glu
                645                 650                 655

Asn Ser Lys Met Met Leu Glu Leu Asp Pro Pro Phe Gly Asp Ser Tyr
            660                 665                 670

Ile Val Ile Gly Val Gly Glu Lys Lys Ile Thr His His Trp His Arg
        675                 680                 685

Ser Gly Ser Thr Ile Gly Lys Ala Phe Glu Ala Thr Val Arg Gly Ala
    690                 695                 700

Lys Arg Met Ala Val Leu Gly Asp Thr Ala Trp Asp Phe Gly Ser Val
705                 710                 715                 720

Gly Gly Ala Leu Asn Ser Leu Gly Lys Gly Ile His Gln Ile Phe Gly
                725                 730                 735

Ala Ala Phe Lys Ser Leu Phe Gly Gly Met Ser Trp Phe Ser Arg Ile
            740                 745                 750

Leu Ile Gly Thr Leu Leu Met Trp Leu Gly Leu Asn Thr Lys Asn Gly
        755                 760                 765

Ser Thr Ser Leu Met Cys Leu Ala Ala Gly Phe Val Thr Leu Tyr Leu
    770                 775                 780
```

```
Gly Val Met Val Gln Ala Asp Ser Gly Cys Val Val Ser Trp Lys Asn
785                 790                 795                 800

Lys Glu Leu Lys Cys Gly Ser Gly Ile Phe Ile Thr Asp Asn Val His
                805                 810                 815

Thr Trp Thr Glu Gln Tyr Lys Phe Gln Pro Glu Ser Pro Ser Lys Leu
            820                 825                 830

Ala Ser Ala Ile Gln Lys Ala His Glu Glu Gly Ile Cys Gly Ile Arg
        835                 840                 845

Ser Val Thr Arg Leu Glu Asn Leu Met Trp Lys Gln Ile Thr Pro Glu
    850                 855                 860

Leu Asn His Ile Leu Ser Glu Asn Glu Val Lys Leu Thr Ile Met Thr
865                 870                 875                 880

Gly Asp Ile Lys Gly Ile Met Gln Ala Gly Lys Arg Ser Leu Arg Pro
                885                 890                 895

Gln Pro Thr Glu Leu Lys Tyr Ser Trp Lys Thr Trp Gly Lys Ala Lys
            900                 905                 910

Met Leu Ser Thr Glu Ser His Asn Gln Thr Phe Leu Ile Asp Gly Pro
        915                 920                 925

Glu Thr Ala Glu Cys Pro Asn Thr Asn Arg Ala Trp Asn Ser Leu Glu
    930                 935                 940

Val Glu Asp Tyr Gly Phe Gly Val Phe Thr Thr Asn Ile Trp Leu Lys
945                 950                 955                 960

Leu Lys Glu Lys Gln Asp Val Phe Cys Asp Ser Lys Leu Met Ser Ala
                965                 970                 975

Ala Ile Lys Asp Asn Arg Ala Val His Ala Asp Met Gly Tyr Trp Ile
            980                 985                 990

Glu Ser Ala Leu Asn Asp Thr Trp  Lys Ile Glu Lys Ala  Ser Phe Ile
        995                 1000                 1005

Glu Val  Lys Asn Cys His Trp  Pro Lys Ser His Thr  Leu Trp Ser
    1010                 1015                 1020

Asn Gly  Val Leu Glu Ser Glu  Met Ile Ile Pro Lys  Asn Leu Ala
    1025                 1030                 1035

Gly Pro  Val Ser Gln His Asn  Tyr Arg Pro Gly Tyr  His Thr Gln
    1040                 1045                 1050

Ile Thr  Gly Pro Trp His Leu  Gly Lys Leu Glu Met  Asp Phe Asp
    1055                 1060                 1065

Phe Cys  Asp Gly Thr Thr Val  Val Val Thr Glu Asp  Cys Gly Asn
    1070                 1075                 1080

Arg Gly  Pro Ser Leu Arg Thr  Thr Thr Ala Ser Gly  Lys Leu Ile
    1085                 1090                 1095

Thr Glu  Trp Cys Cys Arg Ser  Cys Thr Leu Pro Pro  Leu Arg Tyr
    1100                 1105                 1110

Arg Gly  Glu Asp Gly Cys Trp  Tyr Gly Met Glu Ile  Arg Pro Leu
    1115                 1120                 1125

Lys Glu  Lys Glu Glu Asn Leu  Val Asn Ser Leu Val  Thr Ala Gly
    1130                 1135                 1140

His Gly  Gln Val Asp Asn Phe  Ser Leu Gly Val Leu  Gly Met Ala
    1145                 1150                 1155

Leu Phe  Leu Glu Glu Met Leu  Arg Thr Arg Val Gly  Thr Lys His
    1160                 1165                 1170

Ala Ile  Leu Leu Val Ala Val  Ser Phe Val Thr Leu  Ile Thr Gly
    1175                 1180                 1185

Asn Met  Ser Phe Arg Asp Leu  Gly Arg Val Met Val  Met Val Gly
```

```
    1190                1195                1200

Ala Thr  Met Thr Asp Asp Ile  Gly Met Gly Val Thr  Tyr Leu Ala
    1205                1210                1215

Leu Leu  Ala Ala Phe Lys Val  Arg Pro Thr Phe Ala  Ala Gly Leu
    1220                1225                1230

Leu Leu  Arg Lys Leu Thr Ser  Asn Glu Leu Met Met  Thr Thr Ile
    1235                1240                1245

Gly Ile  Val Leu Leu Ser Gln  Ser Thr Ile Pro Glu  Thr Ile Leu
    1250                1255                1260

Glu Leu  Thr Asp Ala Leu Ala  Leu Gly Met Met Val  Leu Lys Met
    1265                1270                1275

Val Arg  Asn Met Glu Lys Tyr  Gln Leu Ala Val Thr  Ile Met Ala
    1280                1285                1290

Ile Leu  Cys Val Pro Asn Ala  Val Ile Leu Gln Asn  Ala Trp Lys
    1295                1300                1305

Val Ser  Cys Thr Ile Leu Ala  Val Val Ser Val Ser  Pro Leu Leu
    1310                1315                1320

Leu Thr  Ser Ser Gln Gln Lys  Thr Asp Trp Ile Pro  Leu Ala Leu
    1325                1330                1335

Thr Ile  Lys Gly Leu Asn Pro  Thr Ala Ile Phe Leu  Thr Thr Leu
    1340                1345                1350

Ser Arg  Thr Ser Lys Lys Arg  Ser Trp Pro Leu Asn  Glu Ala Ile
    1355                1360                1365

Met Ala  Val Gly Met Val Ser  Ile Leu Ala Ser Ser  Leu Leu Lys
    1370                1375                1380

Asn Asp  Ile Pro Met Thr Gly  Pro Leu Val Ala Gly  Gly Leu Leu
    1385                1390                1395

Thr Val  Cys Tyr Val Leu Thr  Gly Arg Ser Ala Asp  Leu Glu Leu
    1400                1405                1410

Glu Arg  Ala Ala Asp Val Lys  Trp Glu Asp Gln Ala  Glu Ile Ser
    1415                1420                1425

Gly Ser  Ser Pro Ile Leu Ser  Ile Thr Ile Ser Glu  Asp Gly Ser
    1430                1435                1440

Met Ser  Ile Lys Asn Glu Glu  Glu Glu Gln Thr Leu  Thr Ile Leu
    1445                1450                1455

Ile Arg  Thr Gly Leu Leu Val  Ile Ser Gly Leu Phe  Pro Val Ser
    1460                1465                1470

Ile Pro  Ile Thr Ala Ala Ala  Trp Tyr Leu Trp Glu  Val Lys Lys
    1475                1480                1485

Gln Arg  Ala Gly Val Leu Trp  Asp Val Pro Ser Pro  Pro Pro Met
    1490                1495                1500

Gly Lys  Ala Glu Leu Glu Asp  Gly Ala Tyr Arg Ile  Lys Gln Lys
    1505                1510                1515

Gly Ile  Leu Gly Tyr Ser Gln  Ile Gly Ala Gly Val  Tyr Lys Glu
    1520                1525                1530

Gly Thr  Phe His Thr Met Trp  His Val Thr Arg Gly  Ala Val Leu
    1535                1540                1545

Met His  Lys Gly Lys Arg Ile  Glu Pro Ser Trp Ala  Asp Val Lys
    1550                1555                1560

Lys Asp  Leu Ile Ser Tyr Gly  Gly Gly Trp Lys Leu  Glu Gly Glu
    1565                1570                1575

Trp Lys  Glu Gly Glu Glu Val  Gln Val Leu Ala Leu  Glu Pro Gly
    1580                1585                1590
```

```
Lys Asn  Pro Arg Ala Val Gln  Thr Lys Pro Gly Leu  Phe Lys Thr
    1595                 1600                 1605

Asn Ala  Gly Thr Ile Gly Ala  Val Ser Leu Asp Phe  Ser Pro Gly
    1610                 1615                 1620

Thr Ser  Gly Ser Pro Ile Ile  Asp Lys Lys Gly Lys  Val Val Gly
    1625                 1630                 1635

Leu Tyr  Gly Asn Gly Val Val  Thr Arg Ser Gly Ala  Tyr Val Ser
    1640                 1645                 1650

Ala Ile  Ala Gln Thr Glu Lys  Ser Ile Glu Asp Asn  Pro Glu Ile
    1655                 1660                 1665

Glu Asp  Asp Ile Phe Arg Lys  Arg Arg Leu Thr Ile  Met Asp Leu
    1670                 1675                 1680

His Pro  Gly Ala Gly Lys Thr  Lys Arg Tyr Leu Pro  Ala Ile Val
    1685                 1690                 1695

Arg Glu  Ala Ile Lys Arg Gly  Leu Arg Thr Leu Ile  Leu Ala Pro
    1700                 1705                 1710

Thr Arg  Val Val Ala Ala Glu  Met Glu Glu Ala Leu  Arg Gly Leu
    1715                 1720                 1725

Pro Ile  Arg Tyr Gln Thr Pro  Ala Ile Arg Ala Glu  His Thr Gly
    1730                 1735                 1740

Arg Glu  Ile Val Asp Leu Met  Cys His Ala Thr Phe  Thr Met Arg
    1745                 1750                 1755

Leu Leu  Ser Pro Val Arg Val  Pro Asn Tyr Asn Leu  Ile Ile Met
    1760                 1765                 1770

Asp Glu  Ala His Phe Thr Asp  Pro Ala Ser Ile Ala  Ala Arg Gly
    1775                 1780                 1785

Tyr Ile  Ser Thr Arg Val Glu  Met Gly Glu Ala Ala  Gly Ile Phe
    1790                 1795                 1800

Met Thr  Ala Thr Pro Pro Gly  Ser Arg Asp Pro Phe  Pro Gln Ser
    1805                 1810                 1815

Asn Ala  Pro Ile Ile Asp Glu  Glu Arg Glu Ile Pro  Glu Arg Ser
    1820                 1825                 1830

Trp Asn  Ser Gly His Glu Trp  Val Thr Asp Phe Lys  Gly Lys Thr
    1835                 1840                 1845

Val Trp  Phe Val Pro Ser Ile  Lys Ala Gly Asn Asp  Ile Ala Ala
    1850                 1855                 1860

Cys Leu  Arg Lys Asn Gly Lys  Lys Val Ile Gln Leu  Ser Arg Lys
    1865                 1870                 1875

Thr Phe  Asp Ser Glu Tyr Val  Lys Thr Arg Thr Asn  Asp Trp Asp
    1880                 1885                 1890

Phe Val  Val Thr Thr Asp Ile  Ser Glu Met Gly Ala  Asn Phe Lys
    1895                 1900                 1905

Ala Glu  Arg Val Ile Asp Pro  Arg Arg Cys Met Lys  Pro Val Ile
    1910                 1915                 1920

Leu Thr  Asp Gly Glu Glu Arg  Val Ile Leu Ala Gly  Pro Met Pro
    1925                 1930                 1935

Val Thr  His Ser Ser Ala Ala  Gln Arg Arg Gly Arg  Ile Gly Arg
    1940                 1945                 1950

Asn Pro  Lys Asn Glu Asn Asp  Gln Tyr Ile Tyr Met  Gly Glu Pro
    1955                 1960                 1965

Leu Glu  Asn Asp Glu Asp Cys  Ala His Trp Lys Glu  Ala Lys Met
    1970                 1975                 1980
```

```
Leu Leu  Asp Asn Ile Asn Thr  Pro Glu Gly Ile Ile  Pro Ser Met
    1985                 1990                 1995

Phe Glu  Pro Glu Arg Glu Lys  Val Asp Ala Ile Asp  Gly Glu Tyr
    2000                 2005                 2010

Arg Leu  Arg Gly Glu Ala Arg  Lys Thr Phe Val Asp  Leu Met Arg
    2015                 2020                 2025

Arg Gly  Asp Leu Pro Val Trp  Leu Ala Tyr Arg Val  Ala Ala Glu
    2030                 2035                 2040

Gly Ile  Asn Tyr Ala Asp Arg  Arg Trp Cys Phe Asp  Gly Val Lys
    2045                 2050                 2055

Asn Asn  Gln Ile Leu Glu Glu  Asn Val Glu Val Glu  Ile Trp Thr
    2060                 2065                 2070

Lys Glu  Gly Glu Arg Lys Lys  Leu Lys Pro Arg Trp  Leu Asp Ala
    2075                 2080                 2085

Arg Ile  Tyr Ser Asp Pro Leu  Ala Leu Lys Glu Phe  Lys Glu Phe
    2090                 2095                 2100

Ala Ala  Gly Arg Lys Ser Leu  Thr Leu Asn Leu Ile  Thr Glu Met
    2105                 2110                 2115

Gly Arg  Leu Pro Thr Phe Met  Thr Gln Lys Ala Arg  Asp Ala Leu
    2120                 2125                 2130

Asp Asn  Leu Ala Val Leu His  Thr Ala Glu Ala Gly  Gly Arg Ala
    2135                 2140                 2145

Tyr Asn  His Ala Leu Ser Glu  Leu Pro Glu Thr Leu  Glu Thr Leu
    2150                 2155                 2160

Leu Leu  Leu Thr Leu Leu Ala  Thr Val Thr Gly Gly  Ile Phe Leu
    2165                 2170                 2175

Phe Leu  Met Ser Gly Arg Gly  Ile Gly Lys Met Thr  Leu Gly Met
    2180                 2185                 2190

Cys Cys  Ile Ile Thr Ala Ser  Ile Leu Leu Trp Tyr  Ala Gln Ile
    2195                 2200                 2205

Gln Pro  His Trp Ile Ala Ala  Ser Ile Ile Leu Glu  Phe Phe Leu
    2210                 2215                 2220

Ile Val  Leu Leu Ile Pro Glu  Pro Glu Lys Gln Arg  Thr Pro Gln
    2225                 2230                 2235

Asp Asn  Gln Leu Thr Tyr Val  Val Ile Ala Ile Leu  Thr Val Val
    2240                 2245                 2250

Ala Ala  Thr Met Ala Asn Glu  Met Gly Phe Leu Glu  Lys Thr Lys
    2255                 2260                 2265

Lys Asp  Leu Gly Leu Gly Ser  Ile Ala Thr Gln Gln  Pro Glu Ser
    2270                 2275                 2280

Asn Ile  Leu Asp Ile Asp Leu  Arg Pro Ala Ser Ala  Trp Thr Leu
    2285                 2290                 2295

Tyr Ala  Val Ala Thr Thr Phe  Val Thr Pro Met Leu  Arg His Ser
    2300                 2305                 2310

Ile Glu  Asn Ser Ser Val Asn  Val Ser Leu Thr Ala  Ile Ala Asn
    2315                 2320                 2325

Gln Ala  Thr Val Leu Met Gly  Leu Gly Lys Gly Trp  Pro Leu Ser
    2330                 2335                 2340

Lys Met  Asp Ile Gly Val Pro  Leu Leu Ala Ile Gly  Cys Tyr Ser
    2345                 2350                 2355

Gln Val  Asn Pro Ile Thr Leu  Thr Ala Ala Leu Phe  Leu Leu Val
    2360                 2365                 2370

Ala His  Tyr Ala Ile Ile Gly  Pro Gly Leu Gln Ala  Lys Ala Thr
```

```
    2375                2380                2385

Arg Glu  Ala Gln Lys Arg Ala  Ala Ala Gly Ile Met  Lys Asn Pro
    2390                2395                2400

Thr Val  Asp Gly Ile Thr Val  Ile Asp Leu Asp Pro  Ile Pro Tyr
    2405                2410                2415

Asp Pro  Lys Phe Glu Lys Gln  Leu Gly Gln Val Met  Leu Leu Val
    2420                2425                2430

Leu Cys  Val Thr Gln Val Leu  Met Met Arg Thr Thr  Trp Ala Leu
    2435                2440                2445

Cys Glu  Ala Leu Thr Leu Ala  Thr Gly Pro Ile Ser  Thr Leu Trp
    2450                2455                2460

Glu Gly  Asn Pro Gly Arg Phe  Trp Asn Thr Thr Ile  Ala Val Ser
    2465                2470                2475

Met Ala  Asn Ile Phe Arg Gly  Ser Tyr Leu Ala Gly  Ala Gly Leu
    2480                2485                2490

Leu Phe  Ser Ile Met Lys Asn  Thr Thr Asn Thr Arg  Arg Gly Thr
    2495                2500                2505

Gly Asn  Ile Gly Glu Thr Leu  Gly Glu Lys Trp Lys  Ser Arg Leu
    2510                2515                2520

Asn Ala  Leu Gly Lys Ser Glu  Phe Gln Ile Tyr Lys  Lys Ser Gly
    2525                2530                2535

Ile Gln  Glu Val Asp Arg Thr  Leu Ala Lys Glu Gly  Ile Lys Arg
    2540                2545                2550

Gly Glu  Thr Asp His His Ala  Val Ser Arg Gly Ser  Ala Lys Leu
    2555                2560                2565

Arg Trp  Phe Val Glu Arg Asn  Met Val Thr Pro Glu  Gly Lys Val
    2570                2575                2580

Val Asp  Leu Gly Cys Gly Arg  Gly Gly Trp Ser Tyr  Tyr Cys Gly
    2585                2590                2595

Gly Leu  Lys Asn Val Arg Glu  Val Lys Gly Leu Thr  Lys Gly Gly
    2600                2605                2610

Pro Gly  His Glu Glu Pro Ile  Pro Met Ser Thr Tyr  Gly Trp Asn
    2615                2620                2625

Leu Val  Arg Leu Gln Ser Gly  Val Asp Val Phe Phe  Ile Pro Pro
    2630                2635                2640

Glu Lys  Cys Asp Thr Leu Leu  Cys Asp Ile Gly Glu  Ser Ser Pro
    2645                2650                2655

Asn Pro  Thr Val Glu Ala Gly  Arg Thr Leu Arg Val  Leu Asn Leu
    2660                2665                2670

Val Glu  Asn Trp Leu Asn Asn  Asn Thr Gln Phe Cys  Ile Lys Val
    2675                2680                2685

Leu Asn  Pro Tyr Met Pro Ser  Val Ile Glu Lys Met  Glu Ala Leu
    2690                2695                2700

Gln Arg  Lys Tyr Gly Gly Ala  Leu Val Arg Asn Pro  Leu Ser Arg
    2705                2710                2715

Asn Ser  Thr His Glu Met Tyr  Trp Val Ser Asn Ala  Ser Gly Asn
    2720                2725                2730

Ile Val  Ser Ser Val Asn Met  Ile Ser Arg Met Leu  Ile Asn Arg
    2735                2740                2745

Phe Thr  Met Arg Tyr Lys Lys  Ala Thr Tyr Glu Pro  Asp Val Asp
    2750                2755                2760

Leu Gly  Ser Gly Thr Arg Asn  Ile Gly Ile Glu Ser  Glu Ile Pro
    2765                2770                2775
```

```
Asn Leu  Asp Ile Ile Gly Lys  Arg Ile Glu Lys Ile  Lys Gln Glu
    2780                 2785                 2790

His Glu  Thr Ser Trp His Tyr  Asp Gln Asp His Pro  Tyr Lys Thr
    2795                 2800                 2805

Trp Ala  Tyr His Gly Ser Tyr  Glu Thr Lys Gln Thr  Gly Ser Ala
    2810                 2815                 2820

Ser Ser  Met Val Asn Gly Val  Val Arg Leu Leu Thr  Lys Pro Trp
    2825                 2830                 2835

Asp Val  Val Pro Met Val Thr  Gln Met Ala Met Thr  Asp Thr Thr
    2840                 2845                 2850

Pro Phe  Gly Gln Gln Arg Val  Phe Lys Glu Lys Val  Asp Thr Arg
    2855                 2860                 2865

Thr Gln  Glu Pro Lys Glu Gly  Thr Lys Lys Leu Met  Lys Ile Thr
    2870                 2875                 2880

Ala Glu  Trp Leu Trp Lys Glu  Leu Gly Lys Lys Lys  Thr Pro Arg
    2885                 2890                 2895

Met Cys  Thr Arg Glu Glu Phe  Thr Arg Lys Val Arg  Ser Asn Ala
    2900                 2905                 2910

Ala Leu  Gly Ala Ile Phe Thr  Asp Glu Asn Lys Trp  Lys Ser Ala
    2915                 2920                 2925

Arg Glu  Ala Val Glu Asp Ser  Arg Phe Trp Glu Leu  Val Asp Lys
    2930                 2935                 2940

Glu Arg  Asn Leu His Leu Glu  Gly Lys Cys Glu Thr  Cys Val Tyr
    2945                 2950                 2955

Asn Met  Met Gly Lys Arg Glu  Lys Lys Leu Gly Glu  Phe Gly Lys
    2960                 2965                 2970

Ala Lys  Gly Ser Arg Ala Ile  Trp Tyr Met Trp Leu  Gly Ala Arg
    2975                 2980                 2985

Phe Leu  Glu Phe Glu Ala Leu  Gly Phe Leu Asn Glu  Asp His Trp
    2990                 2995                 3000

Phe Ser  Arg Glu Asn Ser Leu  Ser Gly Val Glu Gly  Glu Gly Leu
    3005                 3010                 3015

His Lys  Leu Gly Tyr Ile Leu  Arg Asp Val Ser Lys  Lys Glu Gly
    3020                 3025                 3030

Gly Ala  Met Tyr Ala Asp Asp  Thr Ala Gly Trp Asp  Thr Arg Ile
    3035                 3040                 3045

Thr Leu  Glu Asp Leu Lys Asn  Glu Glu Met Val Thr  Asn His Met
    3050                 3055                 3060

Glu Gly  Glu His Lys Lys Leu  Ala Glu Ala Ile Phe  Lys Leu Thr
    3065                 3070                 3075

Tyr Gln  Asn Lys Val Val Arg  Val Gln Arg Pro Thr  Pro Arg Gly
    3080                 3085                 3090

Thr Val  Met Asp Ile Ile Ser  Arg Arg Asp Gln Arg  Gly Ser Gly
    3095                 3100                 3105

Gln Val  Gly Thr Tyr Gly Leu  Asn Thr Phe Thr Asn  Met Glu Ala
    3110                 3115                 3120

Gln Leu  Ile Arg Gln Met Glu  Gly Glu Gly Val Phe  Lys Ser Ile
    3125                 3130                 3135

Gln His  Leu Thr Ile Thr Glu  Glu Ile Ala Val Gln  Asn Trp Leu
    3140                 3145                 3150

Ala Arg  Val Gly Arg Glu Arg  Leu Ser Arg Met Ala  Ile Ser Gly
    3155                 3160                 3165
```

```
Asp Asp  Cys Val Val Lys Pro  Leu Asp Asp Arg Phe  Ala Ser Ala
    3170                 3175                 3180

Leu Thr  Ala Leu Asn Asp Met  Gly Lys Ile Arg Lys  Asp Ile Gln
    3185                 3190                 3195

Gln Trp  Glu Pro Ser Arg Gly  Trp Asn Asp Trp Thr  Gln Val Pro
    3200                 3205                 3210

Phe Cys  Ser His His Phe His  Glu Leu Ile Met Lys  Asp Gly Arg
    3215                 3220                 3225

Val Leu  Val Val Pro Cys Arg  Asn Gln Asp Glu Leu  Ile Gly Arg
    3230                 3235                 3240

Ala Arg  Ile Ser Gln Gly Ala  Gly Trp Ser Leu Arg  Glu Thr Ala
    3245                 3250                 3255

Cys Leu  Gly Lys Ser Tyr Ala  Gln Met Trp Ser Leu  Met Tyr Phe
    3260                 3265                 3270

His Arg  Arg Asp Leu Arg Leu  Ala Ala Asn Ala Ile  Cys Ser Ala
    3275                 3280                 3285

Val Pro  Ser His Trp Val Pro  Thr Ser Arg Thr Thr  Trp Ser Ile
    3290                 3295                 3300

His Ala  Lys His Glu Trp Met  Thr Thr Glu Asp Met  Leu Thr Val
    3305                 3310                 3315

Trp Asn  Arg Val Trp Ile Gln  Glu Asn Pro Trp Met  Glu Asp Lys
    3320                 3325                 3330

Thr Pro  Val Glu Ser Trp Glu  Glu Ile Pro Tyr Leu  Gly Lys Arg
    3335                 3340                 3345

Glu Asp  Gln Trp Cys Gly Ser  Leu Ile Gly Leu Thr  Ser Arg Ala
    3350                 3355                 3360

Thr Trp  Ala Lys Asn Ile Gln  Ala Ala Ile Asn Gln  Val Arg Ser
    3365                 3370                 3375

Leu Ile  Gly Asn Glu Glu Tyr  Thr Asp Tyr Met Pro  Ser Met Lys
    3380                 3385                 3390

Arg Phe  Arg Arg Glu Glu Glu  Glu Ala Gly Val Leu  Trp
    3395                 3400                 3405
```

<210> SEQ ID NO 21
<211> LENGTH: 10768
<212> TYPE: DNA
<213> ORGANISM: Artificial Sequence
<220> FEATURE:
<223> OTHER INFORMATION: Synthetic construct

<400> SEQUENCE: 21

```
agttgttagt ctacgtggac cgacaaagac agattctttg agggagctaa gctcaatgta     60

gttctaacag ttttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatccg cgggtactag tgtcggaatt    420

gttggcctcc tgctgaccac agctatggca gcggaggtca ctagacgtgg gagtgcatac    480

tatatgtact tggacagaaa cgatgctggg gaggccatat cttttccaac cacattgggg    540

atgaataagt gttatataca gatcatggat cttggacaca tgtgtgatgc caccatgagc    600

tatgaatgcc ctatgctgga tgagggggtg gaaccagatg acgtcgattg ttggtgcaac    660
```

```
acgacgtcaa cttgggttgt gtacggaacc tgccatcaca aaaaaggtga agcacggaga    720
agtagaagag ctgtgacgct cccctcccat tccactagga agctgcaaac gcggtcgcaa    780
acctggttgg aatcaagaga atacacaaag cacttgatta gagtcgaaaa ttggatattc    840
aggaaccctg gcttcgcgtt agcagcagct gccatcgctt ggcttttggg aagctcaacg    900
agccaaaaag tcatatactt ggtcatgata ctgctgattg ccccggcata cagcatcagg    960
tgcataggag tcagcaatag ggactttgtg gaaggtatgt caggtgggac ttgggttgat   1020
attgtcttgg aacatggagg ttgtgtcacc gtaatggcac aggacaaacc gactgtcgac   1080
atagagctgg ttacaacaac agtcagcaac atggcggagg taagatccta ctgctatgag   1140
gcatcaatat cagacatggc ttcggacagc cgctgcccaa cacaaggtga agcctacctt   1200
gacaagcaat cagacactca atatgtctgc aaaagaacgt tagtggacag aggctgggga   1260
aatggatgtg gactttttgg caaagggagt ctggtgacat gcgctaagtt tgcatgctcc   1320
aagaaaatga ccgggaagag catccagcca gagaatctgg agtaccggat aatgctgtca   1380
gttcatggct cccagcacag tgggatgatc gttaatgaca caggacatga aactgatgag   1440
aatagagcga aggttgagat aacgcccaat tcaccaagag ccgaagccac cctggggggt   1500
tttggaagcc taggacttga ttgtgaaccg aggacaggcc ttgacttttc agatttgtat   1560
tacttgacta tgaataacaa gcactggttg gttcacaagg agtggttcca cgacattcca   1620
ttaccttggc acgctggggc agacaccgga actccacact ggaacaacaa agaagcactg   1680
gtagagttca aggacgcaca tgccaaaagg caaactgtcg tggttctagg gagtcaagaa   1740
ggagcagttc acacggccct tgctggagct ctggaggctg agatggatgg tgcaaaggga   1800
aggctgtcct ctggccactt gaaatgtcgc ctgaaaatgg ataaacttag attgaagggc   1860
gtgtcatact ccttgtgtac cgcagcgttc acattcacca agatcccggc tgaaacactg   1920
cacgggacag tcacagtgga ggtacagtac gcagggacag atggaccttg caaggttcca   1980
gctcagatgg cggtggacat gcaaactctg accccagttg ggaggttgat aaccgctaac   2040
cccgtaatca ctgaaagcac tgagaactct aagatgatgc tggaacttga tccaccattt   2100
ggggactctt acattgtcat aggagtcggg gagaagaaga tcacccacca ctggcacagg   2160
agtggcagca ccattggaaa agcatttgaa gccactgtga gaggtgccaa gagaatggca   2220
gtcttgggag acacagcctg ggactttgga tcagttggag gcgctctcaa ctcattgggc   2280
aagggcatcc atcaaatttt tggagcagct ttcaaatcat tgtttggagg aatgtcctgg   2340
ttctcaagaa ttctcattgg aacgttgctg atgtggttgg gtctgaacac aaagaatgga   2400
tctacttccc ttatgtgctt ggccgccggc tttgtgacac tgtatttggg agtcatggtg   2460
caggccgata gtggttgcgt tgtgagctgg aaaaacaaag aactgaaatg tggcagtggg   2520
attttcatca cagacaacgt gcacacatgg acagaacaat acaagttcca accagaatcc   2580
ccttcaaaac tagcttcagc tatccagaaa gcccatgaag aggacatttg tggaatccgc   2640
tcagtaacaa gactggagaa tctgatgtgg aaacaaataa caccagaatt gaatcacatt   2700
ctatcagaaa atgaggtgaa gttaactatt atgacaggag acatcaaagg aatcatgcag   2760
gcaggaaaac gatctctgcg gcctcagccc actgagctga agtattcatg gaaaacatgg   2820
ggcaaagcaa aaatgctctc tacagagtct cataaccaga cctttctcat tgatggcccc   2880
gaaacagcag aatgccccaa cacaaataga gcttggaatt cgttggaagt tgaagactat   2940
ggctttggag tattcaccac caatatatgg ctaaaattga aagaaaaaca ggatgtattc   3000
```

```
tgcgactcaa aactcatgtc agcggccata aaagacaaca gagccgtcca tgccgatatg   3060
ggttattgga tagaaagtgc actcaatgac acatggaaga tagagaaagc ctctttcatt   3120
gaagttaaaa actgccactg gccaaaatca cacaccctct ggagcaatgg agtgctagaa   3180
agtgagatga taattccaaa gaatctcgct ggaccagtgt ctcaacacaa ctatagacca   3240
ggctaccata cacaaataac aggaccatgg catctaggta agcttgagat ggactttgat   3300
ttctgtgatg gaacaacagt ggtagtgact gaggactgcg gaaatagagg accctctttg   3360
agaacaacca ctgcctctgg aaaactcata acagaatggt gctgccgatc ttgcacatta   3420
ccaccgctaa gatacagagg tgaggatggg tgctggtacg ggatggaaat cagaccattg   3480
aaggagaaag aagagaattt ggtcaactcc ttggtcacag ctggacatgg gcaggtcgac   3540
aacttttcac taggagtctt gggaatggca ttgttcctgg aggaaatgct taggacccga   3600
gtaggaacga aacatgcaat actactagtt gcagtttctt ttgtgacatt gatcacaggg   3660
aacatgtcct ttagagacct gggaagagtg atggttatgg taggcgccac tatgacggat   3720
gacataggta tgggcgtgac ttatcttgcc ctactagcag ccttcaaagt cagaccaact   3780
tttgcagctg gactactctt gagaaagctg acctccaatg aattgatgat gactactata   3840
ggaattgtac tcctctccca gagcaccata ccagagacca ttcttgagtt gactgatgcg   3900
ttagccttag gcatgatggt cctcaaaatg gtgagaaata tggaaaagta tcaattggca   3960
gtgactatca tggctatctt gtgcgtccca aacgcagtga tattacaaaa cgcatggaaa   4020
gtgagttgca caatattggc agtggtgtcc gtttccccac tgttcttaac atcctcacag   4080
caaaaaacag attggatacc attagcattg acgatcaaag gtctcaatcc aacagctatt   4140
tttctaacaa ccctctcaag aaccagcaag aaaaggagct ggccattaaa tgaggctatc   4200
atggcagtcg ggatggtgag cattttagcc agttctctcc taaaaaatga tattcccatg   4260
acaggaccat tagtggctgg agggctcctc actgtgtgct acgtgctcac tggacgatcg   4320
gccgatttgg aactggagag agcagccgat gtcaaatggg aagaccaggc agagatatca   4380
ggaagcagtc caatcctgtc aataacaata tcagaagatg gtagcatgtc gataaaaaat   4440
gaagaggaag aacaaacact gaccatactc attagaacag gattgctggt gatctcagga   4500
ctttttcctg tatcaatacc aatcacggca gcagcatggt acctgtggga agtgaagaaa   4560
caacgggccg gagtattgtg ggatgttcct tcacccccac ccatgggaaa ggctgaactg   4620
gaagatggag cctatagaat taagcaaaaa gggattcttg gatattccca gatcggagcc   4680
ggagtttaca aagaaggaac attccataca atgtggcatg tcacacgtgg cgctgttcta   4740
atgcataaag gaaagaggat tgaaccatca tgggcggacg tcaagaaaga cctaatatca   4800
tatggaggag gctggaagtt agaaggagaa tggaaggaag gagaagaagt ccaggtattg   4860
gcactggagc ctggaaaaaa tccaagagcc gtccaaacga aacctggtct tttcaaaacc   4920
aacgccggaa caataggtgc tgtatctctg gacttttctc ctggaacgtc aggatctcca   4980
attatcgaca aaaaaggaaa agttgtgggt ctttatggta atggtgttgt tacaaggagt   5040
ggagcatatg tgagtgctat agcccagact gaaaaaagca ttgaagacaa cccagagatc   5100
gaagatgaca ttttccgaaa gagaagactg accatcatgg acctccaccc aggagcggga   5160
aagacgaaga gataccttcc ggccatagtc agagaagcta taaaacgggg tttgagaaca   5220
ttaatcttgg cccccactag agttgtggca gctgaaatgg aggaagccct tagaggactt   5280
ccaataagat accagacccc agccatcaga gctgtgcaca ccgggcggga gattgtggac   5340
ctaatgtgtc atgccacatt taccatgagg ctgctatcac cagttagagt gccaaactac   5400
```

```
aacctgatta tcatggacga agcccatttc acagacccag caagtatagc agctagagga   5460
tacatctcaa ctcgagtgga gatgggtgag gcagctggga tttttatgac agccactccc   5520
ccgggaagca gagacccatt tcctcagagc aatgcaccaa tcatagatga agaaagagaa   5580
atccctgaac gctcgtggaa ttccggacat gaatgggtca cggattttaa agggaagact   5640
gtttggttcg ttccaagtat aaaagcagga aatgatatag cagcttgcct gaggaaaaat   5700
ggaaagaaag tgatacaact cagtaggaag acctttgatt ctgagtatgt caagactaga   5760
accaatgatt gggacttcgt ggttacaact gacatttcag aaatgggtgc caatttcaag   5820
gctgagaggg ttatagaccc cagacgctgc atgaaaccag tcatactaac agatggtgaa   5880
gagcgggtga ttctggcagg acctatgcca gtgacccact ctagtgcagc acaaagaaga   5940
gggagaatag gaagaaatcc aaaaaatgag aatgaccagt acatatacat gggggaacct   6000
ctggaaaatg atgaagactg tgcacactgg aaagaagcta aaatgctcct agataacatc   6060
aacacgccag aaggaatcat tcctagcatg ttcgaaccag agcgtgaaaa ggtggatgcc   6120
attgatggcg aataccgctt gagaggagaa gcaaggaaaa cctttgtaga cttaatgaga   6180
agaggagacc taccagtctg gttggcctac agagtggcag ctgaaggcat caactacgca   6240
gacagaaggt ggtgttttga tggagtcaag aacaaccaaa tcctagaaga aaacgtggaa   6300
gttgaaatct ggacaaaaga aggggaaagg aagaaattga aacccagatg gttggatgct   6360
aggatctatt ctgacccact ggcgctaaaa gaatttaagg aatttgcagc cggaagaaag   6420
tctctgaccc tgaacctaat cacagaaatg ggtaggctcc caaccttcat gactcagaag   6480
gcaagagacg cactggacaa cttagcagtg ctgcacacgg ctgaggcagg tggaagggcg   6540
tacaaccatg ctctcagtga actgccggag accctggaga cattgctttt actgacactt   6600
ctggctacag tcacgggagg gatcttttta ttcttgatga gcgcaagggg catagggaag   6660
atgaccctgg gaatgtgctg cataatcacg gctagcatcc tcctatggta cgcacaaata   6720
cagccacact ggatagcagc ttcaataata ctggagtttt ttctcatagt tttgcttatt   6780
ccagaacctg aaaaacagag aacaccccaa gacaaccaac tgacctacgt tgtcatagcc   6840
atcctcacag tggtggccgc aaccatggca aacgagatgg gtttcctaga aaaaacgaag   6900
aaagatctcg gattgggaag cattgcaacc cagcaacccg agagcaacat cctggacata   6960
gatctacgtc ctgcatcagc atggacgctg tatgccgtgg ccacaacatt tgttacacca   7020
atgttgagac atagcattga aaattcctca gtgaatgtgt ccctaacagc tatagccaac   7080
caagccacag tgttaatggg tctcgggaaa ggatggccat tgtcaaagat ggacatcgga   7140
gttccccttc tcgccattgg atgctactca caagtcaacc ccataactct cacagcagct   7200
cttttcttat tggtagcaca ttatgccatc atagggccag gactccaagc aaaagcaacc   7260
agagaagctc agaaaagagc agcggcgggc atcatgaaaa acccaactgt cgatggaata   7320
acagtgattg acctagatcc aataccttat gatccaaagt ttgaaaagca gttgggacaa   7380
gtaatgctcc tagtcctctg cgtgactcaa gtattgatga tgaggactac atgggctctg   7440
tgtgaggctt taaccttagc taccgggccc atctccacat tgtgggaagg aaatccaggg   7500
aggttttgga acactaccat tgcggtgtca atggctaaca tttttagagg gagttacttg   7560
gccggagctg gacttctctt ttctattatg aagaacacaa ccaacacaag aaggggaact   7620
ggcaacatag gagagacgct tggagagaaa tggaaaagcc gattgaacgc attgggaaaa   7680
agtgaattcc agatctacaa gaaaagtgga atccaggaag tggatagaac cttagcaaaa   7740
```

```
gaaggcatta aaagaggaga aacggaccat cacgctgtgt cgcgaggctc agcaaaactg   7800

agatggttcg ttgagagaaa catggtcaca ccagaaggga aagtagtgga cctcggttgt   7860

ggcagaggag gctggtcata ctattgtgga ggactaaaga atgtaagaga agtcaaaggc   7920

ctaacaaaag gaggaccagg acacgaagaa cccatcccca tgtcaacata tgggtggaat   7980

ctagtgcgtc ttcaaagtgg agttgacgtt ttcttcatcc cgccagaaaa gtgtgacaca   8040

ttattgtgtg acataggggga gtcatcacca aatcccacag tggaagcagg acgaacactc   8100

agagtcctta acttagtaga aaattggttg aacaacaaca ctcaattttg cataaaggtt   8160

ctcaacccat atatgccctc agtcatagaa aaaatggaag cactacaaag gaaatatgga   8220

ggagccttag tgaggaatcc actctcacga aactccacac atgagatgta ctgggtatcc   8280

aatgcttccg ggaacatagt gtcatcagtg aacatgattt caaggatgtt gatcaacaga   8340

tttacaatga gatacaagaa agccacttac gagccggatg ttgacctcgg aagcggaacc   8400

cgtaacatcg ggattgaaag tgagatacca aacctagata taattgggaa aagaatagaa   8460

aaaataaagc aagagcatga aacatcatgg cactatgacc aagaccaccc atacaaaacg   8520

tgggcatacc atggtagcta tgaaacaaaa cagactggat cagcatcatc catggtcaac   8580

ggagtggtca ggctgctgac aaaaccttgg gacgtcgtcc ccatggtgac acagatggca   8640

atgacagaca cgactccatt tggacaacag cgcgtttttta aagagaaagt ggacacgaga   8700

acccaagaac cgaaagaagg cacgaagaaa ctaatgaaaa taacagcaga gtggctttgg   8760

aaagaattag ggaagaaaaa gacacccagg atgtgcacca gagaagaatt cacaagaaag   8820

gtgagaagca atgcagcctt gggggccata ttcactgatg agaacaagtg gaagtcggca   8880

cgtgaggctg ttgaagatag taggttttgg gagctggttg acaaggaaag gaatctccat   8940

cttgaaggaa agtgtgaaac atgtgtgtac aacatgatgg gaaaaagaga gaagaagcta   9000

ggggaattcg gcaaggcaaa aggcagcaga gccatatggt acatgtggct tggagcacgc   9060

ttcttagagt ttgaagccct aggattctta aatgaagatc actggttctc cagagagaac   9120

tccctgagtg gagtggaagg agaagggctg cacaagctag gttacattct aagagacgtg   9180

agcaagaaag agggaggagc aatgtatgcc gatgacaccg caggatggga tacaagaatc   9240

acactagaag acctaaaaaa tgaagaaatg gtaacaaacc acatggaagg agaacacaag   9300

aaactagccg aggccatttt caaactaacg taccaaaaca aggtggtgcg tgtgcaaaga   9360

ccaacaccaa gaggcacagt aatggacatc atatcgagaa gagaccaaag aggtagtgga   9420

caagttggca cctatggact caatactttc accaatatgg aagcccaact aatcagacag   9480

atggagggag aaggagtctt taaaagcatt cagcacctaa caatcacaga agaaatcgct   9540

gtgcaaaact ggttagcaag agtggggcgc gaaaggttat caagaatggc catcagtgga   9600

gatgattgtg ttgtgaaacc tttagatgac aggttcgcaa gcgctttaac agctctaaat   9660

gacatgggaa agattaggaa agacatacaa caatgggaac cttcaagagg atggaatgat   9720

tggacacaag tgcccttctg ttcacaccat ttccatgagt taatcatgaa agacggtcgc   9780

gtactcgttg ttccatgtag aaaccaagat gaactgattg gcagagcccg aatctcccaa   9840

ggagcagggt ggtctttgcg ggagacggcc tgtttgggga agtcttacgc ccaaatgtgg   9900

agcttgatgt acttccacag acgcgacctc aggctggcgg caaatgctat ttgctcggca   9960

gtaccatcac attgggttcc aacaagtcga acaacctggt ccatacatgc taaacatgaa  10020

tggatgacaa cggaagacat gctgacagtc tggaacaggg tgtggattca agaaaaccca  10080

tggatggaag acaaaactcc agtggaatca tgggaggaaa tcccatactt ggggaaaaga  10140
```

```
gaagaccaat ggtgcggctc attgattggg ttaacaagca gggccacctg ggcaaagaac  10200

atccaagcag caataaatca agttagatcc cttataggca atgaagaata cacagattac  10260

atgccatcca tgaaaagatt cagaagagaa gaggaagaag caggagttct gtggtagaaa  10320

gcaaaactaa catgaaacaa ggctagaagt caggtcggat taagccatag tacggaaaaa  10380

actatgctac ctgtgagccc cgtccaagga cgttaaaaga agtcaggcca tcataaatgc  10440

catagcttga gtaaactatg cagcctgtag ctccacctga gaaggtgtaa aaaatccggg  10500

aggccacaaa ccatggaagc tgtacgcatg gcgtagtgga ctagcggtta gaggagaccc  10560

ctcccttaca aatcgcagca acaatggggg cccaaggcga gatgaagctg tagtctcgct  10620

ggaaggacta gaggttagag gagacccccc cgaaacaaaa aacagcatat tgacgctggg  10680

aaagaccaga gatcctgctg tctcctcagc atcattccag gcacagaacg ccagaaaatg  10740

gaatggtgct gttgaatcaa caggttct                                    10768
```

<210> SEQ ID NO 22
<211> LENGTH: 3406
<212> TYPE: PRT
<213> ORGANISM: Artificial Sequence
<220> FEATURE:
<223> OTHER INFORMATION: Synthetic polypeptide

<400> SEQUENCE: 22

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Thr Ser Val Gly Ile Val Gly Leu Leu
            100                 105                 110

Leu Thr Thr Ala Met Ala Ala Glu Val Thr Arg Arg Gly Ser Ala Tyr
        115                 120                 125

Tyr Met Tyr Leu Asp Arg Asn Asp Ala Gly Glu Ala Ile Ser Phe Pro
    130                 135                 140

Thr Thr Leu Gly Met Asn Lys Cys Tyr Ile Gln Ile Met Asp Leu Gly
145                 150                 155                 160

His Met Cys Asp Ala Thr Met Ser Tyr Glu Cys Pro Met Leu Asp Glu
                165                 170                 175

Gly Val Glu Pro Asp Asp Val Asp Cys Trp Cys Asn Thr Thr Ser Thr
            180                 185                 190

Trp Val Val Tyr Gly Thr Cys His His Lys Lys Gly Glu Ala Arg Arg
        195                 200                 205

Ser Arg Arg Ala Val Thr Leu Pro Ser His Ser Thr Arg Lys Leu Gln
    210                 215                 220

Thr Arg Ser Gln Thr Trp Leu Glu Ser Arg Glu Tyr Thr Lys His Leu
225                 230                 235                 240

Ile Arg Val Glu Asn Trp Ile Phe Arg Asn Pro Gly Phe Ala Leu Ala
```

```
                245                 250                 255

Ala Ala Ala Ile Ala Trp Leu Leu Gly Ser Ser Thr Ser Gln Lys Val
            260                 265                 270

Ile Tyr Leu Val Met Ile Leu Leu Ile Ala Pro Ala Tyr Ser Ile Arg
        275                 280                 285

Cys Ile Gly Val Ser Asn Arg Asp Phe Val Glu Gly Met Ser Gly Gly
    290                 295                 300

Thr Trp Val Asp Ile Val Leu Glu His Gly Gly Cys Val Thr Val Met
305                 310                 315                 320

Ala Gln Asp Lys Pro Thr Val Asp Ile Glu Leu Val Thr Thr Thr Val
                325                 330                 335

Ser Asn Met Ala Glu Val Arg Ser Tyr Cys Tyr Glu Ala Ser Ile Ser
            340                 345                 350

Asp Met Ala Ser Asp Ser Arg Cys Pro Thr Gln Gly Glu Ala Tyr Leu
        355                 360                 365

Asp Lys Gln Ser Asp Thr Gln Tyr Val Cys Lys Arg Thr Leu Val Asp
    370                 375                 380

Arg Gly Trp Gly Asn Gly Cys Gly Leu Phe Gly Lys Gly Ser Leu Val
385                 390                 395                 400

Thr Cys Ala Lys Phe Ala Cys Ser Lys Lys Met Thr Gly Lys Ser Ile
                405                 410                 415

Gln Pro Glu Asn Leu Glu Tyr Arg Ile Met Leu Ser Val His Gly Ser
            420                 425                 430

Gln His Ser Gly Met Ile Val Asn Asp Thr Gly His Glu Thr Asp Glu
        435                 440                 445

Asn Arg Ala Lys Val Glu Ile Thr Pro Asn Ser Pro Arg Ala Glu Ala
    450                 455                 460

Thr Leu Gly Gly Phe Gly Ser Leu Gly Leu Asp Cys Glu Pro Arg Thr
465                 470                 475                 480

Gly Leu Asp Phe Ser Asp Leu Tyr Tyr Leu Thr Met Asn Asn Lys His
                485                 490                 495

Trp Leu Val His Lys Glu Trp Phe His Asp Ile Pro Leu Pro Trp His
            500                 505                 510

Ala Gly Ala Asp Thr Gly Thr Pro His Trp Asn Asn Lys Glu Ala Leu
        515                 520                 525

Val Glu Phe Lys Asp Ala His Ala Lys Arg Gln Thr Val Val Val Leu
    530                 535                 540

Gly Ser Gln Glu Gly Ala Val His Thr Ala Leu Ala Gly Ala Leu Glu
545                 550                 555                 560

Ala Glu Met Asp Gly Ala Lys Gly Arg Leu Ser Ser Gly His Leu Lys
                565                 570                 575

Cys Arg Leu Lys Met Asp Lys Leu Arg Leu Lys Gly Val Ser Tyr Ser
            580                 585                 590

Leu Cys Thr Ala Ala Phe Thr Phe Thr Lys Ile Pro Ala Glu Thr Leu
        595                 600                 605

His Gly Thr Val Thr Val Glu Val Gln Tyr Ala Gly Thr Asp Gly Pro
    610                 615                 620

Cys Lys Val Pro Ala Gln Met Ala Val Asp Met Gln Thr Leu Thr Pro
625                 630                 635                 640

Val Gly Arg Leu Ile Thr Ala Asn Pro Val Ile Thr Glu Ser Thr Glu
                645                 650                 655

Asn Ser Lys Met Met Leu Glu Leu Asp Pro Pro Phe Gly Asp Ser Tyr
            660                 665                 670
```

```
Ile Val Ile Gly Val Gly Glu Lys Lys Ile Thr His His Trp His Arg
        675                 680                 685

Ser Gly Ser Thr Ile Gly Lys Ala Phe Glu Ala Thr Val Arg Gly Ala
    690                 695                 700

Lys Arg Met Ala Val Leu Gly Asp Thr Ala Trp Asp Phe Gly Ser Val
705                 710                 715                 720

Gly Gly Ala Leu Asn Ser Leu Gly Lys Gly Ile His Gln Ile Phe Gly
                725                 730                 735

Ala Ala Phe Lys Ser Leu Phe Gly Gly Met Ser Trp Phe Ser Arg Ile
            740                 745                 750

Leu Ile Gly Thr Leu Leu Met Trp Leu Gly Leu Asn Thr Lys Asn Gly
        755                 760                 765

Ser Thr Ser Leu Met Cys Leu Ala Ala Gly Phe Val Thr Leu Tyr Leu
    770                 775                 780

Gly Val Met Val Gln Ala Asp Ser Gly Cys Val Val Ser Trp Lys Asn
785                 790                 795                 800

Lys Glu Leu Lys Cys Gly Ser Gly Ile Phe Ile Thr Asp Asn Val His
                805                 810                 815

Thr Trp Thr Glu Gln Tyr Lys Phe Gln Pro Glu Ser Pro Ser Lys Leu
            820                 825                 830

Ala Ser Ala Ile Gln Lys Ala His Glu Glu Asp Ile Cys Gly Ile Arg
        835                 840                 845

Ser Val Thr Arg Leu Glu Asn Leu Met Trp Lys Gln Ile Thr Pro Glu
    850                 855                 860

Leu Asn His Ile Leu Ser Glu Asn Glu Val Lys Leu Thr Ile Met Thr
865                 870                 875                 880

Gly Asp Ile Lys Gly Ile Met Gln Ala Gly Lys Arg Ser Leu Arg Pro
                885                 890                 895

Gln Pro Thr Glu Leu Lys Tyr Ser Trp Lys Thr Trp Gly Lys Ala Lys
            900                 905                 910

Met Leu Ser Thr Glu Ser His Asn Gln Thr Phe Leu Ile Asp Gly Pro
        915                 920                 925

Glu Thr Ala Glu Cys Pro Asn Thr Asn Arg Ala Trp Asn Ser Leu Glu
    930                 935                 940

Val Glu Asp Tyr Gly Phe Gly Val Phe Thr Thr Asn Ile Trp Leu Lys
945                 950                 955                 960

Leu Lys Glu Lys Gln Asp Val Phe Cys Asp Ser Lys Leu Met Ser Ala
                965                 970                 975

Ala Ile Lys Asp Asn Arg Ala Val His Ala Asp Met Gly Tyr Trp Ile
            980                 985                 990

Glu Ser Ala Leu Asn Asp Thr Trp  Lys Ile Glu Lys Ala  Ser Phe Ile
        995                 1000                1005

Glu Val  Lys Asn Cys His Trp  Pro Lys Ser His Thr  Leu Trp Ser
    1010                1015                1020

Asn Gly  Val Leu Glu Ser Glu  Met Ile Ile Pro Lys  Asn Leu Ala
    1025                1030                1035

Gly Pro  Val Ser Gln His Asn  Tyr Arg Pro Gly Tyr  His Thr Gln
    1040                1045                1050

Ile Thr  Gly Pro Trp His Leu  Gly Lys Leu Glu Met  Asp Phe Asp
    1055                1060                1065

Phe Cys  Asp Gly Thr Thr Val  Val Val Thr Glu Asp  Cys Gly Asn
    1070                1075                1080
```

```
Arg Gly  Pro Ser Leu Arg Thr  Thr Thr Ala Ser Gly  Lys Leu Ile
    1085                 1090                 1095

Thr Glu  Trp Cys Cys Arg Ser  Cys Thr Leu Pro Pro  Leu Arg Tyr
    1100                 1105                 1110

Arg Gly  Glu Asp Gly Cys Trp  Tyr Gly Met Glu Ile  Arg Pro Leu
    1115                 1120                 1125

Lys Glu  Lys Glu Glu Asn Leu  Val Asn Ser Leu Val  Thr Ala Gly
    1130                 1135                 1140

His Gly  Gln Val Asp Asn Phe  Ser Leu Gly Val Leu  Gly Met Ala
    1145                 1150                 1155

Leu Phe  Leu Glu Glu Met Leu  Arg Thr Arg Val Gly  Thr Lys His
    1160                 1165                 1170

Ala Ile  Leu Leu Val Ala Val  Ser Phe Val Thr Leu  Ile Thr Gly
    1175                 1180                 1185

Asn Met  Ser Phe Arg Asp Leu  Gly Arg Val Met Val  Met Val Gly
    1190                 1195                 1200

Ala Thr  Met Thr Asp Asp Ile  Gly Met Gly Val Thr  Tyr Leu Ala
    1205                 1210                 1215

Leu Leu  Ala Ala Phe Lys Val  Arg Pro Thr Phe Ala  Ala Gly Leu
    1220                 1225                 1230

Leu Leu  Arg Lys Leu Thr Ser  Asn Glu Leu Met Met  Thr Thr Ile
    1235                 1240                 1245

Gly Ile  Val Leu Leu Ser Gln  Ser Thr Ile Pro Glu  Thr Ile Leu
    1250                 1255                 1260

Glu Leu  Thr Asp Ala Leu Ala  Leu Gly Met Met Val  Leu Lys Met
    1265                 1270                 1275

Val Arg  Asn Met Glu Lys Tyr  Gln Leu Ala Val Thr  Ile Met Ala
    1280                 1285                 1290

Ile Leu  Cys Val Pro Asn Ala  Val Ile Leu Gln Asn  Ala Trp Lys
    1295                 1300                 1305

Val Ser  Cys Thr Ile Leu Ala  Val Val Ser Val Ser  Pro Leu Phe
    1310                 1315                 1320

Leu Thr  Ser Ser Gln Gln Lys  Thr Asp Trp Ile Pro  Leu Ala Leu
    1325                 1330                 1335

Thr Ile  Lys Gly Leu Asn Pro  Thr Ala Ile Phe Leu  Thr Thr Leu
    1340                 1345                 1350

Ser Arg  Thr Ser Lys Lys Arg  Ser Trp Pro Leu Asn  Glu Ala Ile
    1355                 1360                 1365

Met Ala  Val Gly Met Val Ser  Ile Leu Ala Ser Ser  Leu Leu Lys
    1370                 1375                 1380

Asn Asp  Ile Pro Met Thr Gly  Pro Leu Val Ala Gly  Gly Leu Leu
    1385                 1390                 1395

Thr Val  Cys Tyr Val Leu Thr  Gly Arg Ser Ala Asp  Leu Glu Leu
    1400                 1405                 1410

Glu Arg  Ala Ala Asp Val Lys  Trp Glu Asp Gln Ala  Glu Ile Ser
    1415                 1420                 1425

Gly Ser  Ser Pro Ile Leu Ser  Ile Thr Ile Ser Glu  Asp Gly Ser
    1430                 1435                 1440

Met Ser  Ile Lys Asn Glu Glu  Glu Glu Gln Thr Leu  Thr Ile Leu
    1445                 1450                 1455

Ile Arg  Thr Gly Leu Leu Val  Ile Ser Gly Leu Phe  Pro Val Ser
    1460                 1465                 1470

Ile Pro  Ile Thr Ala Ala Ala  Trp Tyr Leu Trp Glu  Val Lys Lys
```

```
    1475                1480                1485

Gln Arg  Ala Gly Val Leu Trp  Asp Val Pro Ser Pro  Pro Pro Met
    1490                1495                1500

Gly Lys  Ala Glu Leu Glu Asp  Gly Ala Tyr Arg Ile  Lys Gln Lys
    1505                1510                1515

Gly Ile  Leu Gly Tyr Ser Gln  Ile Gly Ala Gly Val  Tyr Lys Glu
    1520                1525                1530

Gly Thr  Phe His Thr Met Trp  His Val Thr Arg Gly  Ala Val Leu
    1535                1540                1545

Met His  Lys Gly Lys Arg Ile  Glu Pro Ser Trp Ala  Asp Val Lys
    1550                1555                1560

Lys Asp  Leu Ile Ser Tyr Gly  Gly Gly Trp Lys Leu  Glu Gly Glu
    1565                1570                1575

Trp Lys  Glu Gly Glu Glu Val  Gln Val Leu Ala Leu  Glu Pro Gly
    1580                1585                1590

Lys Asn  Pro Arg Ala Val Gln  Thr Lys Pro Gly Leu  Phe Lys Thr
    1595                1600                1605

Asn Ala  Gly Thr Ile Gly Ala  Val Ser Leu Asp Phe  Ser Pro Gly
    1610                1615                1620

Thr Ser  Gly Ser Pro Ile Ile  Asp Lys Lys Gly Lys  Val Val Gly
    1625                1630                1635

Leu Tyr  Gly Asn Gly Val Val  Thr Arg Ser Gly Ala  Tyr Val Ser
    1640                1645                1650

Ala Ile  Ala Gln Thr Glu Lys  Ser Ile Glu Asp Asn  Pro Glu Ile
    1655                1660                1665

Glu Asp  Asp Ile Phe Arg Lys  Arg Arg Leu Thr Ile  Met Asp Leu
    1670                1675                1680

His Pro  Gly Ala Gly Lys Thr  Lys Arg Tyr Leu Pro  Ala Ile Val
    1685                1690                1695

Arg Glu  Ala Ile Lys Arg Gly  Leu Arg Thr Leu Ile  Leu Ala Pro
    1700                1705                1710

Thr Arg  Val Val Ala Ala Glu  Met Glu Glu Ala Leu  Arg Gly Leu
    1715                1720                1725

Pro Ile  Arg Tyr Gln Thr Pro  Ala Ile Arg Ala Val  His Thr Gly
    1730                1735                1740

Arg Glu  Ile Val Asp Leu Met  Cys His Ala Thr Phe  Thr Met Arg
    1745                1750                1755

Leu Leu  Ser Pro Val Arg Val  Pro Asn Tyr Asn Leu  Ile Ile Met
    1760                1765                1770

Asp Glu  Ala His Phe Thr Asp  Pro Ala Ser Ile Ala  Ala Arg Gly
    1775                1780                1785

Tyr Ile  Ser Thr Arg Val Glu  Met Gly Glu Ala Ala  Gly Ile Phe
    1790                1795                1800

Met Thr  Ala Thr Pro Pro Gly  Ser Arg Asp Pro Phe  Pro Gln Ser
    1805                1810                1815

Asn Ala  Pro Ile Ile Asp Glu  Glu Arg Glu Ile Pro  Glu Arg Ser
    1820                1825                1830

Trp Asn  Ser Gly His Glu Trp  Val Thr Asp Phe Lys  Gly Lys Thr
    1835                1840                1845

Val Trp  Phe Val Pro Ser Ile  Lys Ala Gly Asn Asp  Ile Ala Ala
    1850                1855                1860

Cys Leu  Arg Lys Asn Gly Lys  Lys Val Ile Gln Leu  Ser Arg Lys
    1865                1870                1875
```

```
Thr Phe  Asp Ser Glu Tyr Val  Lys Thr Arg Thr Asn  Asp Trp Asp
    1880                 1885                 1890

Phe Val  Val Thr Thr Asp Ile  Ser Glu Met Gly Ala  Asn Phe Lys
    1895                 1900                 1905

Ala Glu  Arg Val Ile Asp Pro  Arg Arg Cys Met Lys  Pro Val Ile
    1910                 1915                 1920

Leu Thr  Asp Gly Glu Glu Arg  Val Ile Leu Ala Gly  Pro Met Pro
    1925                 1930                 1935

Val Thr  His Ser Ser Ala Ala  Gln Arg Arg Gly Arg  Ile Gly Arg
    1940                 1945                 1950

Asn Pro  Lys Asn Glu Asn Asp  Gln Tyr Ile Tyr Met  Gly Glu Pro
    1955                 1960                 1965

Leu Glu  Asn Asp Glu Asp Cys  Ala His Trp Lys Glu  Ala Lys Met
    1970                 1975                 1980

Leu Leu  Asp Asn Ile Asn Thr  Pro Glu Gly Ile Ile  Pro Ser Met
    1985                 1990                 1995

Phe Glu  Pro Glu Arg Glu Lys  Val Asp Ala Ile Asp  Gly Glu Tyr
    2000                 2005                 2010

Arg Leu  Arg Gly Glu Ala Arg  Lys Thr Phe Val Asp  Leu Met Arg
    2015                 2020                 2025

Arg Gly  Asp Leu Pro Val Trp  Leu Ala Tyr Arg Val  Ala Ala Glu
    2030                 2035                 2040

Gly Ile  Asn Tyr Ala Asp Arg  Arg Trp Cys Phe Asp  Gly Val Lys
    2045                 2050                 2055

Asn Asn  Gln Ile Leu Glu Glu  Asn Val Glu Val Glu  Ile Trp Thr
    2060                 2065                 2070

Lys Glu  Gly Glu Arg Lys Lys  Leu Lys Pro Arg Trp  Leu Asp Ala
    2075                 2080                 2085

Arg Ile  Tyr Ser Asp Pro Leu  Ala Leu Lys Glu Phe  Lys Glu Phe
    2090                 2095                 2100

Ala Ala  Gly Arg Lys Ser Leu  Thr Leu Asn Leu Ile  Thr Glu Met
    2105                 2110                 2115

Gly Arg  Leu Pro Thr Phe Met  Thr Gln Lys Ala Arg  Asp Ala Leu
    2120                 2125                 2130

Asp Asn  Leu Ala Val Leu His  Thr Ala Glu Ala Gly  Gly Arg Ala
    2135                 2140                 2145

Tyr Asn  His Ala Leu Ser Glu  Leu Pro Glu Thr Leu  Glu Thr Leu
    2150                 2155                 2160

Leu Leu  Leu Thr Leu Leu Ala  Thr Val Thr Gly Gly  Ile Phe Leu
    2165                 2170                 2175

Phe Leu  Met Ser Ala Arg Gly  Ile Gly Lys Met Thr  Leu Gly Met
    2180                 2185                 2190

Cys Cys  Ile Ile Thr Ala Ser  Ile Leu Leu Trp Tyr  Ala Gln Ile
    2195                 2200                 2205

Gln Pro  His Trp Ile Ala Ala  Ser Ile Ile Leu Glu  Phe Phe Leu
    2210                 2215                 2220

Ile Val  Leu Leu Ile Pro Glu  Pro Glu Lys Gln Arg  Thr Pro Gln
    2225                 2230                 2235

Asp Asn  Gln Leu Thr Tyr Val  Val Ile Ala Ile Leu  Thr Val Val
    2240                 2245                 2250

Ala Ala  Thr Met Ala Asn Glu  Met Gly Phe Leu Glu  Lys Thr Lys
    2255                 2260                 2265
```

```
Lys Asp Leu Gly Leu Gly Ser Ile Ala Thr Gln Gln Pro Glu Ser
    2270                2275                2280

Asn Ile Leu Asp Ile Asp Leu Arg Pro Ala Ser Ala Trp Thr Leu
    2285                2290                2295

Tyr Ala Val Ala Thr Thr Phe Val Thr Pro Met Leu Arg His Ser
    2300                2305                2310

Ile Glu Asn Ser Ser Val Asn Val Ser Leu Thr Ala Ile Ala Asn
    2315                2320                2325

Gln Ala Thr Val Leu Met Gly Leu Gly Lys Gly Trp Pro Leu Ser
    2330                2335                2340

Lys Met Asp Ile Gly Val Pro Leu Leu Ala Ile Gly Cys Tyr Ser
    2345                2350                2355

Gln Val Asn Pro Ile Thr Leu Thr Ala Ala Leu Phe Leu Leu Val
    2360                2365                2370

Ala His Tyr Ala Ile Ile Gly Pro Gly Leu Gln Ala Lys Ala Thr
    2375                2380                2385

Arg Glu Ala Gln Lys Arg Ala Ala Ala Gly Ile Met Lys Asn Pro
    2390                2395                2400

Thr Val Asp Gly Ile Thr Val Ile Asp Leu Asp Pro Ile Pro Tyr
    2405                2410                2415

Asp Pro Lys Phe Glu Lys Gln Leu Gly Gln Val Met Leu Leu Val
    2420                2425                2430

Leu Cys Val Thr Gln Val Leu Met Met Arg Thr Thr Trp Ala Leu
    2435                2440                2445

Cys Glu Ala Leu Thr Leu Ala Thr Gly Pro Ile Ser Thr Leu Trp
    2450                2455                2460

Glu Gly Asn Pro Gly Arg Phe Trp Asn Thr Thr Ile Ala Val Ser
    2465                2470                2475

Met Ala Asn Ile Phe Arg Gly Ser Tyr Leu Ala Gly Ala Gly Leu
    2480                2485                2490

Leu Phe Ser Ile Met Lys Asn Thr Thr Asn Thr Arg Arg Gly Thr
    2495                2500                2505

Gly Asn Ile Gly Glu Thr Leu Gly Glu Lys Trp Lys Ser Arg Leu
    2510                2515                2520

Asn Ala Leu Gly Lys Ser Glu Phe Gln Ile Tyr Lys Lys Ser Gly
    2525                2530                2535

Ile Gln Glu Val Asp Arg Thr Leu Ala Lys Glu Gly Ile Lys Arg
    2540                2545                2550

Gly Glu Thr Asp His His Ala Val Ser Arg Gly Ser Ala Lys Leu
    2555                2560                2565

Arg Trp Phe Val Glu Arg Asn Met Val Thr Pro Glu Gly Lys Val
    2570                2575                2580

Val Asp Leu Gly Cys Gly Arg Gly Gly Trp Ser Tyr Tyr Cys Gly
    2585                2590                2595

Gly Leu Lys Asn Val Arg Glu Val Lys Gly Leu Thr Lys Gly Gly
    2600                2605                2610

Pro Gly His Glu Glu Pro Ile Pro Met Ser Thr Tyr Gly Trp Asn
    2615                2620                2625

Leu Val Arg Leu Gln Ser Gly Val Asp Val Phe Phe Ile Pro Pro
    2630                2635                2640

Glu Lys Cys Asp Thr Leu Leu Cys Asp Ile Gly Glu Ser Ser Pro
    2645                2650                2655

Asn Pro Thr Val Glu Ala Gly Arg Thr Leu Arg Val Leu Asn Leu
```

```
    2660                2665                2670

Val Glu  Asn Trp Leu Asn Asn  Asn Thr Gln Phe Cys  Ile Lys Val
    2675                2680                2685

Leu Asn  Pro Tyr Met Pro Ser  Val Ile Glu Lys Met  Glu Ala Leu
    2690                2695                2700

Gln Arg  Lys Tyr Gly Gly Ala  Leu Val Arg Asn Pro  Leu Ser Arg
    2705                2710                2715

Asn Ser  Thr His Glu Met Tyr  Trp Val Ser Asn Ala  Ser Gly Asn
    2720                2725                2730

Ile Val  Ser Ser Val Asn Met  Ile Ser Arg Met Leu  Ile Asn Arg
    2735                2740                2745

Phe Thr  Met Arg Tyr Lys Lys  Ala Thr Tyr Glu Pro  Asp Val Asp
    2750                2755                2760

Leu Gly  Ser Gly Thr Arg Asn  Ile Gly Ile Glu Ser  Glu Ile Pro
    2765                2770                2775

Asn Leu  Asp Ile Ile Gly Lys  Arg Ile Glu Lys Ile  Lys Gln Glu
    2780                2785                2790

His Glu  Thr Ser Trp His Tyr  Asp Gln Asp His Pro  Tyr Lys Thr
    2795                2800                2805

Trp Ala  Tyr His Gly Ser Tyr  Glu Thr Lys Gln Thr  Gly Ser Ala
    2810                2815                2820

Ser Ser  Met Val Asn Gly Val  Val Arg Leu Leu Thr  Lys Pro Trp
    2825                2830                2835

Asp Val  Val Pro Met Val Thr  Gln Met Ala Met Thr  Asp Thr Thr
    2840                2845                2850

Pro Phe  Gly Gln Gln Arg Val  Phe Lys Glu Lys Val  Asp Thr Arg
    2855                2860                2865

Thr Gln  Glu Pro Lys Glu Gly  Thr Lys Lys Leu Met  Lys Ile Thr
    2870                2875                2880

Ala Glu  Trp Leu Trp Lys Glu  Leu Gly Lys Lys Lys  Thr Pro Arg
    2885                2890                2895

Met Cys  Thr Arg Glu Glu Phe  Thr Arg Lys Val Arg  Ser Asn Ala
    2900                2905                2910

Ala Leu  Gly Ala Ile Phe Thr  Asp Glu Asn Lys Trp  Lys Ser Ala
    2915                2920                2925

Arg Glu  Ala Val Glu Asp Ser  Arg Phe Trp Glu Leu  Val Asp Lys
    2930                2935                2940

Glu Arg  Asn Leu His Leu Glu  Gly Lys Cys Glu Thr  Cys Val Tyr
    2945                2950                2955

Asn Met  Met Gly Lys Arg Glu  Lys Lys Leu Gly Glu  Phe Gly Lys
    2960                2965                2970

Ala Lys  Gly Ser Arg Ala Ile  Trp Tyr Met Trp Leu  Gly Ala Arg
    2975                2980                2985

Phe Leu  Glu Phe Glu Ala Leu  Gly Phe Leu Asn Glu  Asp His Trp
    2990                2995                3000

Phe Ser  Arg Glu Asn Ser Leu  Ser Gly Val Glu Gly  Glu Gly Leu
    3005                3010                3015

His Lys  Leu Gly Tyr Ile Leu  Arg Asp Val Ser Lys  Lys Glu Gly
    3020                3025                3030

Gly Ala  Met Tyr Ala Asp Asp  Thr Ala Gly Trp Asp  Thr Arg Ile
    3035                3040                3045

Thr Leu  Glu Asp Leu Lys Asn  Glu Glu Met Val Thr  Asn His Met
    3050                3055                3060
```

```
Glu Gly  Glu His Lys Lys Leu  Ala Glu Ala Ile Phe  Lys Leu Thr
    3065                 3070                 3075

Tyr Gln  Asn Lys Val Val Arg  Val Gln Arg Pro Thr  Pro Arg Gly
    3080                 3085                 3090

Thr Val  Met Asp Ile Ile Ser  Arg Arg Asp Gln Arg  Gly Ser Gly
    3095                 3100                 3105

Gln Val  Gly Thr Tyr Gly Leu  Asn Thr Phe Thr Asn  Met Glu Ala
    3110                 3115                 3120

Gln Leu  Ile Arg Gln Met Glu  Gly Glu Gly Val Phe  Lys Ser Ile
    3125                 3130                 3135

Gln His  Leu Thr Ile Thr Glu  Glu Ile Ala Val Gln  Asn Trp Leu
    3140                 3145                 3150

Ala Arg  Val Gly Arg Glu Arg  Leu Ser Arg Met Ala  Ile Ser Gly
    3155                 3160                 3165

Asp Asp  Cys Val Val Lys Pro  Leu Asp Asp Arg Phe  Ala Ser Ala
    3170                 3175                 3180

Leu Thr  Ala Leu Asn Asp Met  Gly Lys Ile Arg Lys  Asp Ile Gln
    3185                 3190                 3195

Gln Trp  Glu Pro Ser Arg Gly  Trp Asn Asp Trp Thr  Gln Val Pro
    3200                 3205                 3210

Phe Cys  Ser His His Phe His  Glu Leu Ile Met Lys  Asp Gly Arg
    3215                 3220                 3225

Val Leu  Val Val Pro Cys Arg  Asn Gln Asp Glu Leu  Ile Gly Arg
    3230                 3235                 3240

Ala Arg  Ile Ser Gln Gly Ala  Gly Trp Ser Leu Arg  Glu Thr Ala
    3245                 3250                 3255

Cys Leu  Gly Lys Ser Tyr Ala  Gln Met Trp Ser Leu  Met Tyr Phe
    3260                 3265                 3270

His Arg  Arg Asp Leu Arg Leu  Ala Ala Asn Ala Ile  Cys Ser Ala
    3275                 3280                 3285

Val Pro  Ser His Trp Val Pro  Thr Ser Arg Thr Thr  Trp Ser Ile
    3290                 3295                 3300

His Ala  Lys His Glu Trp Met  Thr Thr Glu Asp Met  Leu Thr Val
    3305                 3310                 3315

Trp Asn  Arg Val Trp Ile Gln  Glu Asn Pro Trp Met  Glu Asp Lys
    3320                 3325                 3330

Thr Pro  Val Glu Ser Trp Glu  Glu Ile Pro Tyr Leu  Gly Lys Arg
    3335                 3340                 3345

Glu Asp  Gln Trp Cys Gly Ser  Leu Ile Gly Leu Thr  Ser Arg Ala
    3350                 3355                 3360

Thr Trp  Ala Lys Asn Ile Gln  Ala Ala Ile Asn Gln  Val Arg Ser
    3365                 3370                 3375

Leu Ile  Gly Asn Glu Glu Tyr  Thr Asp Tyr Met Pro  Ser Met Lys
    3380                 3385                 3390

Arg Phe  Arg Arg Glu Glu Glu  Glu Ala Gly Val Leu  Trp
    3395                 3400                 3405
```

<210> SEQ ID NO 23
<211> LENGTH: 10768
<212> TYPE: DNA
<213> ORGANISM: Artificial Sequence
<220> FEATURE:
<223> OTHER INFORMATION: Synthetic construct

<400> SEQUENCE: 23

```
agttgttagt ctacgtggac cgacaaagac agattctttg agggagctaa gctcaacgta     60
gttctaacag tttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagatccg cgggtactag tgtcggaatt    420
gttggcctcc tgctgaccac agctatggca gcggaggtca ctagacgtgg gagtgcatac    480
tatatgtact tggacagaaa cgatgctggg gaggccatat cttttccaac cacattgggg    540
atgaataagt gttatataca gatcatggat cttggacaca tgtgtgatgc caccatgagc    600
tatgaatgcc ctatgctgga tgagggggtg gaaccagatg acgtcgattg ttggtgcaac    660
acgacgtcaa cttgggttgt gtacggaacc tgccatcaca aaaaaggtga agcacggaga    720
agtagaagag ctgtgacgct cccctcccat tccactagga agctgcaaac gcggtcgcaa    780
acctggttgg aatcaagaga atacacaaag cacttgatta gagtcgaaaa ttggatattc    840
aggaaccctg gcttcgcgtt agcagcagct gccatcgctt ggcttttggg aagctcaacg    900
agccaaaaag tcatatactt ggtcatgata ctgctgattg ccccggcata cagcatcagg    960
tgcataggag tcagcaatag ggactttgtg gaaggtatgt caggtgggac ttgggttgat   1020
attgtcttgg aacatggagg ttgtgtcacc gtaatggcac aggacaaacc gactgtcgac   1080
atagagctgg ttacaacaac agtcagcaac atggcggagg taagatccta ctgctatgag   1140
gcatcaatat cagacatggc ttcggacagc cgctgcccaa cacaaggtga agcctacctt   1200
gacaagcaat cagacactca atatgtctgc aaaagaacgt tagtggacag aggctgggga   1260
aatggatgtg gactttttgg caaagggagt ctggtgacat gcgctaagtt tgcatgctcc   1320
aagaaaatga ccgggaagag catccagcca gagaatctgg agtaccggat aatgctgtca   1380
gttcatggct cccagcacag tgggatgatc gttaatgaca caggacatga aactgatgag   1440
aatagagcga aggttgagat aacgcccaat tcaccaagag ccgaagccac cctgggggt   1500
tttggaagcc taggacttga ttgtgaaccg aggacaggcc ttgacttttc agatttgtat   1560
tacttgacta tgaataacaa gcactggttg gttcacaagg agtggttcca cgacattcca   1620
ttaccttggc acgctggggc agacaccgga actccacact ggaacaacaa agaagcactg   1680
gtagagttca aggacgcaca tgccaaaagg caaactgtcg tggttctagg gagtcaagaa   1740
ggagcagttc acacggccct tgctggagct ctggaggctg agatggatgg tgcaaaggga   1800
aggctgtcct ctggccactt gaaatgtcgc ctgaaaatgg ataaacttag attgaagggc   1860
gtgtcatact ccttgtgtac cgcagcgttc acattcacca agatcccggc tgaaacactg   1920
cacgggacag tcacagtgga ggtacagtac gcagggacag atggaccttg caaggttcca   1980
gctcagatgg cggtggacat gcaaactctg accccagttg ggaggttgat aaccgctaac   2040
cccgtaatca ctgaaagcac tgagaactct aagatgatgc tggaacttga tccaccattt   2100
ggggactctt acattgtcat aggagtcggg gagaagaaga tcacccacca ctggcacagg   2160
agtggcagca ccattggaaa agcatttgaa gccactgtga gaggtgccaa gagaatggca   2220
gtcttgggag acacagcctg ggactttgga tcagttggag gcgctctcaa ctcattgggc   2280
aagggcatcc atcaaatttt tggagcagct ttcaaatcat tgtttggagg aatgtcctgg   2340
```

```
ttctcaagaa ttctcattgg aacgttgctg atgtggttgg gtctgaacac aaagaatgga   2400
tctacttccc ttatgtgctt ggccgccggc tttgtgacac tgtatttggg ggtcatggtg   2460
caggccgata gtggttgcgt tgtgagctgg aaaaacaaag aactgaaatg tggcagtggg   2520
attttcatca cagacaacgt gcacacatgg acagaacaat acaagttcca accagaatcc   2580
ccttcaaaac tagcttcagc tatccagaaa gcccatgaag agggcatttg tggaatccgc   2640
tcagtaacaa gactggagaa tctgatgtgg aaacaaataa caccagaatt gaatcacatt   2700
ctatcagaaa atgaggtgaa gttaactatt atgacaggag acatcaaagg aatcatgcag   2760
gcaggaaaac gatctctgcg gcctcagccc actgagctga agtattcatg gaaaacatgg   2820
ggcaaagcaa aaatgctctc tacagagtct cataaccaga cctttctcat tgatggcccc   2880
gaaacagcag aatgccccaa cacaaataga gcttggaatt cgttggaagt tgaagactat   2940
ggctttggag tattcaccac caatatatgg ctaaaattga aagaaaaaca ggatgtattc   3000
tgcgactcaa aactcatgtc agcggccata aaagacaaca gagccgtcca tgccgatatg   3060
ggttattgga tagaaagtgc actcaatgac acatggaaga tagagaaagc ctctttcatt   3120
gaagttaaaa actgccactg gccaaaatca cacaccctct ggagcaatgg agtgctagaa   3180
agtgagatga taattccaaa gaatctcgct ggaccagtgt ctcaacacaa ctatagacca   3240
ggctaccata cacaaataac aggaccatgg catctaggta agcttgagat ggactttgat   3300
ttctgtgatg gaacaacagt ggtagtgact gaggactgcg gaaatagagg accctctttg   3360
agaacaacca ctgcctctgg aaaactcata acagaatggt gctgccgatc ttgcacatta   3420
ccaccgctaa gatacagagg tgaggatggg tgctggtacg ggatggaaat cagaccattg   3480
aaggagaaag aagagaattt ggtcaactcc ttggtcacag ctggacatgg gcaggtcgac   3540
aacttttcac taggagtctt gggaatggca ttgttcctgg aggaaatgct taggacccga   3600
gtaggaacga aacatgcaat actactagtt gcagtttctt ttgtgacatt gatcacaggg   3660
aacatgtcct ttagagacct gggaagagtg atggttatgg taggcgccac tatgacggat   3720
gacataggta tgggcgtgac ttatcttgcc ctactagcag ccttcaaagt cagaccaact   3780
tttgcagctg gactactctt gagaaagctg acctccaatg aattgatgat gactactata   3840
ggaattgtac tcctctccca gagcaccata ccagagacca ttcttgagtt gactgatgcg   3900
ttagccttag gcatgatggt cctcaaaatg gtgagaaata tggaaaagta tcaattggca   3960
gtgactatca tggctatctt gtgcgtccca aacgcagtga tattacaaaa cgcatggaaa   4020
gtgagttgca caatattggc agtggtgtcc gtttccccac tgctcttaac atcctcacag   4080
caaaaaacag attggatacc attagcattg acgatcaaag gtctcaatcc aacagctatt   4140
tttctaacaa ccctctcaag aaccagcaag aaaaggagct ggccattaaa tgaggctatc   4200
atggcagtcg ggatggtgag cattttagcc agttctctcc taaaaaatga tattcccatg   4260
acaggaccat tagtggctgg agggctcctc actgtgtgct acgtgctcac tggacgatcg   4320
gccgatttgg aactggagag agcagccgat gtcaaatggg aagaccaggc agagatatca   4380
ggaagcagtc caatcctgtc aataacaata tcagaagatg gtagcatgtc gataaaaaat   4440
gaagaggaag aacaaacact gaccatactc attagaacag gattgctggt gatctcagga   4500
ctttttcctg tatcaatacc aatcacggca gcagcatggt acctgtggga agtgaagaaa   4560
caacgggccg gagtattgtg ggatgttcct tcacccccac ccatgggaaa ggctgaactg   4620
gaagatggag cctatagaat taagcaaaaa gggattcttg gatattccca gatcggagcc   4680
ggagtttaca aagaaggaac attccataca atgtggcatg tcacacgtgg cgctgttcta   4740
```

```
atgcataaag gaaagaggat tgaaccatca tgggcggacg tcaagaaaga cctaatatca   4800
tatggaggag gctggaagtt agaaggagaa tggaaggaag gagaagaagt ccaggtattg   4860
gcactggagc ctggaaaaaa tccaagagcc gtccaaacga aacctggtct tttcaaaacc   4920
aacgccggaa caataggtgc tgtatctctg gacttttctc ctggaacgtc aggatctcca   4980
attatcgaca aaaaaggaaa agttgtgggt ctttatggta atggtgttgt tacaaggagt   5040
ggagcatatg tgagtgctat agcccagact gaaaaaagca ttgaagacaa cccagagatc   5100
gaagatgaca ttttccgaaa gagaagactg accatcatgg acctccaccc aggagcggga   5160
aagacgaaga gataccttcc ggccatagtc agagaagcta taaaacgggg tttgagaaca   5220
ttaatcttgg cccccactag agttgtggca gctgaaatgg aggaagccct tagaggactt   5280
ccaataagat accagacccc agccatcaga gctgagcaca ccgggcggga gattgtggac   5340
ctaatgtgtc atgccacatt taccatgagg ctgctatcac cagttagagt gccaaactac   5400
aacctgatta tcatggacga agcccatttc acagacccag caagtatagc agctagagga   5460
tacatctcaa ctcgagtgga gatgggtgag gcagctggga tttttatgac agccactccc   5520
ccgggaagca gagacccatt tcctcagagc aatgcaccaa tcatagatga agaaagagaa   5580
atccctgaac gttcgtggaa ttccggacat gaatgggtca cggattttaa agggaagact   5640
gtttggttcg ttccaagtat aaaagcagga aatgatatag cagcttgcct gaggaaaaat   5700
ggaaagaaag tgatacaact cagtaggaag acctttgatt ctgagtatgt caagactaga   5760
accaatgatt gggacttcgt ggttacaact gacatttcag aaatgggtgc caatttcaag   5820
gctgagaggg ttatagaccc cagacgctgc atgaaaccag tcatactaac agatggtgaa   5880
gagcgggtga ttctggcagg acctatgcca gtgacccact ctagtgcagc acaaagaaga   5940
gggagaatag gaagaaatcc aaaaaatgag aatgaccagt acatatacat gggggaacct   6000
ctggaaaatg atgaagactg tgcacactgg aaagaagcta aaatgctcct agataacatc   6060
aacacgccag aaggaatcat tcctagcatg ttcgaaccag agcgtgaaaa ggtggatgcc   6120
attgatggcg aataccgctt gagaggagaa gcaaggaaaa cctttgtaga cttaatgaga   6180
agaggagacc taccagtctg gttggcctac agagtggcag ctgaaggcat caactacgca   6240
gacagaaggt ggtgttttga tggagtcaag aacaaccaaa tcctagaaga aaacgtggaa   6300
gttgaaatct ggacaaaaga aggggaaagg aagaaattga aacccagatg gttggatgct   6360
aggatctatt ctgacccact ggcgctaaaa gaatttaagg aatttgcagc cggaagaaag   6420
tctctgaccc tgaacctaat cacagaaatg ggtaggctcc caaccttcat gactcagaag   6480
gcaagaaacg cactggacaa cttagcagtg ctgcacacgg ctgaggcagg tggaagggcg   6540
tacaaccatg ctctcagtga actgccggag accctggaga cattgctttt actgacactt   6600
ctggctacag tcacgggagg gatcttttta ttcttgatga gcggaagggg catagggaag   6660
atgaccctgg gaatgtgctg cataatcacg gctagcatcc tcctatggta cgcacaaata   6720
cagccacact ggatagcagc ttcaataata ctggagtttt ttctcatagt tttgcttatt   6780
ccagaacctg aaaaacagag aacaccccaa gacaaccaac tgacctacgt tgtcatagcc   6840
atcctcacag tggtggccgc aaccatggca aacgagatgg gtttcctaga aaaaacgaag   6900
aaagatctcg gattgggaag cattgcaacc cagcaacccg agagcaacat cctggacata   6960
gatctacgtc ctgcatcagc atggacgctg tatgccgtgg ccacaacatt tgttacacca   7020
atgttgagac atagcattga aaattcctca gtgaatgtgt ccctaacagc tatagccaac   7080
```

```
caagccacag tgttaatggg tctcgggaaa ggatggccat tgtcaaagat ggacatcgga   7140
gttccccttc tcgccattgg atgctactca caagtcaacc ccataactct cacagcagct   7200
cttttcttat tggtagcaca ttatgccatc atagggccag gactccaagc aaaagcaacc   7260
agagaagctc agaaaagagc agcggcgggc atcatgaaaa acccaactgt cgatggaata   7320
acagtgattg acctagatcc aataccttat gatccaaagt ttgaaaagca gttgggacaa   7380
gtaatgctcc tagtcctctg cgtgactcaa gtattgatga tgaggactac atgggctctg   7440
tgtgaggctt taaccttagc taccgggccc atctccacat tgtgggaagg aaatccaggg   7500
aggttttgga acactaccat tgcggtgtca atggctaaca tttttagagg gagttacttg   7560
gccggagctg gacttctctt ttctattatg aagaacacaa ccaacacaag aaggggaact   7620
ggcaacatag gagagacgct tggagagaaa tggaaaagcc gattgaacgc attgggaaaa   7680
agtgaattcc agatctacaa gaaaagtgga atccaggaag tggatagaac cttagcaaaa   7740
gaaggcatta aaagaggaga aacggaccat cacgctgtgt cgcgaggctc agcaaaactg   7800
agatggttcg ttgagagaaa catggtcaca ccagaaggga aagtagtgga cctcggttgt   7860
ggcagaggag gctggtcata ctattgtgga ggactaaaga atgtaagaga agtcaaaggc   7920
ctaacaaaag gaggaccagg acacgaagaa cccatcccca tgtcaacata tgggtggaat   7980
ctagtgcgtc ttcaaagtgg agttgacgtt ttcttcatcc cgccagaaaa gtgtgacaca   8040
ttattgtgtg acatagggga gtcatcacca aatcccacag tggaagcagg acgaacactc   8100
agagtcctta acttagtaga aaattggttg aacaacaaca ctcaattttg cataaaggtt   8160
ctcaacccat atatgccctc agtcatagaa aaaatggaag cactacaaag gaaatatgga   8220
ggagccttag tgaggaatcc actctcacga aactccacac atgagatgta ctgggtatcc   8280
aatgcttccg ggaacatagt gtcatcagtg aacatgattt caaggatgtt gatcaacaga   8340
tttacaatga gatacaagaa agccacttac gagccggatg ttgacctcgg aagcggaacc   8400
cgtaacatcg ggattgaaag tgagatacca aacctagata taattgggaa aagaatagaa   8460
aaaataaagc aagagcatga aacatcatgg cactatgacc aagaccaccc atacaaaacg   8520
tgggcatacc atggtagcta tgaaacaaaa cagactggat cagcatcatc catggtcaac   8580
ggagtggtca ggctgctgac aaaaccttgg gacgtcgtcc ccatggtgac acagatggca   8640
atgacagaca cgactccatt tggacaacag cgcgtttttta aagagaaagt ggacacgaga   8700
acccaagaac cgaaagaagg cacgaagaaa ctaatgaaaa taacagcaga gtggctttgg   8760
aaagaattag ggaagaaaaa gacacccagg atgtgcacca gagaagaatt cacaagaaag   8820
gtgagaagca atgcagcctt gggggccata ttcactgatg agaacaagtg gaagtcggca   8880
cgtgaggctg ttgaagatag taggttttgg gagctggttg acaaggaaag gaatctccat   8940
cttgaaggaa agtgtgaaac atgtgtgtac aacatgatgg gaaaaagaga gaagaagcta   9000
ggggaattcg gcaaggcaaa aggcagcaga gccatatggt acatgtggct tggagcacgc   9060
ttcttagagt ttgaagccct aggattctta aatgaagatc actggttctc cagagagaac   9120
tccctgagtg gagtggaagg agaagggctg cacaagctag gttacattct aagagacgtg   9180
agcaagaaag agggaggagc aatgtatgcc gatgacaccg caggatggga tacaagaatc   9240
acactagaag acctaaaaaa tgaagaaatg gtaacaaacc acatggaagg agaacacaag   9300
aaactagccg aggccatttt caaactaacg taccaaaaca aggtggtgcg tgtgcaaaga   9360
ccaacaccaa gaggcacagt aatggacatc atatcgagaa gagaccaaag aggtagtgga   9420
caagttggca cctatggact caatactttc accaatatgg aagcccaact aatcagacag   9480
```

```
atggagggag aaggagtctt taaaagcatt cagcacctaa caatcacaga agaaatcgct   9540
gtgcaaaact ggttagcaag agtggggcgc gaaaggttat caagaatggc catcagtgga   9600
gatgattgtg ttgtgaaacc tttagatgac aggttcgcaa gcgctttaac agctctaaat   9660
gacatgggaa agattaggaa agacatacaa caatgggaac cttcaagagg atggaatgat   9720
tggacacaag tgcccttctg ttcacaccat ttccatgagt taatcatgaa agacggtcgc   9780
gtactcgttg ttccatgtag aaaccaagat gaactgattg gcagagcccg aatctcccaa   9840
ggagcagggt ggtctttgcg ggagacggcc tgtttgggga agtcttacgc ccaaatgtgg   9900
agcttgatgt acttccacag acgcgacctc aggctggcgg caaatgctat ttgctcggca   9960
gtaccatcac attgggttcc aacaagtcga acaacctggt ccatacatgc taaacatgaa  10020
tggatgacaa cggaagacat gctgacagtc tggaacaggg tgtggattca agaaaaccca  10080
tggatggaag acaaaactcc agtggaatca tgggaggaaa tcccatactt ggggaaaaga  10140
gaagaccaat ggtgcggctc attgattggg ttaacaagca gggccacctg ggcaaagaac  10200
atccaagcag caataaatca agttagatcc cttataggca atgaagaata cacagattac  10260
atgccatcca tgaaaagatt cagaagagaa gaggaagaag caggagttct gtggtagaaa  10320
gcaaaactaa catgaaacaa ggctagaagt caggtcggat taagccatag tacggaaaaa  10380
actatgctac ctgtgagccc cgtccaagga cgttaaaaga agtcaggcca tcataaatgc  10440
catagcttga gtaaactatg cagcctgtag ctccacctga gaaggtgtaa aaaatccggg  10500
aggccacaaa ccatggaagc tgtacgcatg gcgtagtgga ctagcggtta gaggagaccc  10560
ctcccttaca aatcgcagca acaatggggg cccaaggcga gatgaagctg tagtctcgct  10620
ggaaggacta gaggttagag gagacccccc cgaaacaaaa aacagcatat tgacgctggg  10680
aaagaccaga gatcctgctg tctcctcagc atcattccag gcacagaacg ccagaaaatg  10740
gaatggtgct gttgaatcaa caggttct                                    10768
```

<210> SEQ ID NO 24
<211> LENGTH: 3406
<212> TYPE: PRT
<213> ORGANISM: Artificial Sequence
<220> FEATURE:
<223> OTHER INFORMATION: Synthetic polypeptide

<400> SEQUENCE: 24

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Thr Ser Val Gly Ile Val Gly Leu Leu
            100                 105                 110

Leu Thr Thr Ala Met Ala Ala Glu Val Thr Arg Arg Gly Ser Ala Tyr
        115                 120                 125
```

```
Tyr Met Tyr Leu Asp Arg Asn Asp Ala Gly Glu Ala Ile Ser Phe Pro
    130                 135                 140

Thr Thr Leu Gly Met Asn Lys Cys Tyr Ile Gln Ile Met Asp Leu Gly
145                 150                 155                 160

His Met Cys Asp Ala Thr Met Ser Tyr Glu Cys Pro Met Leu Asp Glu
                165                 170                 175

Gly Val Glu Pro Asp Asp Val Asp Cys Trp Cys Asn Thr Thr Ser Thr
            180                 185                 190

Trp Val Val Tyr Gly Thr Cys His His Lys Lys Gly Glu Ala Arg Arg
        195                 200                 205

Ser Arg Arg Ala Val Thr Leu Pro Ser His Ser Thr Arg Lys Leu Gln
    210                 215                 220

Thr Arg Ser Gln Thr Trp Leu Glu Ser Arg Glu Tyr Thr Lys His Leu
225                 230                 235                 240

Ile Arg Val Glu Asn Trp Ile Phe Arg Asn Pro Gly Phe Ala Leu Ala
                245                 250                 255

Ala Ala Ala Ile Ala Trp Leu Leu Gly Ser Ser Thr Ser Gln Lys Val
            260                 265                 270

Ile Tyr Leu Val Met Ile Leu Leu Ile Ala Pro Ala Tyr Ser Ile Arg
        275                 280                 285

Cys Ile Gly Val Ser Asn Arg Asp Phe Val Glu Gly Met Ser Gly Gly
    290                 295                 300

Thr Trp Val Asp Ile Val Leu Glu His Gly Gly Cys Val Thr Val Met
305                 310                 315                 320

Ala Gln Asp Lys Pro Thr Val Asp Ile Glu Leu Val Thr Thr Thr Val
                325                 330                 335

Ser Asn Met Ala Glu Val Arg Ser Tyr Cys Tyr Glu Ala Ser Ile Ser
            340                 345                 350

Asp Met Ala Ser Asp Ser Arg Cys Pro Thr Gln Gly Glu Ala Tyr Leu
        355                 360                 365

Asp Lys Gln Ser Asp Thr Gln Tyr Val Cys Lys Arg Thr Leu Val Asp
    370                 375                 380

Arg Gly Trp Gly Asn Gly Cys Gly Leu Phe Gly Lys Gly Ser Leu Val
385                 390                 395                 400

Thr Cys Ala Lys Phe Ala Cys Ser Lys Lys Met Thr Gly Lys Ser Ile
                405                 410                 415

Gln Pro Glu Asn Leu Glu Tyr Arg Ile Met Leu Ser Val His Gly Ser
            420                 425                 430

Gln His Ser Gly Met Ile Val Asn Asp Thr Gly His Glu Thr Asp Glu
        435                 440                 445

Asn Arg Ala Lys Val Glu Ile Thr Pro Asn Ser Pro Arg Ala Glu Ala
    450                 455                 460

Thr Leu Gly Gly Phe Gly Ser Leu Gly Leu Asp Cys Glu Pro Arg Thr
465                 470                 475                 480

Gly Leu Asp Phe Ser Asp Leu Tyr Tyr Leu Thr Met Asn Asn Lys His
                485                 490                 495

Trp Leu Val His Lys Glu Trp Phe His Asp Ile Pro Leu Pro Trp His
            500                 505                 510

Ala Gly Ala Asp Thr Gly Thr Pro His Trp Asn Asn Lys Glu Ala Leu
        515                 520                 525

Val Glu Phe Lys Asp Ala His Ala Lys Arg Gln Thr Val Val Val Leu
    530                 535                 540

Gly Ser Gln Glu Gly Ala Val His Thr Ala Leu Ala Gly Ala Leu Glu
```

```
545                 550                 555                 560

Ala Glu Met Asp Gly Ala Lys Gly Arg Leu Ser Ser Gly His Leu Lys
                565                 570                 575

Cys Arg Leu Lys Met Asp Lys Leu Arg Leu Lys Gly Val Ser Tyr Ser
            580                 585                 590

Leu Cys Thr Ala Ala Phe Thr Phe Thr Lys Ile Pro Ala Glu Thr Leu
        595                 600                 605

His Gly Thr Val Thr Val Glu Val Gln Tyr Ala Gly Thr Asp Gly Pro
    610                 615                 620

Cys Lys Val Pro Ala Gln Met Ala Val Asp Met Gln Thr Leu Thr Pro
625                 630                 635                 640

Val Gly Arg Leu Ile Thr Ala Asn Pro Val Ile Thr Glu Ser Thr Glu
                645                 650                 655

Asn Ser Lys Met Met Leu Glu Leu Asp Pro Pro Phe Gly Asp Ser Tyr
            660                 665                 670

Ile Val Ile Gly Val Gly Glu Lys Lys Ile Thr His His Trp His Arg
        675                 680                 685

Ser Gly Ser Thr Ile Gly Lys Ala Phe Glu Ala Thr Val Arg Gly Ala
    690                 695                 700

Lys Arg Met Ala Val Leu Gly Asp Thr Ala Trp Asp Phe Gly Ser Val
705                 710                 715                 720

Gly Gly Ala Leu Asn Ser Leu Gly Lys Gly Ile His Gln Ile Phe Gly
                725                 730                 735

Ala Ala Phe Lys Ser Leu Phe Gly Gly Met Ser Trp Phe Ser Arg Ile
            740                 745                 750

Leu Ile Gly Thr Leu Leu Met Trp Leu Gly Leu Asn Thr Lys Asn Gly
        755                 760                 765

Ser Thr Ser Leu Met Cys Leu Ala Ala Gly Phe Val Thr Leu Tyr Leu
    770                 775                 780

Gly Val Met Val Gln Ala Asp Ser Gly Cys Val Val Ser Trp Lys Asn
785                 790                 795                 800

Lys Glu Leu Lys Cys Gly Ser Gly Ile Phe Ile Thr Asp Asn Val His
                805                 810                 815

Thr Trp Thr Glu Gln Tyr Lys Phe Gln Pro Glu Ser Pro Ser Lys Leu
            820                 825                 830

Ala Ser Ala Ile Gln Lys Ala His Glu Glu Gly Ile Cys Gly Ile Arg
        835                 840                 845

Ser Val Thr Arg Leu Glu Asn Leu Met Trp Lys Gln Ile Thr Pro Glu
    850                 855                 860

Leu Asn His Ile Leu Ser Glu Asn Glu Val Lys Leu Thr Ile Met Thr
865                 870                 875                 880

Gly Asp Ile Lys Gly Ile Met Gln Ala Gly Lys Arg Ser Leu Arg Pro
                885                 890                 895

Gln Pro Thr Glu Leu Lys Tyr Ser Trp Lys Thr Trp Gly Lys Ala Lys
            900                 905                 910

Met Leu Ser Thr Glu Ser His Asn Gln Thr Phe Leu Ile Asp Gly Pro
        915                 920                 925

Glu Thr Ala Glu Cys Pro Asn Thr Asn Arg Ala Trp Asn Ser Leu Glu
    930                 935                 940

Val Glu Asp Tyr Gly Phe Gly Val Phe Thr Thr Asn Ile Trp Leu Lys
945                 950                 955                 960

Leu Lys Glu Lys Gln Asp Val Phe Cys Asp Ser Lys Leu Met Ser Ala
                965                 970                 975
```

```
Ala Ile Lys Asp Asn Arg Ala Val His Ala Asp Met Gly Tyr Trp Ile
            980                 985                 990

Glu Ser Ala Leu Asn Asp Thr Trp  Lys Ile Glu Lys Ala  Ser Phe Ile
        995                 1000                1005

Glu Val  Lys Asn Cys His Trp  Pro Lys Ser His Thr  Leu Trp Ser
    1010                 1015                 1020

Asn Gly  Val Leu Glu Ser Glu  Met Ile Ile Pro Lys  Asn Leu Ala
    1025                 1030                 1035

Gly Pro  Val Ser Gln His Asn  Tyr Arg Pro Gly Tyr  His Thr Gln
    1040                 1045                 1050

Ile Thr  Gly Pro Trp His Leu  Gly Lys Leu Glu Met  Asp Phe Asp
    1055                 1060                 1065

Phe Cys  Asp Gly Thr Thr Val  Val Val Thr Glu Asp  Cys Gly Asn
    1070                 1075                 1080

Arg Gly  Pro Ser Leu Arg Thr  Thr Thr Ala Ser Gly  Lys Leu Ile
    1085                 1090                 1095

Thr Glu  Trp Cys Cys Arg Ser  Cys Thr Leu Pro Pro  Leu Arg Tyr
    1100                 1105                 1110

Arg Gly  Glu Asp Gly Cys Trp  Tyr Gly Met Glu Ile  Arg Pro Leu
    1115                 1120                 1125

Lys Glu  Lys Glu Glu Asn Leu  Val Asn Ser Leu Val  Thr Ala Gly
    1130                 1135                 1140

His Gly  Gln Val Asp Asn Phe  Ser Leu Gly Val Leu  Gly Met Ala
    1145                 1150                 1155

Leu Phe  Leu Glu Glu Met Leu  Arg Thr Arg Val Gly  Thr Lys His
    1160                 1165                 1170

Ala Ile  Leu Leu Val Ala Val  Ser Phe Val Thr Leu  Ile Thr Gly
    1175                 1180                 1185

Asn Met  Ser Phe Arg Asp Leu  Gly Arg Val Met Val  Met Val Gly
    1190                 1195                 1200

Ala Thr  Met Thr Asp Asp Ile  Gly Met Gly Val Thr  Tyr Leu Ala
    1205                 1210                 1215

Leu Leu  Ala Ala Phe Lys Val  Arg Pro Thr Phe Ala  Ala Gly Leu
    1220                 1225                 1230

Leu Leu  Arg Lys Leu Thr Ser  Asn Glu Leu Met Met  Thr Thr Ile
    1235                 1240                 1245

Gly Ile  Val Leu Leu Ser Gln  Ser Thr Ile Pro Glu  Thr Ile Leu
    1250                 1255                 1260

Glu Leu  Thr Asp Ala Leu Ala  Leu Gly Met Met Val  Leu Lys Met
    1265                 1270                 1275

Val Arg  Asn Met Glu Lys Tyr  Gln Leu Ala Val Thr  Ile Met Ala
    1280                 1285                 1290

Ile Leu  Cys Val Pro Asn Ala  Val Ile Leu Gln Asn  Ala Trp Lys
    1295                 1300                 1305

Val Ser  Cys Thr Ile Leu Ala  Val Val Ser Val Ser  Pro Leu Leu
    1310                 1315                 1320

Leu Thr  Ser Ser Gln Gln Lys  Thr Asp Trp Ile Pro  Leu Ala Leu
    1325                 1330                 1335

Thr Ile  Lys Gly Leu Asn Pro  Thr Ala Ile Phe Leu  Thr Thr Leu
    1340                 1345                 1350

Ser Arg  Thr Ser Lys Lys Arg  Ser Trp Pro Leu Asn  Glu Ala Ile
    1355                 1360                 1365
```

```
Met Ala  Val Gly Met Val Ser  Ile Leu Ala Ser Ser  Leu Leu Lys
    1370                 1375                 1380

Asn Asp  Ile Pro Met Thr Gly  Pro Leu Val Ala Gly  Gly Leu Leu
    1385                 1390                 1395

Thr Val  Cys Tyr Val Leu Thr  Gly Arg Ser Ala Asp  Leu Glu Leu
    1400                 1405                 1410

Glu Arg  Ala Ala Asp Val Lys  Trp Glu Asp Gln Ala  Glu Ile Ser
    1415                 1420                 1425

Gly Ser  Ser Pro Ile Leu Ser  Ile Thr Ile Ser Glu  Asp Gly Ser
    1430                 1435                 1440

Met Ser  Ile Lys Asn Glu Glu  Glu Glu Gln Thr Leu  Thr Ile Leu
    1445                 1450                 1455

Ile Arg  Thr Gly Leu Leu Val  Ile Ser Gly Leu Phe  Pro Val Ser
    1460                 1465                 1470

Ile Pro  Ile Thr Ala Ala Ala  Trp Tyr Leu Trp Glu  Val Lys Lys
    1475                 1480                 1485

Gln Arg  Ala Gly Val Leu Trp  Asp Val Pro Ser Pro  Pro Pro Met
    1490                 1495                 1500

Gly Lys  Ala Glu Leu Glu Asp  Gly Ala Tyr Arg Ile  Lys Gln Lys
    1505                 1510                 1515

Gly Ile  Leu Gly Tyr Ser Gln  Ile Gly Ala Gly Val  Tyr Lys Glu
    1520                 1525                 1530

Gly Thr  Phe His Thr Met Trp  His Val Thr Arg Gly  Ala Val Leu
    1535                 1540                 1545

Met His  Lys Gly Lys Arg Ile  Glu Pro Ser Trp Ala  Asp Val Lys
    1550                 1555                 1560

Lys Asp  Leu Ile Ser Tyr Gly  Gly Gly Trp Lys Leu  Glu Gly Glu
    1565                 1570                 1575

Trp Lys  Glu Gly Glu Glu Val  Gln Val Leu Ala Leu  Glu Pro Gly
    1580                 1585                 1590

Lys Asn  Pro Arg Ala Val Gln  Thr Lys Pro Gly Leu  Phe Lys Thr
    1595                 1600                 1605

Asn Ala  Gly Thr Ile Gly Ala  Val Ser Leu Asp Phe  Ser Pro Gly
    1610                 1615                 1620

Thr Ser  Gly Ser Pro Ile Ile  Asp Lys Lys Gly Lys  Val Val Gly
    1625                 1630                 1635

Leu Tyr  Gly Asn Gly Val Val  Thr Arg Ser Gly Ala  Tyr Val Ser
    1640                 1645                 1650

Ala Ile  Ala Gln Thr Glu Lys  Ser Ile Glu Asp Asn  Pro Glu Ile
    1655                 1660                 1665

Glu Asp  Asp Ile Phe Arg Lys  Arg Arg Leu Thr Ile  Met Asp Leu
    1670                 1675                 1680

His Pro  Gly Ala Gly Lys Thr  Lys Arg Tyr Leu Pro  Ala Ile Val
    1685                 1690                 1695

Arg Glu  Ala Ile Lys Arg Gly  Leu Arg Thr Leu Ile  Leu Ala Pro
    1700                 1705                 1710

Thr Arg  Val Val Ala Ala Glu  Met Glu Glu Ala Leu  Arg Gly Leu
    1715                 1720                 1725

Pro Ile  Arg Tyr Gln Thr Pro  Ala Ile Arg Ala Glu  His Thr Gly
    1730                 1735                 1740

Arg Glu  Ile Val Asp Leu Met  Cys His Ala Thr Phe  Thr Met Arg
    1745                 1750                 1755

Leu Leu  Ser Pro Val Arg Val  Pro Asn Tyr Asn Leu  Ile Ile Met
```

```
    1760                1765                1770

Asp Glu  Ala His Phe Thr Asp  Pro Ala Ser Ile Ala  Ala Arg Gly
    1775                1780                1785

Tyr Ile  Ser Thr Arg Val Glu  Met Gly Glu Ala Ala  Gly Ile Phe
    1790                1795                1800

Met Thr  Ala Thr Pro Pro Gly  Ser Arg Asp Pro Phe  Pro Gln Ser
    1805                1810                1815

Asn Ala  Pro Ile Ile Asp Glu  Glu Arg Glu Ile Pro  Glu Arg Ser
    1820                1825                1830

Trp Asn  Ser Gly His Glu Trp  Val Thr Asp Phe Lys  Gly Lys Thr
    1835                1840                1845

Val Trp  Phe Val Pro Ser Ile  Lys Ala Gly Asn Asp  Ile Ala Ala
    1850                1855                1860

Cys Leu  Arg Lys Asn Gly Lys  Lys Val Ile Gln Leu  Ser Arg Lys
    1865                1870                1875

Thr Phe  Asp Ser Glu Tyr Val  Lys Thr Arg Thr Asn  Asp Trp Asp
    1880                1885                1890

Phe Val  Val Thr Thr Asp Ile  Ser Glu Met Gly Ala  Asn Phe Lys
    1895                1900                1905

Ala Glu  Arg Val Ile Asp Pro  Arg Arg Cys Met Lys  Pro Val Ile
    1910                1915                1920

Leu Thr  Asp Gly Glu Glu Arg  Val Ile Leu Ala Gly  Pro Met Pro
    1925                1930                1935

Val Thr  His Ser Ser Ala Ala  Gln Arg Arg Gly Arg  Ile Gly Arg
    1940                1945                1950

Asn Pro  Lys Asn Glu Asn Asp  Gln Tyr Ile Tyr Met  Gly Glu Pro
    1955                1960                1965

Leu Glu  Asn Asp Glu Asp Cys  Ala His Trp Lys Glu  Ala Lys Met
    1970                1975                1980

Leu Leu  Asp Asn Ile Asn Thr  Pro Glu Gly Ile Ile  Pro Ser Met
    1985                1990                1995

Phe Glu  Pro Glu Arg Glu Lys  Val Asp Ala Ile Asp  Gly Glu Tyr
    2000                2005                2010

Arg Leu  Arg Gly Glu Ala Arg  Lys Thr Phe Val Asp  Leu Met Arg
    2015                2020                2025

Arg Gly  Asp Leu Pro Val Trp  Leu Ala Tyr Arg Val  Ala Ala Glu
    2030                2035                2040

Gly Ile  Asn Tyr Ala Asp Arg  Arg Trp Cys Phe Asp  Gly Val Lys
    2045                2050                2055

Asn Asn  Gln Ile Leu Glu Glu  Asn Val Glu Val Glu  Ile Trp Thr
    2060                2065                2070

Lys Glu  Gly Glu Arg Lys Lys  Leu Lys Pro Arg Trp  Leu Asp Ala
    2075                2080                2085

Arg Ile  Tyr Ser Asp Pro Leu  Ala Leu Lys Glu Phe  Lys Glu Phe
    2090                2095                2100

Ala Ala  Gly Arg Lys Ser Leu  Thr Leu Asn Leu Ile  Thr Glu Met
    2105                2110                2115

Gly Arg  Leu Pro Thr Phe Met  Thr Gln Lys Ala Arg  Asn Ala Leu
    2120                2125                2130

Asp Asn  Leu Ala Val Leu His  Thr Ala Glu Ala Gly  Gly Arg Ala
    2135                2140                2145

Tyr Asn  His Ala Leu Ser Glu  Leu Pro Glu Thr Leu  Glu Thr Leu
    2150                2155                2160
```

```
Leu Leu  Leu Thr Leu Leu Ala  Thr Val Thr Gly Gly  Ile Phe Leu
    2165                 2170                 2175

Phe Leu  Met Ser Gly Arg Gly  Ile Gly Lys Met Thr  Leu Gly Met
    2180                 2185                 2190

Cys Cys  Ile Ile Thr Ala Ser  Ile Leu Leu Trp Tyr  Ala Gln Ile
    2195                 2200                 2205

Gln Pro  His Trp Ile Ala Ala  Ser Ile Ile Leu Glu  Phe Phe Leu
    2210                 2215                 2220

Ile Val  Leu Leu Ile Pro Glu  Pro Glu Lys Gln Arg  Thr Pro Gln
    2225                 2230                 2235

Asp Asn  Gln Leu Thr Tyr Val  Val Ile Ala Ile Leu  Thr Val Val
    2240                 2245                 2250

Ala Ala  Thr Met Ala Asn Glu  Met Gly Phe Leu Glu  Lys Thr Lys
    2255                 2260                 2265

Lys Asp  Leu Gly Leu Gly Ser  Ile Ala Thr Gln Gln  Pro Glu Ser
    2270                 2275                 2280

Asn Ile  Leu Asp Ile Asp Leu  Arg Pro Ala Ser Ala  Trp Thr Leu
    2285                 2290                 2295

Tyr Ala  Val Ala Thr Thr Phe  Val Thr Pro Met Leu  Arg His Ser
    2300                 2305                 2310

Ile Glu  Asn Ser Ser Val Asn  Val Ser Leu Thr Ala  Ile Ala Asn
    2315                 2320                 2325

Gln Ala  Thr Val Leu Met Gly  Leu Gly Lys Gly Trp  Pro Leu Ser
    2330                 2335                 2340

Lys Met  Asp Ile Gly Val Pro  Leu Leu Ala Ile Gly  Cys Tyr Ser
    2345                 2350                 2355

Gln Val  Asn Pro Ile Thr Leu  Thr Ala Ala Leu Phe  Leu Leu Val
    2360                 2365                 2370

Ala His  Tyr Ala Ile Ile Gly  Pro Gly Leu Gln Ala  Lys Ala Thr
    2375                 2380                 2385

Arg Glu  Ala Gln Lys Arg Ala  Ala Ala Gly Ile Met  Lys Asn Pro
    2390                 2395                 2400

Thr Val  Asp Gly Ile Thr Val  Ile Asp Leu Asp Pro  Ile Pro Tyr
    2405                 2410                 2415

Asp Pro  Lys Phe Glu Lys Gln  Leu Gly Gln Val Met  Leu Leu Val
    2420                 2425                 2430

Leu Cys  Val Thr Gln Val Leu  Met Met Arg Thr Thr  Trp Ala Leu
    2435                 2440                 2445

Cys Glu  Ala Leu Thr Leu Ala  Thr Gly Pro Ile Ser  Thr Leu Trp
    2450                 2455                 2460

Glu Gly  Asn Pro Gly Arg Phe  Trp Asn Thr Thr Ile  Ala Val Ser
    2465                 2470                 2475

Met Ala  Asn Ile Phe Arg Gly  Ser Tyr Leu Ala Gly  Ala Gly Leu
    2480                 2485                 2490

Leu Phe  Ser Ile Met Lys Asn  Thr Thr Asn Thr Arg  Arg Gly Thr
    2495                 2500                 2505

Gly Asn  Ile Gly Glu Thr Leu  Gly Glu Lys Trp Lys  Ser Arg Leu
    2510                 2515                 2520

Asn Ala  Leu Gly Lys Ser Glu  Phe Gln Ile Tyr Lys  Lys Ser Gly
    2525                 2530                 2535

Ile Gln  Glu Val Asp Arg Thr  Leu Ala Lys Glu Gly  Ile Lys Arg
    2540                 2545                 2550
```

```
Gly Glu  Thr Asp His His Ala  Val Ser Arg Gly Ser  Ala Lys Leu
    2555                 2560                 2565

Arg Trp  Phe Val Glu Arg Asn  Met Val Thr Pro Glu  Gly Lys Val
    2570                 2575                 2580

Val Asp  Leu Gly Cys Gly Arg  Gly Gly Trp Ser Tyr  Tyr Cys Gly
    2585                 2590                 2595

Gly Leu  Lys Asn Val Arg Glu  Val Lys Gly Leu Thr  Lys Gly Gly
    2600                 2605                 2610

Pro Gly  His Glu Glu Pro Ile  Pro Met Ser Thr Tyr  Gly Trp Asn
    2615                 2620                 2625

Leu Val  Arg Leu Gln Ser Gly  Val Asp Val Phe Phe  Ile Pro Pro
    2630                 2635                 2640

Glu Lys  Cys Asp Thr Leu Leu  Cys Asp Ile Gly Glu  Ser Ser Pro
    2645                 2650                 2655

Asn Pro  Thr Val Glu Ala Gly  Arg Thr Leu Arg Val  Leu Asn Leu
    2660                 2665                 2670

Val Glu  Asn Trp Leu Asn Asn  Asn Thr Gln Phe Cys  Ile Lys Val
    2675                 2680                 2685

Leu Asn  Pro Tyr Met Pro Ser  Val Ile Glu Lys Met  Glu Ala Leu
    2690                 2695                 2700

Gln Arg  Lys Tyr Gly Gly Ala  Leu Val Arg Asn Pro  Leu Ser Arg
    2705                 2710                 2715

Asn Ser  Thr His Glu Met Tyr  Trp Val Ser Asn Ala  Ser Gly Asn
    2720                 2725                 2730

Ile Val  Ser Ser Val Asn Met  Ile Ser Arg Met Leu  Ile Asn Arg
    2735                 2740                 2745

Phe Thr  Met Arg Tyr Lys Lys  Ala Thr Tyr Glu Pro  Asp Val Asp
    2750                 2755                 2760

Leu Gly  Ser Gly Thr Arg Asn  Ile Gly Ile Glu Ser  Glu Ile Pro
    2765                 2770                 2775

Asn Leu  Asp Ile Ile Gly Lys  Arg Ile Glu Lys Ile  Lys Gln Glu
    2780                 2785                 2790

His Glu  Thr Ser Trp His Tyr  Asp Gln Asp His Pro  Tyr Lys Thr
    2795                 2800                 2805

Trp Ala  Tyr His Gly Ser Tyr  Glu Thr Lys Gln Thr  Gly Ser Ala
    2810                 2815                 2820

Ser Ser  Met Val Asn Gly Val  Val Arg Leu Leu Thr  Lys Pro Trp
    2825                 2830                 2835

Asp Val  Val Pro Met Val Thr  Gln Met Ala Met Thr  Asp Thr Thr
    2840                 2845                 2850

Pro Phe  Gly Gln Gln Arg Val  Phe Lys Glu Lys Val  Asp Thr Arg
    2855                 2860                 2865

Thr Gln  Glu Pro Lys Glu Gly  Thr Lys Lys Leu Met  Lys Ile Thr
    2870                 2875                 2880

Ala Glu  Trp Leu Trp Lys Glu  Leu Gly Lys Lys Lys  Thr Pro Arg
    2885                 2890                 2895

Met Cys  Thr Arg Glu Glu Phe  Thr Arg Lys Val Arg  Ser Asn Ala
    2900                 2905                 2910

Ala Leu  Gly Ala Ile Phe Thr  Asp Glu Asn Lys Trp  Lys Ser Ala
    2915                 2920                 2925

Arg Glu  Ala Val Glu Asp Ser  Arg Phe Trp Glu Leu  Val Asp Lys
    2930                 2935                 2940

Glu Arg  Asn Leu His Leu Glu  Gly Lys Cys Glu Thr  Cys Val Tyr
```

```
    2945                2950                2955

Asn Met Met Gly Lys Arg Glu Lys Lys Leu Gly Glu Phe Gly Lys
    2960                2965                2970

Ala Lys Gly Ser Arg Ala Ile Trp Tyr Met Trp Leu Gly Ala Arg
    2975                2980                2985

Phe Leu Glu Phe Glu Ala Leu Gly Phe Leu Asn Glu Asp His Trp
    2990                2995                3000

Phe Ser Arg Glu Asn Ser Leu Ser Gly Val Glu Gly Glu Gly Leu
    3005                3010                3015

His Lys Leu Gly Tyr Ile Leu Arg Asp Val Ser Lys Lys Glu Gly
    3020                3025                3030

Gly Ala Met Tyr Ala Asp Asp Thr Ala Gly Trp Asp Thr Arg Ile
    3035                3040                3045

Thr Leu Glu Asp Leu Lys Asn Glu Glu Met Val Thr Asn His Met
    3050                3055                3060

Glu Gly Glu His Lys Lys Leu Ala Glu Ala Ile Phe Lys Leu Thr
    3065                3070                3075

Tyr Gln Asn Lys Val Val Arg Val Gln Arg Pro Thr Pro Arg Gly
    3080                3085                3090

Thr Val Met Asp Ile Ile Ser Arg Arg Asp Gln Arg Gly Ser Gly
    3095                3100                3105

Gln Val Gly Thr Tyr Gly Leu Asn Thr Phe Thr Asn Met Glu Ala
    3110                3115                3120

Gln Leu Ile Arg Gln Met Glu Gly Glu Gly Val Phe Lys Ser Ile
    3125                3130                3135

Gln His Leu Thr Ile Thr Glu Glu Ile Ala Val Gln Asn Trp Leu
    3140                3145                3150

Ala Arg Val Gly Arg Glu Arg Leu Ser Arg Met Ala Ile Ser Gly
    3155                3160                3165

Asp Asp Cys Val Val Lys Pro Leu Asp Asp Arg Phe Ala Ser Ala
    3170                3175                3180

Leu Thr Ala Leu Asn Asp Met Gly Lys Ile Arg Lys Asp Ile Gln
    3185                3190                3195

Gln Trp Glu Pro Ser Arg Gly Trp Asn Asp Trp Thr Gln Val Pro
    3200                3205                3210

Phe Cys Ser His His Phe His Glu Leu Ile Met Lys Asp Gly Arg
    3215                3220                3225

Val Leu Val Val Pro Cys Arg Asn Gln Asp Glu Leu Ile Gly Arg
    3230                3235                3240

Ala Arg Ile Ser Gln Gly Ala Gly Trp Ser Leu Arg Glu Thr Ala
    3245                3250                3255

Cys Leu Gly Lys Ser Tyr Ala Gln Met Trp Ser Leu Met Tyr Phe
    3260                3265                3270

His Arg Arg Asp Leu Arg Leu Ala Ala Asn Ala Ile Cys Ser Ala
    3275                3280                3285

Val Pro Ser His Trp Val Pro Thr Ser Arg Thr Thr Trp Ser Ile
    3290                3295                3300

His Ala Lys His Glu Trp Met Thr Thr Glu Asp Met Leu Thr Val
    3305                3310                3315

Trp Asn Arg Val Trp Ile Gln Glu Asn Pro Trp Met Glu Asp Lys
    3320                3325                3330

Thr Pro Val Glu Ser Trp Glu Glu Ile Pro Tyr Leu Gly Lys Arg
    3335                3340                3345
```

```
Glu Asp  Gln Trp Cys Gly Ser  Leu Ile Gly Leu Thr  Ser Arg Ala
    3350                3355                3360

Thr Trp  Ala Lys Asn Ile Gln  Ala Ala Ile Asn Gln  Val Arg Ser
    3365                3370                3375

Leu Ile  Gly Asn Glu Glu Tyr  Thr Asp Tyr Met Pro  Ser Met Lys
    3380                3385                3390

Arg Phe  Arg Arg Glu Glu Glu  Glu Ala Gly Val Leu  Trp
    3395                3400                3405
```

```
<210> SEQ ID NO 25
<211> LENGTH: 10768
<212> TYPE: DNA
<213> ORGANISM: Artificial Sequence
<220> FEATURE:
<223> OTHER INFORMATION: Synthetic construct

<400> SEQUENCE: 25

agttgttagt ctacgtggac cgacaaagac agattctttg agggagctaa gctcaatgta     60

gttctaacag tttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatccg cgggtactag tgtcggaatt    420

gttggcctcc tgctgaccac agctatggca gcggaggtca ctagacgtgg gagtgcatac    480

tatatgtact tggacagaaa cgatgctggg gaggccatat cttttccaac cacattgggg    540

atgaataagt gttatataca gatcatggat cttggacaca tgtgtgatgc caccatgagc    600

tatgaatgcc ctatgctgga tgagggggtg gaaccagatg acgtcgattg ttggtgcaac    660

acgacgtcaa cttgggttgt gtacggaacc tgccatcaca aaaaaggtga agcacggaga    720

agtagaagag ctgtgacgct cccctcccat tccactagga agctgcaaac gcggtcgcaa    780

acctggttgg aatcaagaga atacacaaag cacttgatta gagtcgaaaa ttggatattc    840

aggaaccctg gcttcgcgtt agcagcagct gccatcgctt ggcttttggg aagctcaacg    900

agccaaaaag tcatatactt ggtcatgata ctgctgattg ccccggcata cagcatcagg    960

tgcataggag tcagcaatag ggactttgtg gaaggtatgt caggtgggac ttgggttgat   1020

attgtcttgg aacatggagg ttgtgtcacc gtaatggcac aggacaaacc gactgtcgac   1080

atagagctgg ttacaacaac agtcagcaac atggcggagg taagatccta ctgctatgag   1140

gcatcaatat cagacatggc ttcggacagc cgctgcccaa cacaaggtga agcctacctt   1200

gacaagcaat cagacactca atatgtctgc aaaagaacgt tagtggacag aggctgggga   1260

aatggatgtg gacttttttgg caaagggagt ctggtgacat gcgctaagtt tgcatgctcc   1320

aagaaaatga ccgggaagag catccagcca gagaatctgg agtaccggat aatgctgtca   1380

gttcatggct cccagcacag tgggatgatc gttaatgaca caggacatga aactgatgag   1440

aatagagcga aggttgagat aacgcccaat tcaccaagag ccgaagccac cctgggggggt   1500

tttggaagcc taggacttga ttgtgaaccg aggacaggcc ttgacttttc agatttgtat   1560

tacttgacta tgaataacaa gcactggttg gttcacaagg agtggttcca cgacattcca   1620

ttaccttggc acgctggggc agacaccgga actccacact ggaacaacaa agaagcactg   1680
```

```
gtagagttca aggacgcaca tgccaaaagg caaactgtcg tggttctagg gagtcaagaa   1740
ggagcagttc acacggccct tgctggagct ctggaggctg agatggatgg tgcaaaggga   1800
aggctgtcct ctggccactt gaaatgtcgc ctgaaaatgg ataaacttag attgaagggc   1860
gtgtcatact ccttgtgtac cgcagcgttc acattcacca agatcccggc tgaaacactg   1920
cacgggacag tcacagtgga ggtacagtac gcagggacag atggaccttg caaggttcca   1980
gctcagatgg cggtggacat gcaaactctg accccagttg ggaggttgat aaccgctaac   2040
cccgtaatca ctgaaagcac tgagaactct aagatgatgc tggaacttga tccaccattt   2100
ggggactctt acattgtcat aggagtcggg gagaagaaga tcacccacca ctggcacagg   2160
agtggcagca ccattggaaa agcatttgaa gccactgtga gaggtgccaa gagaatggca   2220
gtcttgggag acacagcctg ggactttgga tcagttggag gcgctctcaa ctcattgggc   2280
aagggcatcc atcaaatttt tggagcagct ttcaaatcat tgtttggagg aatgtcctgg   2340
ttctcaagaa ttctcattgg aacgttgctg atgtggttgg gtctgaacac aaagaatgga   2400
tctacttccc ttatgtgctt ggccgccggc tttgtgacac tgtatttggg agtcatggtg   2460
caggccgata gtggttgcgt tgtgagctgg aaaaacaaag aactgaaatg tggcagtggg   2520
attttcatca cagacaacgt gcacacatgg acagaacaat acaagttcca accagaatcc   2580
ccttcaaaac tagcttcagc tatccagaaa gcccatgaag aggacatttg tggaatccgc   2640
tcagtaacaa gactggagaa tctgatgtgg aaacaaataa caccagaatt gaatcacatt   2700
ctatcagaaa atgaggtgaa gttaactatt atgacaggag acatcaaagg aatcatgcag   2760
gcaggaaaac gatctctgcg gcctcagccc actgagctga agtattcatg gaaaacatgg   2820
ggcaaagcaa aaatgctctc tacagagtct cataaccaga cctttctcat tgatggcccc   2880
gaaacagcag aatgccccaa cacaaataga gcttggaatt cgttggaagt tgaagactat   2940
ggctttggag tattcaccac caatatatgg ctaaaattga aagaaaaaca ggatgtattc   3000
tgcgactcaa aactcatgtc agcggccata aaagacaaca gagccgtcca tgccgatatg   3060
ggttattgga tagaaagtgc actcaatgac acatggaaga tagagaaagc ctctttcatt   3120
gaagttaaaa actgccactg gccaaaatca cacaccctct ggagcaatgg agtgctagaa   3180
agtgagatga taattccaaa gaatctcgct ggaccagtgt ctcaacacaa ctatagacca   3240
ggctaccata cacaaataac aggaccatgg catctaggta agcttgagat ggactttgat   3300
ttctgtgatg gaacaacagt ggtagtgact gaggactgcg gaaatagagg accctctttg   3360
agaacaacca ctgcctctgg aaaactcata acagaatggt gctgccgatc ttgcacatta   3420
ccaccgctaa gatacagagg tgaggatggg tgctggtacg ggatggaaat cagaccattg   3480
aaggagaaag aagagaattt ggtcaactcc ttggtcacag ctggacatgg gcaggtcgac   3540
aacttttcac taggagtctt gggaatggca ttgttcctgg aggaaatgct taggacccga   3600
gtaggaacga aacatgcaat actactagtt gcagtttctt ttgtgacatt gatcacaggg   3660
aacatgtcct ttagagacct gggaagagtg atggttatgg taggcgccac tatgacggat   3720
gacataggta tgggcgtgac ttatcttgcc ctactagcag ccttcaaagt cagaccaact   3780
tttgcagctg gactactctt gagaaagctg acctccaatg aattgatgat gactactata   3840
ggaattgtac tcctctccca gagcaccata ccagagacca ttcttgagtt gactgatgcg   3900
ttagccttag gcatgatggt cctcaaaatg gtgagaaata tggaaaagta tcaattggca   3960
gtgactatca tggctatctt gtgcgtccca aacgcagtga tattacaaaa cgcatggaaa   4020
gtgagttgca caatattggc agtggtgtcc gtttccccac tgttcttaac atcctcacag   4080
```

```
caaaaaacag attggatacc attagcattg acgatcaaag gtctcaatcc aacagctatt   4140
tttctaacaa ccctctcaag aaccagcaag aaaaggagct ggccattaaa tgaggctatc   4200
atggcagtcg ggatggtgag cattttagcc agttctctcc taaaaaatga tattcccatg   4260
acaggaccat tagtggctgg agggctcctc actgtgtgct acgtgctcac tggacgatcg   4320
gccgatttgg aactggagag agcagccgat gtcaaatggg aagaccaggc agagatatca   4380
ggaagcagtc caatcctgtc aataacaata tcagaagatg gtagcatgtc gataaaaaat   4440
gaagaggaag aacaaacact gaccatactc attagaacag gattgctggt gatctcagga   4500
ctttttcctg tatcaatacc aatcacggca gcagcatggt acctgtggga agtgaagaaa   4560
caacgggccg gagtattgtg ggatgttcct tcacccccac ccatgggaaa ggctgaactg   4620
gaagatggag cctatagaat taagcaaaaa gggattcttg gatattccca gatcggagcc   4680
ggagtttaca aagaaggaac attccataca atgtggcatg tcacacgtgg cgctgttcta   4740
atgcataaag gaaagaggat tgaaccatca tgggcggacg tcaagaaaga cctaatatca   4800
tatggaggag gctggaagtt agaaggagaa tggaaggaag gagaagaagt ccaggtattg   4860
gcactggagc ctggaaaaaa tccaagagcc gtccaaacga aacctggtct tttcaaaacc   4920
aacgccggaa caataggtgc tgtatctctg gacttttctc ctggaacgtc aggatctcca   4980
attatcgaca aaaaaggaaa agttgtgggt ctttatggta atggtgttgt tacaaggagt   5040
ggagcatatg tgagtgctat agcccagact gaaaaaagca ttgaagacaa cccagagatc   5100
gaagatgaca ttttccgaaa gagaagactg accatcatgg acctccaccc aggagcggga   5160
aagacgaaga gataccttcc ggccatagtc agagaagcta taaaacgggg tttgagaaca   5220
ttaatcttgg cccccactag agttgtggca gctgaaatgg aggaagccct tagaggactt   5280
ccaataagat accagacccc agccatcaga gctgtgcaca ccgggcggga gattgtggac   5340
ctaatgtgtc atgccacatt taccatgagg ctgctatcac cagttagagt gccaaactac   5400
aacctgatta tcatggacga agcccatttc acagacccag caagtatagc agctagagga   5460
tacatctcaa ctcgagtgga gatgggtgag gcagctggga tttttatgac agccactccc   5520
ccgggaagca gagacccatt tcctcagagc aatgcaccaa tcatagatga agaaagagaa   5580
atccctgaac gctcgtggaa ttccggacat gaatgggtca cggattttaa agggaagact   5640
gtttggttcg ttccaagtat aaaagcagga aatgatatag cagcttgcct gaggaaaaat   5700
ggaaagaaag tgatacaact cagtaggaag acctttgatt ctgagtatgt caagactaga   5760
accaatgatt gggacttcgt ggttacaact gacatttcag aaatgggtgc caatttcaag   5820
gctgagaggg ttatagaccc cagacgctgc atgaaaccag tcatactaac agatggtgaa   5880
gagcgggtga ttctggcagg acctatgcca gtgacccact ctagtgcagc acaaagaaga   5940
gggagaatag gaagaaatcc aaaaaatgag aatgaccagt acatatacat gggggaacct   6000
ctggaaaatg atgaagactg tgcacactgg aaagaagcta aaatgctcct agataacatc   6060
aacacgccag aaggaatcat tcctagcatg ttcgaaccag agcgtgaaaa ggtggatgcc   6120
attgatggcg aataccgctt gagaggagaa gcaaggaaaa cctttgtaga cttaatgaga   6180
agaggagacc taccagtctg gttggcctac agagtggcag ctgaaggcat caactacgca   6240
gacagaaggt ggtgttttga tggagtcaag aacaaccaaa tcctagaaga aaacgtggaa   6300
gttgaaatct ggacaaaaga aggggaaagg aagaaattga aacccagatg gttggatgct   6360
aggatctatt ctgacccact ggcgctaaaa gaatttaagg aatttgcagc cggaagaaag   6420
```

```
tctctgaccc tgaacctaat cacagaaatg ggtaggctcc caaccttcat gactcagaag   6480

gcaagaaacg cactggacaa cttagcagtg ctgcacacgg ctgaggcagg tggaagggcg   6540

tacaaccatg ctctcagtga actgccggag accctggaga cattgctttt actgacactt   6600

ctggctacag tcacgggagg gatcttttta ttcttgatga gcgcaagggg catagggaag   6660

atgaccctgg gaatgtgctg cataatcacg gctagcatcc tcctatggta cgcacaaata   6720

cagccacact ggatagcagc ttcaataata ctggagtttt ttctcatagt tttgcttatt   6780

ccagaacctg aaaaacagag aacaccccaa gacaaccaac tgacctacgt tgtcatagcc   6840

atcctcacag tggtggccgc aaccatggca aacgagatgg gtttcctaga aaaaacgaag   6900

aaagatctcg gattgggaag cattgcaacc cagcaacccg agagcaacat cctggacata   6960

gatctacgtc ctgcatcagc atggacgctg tatgccgtgg ccacaacatt tgttacacca   7020

atgttgagac atagcattga aaattcctca gtgaatgtgt ccctaacagc tatagccaac   7080

caagccacag tgttaatggg tctcgggaaa ggatggccat tgtcaaagat ggacatcgga   7140

gttccccttc tcgccattgg atgctactca caagtcaacc ccataactct cacagcagct   7200

cttttcttat tggtagcaca ttatgccatc atagggccag gactccaagc aaaagcaacc   7260

agagaagctc agaaaagagc agcggcgggc atcatgaaaa acccaactgt cgatggaata   7320

acagtgattg acctagatcc aataccttat gatccaaagt ttgaaaagca gttgggacaa   7380

gtaatgctcc tagtcctctg cgtgactcaa gtattgatga tgaggactac atgggctctg   7440

tgtgaggctt taaccttagc taccgggccc atctccacat tgtgggaagg aaatccaggg   7500

aggttttgga acactaccat tgcggtgtca atggctaaca tttttagagg gagttacttg   7560

gccggagctg gacttctctt ttctattatg aagaacacaa ccaacacaag aaggggaact   7620

ggcaacatag gagagacgct tggagagaaa tggaaaagcc gattgaacgc attgggaaaa   7680

agtgaattcc agatctacaa gaaaagtgga atccaggaag tggatagaac cttagcaaaa   7740

gaaggcatta aaagaggaga aacggaccat cacgctgtgt cgcgaggctc agcaaaactg   7800

agatggttcg ttgagagaaa catggtcaca ccagaaggga aagtagtgga cctcggttgt   7860

ggcagaggag gctggtcata ctattgtgga ggactaaaga atgtaagaga agtcaaaggc   7920

ctaacaaaag gaggaccagg acacgaagaa cccatcccca tgtcaacata tgggtggaat   7980

ctagtgcgtc ttcaaagtgg agttgacgtt ttcttcatcc cgccagaaaa gtgtgacaca   8040

ttattgtgtg acatagggga gtcatcacca aatcccacag tggaagcagg acgaacactc   8100

agagtcctta acttagtaga aaattggttg aacaacaaca ctcaattttg cataaaggtt   8160

ctcaacccat atatgccctc agtcatagaa aaaatggaag cactacaaag gaaatatgga   8220

ggagccttag tgaggaatcc actctcacga aactccacac atgagatgta ctgggtatcc   8280

aatgcttccg ggaacatagt gtcatcagtg aacatgattt caaggatgtt gatcaacaga   8340

tttacaatga gatacaagaa agccacttac gagccggatg ttgacctcgg aagcggaacc   8400

cgtaacatcg ggattgaaag tgagatacca aacctagata taattgggaa aagaatagaa   8460

aaaataaagc aagagcatga aacatcatgg cactatgacc aagaccaccc atacaaaacg   8520

tgggcatacc atggtagcta tgaaacaaaa cagactggat cagcatcatc catggtcaac   8580

ggagtggtca ggctgctgac aaaaccttgg gacgtcgtcc ccatggtgac acagatggca   8640

atgacagaca cgactccatt tggacaacag cgcgttttta aagagaaagt ggacacgaga   8700

acccaagaac cgaaagaagg cacgaagaaa ctaatgaaaa taacagcaga gtggctttgg   8760

aaagaattag ggaagaaaaa gacacccagg atgtgcacca gagaagaatt cacaagaaag   8820
```

```
gtgagaagca atgcagcctt gggggccata ttcactgatg agaacaagtg gaagtcggca   8880

cgtgaggctg ttgaagatag taggttttgg gagctggttg acaaggaaag gaatctccat   8940

cttgaaggaa agtgtgaaac atgtgtgtac aacatgatgg gaaaaagaga gaagaagcta   9000

ggggaattcg gcaaggcaaa aggcagcaga gccatatggt acatgtggct tggagcacgc   9060

ttcttagagt ttgaagccct aggattctta aatgaagatc actggttctc cagagagaac   9120

tccctgagtg gagtggaagg agaagggctg cacaagctag gttacattct aagagacgtg   9180

agcaagaaag agggaggagc aatgtatgcc gatgacaccg caggatggga tacaagaatc   9240

acactagaag acctaaaaaa tgaagaaatg gtaacaaacc acatggaagg agaacacaag   9300

aaactagccg aggccatttt caaactaacg taccaaaaca aggtggtgcg tgtgcaaaga   9360

ccaacaccaa gaggcacagt aatggacatc atatcgagaa gagaccaaag aggtagtgga   9420

caagttggca cctatggact caatactttc accaatatgg aagcccaact aatcagacag   9480

atggagggag aaggagtctt taaaagcatt cagcacctaa caatcacaga agaaatcgct   9540

gtgcaaaact ggttagcaag agtggggcgc gaaaggttat caagaatggc catcagtgga   9600

gatgattgtg ttgtgaaacc tttagatgac aggttcgcaa gcgctttaac agctctaaat   9660

gacatgggaa agattaggaa agacatacaa caatgggaac cttcaagagg atggaatgat   9720

tggacacaag tgcccttctg ttcacaccat ttccatgagt taatcatgaa agacggtcgc   9780

gtactcgttg ttccatgtag aaaccaagat gaactgattg gcagagcccg aatctcccaa   9840

ggagcagggt ggtctttgcg ggagacggcc tgtttgggga agtcttacgc ccaaatgtgg   9900

agcttgatgt acttccacag acgcgacctc aggctggcgg caaatgctat ttgctcggca   9960

gtaccatcac attgggttcc aacaagtcga acaacctggt ccatacatgc taaacatgaa  10020

tggatgacaa cggaagacat gctgacagtc tggaacaggg tgtggattca agaaaaccca  10080

tggatggaag acaaaactcc agtggaatca tgggaggaaa tcccatactt ggggaaaaga  10140

gaagaccaat ggtgcggctc attgattggg ttaacaagca gggccacctg ggcaaagaac  10200

atccaagcag caataaatca agttagatcc cttataggca atgaagaata cacagattac  10260

atgccatcca tgaaaagatt cagaagagaa gaggaagaag caggagttct gtggtagaaa  10320

gcaaaactaa catgaaacaa ggctagaagt caggtcggat taagccatag tacggaaaaa  10380

actatgctac ctgtgagccc cgtccaagga cgttaaaaga agtcaggcca tcataaatgc  10440

catagcttga gtaaactatg cagcctgtag ctccacctga gaaggtgtaa aaaatccggg  10500

aggccacaaa ccatggaagc tgtacgcatg gcgtagtgga ctagcggtta gaggagaccc  10560

ctcccttaca aatcgcagca acaatggggg cccaaggcga gatgaagctg tagtctcgct  10620

ggaaggacta gaggttagag gagacccccc cgaaacaaaa aacagcatat tgacgctggg  10680

aaagaccaga gatcctgctg tctcctcagc atcattccag gcacagaacg ccagaaaatg  10740

gaatggtgct gttgaatcaa caggttct                                    10768
```

<210> SEQ ID NO 26
<211> LENGTH: 3406
<212> TYPE: PRT
<213> ORGANISM: Artificial Sequence
<220> FEATURE:
<223> OTHER INFORMATION: Synthetic polypeptide

<400> SEQUENCE: 26

```
Met Asn Asn Gln Arg Lys Lys Ala Lys Asn Thr Pro Phe Asn Met Leu
1               5                   10                  15
```

```
Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Thr Ser Val Gly Ile Val Gly Leu Leu
            100                 105                 110

Leu Thr Thr Ala Met Ala Ala Glu Val Thr Arg Arg Gly Ser Ala Tyr
        115                 120                 125

Tyr Met Tyr Leu Asp Arg Asn Asp Ala Gly Glu Ala Ile Ser Phe Pro
    130                 135                 140

Thr Thr Leu Gly Met Asn Lys Cys Tyr Ile Gln Ile Met Asp Leu Gly
145                 150                 155                 160

His Met Cys Asp Ala Thr Met Ser Tyr Glu Cys Pro Met Leu Asp Glu
                165                 170                 175

Gly Val Glu Pro Asp Asp Val Asp Cys Trp Cys Asn Thr Thr Ser Thr
            180                 185                 190

Trp Val Val Tyr Gly Thr Cys His His Lys Lys Gly Glu Ala Arg Arg
        195                 200                 205

Ser Arg Arg Ala Val Thr Leu Pro Ser His Ser Thr Arg Lys Leu Gln
    210                 215                 220

Thr Arg Ser Gln Thr Trp Leu Glu Ser Arg Glu Tyr Thr Lys His Leu
225                 230                 235                 240

Ile Arg Val Glu Asn Trp Ile Phe Arg Asn Pro Gly Phe Ala Leu Ala
                245                 250                 255

Ala Ala Ala Ile Ala Trp Leu Leu Gly Ser Ser Thr Ser Gln Lys Val
            260                 265                 270

Ile Tyr Leu Val Met Ile Leu Leu Ile Ala Pro Ala Tyr Ser Ile Arg
        275                 280                 285

Cys Ile Gly Val Ser Asn Arg Asp Phe Val Glu Gly Met Ser Gly Gly
    290                 295                 300

Thr Trp Val Asp Ile Val Leu Glu His Gly Gly Cys Val Thr Val Met
305                 310                 315                 320

Ala Gln Asp Lys Pro Thr Val Asp Ile Glu Leu Val Thr Thr Thr Val
                325                 330                 335

Ser Asn Met Ala Glu Val Arg Ser Tyr Cys Tyr Glu Ala Ser Ile Ser
            340                 345                 350

Asp Met Ala Ser Asp Ser Arg Cys Pro Thr Gln Gly Glu Ala Tyr Leu
        355                 360                 365

Asp Lys Gln Ser Asp Thr Gln Tyr Val Cys Lys Arg Thr Leu Val Asp
    370                 375                 380

Arg Gly Trp Gly Asn Gly Cys Gly Leu Phe Gly Lys Gly Ser Leu Val
385                 390                 395                 400

Thr Cys Ala Lys Phe Ala Cys Ser Lys Lys Met Thr Gly Lys Ser Ile
                405                 410                 415

Gln Pro Glu Asn Leu Glu Tyr Arg Ile Met Leu Ser Val His Gly Ser
            420                 425                 430
```

```
Gln His Ser Gly Met Ile Val Asn Asp Thr Gly His Glu Thr Asp Glu
        435                 440                 445

Asn Arg Ala Lys Val Glu Ile Thr Pro Asn Ser Pro Arg Ala Glu Ala
    450                 455                 460

Thr Leu Gly Gly Phe Gly Ser Leu Gly Leu Asp Cys Glu Pro Arg Thr
465                 470                 475                 480

Gly Leu Asp Phe Ser Asp Leu Tyr Tyr Leu Thr Met Asn Asn Lys His
                485                 490                 495

Trp Leu Val His Lys Glu Trp Phe His Asp Ile Pro Leu Pro Trp His
            500                 505                 510

Ala Gly Ala Asp Thr Gly Thr Pro His Trp Asn Asn Lys Glu Ala Leu
        515                 520                 525

Val Glu Phe Lys Asp Ala His Ala Lys Arg Gln Thr Val Val Val Leu
    530                 535                 540

Gly Ser Gln Glu Gly Ala Val His Thr Ala Leu Ala Gly Ala Leu Glu
545                 550                 555                 560

Ala Glu Met Asp Gly Ala Lys Gly Arg Leu Ser Ser Gly His Leu Lys
                565                 570                 575

Cys Arg Leu Lys Met Asp Lys Leu Arg Leu Lys Gly Val Ser Tyr Ser
            580                 585                 590

Leu Cys Thr Ala Ala Phe Thr Phe Thr Lys Ile Pro Ala Glu Thr Leu
        595                 600                 605

His Gly Thr Val Thr Val Glu Val Gln Tyr Ala Gly Thr Asp Gly Pro
    610                 615                 620

Cys Lys Val Pro Ala Gln Met Ala Val Asp Met Gln Thr Leu Thr Pro
625                 630                 635                 640

Val Gly Arg Leu Ile Thr Ala Asn Pro Val Ile Thr Glu Ser Thr Glu
                645                 650                 655

Asn Ser Lys Met Met Leu Glu Leu Asp Pro Pro Phe Gly Asp Ser Tyr
            660                 665                 670

Ile Val Ile Gly Val Gly Glu Lys Lys Ile Thr His His Trp His Arg
        675                 680                 685

Ser Gly Ser Thr Ile Gly Lys Ala Phe Glu Ala Thr Val Arg Gly Ala
    690                 695                 700

Lys Arg Met Ala Val Leu Gly Asp Thr Ala Trp Asp Phe Gly Ser Val
705                 710                 715                 720

Gly Gly Ala Leu Asn Ser Leu Gly Lys Gly Ile His Gln Ile Phe Gly
                725                 730                 735

Ala Ala Phe Lys Ser Leu Phe Gly Gly Met Ser Trp Phe Ser Arg Ile
            740                 745                 750

Leu Ile Gly Thr Leu Leu Met Trp Leu Gly Leu Asn Thr Lys Asn Gly
        755                 760                 765

Ser Thr Ser Leu Met Cys Leu Ala Ala Gly Phe Val Thr Leu Tyr Leu
    770                 775                 780

Gly Val Met Val Gln Ala Asp Ser Gly Cys Val Val Ser Trp Lys Asn
785                 790                 795                 800

Lys Glu Leu Lys Cys Gly Ser Gly Ile Phe Ile Thr Asp Asn Val His
                805                 810                 815

Thr Trp Thr Glu Gln Tyr Lys Phe Gln Pro Glu Ser Pro Ser Lys Leu
            820                 825                 830

Ala Ser Ala Ile Gln Lys Ala His Glu Glu Asp Ile Cys Gly Ile Arg
        835                 840                 845

Ser Val Thr Arg Leu Glu Asn Leu Met Trp Lys Gln Ile Thr Pro Glu
```

-continued

```
    850                 855                 860

Leu Asn His Ile Leu Ser Glu Asn Glu Val Lys Leu Thr Ile Met Thr
865                 870                 875                 880

Gly Asp Ile Lys Gly Ile Met Gln Ala Gly Lys Arg Ser Leu Arg Pro
                885                 890                 895

Gln Pro Thr Glu Leu Lys Tyr Ser Trp Lys Thr Trp Gly Lys Ala Lys
            900                 905                 910

Met Leu Ser Thr Glu Ser His Asn Gln Thr Phe Leu Ile Asp Gly Pro
        915                 920                 925

Glu Thr Ala Glu Cys Pro Asn Thr Asn Arg Ala Trp Asn Ser Leu Glu
    930                 935                 940

Val Glu Asp Tyr Gly Phe Gly Val Phe Thr Thr Asn Ile Trp Leu Lys
945                 950                 955                 960

Leu Lys Glu Lys Gln Asp Val Phe Cys Asp Ser Lys Leu Met Ser Ala
                965                 970                 975

Ala Ile Lys Asp Asn Arg Ala Val His Ala Asp Met Gly Tyr Trp Ile
            980                 985                 990

Glu Ser Ala Leu Asn Asp Thr Trp  Lys Ile Glu Lys Ala  Ser Phe Ile
        995                 1000                1005

Glu Val  Lys Asn Cys His Trp  Pro Lys Ser His Thr  Leu Trp Ser
    1010                1015                1020

Asn Gly  Val Leu Glu Ser Glu  Met Ile Ile Pro Lys  Asn Leu Ala
    1025                1030                1035

Gly Pro  Val Ser Gln His Asn  Tyr Arg Pro Gly Tyr  His Thr Gln
    1040                1045                1050

Ile Thr  Gly Pro Trp His Leu  Gly Lys Leu Glu Met  Asp Phe Asp
    1055                1060                1065

Phe Cys  Asp Gly Thr Thr Val  Val Val Thr Glu Asp  Cys Gly Asn
    1070                1075                1080

Arg Gly  Pro Ser Leu Arg Thr  Thr Thr Ala Ser Gly  Lys Leu Ile
    1085                1090                1095

Thr Glu  Trp Cys Cys Arg Ser  Cys Thr Leu Pro Pro  Leu Arg Tyr
    1100                1105                1110

Arg Gly  Glu Asp Gly Cys Trp  Tyr Gly Met Glu Ile  Arg Pro Leu
    1115                1120                1125

Lys Glu  Lys Glu Glu Asn Leu  Val Asn Ser Leu Val  Thr Ala Gly
    1130                1135                1140

His Gly  Gln Val Asp Asn Phe  Ser Leu Gly Val Leu  Gly Met Ala
    1145                1150                1155

Leu Phe  Leu Glu Glu Met Leu  Arg Thr Arg Val Gly  Thr Lys His
    1160                1165                1170

Ala Ile  Leu Leu Val Ala Val  Ser Phe Val Thr Leu  Ile Thr Gly
    1175                1180                1185

Asn Met  Ser Phe Arg Asp Leu  Gly Arg Val Met Val  Met Val Gly
    1190                1195                1200

Ala Thr  Met Thr Asp Asp Ile  Gly Met Gly Val Thr  Tyr Leu Ala
    1205                1210                1215

Leu Leu  Ala Ala Phe Lys Val  Arg Pro Thr Phe Ala  Ala Gly Leu
    1220                1225                1230

Leu Leu  Arg Lys Leu Thr Ser  Asn Glu Leu Met Met  Thr Thr Ile
    1235                1240                1245

Gly Ile  Val Leu Leu Ser Gln  Ser Thr Ile Pro Glu  Thr Ile Leu
    1250                1255                1260
```

```
Glu Leu  Thr Asp Ala Leu Ala  Leu Gly Met Met Val  Leu Lys Met
    1265                 1270                 1275

Val Arg  Asn Met Glu Lys Tyr  Gln Leu Ala Val Thr  Ile Met Ala
    1280                 1285                 1290

Ile Leu  Cys Val Pro Asn Ala  Val Ile Leu Gln Asn  Ala Trp Lys
    1295                 1300                 1305

Val Ser  Cys Thr Ile Leu Ala  Val Val Ser Val Ser  Pro Leu Phe
    1310                 1315                 1320

Leu Thr  Ser Ser Gln Gln Lys  Thr Asp Trp Ile Pro  Leu Ala Leu
    1325                 1330                 1335

Thr Ile  Lys Gly Leu Asn Pro  Thr Ala Ile Phe Leu  Thr Thr Leu
    1340                 1345                 1350

Ser Arg  Thr Ser Lys Lys Arg  Ser Trp Pro Leu Asn  Glu Ala Ile
    1355                 1360                 1365

Met Ala  Val Gly Met Val Ser  Ile Leu Ala Ser Ser  Leu Leu Lys
    1370                 1375                 1380

Asn Asp  Ile Pro Met Thr Gly  Pro Leu Val Ala Gly  Gly Leu Leu
    1385                 1390                 1395

Thr Val  Cys Tyr Val Leu Thr  Gly Arg Ser Ala Asp  Leu Glu Leu
    1400                 1405                 1410

Glu Arg  Ala Ala Asp Val Lys  Trp Glu Asp Gln Ala  Glu Ile Ser
    1415                 1420                 1425

Gly Ser  Ser Pro Ile Leu Ser  Ile Thr Ile Ser Glu  Asp Gly Ser
    1430                 1435                 1440

Met Ser  Ile Lys Asn Glu Glu  Glu Glu Gln Thr Leu  Thr Ile Leu
    1445                 1450                 1455

Ile Arg  Thr Gly Leu Leu Val  Ile Ser Gly Leu Phe  Pro Val Ser
    1460                 1465                 1470

Ile Pro  Ile Thr Ala Ala Ala  Trp Tyr Leu Trp Glu  Val Lys Lys
    1475                 1480                 1485

Gln Arg  Ala Gly Val Leu Trp  Asp Val Pro Ser Pro  Pro Pro Met
    1490                 1495                 1500

Gly Lys  Ala Glu Leu Glu Asp  Gly Ala Tyr Arg Ile  Lys Gln Lys
    1505                 1510                 1515

Gly Ile  Leu Gly Tyr Ser Gln  Ile Gly Ala Gly Val  Tyr Lys Glu
    1520                 1525                 1530

Gly Thr  Phe His Thr Met Trp  His Val Thr Arg Gly  Ala Val Leu
    1535                 1540                 1545

Met His  Lys Gly Lys Arg Ile  Glu Pro Ser Trp Ala  Asp Val Lys
    1550                 1555                 1560

Lys Asp  Leu Ile Ser Tyr Gly  Gly Gly Trp Lys Leu  Glu Gly Glu
    1565                 1570                 1575

Trp Lys  Glu Gly Glu Glu Val  Gln Val Leu Ala Leu  Glu Pro Gly
    1580                 1585                 1590

Lys Asn  Pro Arg Ala Val Gln  Thr Lys Pro Gly Leu  Phe Lys Thr
    1595                 1600                 1605

Asn Ala  Gly Thr Ile Gly Ala  Val Ser Leu Asp Phe  Ser Pro Gly
    1610                 1615                 1620

Thr Ser  Gly Ser Pro Ile Ile  Asp Lys Lys Gly Lys  Val Val Gly
    1625                 1630                 1635

Leu Tyr  Gly Asn Gly Val Val  Thr Arg Ser Gly Ala  Tyr Val Ser
    1640                 1645                 1650
```

```
Ala Ile Ala Gln Thr Glu Lys Ser Ile Glu Asp Asn Pro Glu Ile
    1655                1660                1665

Glu Asp Asp Ile Phe Arg Lys Arg Arg Leu Thr Ile Met Asp Leu
    1670                1675                1680

His Pro Gly Ala Gly Lys Thr Lys Arg Tyr Leu Pro Ala Ile Val
    1685                1690                1695

Arg Glu Ala Ile Lys Arg Gly Leu Arg Thr Leu Ile Leu Ala Pro
    1700                1705                1710

Thr Arg Val Val Ala Ala Glu Met Glu Glu Ala Leu Arg Gly Leu
    1715                1720                1725

Pro Ile Arg Tyr Gln Thr Pro Ala Ile Arg Ala Val His Thr Gly
    1730                1735                1740

Arg Glu Ile Val Asp Leu Met Cys His Ala Thr Phe Thr Met Arg
    1745                1750                1755

Leu Leu Ser Pro Val Arg Val Pro Asn Tyr Asn Leu Ile Ile Met
    1760                1765                1770

Asp Glu Ala His Phe Thr Asp Pro Ala Ser Ile Ala Ala Arg Gly
    1775                1780                1785

Tyr Ile Ser Thr Arg Val Glu Met Gly Glu Ala Ala Gly Ile Phe
    1790                1795                1800

Met Thr Ala Thr Pro Pro Gly Ser Arg Asp Pro Phe Pro Gln Ser
    1805                1810                1815

Asn Ala Pro Ile Ile Asp Glu Glu Arg Glu Ile Pro Glu Arg Ser
    1820                1825                1830

Trp Asn Ser Gly His Glu Trp Val Thr Asp Phe Lys Gly Lys Thr
    1835                1840                1845

Val Trp Phe Val Pro Ser Ile Lys Ala Gly Asn Asp Ile Ala Ala
    1850                1855                1860

Cys Leu Arg Lys Asn Gly Lys Lys Val Ile Gln Leu Ser Arg Lys
    1865                1870                1875

Thr Phe Asp Ser Glu Tyr Val Lys Thr Arg Thr Asn Asp Trp Asp
    1880                1885                1890

Phe Val Val Thr Thr Asp Ile Ser Glu Met Gly Ala Asn Phe Lys
    1895                1900                1905

Ala Glu Arg Val Ile Asp Pro Arg Arg Cys Met Lys Pro Val Ile
    1910                1915                1920

Leu Thr Asp Gly Glu Glu Arg Val Ile Leu Ala Gly Pro Met Pro
    1925                1930                1935

Val Thr His Ser Ser Ala Ala Gln Arg Arg Gly Arg Ile Gly Arg
    1940                1945                1950

Asn Pro Lys Asn Glu Asn Asp Gln Tyr Ile Tyr Met Gly Glu Pro
    1955                1960                1965

Leu Glu Asn Asp Glu Asp Cys Ala His Trp Lys Glu Ala Lys Met
    1970                1975                1980

Leu Leu Asp Asn Ile Asn Thr Pro Glu Gly Ile Ile Pro Ser Met
    1985                1990                1995

Phe Glu Pro Glu Arg Glu Lys Val Asp Ala Ile Asp Gly Glu Tyr
    2000                2005                2010

Arg Leu Arg Gly Glu Ala Arg Lys Thr Phe Val Asp Leu Met Arg
    2015                2020                2025

Arg Gly Asp Leu Pro Val Trp Leu Ala Tyr Arg Val Ala Ala Glu
    2030                2035                2040

Gly Ile Asn Tyr Ala Asp Arg Arg Trp Cys Phe Asp Gly Val Lys
```

```
    2045                2050                2055

Asn Asn  Gln Ile Leu Glu Glu  Asn Val Glu Val Glu  Ile Trp Thr
    2060                2065                2070

Lys Glu  Gly Glu Arg Lys Lys  Leu Lys Pro Arg Trp  Leu Asp Ala
    2075                2080                2085

Arg Ile  Tyr Ser Asp Pro Leu  Ala Leu Lys Glu Phe  Lys Glu Phe
    2090                2095                2100

Ala Ala  Gly Arg Lys Ser Leu  Thr Leu Asn Leu Ile  Thr Glu Met
    2105                2110                2115

Gly Arg  Leu Pro Thr Phe Met  Thr Gln Lys Ala Arg  Asn Ala Leu
    2120                2125                2130

Asp Asn  Leu Ala Val Leu His  Thr Ala Glu Ala Gly  Gly Arg Ala
    2135                2140                2145

Tyr Asn  His Ala Leu Ser Glu  Leu Pro Glu Thr Leu  Glu Thr Leu
    2150                2155                2160

Leu Leu  Leu Thr Leu Leu Ala  Thr Val Thr Gly Gly  Ile Phe Leu
    2165                2170                2175

Phe Leu  Met Ser Ala Arg Gly  Ile Gly Lys Met Thr  Leu Gly Met
    2180                2185                2190

Cys Cys  Ile Ile Thr Ala Ser  Ile Leu Leu Trp Tyr  Ala Gln Ile
    2195                2200                2205

Gln Pro  His Trp Ile Ala Ala  Ser Ile Ile Leu Glu  Phe Phe Leu
    2210                2215                2220

Ile Val  Leu Leu Ile Pro Glu  Pro Glu Lys Gln Arg  Thr Pro Gln
    2225                2230                2235

Asp Asn  Gln Leu Thr Tyr Val  Val Ile Ala Ile Leu  Thr Val Val
    2240                2245                2250

Ala Ala  Thr Met Ala Asn Glu  Met Gly Phe Leu Glu  Lys Thr Lys
    2255                2260                2265

Lys Asp  Leu Gly Leu Gly Ser  Ile Ala Thr Gln Gln  Pro Glu Ser
    2270                2275                2280

Asn Ile  Leu Asp Ile Asp Leu  Arg Pro Ala Ser Ala  Trp Thr Leu
    2285                2290                2295

Tyr Ala  Val Ala Thr Thr Phe  Val Thr Pro Met Leu  Arg His Ser
    2300                2305                2310

Ile Glu  Asn Ser Ser Val Asn  Val Ser Leu Thr Ala  Ile Ala Asn
    2315                2320                2325

Gln Ala  Thr Val Leu Met Gly  Leu Gly Lys Gly Trp  Pro Leu Ser
    2330                2335                2340

Lys Met  Asp Ile Gly Val Pro  Leu Leu Ala Ile Gly  Cys Tyr Ser
    2345                2350                2355

Gln Val  Asn Pro Ile Thr Leu  Thr Ala Ala Leu Phe  Leu Leu Val
    2360                2365                2370

Ala His  Tyr Ala Ile Ile Gly  Pro Gly Leu Gln Ala  Lys Ala Thr
    2375                2380                2385

Arg Glu  Ala Gln Lys Arg Ala  Ala Ala Gly Ile Met  Lys Asn Pro
    2390                2395                2400

Thr Val  Asp Gly Ile Thr Val  Ile Asp Leu Asp Pro  Ile Pro Tyr
    2405                2410                2415

Asp Pro  Lys Phe Glu Lys Gln  Leu Gly Gln Val Met  Leu Leu Val
    2420                2425                2430

Leu Cys  Val Thr Gln Val Leu  Met Met Arg Thr Thr  Trp Ala Leu
    2435                2440                2445
```

```
Cys Glu  Ala Leu Thr Leu Ala  Thr Gly Pro Ile Ser  Thr Leu Trp
    2450                 2455                 2460

Glu Gly  Asn Pro Gly Arg Phe  Trp Asn Thr Thr Ile  Ala Val Ser
    2465                 2470                 2475

Met Ala  Asn Ile Phe Arg Gly  Ser Tyr Leu Ala Gly  Ala Gly Leu
    2480                 2485                 2490

Leu Phe  Ser Ile Met Lys Asn  Thr Thr Asn Thr Arg  Arg Gly Thr
    2495                 2500                 2505

Gly Asn  Ile Gly Glu Thr Leu  Gly Glu Lys Trp Lys  Ser Arg Leu
    2510                 2515                 2520

Asn Ala  Leu Gly Lys Ser Glu  Phe Gln Ile Tyr Lys  Lys Ser Gly
    2525                 2530                 2535

Ile Gln  Glu Val Asp Arg Thr  Leu Ala Lys Glu Gly  Ile Lys Arg
    2540                 2545                 2550

Gly Glu  Thr Asp His His Ala  Val Ser Arg Gly Ser  Ala Lys Leu
    2555                 2560                 2565

Arg Trp  Phe Val Glu Arg Asn  Met Val Thr Pro Glu  Gly Lys Val
    2570                 2575                 2580

Val Asp  Leu Gly Cys Gly Arg  Gly Gly Trp Ser Tyr  Tyr Cys Gly
    2585                 2590                 2595

Gly Leu  Lys Asn Val Arg Glu  Val Lys Gly Leu Thr  Lys Gly Gly
    2600                 2605                 2610

Pro Gly  His Glu Glu Pro Ile  Pro Met Ser Thr Tyr  Gly Trp Asn
    2615                 2620                 2625

Leu Val  Arg Leu Gln Ser Gly  Val Asp Val Phe Phe  Ile Pro Pro
    2630                 2635                 2640

Glu Lys  Cys Asp Thr Leu Leu  Cys Asp Ile Gly Glu  Ser Ser Pro
    2645                 2650                 2655

Asn Pro  Thr Val Glu Ala Gly  Arg Thr Leu Arg Val  Leu Asn Leu
    2660                 2665                 2670

Val Glu  Asn Trp Leu Asn Asn  Asn Thr Gln Phe Cys  Ile Lys Val
    2675                 2680                 2685

Leu Asn  Pro Tyr Met Pro Ser  Val Ile Glu Lys Met  Glu Ala Leu
    2690                 2695                 2700

Gln Arg  Lys Tyr Gly Gly Ala  Leu Val Arg Asn Pro  Leu Ser Arg
    2705                 2710                 2715

Asn Ser  Thr His Glu Met Tyr  Trp Val Ser Asn Ala  Ser Gly Asn
    2720                 2725                 2730

Ile Val  Ser Ser Val Asn Met  Ile Ser Arg Met Leu  Ile Asn Arg
    2735                 2740                 2745

Phe Thr  Met Arg Tyr Lys Lys  Ala Thr Tyr Glu Pro  Asp Val Asp
    2750                 2755                 2760

Leu Gly  Ser Gly Thr Arg Asn  Ile Gly Ile Glu Ser  Glu Ile Pro
    2765                 2770                 2775

Asn Leu  Asp Ile Ile Gly Lys  Arg Ile Glu Lys Ile  Lys Gln Glu
    2780                 2785                 2790

His Glu  Thr Ser Trp His Tyr  Asp Gln Asp His Pro  Tyr Lys Thr
    2795                 2800                 2805

Trp Ala  Tyr His Gly Ser Tyr  Glu Thr Lys Gln Thr  Gly Ser Ala
    2810                 2815                 2820

Ser Ser  Met Val Asn Gly Val  Val Arg Leu Leu Thr  Lys Pro Trp
    2825                 2830                 2835
```

```
Asp Val  Val Pro Met Val Thr  Gln Met Ala Met Thr  Asp Thr Thr
    2840                 2845                 2850

Pro Phe  Gly Gln Gln Arg Val  Phe Lys Glu Lys Val  Asp Thr Arg
    2855                 2860                 2865

Thr Gln  Glu Pro Lys Glu Gly  Thr Lys Lys Leu Met  Lys Ile Thr
    2870                 2875                 2880

Ala Glu  Trp Leu Trp Lys Glu  Leu Gly Lys Lys Lys  Thr Pro Arg
    2885                 2890                 2895

Met Cys  Thr Arg Glu Glu Phe  Thr Arg Lys Val Arg  Ser Asn Ala
    2900                 2905                 2910

Ala Leu  Gly Ala Ile Phe Thr  Asp Glu Asn Lys Trp  Lys Ser Ala
    2915                 2920                 2925

Arg Glu  Ala Val Glu Asp Ser  Arg Phe Trp Glu Leu  Val Asp Lys
    2930                 2935                 2940

Glu Arg  Asn Leu His Leu Glu  Gly Lys Cys Glu Thr  Cys Val Tyr
    2945                 2950                 2955

Asn Met  Met Gly Lys Arg Glu  Lys Lys Leu Gly Glu  Phe Gly Lys
    2960                 2965                 2970

Ala Lys  Gly Ser Arg Ala Ile  Trp Tyr Met Trp Leu  Gly Ala Arg
    2975                 2980                 2985

Phe Leu  Glu Phe Glu Ala Leu  Gly Phe Leu Asn Glu  Asp His Trp
    2990                 2995                 3000

Phe Ser  Arg Glu Asn Ser Leu  Ser Gly Val Glu Gly  Glu Gly Leu
    3005                 3010                 3015

His Lys  Leu Gly Tyr Ile Leu  Arg Asp Val Ser Lys  Lys Glu Gly
    3020                 3025                 3030

Gly Ala  Met Tyr Ala Asp Asp  Thr Ala Gly Trp Asp  Thr Arg Ile
    3035                 3040                 3045

Thr Leu  Glu Asp Leu Lys Asn  Glu Glu Met Val Thr  Asn His Met
    3050                 3055                 3060

Glu Gly  Glu His Lys Lys Leu  Ala Glu Ala Ile Phe  Lys Leu Thr
    3065                 3070                 3075

Tyr Gln  Asn Lys Val Val Arg  Val Gln Arg Pro Thr  Pro Arg Gly
    3080                 3085                 3090

Thr Val  Met Asp Ile Ile Ser  Arg Arg Asp Gln Arg  Gly Ser Gly
    3095                 3100                 3105

Gln Val  Gly Thr Tyr Gly Leu  Asn Thr Phe Thr Asn  Met Glu Ala
    3110                 3115                 3120

Gln Leu  Ile Arg Gln Met Glu  Gly Glu Gly Val Phe  Lys Ser Ile
    3125                 3130                 3135

Gln His  Leu Thr Ile Thr Glu  Glu Ile Ala Val Gln  Asn Trp Leu
    3140                 3145                 3150

Ala Arg  Val Gly Arg Glu Arg  Leu Ser Arg Met Ala  Ile Ser Gly
    3155                 3160                 3165

Asp Asp  Cys Val Val Lys Pro  Leu Asp Asp Arg Phe  Ala Ser Ala
    3170                 3175                 3180

Leu Thr  Ala Leu Asn Asp Met  Gly Lys Ile Arg Lys  Asp Ile Gln
    3185                 3190                 3195

Gln Trp  Glu Pro Ser Arg Gly  Trp Asn Asp Trp Thr  Gln Val Pro
    3200                 3205                 3210

Phe Cys  Ser His His Phe His  Glu Leu Ile Met Lys  Asp Gly Arg
    3215                 3220                 3225

Val Leu  Val Val Pro Cys Arg  Asn Gln Asp Glu Leu  Ile Gly Arg
```

-continued

```
    3230                3235                3240

Ala Arg  Ile Ser Gln Gly Ala  Gly Trp Ser Leu Arg  Glu Thr Ala
    3245                3250                3255

Cys Leu  Gly Lys Ser Tyr Ala  Gln Met Trp Ser Leu  Met Tyr Phe
    3260                3265                3270

His Arg  Arg Asp Leu Arg Leu  Ala Ala Asn Ala Ile  Cys Ser Ala
    3275                3280                3285

Val Pro  Ser His Trp Val Pro  Thr Ser Arg Thr Thr  Trp Ser Ile
    3290                3295                3300

His Ala  Lys His Glu Trp Met  Thr Thr Glu Asp Met  Leu Thr Val
    3305                3310                3315

Trp Asn  Arg Val Trp Ile Gln  Glu Asn Pro Trp Met  Glu Asp Lys
    3320                3325                3330

Thr Pro  Val Glu Ser Trp Glu  Glu Ile Pro Tyr Leu  Gly Lys Arg
    3335                3340                3345

Glu Asp  Gln Trp Cys Gly Ser  Leu Ile Gly Leu Thr  Ser Arg Ala
    3350                3355                3360

Thr Trp  Ala Lys Asn Ile Gln  Ala Ala Ile Asn Gln  Val Arg Ser
    3365                3370                3375

Leu Ile  Gly Asn Glu Glu Tyr  Thr Asp Tyr Met Pro  Ser Met Lys
    3380                3385                3390

Arg Phe  Arg Arg Glu Glu Glu  Glu Ala Gly Val Leu  Trp
    3395                3400                3405
```

NUCLEIC ACIDS ENCODING CHIMERIC DENGUE/ZIKA VIRUSES OPTIMIZED FOR GROWTH AND STABILITY IN VERO CELLS

CROSS REFERENCE TO RELATED APPLICATIONS

This application is the U.S. National Stage of International Application No. PCT/US2017/040820, filed Jul. 6, 2017, published in English under PCT Article 21(2), which claims the benefit of U.S. Provisional Application No. 62/359,812, filed Jul. 8, 2016, which is herein incorporated by reference in its entirety.

FIELD

This disclosure concerns chimeric, attenuated flaviviruses having non-structural proteins from an attenuated or wild-type dengue virus and at least one structural protein from a Zika virus. This disclosure further concerns use of the chimeric flaviviruses in Zika virus vaccine compositions.

BACKGROUND

Zika virus, a flavivirus classified within the Flaviviridae with other important mosquito-borne viruses, including yellow fever, dengue, West Nile and Japanese encephalitis viruses, has spread rapidly in a hemispheric-wide epidemic since the virus was introduced to Brazil in 2015, reaching Central and North Americas, including territories of the United States and now threatening the continental U.S. Initially isolated in 1947 in Uganda, the virus was first linked to human disease in 1952 and has been recognized sporadically as a cause of mild, self-limited febrile illness in Africa and Southeast Asia (Weaver et al., *Antiviral Res* 130:69-80, 2016; Faria et al., *Science* 352(6283):345-349, 2016). However, in 2007, an outbreak appeared in the North Pacific island of Yap, transferred there presumably from Asia, and subsequently disseminated from island to island across the Pacific, leading to an extensive outbreak in 2013-2014 in French Polynesia, with subsequent spread to New Caledonia, the Cook Islands, and ultimately to Easter Island, far to the East. An Asian lineage virus subsequently was transferred to the Western Hemisphere by routes that remain undetermined (Faria et al., *Science* 352(6283):345-349, 2016). The virus is transmitted anthropontically by *Aedes aegypti, A. albopictus* and possibly *A. hensilli* and *A. polynieseinsis* (Weaver et al., *Antiviral Res* 130:69-80, 2016).

In late 2015, a significant increase in fetal abnormalities (e.g. microcephaly) and Guillain-Barré syndrome (GBS) in areas of widespread Zika virus infection raised concerns that Zika virus might be much more virulent than originally thought and prompted the World Health Organization (WHO) to declare a Public Health Emergency of International Concern (PHEIC) (Heymann et al., *Lancet* 387 (10020):719-721, 2016).

SUMMARY

Disclosed herein are chimeric flaviviruses that include non-coding regions, non-structural proteins, a capsid (C) protein and a portion of a premembrane (prM) signal sequence from a dengue serotype 2 virus (DENV-2); and a portion of a prM signal sequence, a prM protein and at least a portion of an envelope (E) protein from a Zika virus (ZIKV). Also described are immunogenic compositions and methods for eliciting an immune response against ZIKV in a subject.

Provided herein are nucleic acid chimeras that include a first nucleic acid molecule comprising a 5' non-coding region, a nucleic acid encoding non-structural proteins and a C protein, and a 3' non-coding region, each from a DENV-2 strain genome, wherein the C protein comprises a portion of a prM signal sequence from the DENV-2 genome and a portion of a prM signal sequence from a ZIKV genome; and a second nucleic acid molecule operably linked to the first nucleic acid molecule, encoding a prM protein and at least a portion of an E protein from the ZIKV genome. In some embodiments, the DENV-2 is an attenuated DENV-2 strain, such as strain PDK-53, or the attenuated strain includes one or more attenuating mutations present in the PDK-53 genome. In other embodiments, the DENV-2 is a wild-type DENV-2, such as strain 16681.

Also provided are chimeric flaviviruses that include a nucleic acid chimera disclosed herein. Immunogenic compositions that include a chimeric DENV-2/ZIKV are further provided.

Further provided herein are methods of eliciting an immune response against ZIKV in a subject by administering to the subject a chimeric flavivirus disclosed herein, or immunogenic composition thereof.

The foregoing and other objects, features, and advantages of the invention will become more apparent from the following detailed description, which proceeds with reference to the accompanying figures.

BRIEF DESCRIPTION OF THE DRAWINGS

(FIG. 2A) In Vero cells, both P5 and V5 chimeras reached peak titers of greater than $1\times10^7$ pfu/ml, but V5 virus grew slightly slower than the P5 virus. Both viruses replicated slightly less than the wt ZIKV pRVABC59 in Vero cells. (FIG. 2B) In C6/36 cells, P5 virus replicated significantly less than the wt ZIKV, and somewhat less than its backbone D2 16681 virus. However, P5 still replicated to greater than $1\times10^8$ pfu/ml. The V5 virus retained the same crippled growth in C6/36 cells as its D2 PDK-53 vaccine backbone virus.

SEQUENCE LISTING

Figure 1:
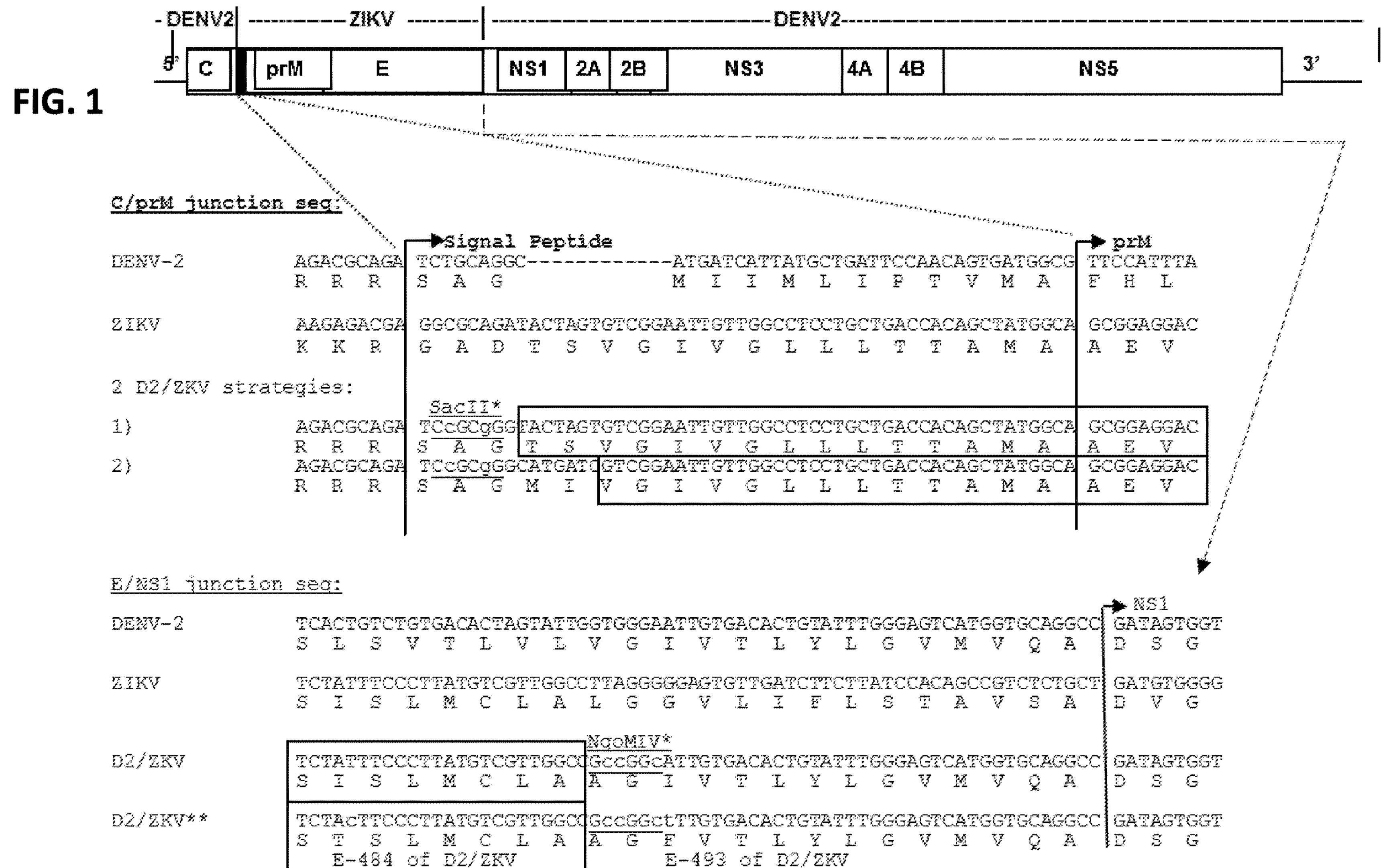
FIG. 1 is a schematic of the genomic structure of chimeric DENV-2/Zika viruses (D2/ZKV). The C/prM and E/NS1 junction site sequences for DENV-2, ZIKV and D2/ZKV are also shown. For the chimeric viruses, ZIKV sequence is indicated by boxes. The C/prM junction sequences shown are from DENV-2 (nucleotides 388-447 of SEQ ID NO: 11; amino acids 98-117 of SEQ ID NO: 12), ZIKV (nucleotides 411-482 of SEQ ID NO: 7; amino acids 102-125 of SEQ ID NO: 8), D2/ZKV Strategy 1 (D2/ZKV-V nucleotides 388-459 of SEQ ID NO: 1 and amino acids 98-121 of SEQ ID NO: 2) and D2/ZKV Strategy 2 (nucleotides 388-459 of SEQ ID NO: 3; amino acids 98-121 of SEQ ID NO: 4). The E/NS1 junction sequences shown are from DENV-2 (nucleotides 2356-2430 of SEQ ID NO: 11; amino acids 754-778 of SEQ ID NO: 12), ZIKV (nucleotides 2424-2498 of SEQ ID NO: 7 and amino acids 773-797 of SEQ ID NO: 8) and D2/ZKV (nucleotides 2401-2475 of SEQ ID NO: 1 and amino acids 769-793 of SEQ ID NO: 2). The introduced NgoMIV in the DENV-2 backbone for the E/NS1 junction site resulted in a Val to Ala substitution at the amino acid 754 (DENV-2 E-482 residue).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jan. 2, 2019, 562 KB, which is incorporated by reference herein. In the accompanying sequence listing:

SEQ ID NOs: 1 and 2 are D2/ZK-V nucleotide and amino acid sequences, respectively.

SEQ ID NOs: 3 and 4 are D2/ZK-5V nucleotide and amino acid sequences, respectively.

SEQ ID NOs: 5 and 6 are D2/ZK-V2A nucleotide and amino acid sequences, respectively.

SEQ ID NOs: 7 and 8 are nucleotide and amino acid sequences of ZIKV strain R103451.

SEQ ID NOs: 9 and 10 are nucleotide and amino acid sequences of DENV-2 16681.

SEQ ID NOs: 11 and 12 are nucleotide and amino acid sequences of DENV-2 PDK-53.

SEQ ID NOs: 13 and 14 are nucleotide and amino acid sequences of ZIKV strain PRVABC59.

SEQ ID NOs: 15 and 16 are D2/ZK-P-RFNN nucleotide and amino acid sequences, respectively.

SEQ ID NOs: 17 and 18 are D2/ZK-V-RFNN nucleotide and amino acid sequences, respectively.

SEQ ID NOs: 19 and 20 are D2/ZK-P4 nucleotide and amino acid sequences, respectively.

SEQ ID NOs: 21 and 22 are D2/ZK-V4 nucleotide and amino acid sequences, respectively.

SEQ ID NOs: 23 and 24 are D2/ZK-P5 nucleotide and amino acid sequences, respectively.

SEQ ID NOs: 25 and 26 are D2/ZK-V5 nucleotide and amino acid sequences, respectively.

DETAILED DESCRIPTION

I. Abbreviations

ASD average survival days
C capsid protein
D2/ZKV chimeric dengue-2/Zika virus
DENY dengue virus
E envelope glycoprotein
GB S Guillain-Barre syndrome
MOI multiplicity of infection
NS non-structural
pfu plaque forming unit
p.i. post-infection
prM premembrane protein
PHEIC Public Health Emergency of International Concern
WHO World Health Organization
ZIKV Zika virus

II. Terms and Methods

Unless otherwise noted, technical terms are used according to conventional usage.

Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: As used herein, administering a composition (e.g. an immunogenic composition, such as a chimeric virus) to a subject means to give, apply or bring the composition into contact with the subject. Administration can be accomplished by any of a number of routes, such as, for example, topical, oral, subcutaneous, intramuscular, intraperitoneal, intravenous, intrathecal and intramuscular.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibodies" includes intact immunoglobulins as well as a number of well-characterized fragments. For instance, Fabs, Fvs, and single-chain Fvs (scFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) $(Fab')_2$, the fragment of the antibody obtained by treating whole antibody with the enzyme pepsin without subsequent reduction; (4) $F(ab')_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibodies for use in the methods and devices of this disclosure can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antibody binding affinity: The strength of binding between a single antibody binding site and a ligand (e.g., an antigen or epitope). The affinity of an antibody binding site X for a ligand Y is represented by the dissociation constant ($K_d$), which is the concentration of Y that is required to occupy half of the binding sites of X present in a solution. A smaller $K_d$ indicates a stronger or higher-affinity interaction between X and Y and a lower concentration of ligand is needed to occupy the sites. In general, antibody binding affinity can be affected by the alteration, modification and/or substitution of one or more amino acids in the epitope recognized by the antibody paratope. In one example, antibody binding affinity is measured by end-point titration in an Ag-ELISA assay.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In one embodiment, an antigen is a virus antigen, such as a flavivirus E protein.

Attenuated: In the context of a live virus, the virus is attenuated if its ability to infect a cell or subject and/or its ability to produce disease is reduced (for example, eliminated) compared to a wild-type virus. Typically, an attenuated virus retains at least some capacity to elicit an immune response following administration to an immunocompetent subject. In some cases, an attenuated virus is capable of eliciting a protective immune response without causing any signs or symptoms of infection. In some embodiments, the ability of an attenuated virus to cause disease in a subject is reduced at least about 10%, at least about 25%, at least about 50%, at least about 75% or at least about 90% relative to wild-type virus. Accordingly, an "attenuating mutation" is a mutation in the viral genome and/or an encoded polypeptide that results in an attenuated virus.

Biological sample: A sample obtained from a subject (such as a human or veterinary subject). Biological samples, include, for example, fluid, cell and/or tissue samples. In some embodiments herein, the biological sample is a fluid sample. Fluid sample include, but are not limited to, serum, blood, plasma, urine, feces, saliva, cerebral spinal fluid (CSF) and bronchoalveolar lavage (BAL) fluid.

Capsid protein (C protein): A flavivirus structural protein that functions to package viral RNA into the nucleocapsid core during virus assembly. The C-terminal portion of the C protein includes an internal signal sequence (referred to herein as either C(ss) or prM signal sequence) for translocation of the prM protein into the endoplasmic reticulum, where cleavage of the C and prM proteins occurs. This signal sequence varies in length among different flaviviruses. For example, the C(ss) of both WNV and ZIKV is 18 amino acids, while the C(ss) of DEN viruses is 14 amino acids.

Chimera: A molecule (e.g., nucleic acid or protein) composed of parts that are of different origin (such as at least two nucleic acids or polypeptides) that, while typically unjoined in their native state, are joined or linked to form a single continuous molecule. A chimera may include nucleic acids or polypeptides that are joined end-to-end (for example, the amino-terminus of one sequence is joined to the carboxyl-terminus of a second sequence) or may include a sequence from one molecule that is embedded within that of another molecule (for example, the amino-terminus and carboxyl-terminus of the chimera are from one molecule, while an intervening sequence comes from another molecule).

A chimera may include a chimeric protein, for example a protein that is composed of amino acids from more than one protein. A chimera may also include a chimeric nucleic acid composed of nucleic acid sequences from more than one source, such as a chimeric nucleic acid which encodes a chimeric protein. In other examples, a chimera may include a chimeric genome, such as a flavivirus genome, which is composed of sequences from two or more flaviviruses. For example, a chimeric flavivirus genome may comprise nucleic acid sequences from more than one flavivirus genome, such as a dengue virus and a Zika virus. In some examples, a chimeric flavivirus includes nucleic acids encoding one or more proteins from a first flavivirus and nucleic acids encoding one or more proteins from a second flavivirus. In particular examples, a chimeric flavivirus is composed of a nucleic acid encoding the non-structural proteins and a C protein or a portion thereof from a dengue virus genome linked to a nucleic acid encoding a prM protein and at least a portion of an E protein (and optionally a portion of a C protein) from a Zika virus genome.

Conservative substitution: A substitution of one amino acid residue in a protein sequence for a different amino acid residue having similar biochemical properties. Typically, conservative substitutions have little to no impact on the activity of a resulting polypeptide. For example, ideally, a flavivirus protein (such as a prM, E, or non-structural protein) including one or more conservative substitutions (for example 1-10, 2-5, or 10-20, or no more than 2, 5, 10, 20, 30, 40, or 50 substitutions) retains the structure and function of the wild-type protein. A polypeptide can be produced to contain one or more conservative substitutions by manipulating the nucleotide sequence that encodes that polypeptide using, for example, standard procedures such as site-directed mutagenesis or PCR. In one example, such variants can be readily selected for additional testing by infecting cells with a virus containing a variant protein and determining its ability to replicate, by producing virus containing a variant protein and determining its neurovirulence or neuroinvasion properties, and/or by testing antibody cross-reactivity.

Contacting: Placement in direct physical association; includes both in solid and liquid form. "Contacting" is often used interchangeably with "exposed." In some cases, "contacting" includes transfecting, such as transfecting a nucleic acid molecule into a cell. In other examples, "contacting" refers to incubating a molecule (such as an antibody) with a biological sample.

Control: A reference standard, for example a positive control or negative control. A positive control is known to provide a positive test result. A negative control is known to provide a negative test result. However, the reference standard can be a theoretical or computed result, for example a result obtained in a population.

Dengue virus (DENY): An RNA virus of the family Flaviviridae, genus Flavivirus. The dengue virus genome encodes the three structural proteins (C, prM and E) that form the virus particle and seven non-structural proteins (NS1, NS2A, NS2B, NS3, NS4A, NS4B, NS5) that are only found in infected host cells, but are required for replication of the virus. There are four serotypes of dengue virus, referred to as DENY-1, DENV-2, DENV-3 and DENV-4. All four serotypes can cause the full spectrum of dengue disease. Infection with one serotype can produce lifelong immunity to that serotype. However, severe complications can occur upon subsequent infection by a different serotype. Dengue virus is primarily transmitted by *Aedes* mosquitoes, particularly *A. aegypti*. Symptoms of dengue virus infection include fever, headache, muscle and joint pain and a skin rash similar to measles. In a small percentage of cases, the infection develops into a life-threatening dengue hemorrhagic fever, typically resulting in bleeding, low platelet levels and blood plasma leakage, or into dengue shock syndrome characterized by dangerously low blood pressure.

Envelope glycoprotein (E protein): A flavivirus structural protein that mediates binding of flavivirus virions to cellular receptors on host cells. The flavivirus E protein is required for membrane fusion, and is the primary antigen inducing protective immunity to flavivirus infection. Flavivirus E protein affects host range, tissue tropism and viral virulence. The flavivirus E protein contains three structural and functional domains, DI-DIII. In mature virus particles the E protein forms head to tail homodimers lying flat and forming a dense lattice on the viral surface.

Flavivirus non-structural protein: There are seven non-structural (NS) proteins of a flavivirus, NS1, NS2A, NS2B, NS3, NS4A, NS4B, and NS5, which are encoded by the portion of the flavivirus genome that is 3' to the structural proteins. NS1 has been implicated in RNA replication and has been shown to be secreted from infected mammalian cells (Post et al., *Virus Res.* 18:291-302, 1991; Mackenzie et al., *Virology* 220:232-240, 1996; Muylaert et al., *Virology* 222:159-168, 1996). NS1 can elicit strong humoral immune responses and is a potential vaccine candidate (Shlesinger et al., *J. Virol.* 60:1153-1155, 1986; Qu et al., *J. Gen. Virol.* 74:89-97, 1993). NS2 is cleaved into NS2A and NS2B. NS2A is involved in RNA replication and virus particle assembly and secretion and NS2B forms a complex with NS3 and functions as a cofactor for the NS3 protease, which cleaves portions of the virus polyprotein. NS3 also functions as an RNA helicase and is used to unwind viral RNA during replication (Li et al., *J. Virol.* 73:3108-3116, 1999). While the exact functions of NS4A and NS4B remain to be elucidated, they are thought to be involved in RNA replication and RNA trafficking (Lindenbach and Rice, In: *Fields Virology*, Knipe and Howley, eds., Lippincott, Williams, and Wilkins, 991-1041, 2001). Finally, the NS5 protein is an RNA-dependent RNA polymerase involved in genome replication (Rice et al., *Science* 229:726-733, 1985). NS5 also shows methyltransferase activity commonly found in RNA capping enzymes (Koonin, *J. Gen. Virol.* 74:733-740, 1993).

Flavivirus structural protein: The capsid (C), premembrane (prM), and envelope (E) proteins of a flavivirus are the viral structural proteins. Flavivirus genomes consist of positive-sense RNAs that are roughly 11 kb in length. The genome has a 5' cap, but lacks a 3' polyadenylated tail (Wengler et al., *Virology* 89:423-437, 1978) and is translated into one polyprotein. The structural proteins (C, prM, and E) are at the amino-terminal end of the polyprotein followed by the non-structural proteins (NS1-5). The polyprotein is cleaved by virus and host derived proteases into individual proteins. The C protein forms the viral capsid while the prM and E proteins are embedded in the surrounding envelope (Russell et al., *The Togaviruses: Biology, Structure, and Replication*, Schlesinger, ed., Academic Press, 1980). The E protein functions in binding to host cell receptors resulting in receptor-mediated endocytosis. In the low pH of the endosome, the E protein undergoes a conformational change causing fusion between the viral envelope and the endosomal membranes. The prM protein is believed to stabilize the E protein until the virus exits the infected cell, at which time prM is cleaved to the mature M protein (Reviewed in Lindenbach and Rice, In: *Fields Virology*, Knipe and Howley, eds., Lippincott, Williams, and Wilkins, 991-1041, 2001).

Heterologous: Originating from a different genetic sources or species.

Immune response: A response of a cell of the immune system, such as a B-cell, T-cell, macrophage or polymorphonucleocyte, to a stimulus such as an antigen. An immune response can include any cell of the body involved in a host defense response for example, an epithelial cell that secretes an interferon or a cytokine. An immune response includes, but is not limited to, an innate immune response or inflammation.

Immunize: To render a subject protected from an infectious disease, such as by vaccination.

Isolated: An "isolated" or "purified" biological component (such as a nucleic acid, peptide, protein, protein complex, or particle) has been substantially separated, produced apart from, or purified away from other components in a preparation or other biological components in the cell of the organism in which the component occurs, that is, other chromosomal and extrachromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages.

Operably linked: A first nucleic acid is operably linked to a second nucleic acid when the first nucleic acid is placed in a functional relationship with the second nucleic acid. Generally, operably linked DNA sequences are contiguous and, where necessary to join two protein coding regions, in the same reading frame. Operably linked nucleic acids include a first nucleic acid contiguous with the 5' or 3' end of a second nucleic acid. In other examples, a second nucleic acid is operably linked to a first nucleic acid when it is embedded within the first nucleic acid, for example, where the nucleic acid construct includes (in order) a portion of the first nucleic acid, the second nucleic acid, and the remainder of the first nucleic acid.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., $21^{st}$ Edition (2005), describes compositions and formulations suitable for pharmaceutical delivery of one or more therapeutic compositions, such as a chimeric virus, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Premembrane protein (prM protein): A flavivirus structural protein. The prM protein is an approximately 25 kDa protein that is the intracellular precursor for the membrane (M) protein. prM is believed to stabilize the E protein during transport of the immature virion to the cell surface. When the virus exits the infected cell, the prM protein is cleaved to the mature M protein, which is part of the viral envelope (Reviewed in Lindenbach and Rice, In: *Fields Virology*, Knipe and Howley, eds., Lippincott, Williams, and Wilkins, 991-1041, 2001).

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of one or more signs or symptoms of a disease.

Purified: The term purified does not require absolute purity; rather, it is intended as a relative term. Thus, for example, a purified nucleic acid preparation is one in which the nucleic acid is more enriched than the nucleic acid is in its natural environment (such as within a cell) or in a preparation or production vessel. In other examples, a purified virus preparation is one in which the virus is more enriched than in a cell or organism, a preparation, or a production vessel. A purified nucleic acid or virus also includes one that is substantially free of undesired components, such as an inactivating agent. Preferably, a preparation is purified such that the nucleic acid or virus represents at least 50% of the total content of the preparation. In some embodiments, a purified preparation contains at least 60%, at least 70%, at least 80%, at least 85%, at least 90%, at least 95%, at least 98%, at least 99%, or more of the nucleic acid or virus.

Recombinant nucleic acid: A nucleic acid molecule (or protein or virus) that is not naturally occurring or has a sequence that is made by an artificial combination of two otherwise separated segments of sequence. This artificial combination is accomplished by chemical synthesis or, more commonly, by the artificial manipulation of isolated segments of nucleic acids, e.g., by genetic engineering techniques such as those described in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989. The term recombinant includes nucleic acids and proteins that have been altered solely by addition, substitution, or deletion of a portion of a natural nucleic acid molecule or protein.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.*, 2:482, 1981); Needleman and Wunsch (*J. Mol. Biol.*, 48:443, 1970); Pearson and Lipman (*Proc. Natl. Acad. Sci.*, 85:2444, 1988); Higgins and Sharp (*Gene*, 73:237-44, 1988); Higgins and Sharp (*CABIOS*, 5:151-53, 1989); Corpet et al. (*Nuc. Acids Res.*, 16:10881-90, 1988); Huang et al. (*Comp. Appls. Biosci.*, 8:155-65, 1992); and Pearson et al. (*Meth. Mol. Biol.*, 24:307-31, 1994). Altschul et al. (*Nature Genet.*, 6:119-29, 1994) presents a detailed consideration of sequence alignment methods and homology calculations.

The alignment tools ALIGN (Myers and Miller, *CABIOS* 4:11-17, 1989) or LFASTA (Pearson and Lipman, *Proc. Natl. Acad. Sci.* 85:2444-2448, 1988) may be used to perform sequence comparisons (Internet Program© 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at the NCSA website. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment should be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J. Mol. Biol.,* 215:403-10, 1990; Gish and States, *Nature Genet.,* 3:266-72, 1993; Madden et al., *Meth. Enzymol.,* 266:131-41, 1996; Altschul et al., *Nucleic Acids Res.,* 25:3389-402, 1997; and Zhang and Madden, *Genome Res.,* 7:649-56, 1997.

Serum: The fluid portion of the blood that separates out from clotted blood. Serum contains many proteins, including antibodies, but does not contain clotting factors.

Subject: Living multi-cellular vertebrate organisms, a category that includes both human and non-human mammals (such as mice, rats, rabbits, sheep, horses, cows, and non-human primates).

Therapeutically effective amount: A quantity of a specified agent (such as a chimeric virus) sufficient to achieve a desired effect in a subject being treated with that agent. For example, this may be the amount of a virus vaccine useful for eliciting an immune response in a subject and/or for preventing infection by the virus. In the context of the present disclosure, a therapeutically effective amount of a Zika virus vaccine, for example, is an amount sufficient to increase resistance to, prevent, ameliorate, and/or treat infection caused by Zika virus in a subject without causing a substantial cytotoxic effect in the subject. The effective amount of a Zika virus vaccine (or Zika virus immunogenic composition) useful for increasing resistance to, preventing, ameliorating, and/or treating infection in a subject will be dependent on, for example, the subject being treated, the manner of administration of the therapeutic composition and other factors.

Transformed: A "transformed" cell is a cell into which has been introduced a nucleic acid molecule (such as a heterologous nucleic acid) by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Vaccine: A preparation of immunogenic material capable of stimulating an immune response, administered for the prevention, inhibition, amelioration, or treatment of infectious or other types of disease. The immunogenic material may include attenuated or inactivated (killed) microorganisms (such as bacteria or viruses), or antigenic proteins, peptides or DNA derived from them. An attenuated virus is a virulent organism that has been modified to produce a less virulent form, but nevertheless retains the ability to elicit antibodies and cell-mediated immunity against the virulent form. An inactivated (killed) virus is a previously virulent organism that has been inactivated with chemicals, heat, or other treatment, but elicits antibodies against the organism. Vaccines may elicit both prophylactic (preventative or protective) and therapeutic responses. Methods of administration vary according to the vaccine, but may include inoculation, ingestion, inhalation or other forms of administration. Vaccines may be administered with an adjuvant to boost the immune response.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of inserted gene or genes.

Zika virus (ZIKV): A member of the virus family Flaviviridae and the genus Flavivirus. Other members of this genus include dengue virus, yellow fever virus, Japanese encephalitis virus (JEV), West Nile virus and Spondweni virus. ZIKV is spread by the daytime-active mosquitoes *Aedes aegypti* and *A. albopictus*. This virus was first isolated from a *Rhesus* macaque from the Zika Forest of Uganda in 1947. Since the 1950s, ZIKV has been known to occur within a narrow equatorial belt from Africa to Asia. The virus spread eastward across the Pacific Ocean in 2013-2014, resulting in ZIKV outbreaks in Oceania to French Polynesia, New Caledonia, the Cook Islands, and Easter Island. In 2015, ZIKV spread to Mexico, Central America, the Caribbean and South America, where ZIKV has reached pandemic levels. Infection by ZIKV generally causes either no symptoms are mild symptoms, including mild headache, maculopapular rash, fever, malaise, conjunctivitis and joint pain. ZIKV causes symptoms in about 20% of infected individuals, and no deaths from the virus have yet been reported. However, ZIKV infection has been linked to the birth of microcephalic infants following maternal infection, as well an increase in cases of GBS. Reports have also indicated that ZIKV has the potential for human blood-borne and sexual transmission. ZIKV has also been found in human saliva and breastmilk. There are currently no available medical countermeasures for the treatment or prevention of Zika virus infection (Malone et al., *PLoS Negl Trop Dis* 10(3):e0004530, 2016).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Disclosed herein are chimeric flaviviruses that include non-coding regions, non-structural proteins, a capsid (C) protein and a portion of a premembrane (prM) signal sequence from a wild-type or attenuated dengue serotype 2 virus (DENV-2); and a portion of a prM signal sequence, a prM protein and at least a portion of an envelope (E) protein from a Zika virus (ZIKV). Tables 1 and 2 below provide start and stop positions of the particular genes and proteins in an exemplary Zika virus (SPH2015) and an exemplary attenuated DENV-2 vaccine strain (PDK-53). These sequences can serve as reference sequences and may be used to identify particular nucleotide or amino acid positions that correspond to positions referred to in the chimeric nucleic acids disclosed herein, or proteins encoded by the chimeric nucleic acids disclosed herein, for example by producing an alignment of a chimera and one of the virus sequences provided herein.

TABLE 1

Start and stop positions of noncoding regions (NCRs), structural proteins and nonstructural proteins in ZIKV strain R103451

| Region | Nucleotide start/ stop position (SEQ ID NO: 7) | Amino acid start/ stop position (SEQ ID NO: 8) |
|---|---|---|
| 5' NCR | 1-107 | — |
| C | 108-473 | 1-122 |
| C(ss) | 420-473 | 105-122 |
| prM | 474-977 | 123-290 |
| M | 753-977 | 216-290 |
| E | 978-2489 | 291-794 |
| NS1 | 2490-3545 | 795-1146 |
| NS2A | 3546-4223 | 1147-1372 |
| NS2B | 4224-4613 | 1373-1502 |
| NS3 | 4614-6464 | 1503-2119 |
| NS4A | 6465-6914 | 2120-2269 |
| NS4B | 6915-7667 | 2270-2520 |
| NS5 | 7668-10376 | 2521-3423 |
| Stop | 10377-10379 | — |
| 3' NCR | 10380-10807 | — |

TABLE 2

Start and stop positions ot NCRs, structural proteins and nonstructural proteins in DENV-2 vaccine strain PDK-53

| Region | Nucleotide start/ stop position (SEQ ID NO: 11) | Amino acid start/ stop position (SEQ ID NO: 12) |
|---|---|---|
| 5' NCR | 1-96 | — |
| C | 97-438 | 1-114 |
| C(ss) | 397-438 | 101-114 |
| prM | 439-936 | 115-280 |
| M | 712-936 | 206-280 |
| E | 937-2421 | 281-775 |
| NS1 | 2422-3477 | 776-1127 |
| NS2A | 3478-4131 | 1128-1345 |
| NS2B | 4132-4521 | 1346-1475 |
| NS3 | 4522-6375 | 1476-2093 |
| NS4A | 6376-6825 | 2094-2243 |
| NS4B | 6826-7569 | 2244-2491 |
| NS5 | 7570-10269 | 2492-3391 |
| 3' NCR | 10270-10723 | |

In the disclosed nucleic acid chimeras, the ZIKV genome can be from any strain of ZIKV, including an African genotype strain or an Asian genotype strain. In some embodiments, the ZIKV is an African genotype strain, such as MR-766. In other embodiments, the ZIKV is an Asian genotype strain, such as SPH2015, PRVABC59, R103451, P6-740 or FSS 13025. In some embodiments, the ZIKV genome is from strain R103451 (SEQ ID NO: 7; or deposited under GenBank Accession No. KX262887.1). The ZIKV genome may be a wild type strain or an attenuated (or vaccine) strain. In some examples, the ZIKV genome sequence is modified, for example to introduce restriction sites for cloning purposes. These modifications can be silent mutations (for example, nucleotide sequence changes that do not alter amino acid sequence) or they may change the amino acid sequence.

ZIKV sequences are publicly available. For example GenBank Accession Nos. KX262887.1, KU321639.1, KU501215.1, KU955595.1, KU955594.1, KU955593.1, KU955592.1, KU955591.1, KU681082.3, KU681081.3 and KX247646.1, all of which are incorporated by reference as included in GenBank on Jun. 14, 2016. In additional examples, the ZIKV genome (or the C signal sequence, prM, and/or E protein from the ZIKV genome) are at least 90%, at least 95%, at least 96%, at least 97%, at least 98%, or at least 99% identical to a publicly available ZIKV sequence.

In some embodiments, the DENV-2 strain genome is an attenuated DENV-2 strain genome. In some examples, the attenuated DENV-2 is strain PDK-53, the genome sequence of which is set forth herein as SEQ ID NO: 11.

In other embodiments, the DENV-2 strain genome is a wild-type DENV-2 strain genome. In some examples, the wild-type DENV-2 is strain 16681, the genome sequence of which is set forth herein as SEQ ID NO: 9.

In some examples, the disclosed D2/ZKV chimeras include one or more nucleic acid substitutions that result in an amino acid substitution that provides a desirable characteristic, for example, increased stability and/or replication in vaccine virus production cell culture (such as Vero cells), or decrease virus replication in mosquito cells (such as C6/36 cells) or live mosquitoes compared to the unsubstituted virus or chimera.

The viruses containing the disclosed nucleic acid chimeras can readily be produced by replication in host cells in culture. Methods of producing viruses are well known in the art (see e.g. *Fields Virology*, Knipe and Howley, eds., Lippincott, Williams, and Wilkins, 2001; Flint et al., *Principles of Virology*, ASM Press, 2000). Host cell lines are generally selected to be easy to infect with virus or transfect with viral genomic RNA, capable of stably maintaining foreign RNA with an unarranged sequence, and have the necessary cellular components for efficient transcription, translation, post-translation modification, virus assembly, and secretion of the protein or virus particle. In addition, cells are typically those having simple media component requirements which can be adapted for growth in suspension culture. In some examples, the host cell line is a mammalian cell line that is adapted to growth in low serum or serum-free medium. Exemplary suitable host cell lines include Vero (monkey), C6/36 (mosquito), BHK21 (hamster), LLC-MK2 (monkey) SK6 (swine), L292 (mouse), HeLa (human), HEK (human), 2fTGH cells (human), HepG2 (human), and PDK (dog) cells. Suitable cell lines can be obtained from the American Type Culture Collection (ATCC), Manassas, Va.

The disclosure also provides D2/ZKV chimeras having one or more nucleic acid or amino acid substitutions, insertions, deletions, or combinations thereof, such that the resulting chimera has improved characteristics, such as improved growth in Vero cells.

Manipulation of the nucleotide sequence of the disclosed chimeric flaviviruses by standard procedures, including for instance site-directed mutagenesis or PCR and M13 primer mutagenesis, can be used to produce variants with improved characteristics (such as increased virus titer or stability in cell culture). Details of these techniques are well known. For instances, protocols are provided in Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989. The simplest modifications involve the substitution of one or more amino acids for amino acids having similar physiochemical and/or structural properties. These so-called conservative substitutions are likely to have minimal impact on the activity and/or structure of the resultant protein. Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl (or vice versa); (b) a cysteine or proline is substituted for (or by) any other residue; (c) a residue having an electropositive side chain, for example, lysyl, arginyl, or histadyl, is substituted for (or by) an electronegative residue, for example, glutamyl or asparty (or vice versa); or (d) a residue having a bulky side chain, for example, phenylalanine, is substituted for (or by) one not having a side chain, for example, glycine (or vice versa).

In addition to targeted mutagenesis to produce variants of the disclosed D2/ZKV chimeras, mutations may accrue upon passage in cell culture that result in variants, some with desirable characteristics. Nucleic acid and amino acid substitutions, insertions, and/or deletions that accrue in chimeric viruses during cell culture passages are readily determined by sequence analysis of the virus amplified from isolated plaques of the virus seed, and can be engineered into infectious clones to generate D2/ZKV chimera variants that have improved characteristics (such as replication to high titer). Consistent mutations identified from multiple seeds or isolated plaques are one indication of a desirable substitution of the chimera in the cell type. Previous studies have successfully identified substitutions which occurred in cell culture and engineered these into different chimeric virus constructs to produce chimeric viruses with improved characteristics (e.g., Huang et al., *J. Virol.* 77:11436-11447, 2003; Huang et al., *J. Virol.* 12:7300-7310, 2005; U.S. Pat. No. 8,715,689; and WO 2015/196094).

Provided herein are flavivirus nucleic acid chimeras. In some embodiments, the nucleic acid chimera includes a first nucleic acid molecule comprising a 5' non-coding region, a nucleic acid encoding non-structural proteins and a C protein, and a 3' non-coding region, each from a DENV-2 strain genome, wherein the C protein comprises a portion of a prM signal sequence from the DENV-2 genome and a portion of a prM signal sequence from a ZIKV genome; and a second nucleic acid molecule operably linked to the first nucleic acid molecule, encoding a prM protein and at least a portion of an E protein from the ZIKV genome.

In some embodiments, the DENV-2 strain genome is an attenuated DENV-2 strain genome. In some examples, the attenuated DENV-2 genome includes a mutation in the 5' non-coding region at nucleotide position 57; a mutation at nucleotide position 2579 that results in the presence of an aspartate at amino acid residue 53 of the NS1 protein; and/or a mutation at nucleotide position 5270 that results in the presence of a valine at amino acid residue 250 of the NS3 protein. In particular examples, the attenuated DENV-2 is strain PDK-53. The attenuated DENV-2 may also include one or more of the mutations listed in Table 4.

In some embodiments, the DENV-2 strain genome is a wild-type DENV-2 strain genome. In some examples, the wild-type DENV-2 is strain 16681.

In some embodiments, the Zika virus is an African genotype virus, such as strain MR-766. In other embodiments, the Zika virus is an Asian genotype virus, such as strain SPH2015, PRVABC59, R103451, P6-740 or FSS 13025.

In some embodiments, the portion of the prM signal sequence from the DENV-2 genome includes the first three amino acids of the DENV-2 prM signal sequence and the portion of the prM signal sequence from the ZIKV genome includes the last 15 amino acids of the ZIKV prM signal sequence (see Strategy 1 in FIG. 1). In some examples, the first three amino acids of the DENV-2 prM signal sequence includes amino acids 101-103 of SEQ ID NO: 12 and/or the last 15 amino acids of the ZIKV prM signal sequence includes amino acids 108-122 of SEQ ID NO: 8.

In other embodiments, the portion of the prM signal sequence from the DENV-2 genome includes the first five amino acids of the DENV-2 prM signal sequence and the portion of the prM signal sequence from the ZIKV genome includes the last 13 amino acids of the ZIKV prM signal sequence (see Strategy 2 in FIG. 1). In some examples, the first five amino acids of the DENV-2 prM signal sequence includes amino acids 101-105 of SEQ ID NO: 12 and/or the last 13 amino acids of the ZIKV prM signal sequence includes amino acids 110-122 of SEQ ID NO: 8.

In other embodiments, the C/prM junction site includes a different number of residues from the DENV-2 and the ZIKV than those listed above.

In some embodiments, a portion of the E protein is from the DENV-2 genome. In some examples, the portion of the E protein from the DENV-2 genome includes the last 14 amino acids of the modified DENV-2 E protein. In specific non-limiting examples, the last 14 amino acids of the DENV-2 E protein includes amino acids 777-790 of SEQ ID NO: 2. In other examples, the E/NS1 junction site in the D2/ZKV chimera may include an alternative number of residues from the DENV-2, such as about 0, about 2, about 4, about 6, about 8, about 10, about 12, about 13, about 14, about 16, about 18 or about 20 residues from the DENV-2.

In some embodiments, the nucleic acid chimera further includes at least one Vero cell adaptation mutation. In some examples, the Vero cell adaptation mutation results in a glutamine to arginine substitution at residue 465 of the D2/ZKV E protein (also E-465 of ZIKV); an isoleucine to threonine substitution at residue 484 of the D2/ZKV E protein (also E-484 of ZIKV); an isoleucine to phenylalanine substitution at residue 493 of the D2/ZKV E protein (as E-484 of the DENV-2); a lysine to asparagine substitution at residue 99 of the NS2A protein (NS2A protein is from DENV-2); and/or an aspartic acid to asparagine substitution at residue 23 of the NS4A protein (NS4A protein is from DENV-2) (Table 3).

In particular examples, nucleic acid chimera includes four Vero cell adaptation mutations, wherein the mutations result in a glutamine to arginine substitution at residue 465 of the D2/ZKV E protein (also E-465 of ZIKV); an isoleucine to phenylalanine substitution at residue 493 of the D2/ZKV E protein (also E-484 of DENV-2); a lysine to asparagine substitution at residue 99 of the NS2A protein (from DENV-2); and an aspartic acid to asparagine substitution at residue 23 of the NS4A protein (from DENV-2).

In other particular examples, nucleic acid chimera includes four Vero cell adaptation mutations, wherein the mutations result in a glutamine to arginine substitution at residue 465 of the D2/ZKV E (also E-465 of ZIKV) protein; an isoleucine to threonine substitution at residue 484 of the D2/ZKV E (also E-484 of ZIKV) protein; an isoleucine to phenylalanine substitution at residue 493 of the D2/ZKV E (also E-484 of DENV-2) protein; and a lysine to asparagine substitution at residue 99 of the NS2A protein (from DENV-2).

In other particular examples, nucleic acid chimera includes five Vero cell adaptation mutations, wherein the mutations result in a glutamine to arginine substitution at residue 465 of the D2/ZIKV E protein (also E-465 of ZIKV); an isoleucine to threonine substitution at residue 484 of the D2/ZIKV E protein (also E-484 of ZIKV); an isoleucine to phenylalanine substitution at residue 493 of the D2/ZIKV E protein (also E-484 of DENV-2); a lysine to asparagine substitution at residue 99 of the NS2A protein (from DENV-2); and an aspartic acid to asparagine substitution at residue 23 of the NS4A protein (from DENV-2).

TABLE 3

Potential amino acid mutations for Vero-cell-fitness enhancement of chimeric DEN-2/Zika viruses

| NT position on | Protein-AA position based on: | | | AA |
|---|---|---|---|---|
| chimeric DENV-2/ZKV | Chimeric DENV-2/ZKV | DENV-2 AA | ZIKV AA | substitution (WT-Mut) |
| 2348 (A to G) | E-465 | NA | E-465 | Gln-Arg |
| 2405 (T to C) | E-484 | NA | E-484 | Ile-Thr |
| 2431 (A to T) | E-493 | E-484* | NA | Ile-Phe |
| 3817 (A to C) | NS2A-99 | NS2A-99 | NA | Lys-Asn |
| 6487 (G to A) | NS4A-23 | NS4A-23 | NA | Asp-Asn |

NA = not applicable; chimeric virus doesn't include the gene of the virus

*The DENV-2 E protein is shorter than the ZIKV E protein, resulting in different residue numbering between chimeric DENV-2/ZKV and DENV-2

In some embodiments, the nucleic acid chimera includes a nucleic acid sequence at least 80%, at least 85%, at least 90%, at least 95%, at least 96%, at least 97%, at least 98% or at least 99% identical to SEQ ID NO: 15, SEQ ID NO: 17, SEQ ID NO: 19, SEQ ID NO: 21, SEQ ID NO: 23 or SEQ ID NO: 25. In some examples, the nucleic acid chimera includes the nucleic acid sequence of SEQ ID NO: 15, SEQ ID NO: 17, SEQ ID NO: 19, SEQ ID NO: 21, SEQ ID NO: 23 or SEQ ID NO: 25.

In some embodiments, the nucleic acid chimera encodes an amino acid sequence at least 80%, at least 85%, at least 90%, at least 95%, at least 96%, at least 97%, at least 98% or at least 99% identical to SEQ ID NO: 16, SEQ ID NO: 18, SEQ ID NO: 20, SEQ ID NO: 22, SEQ ID NO: 24 or SEQ ID NO: 26. In some examples, the nucleic acid chimera encodes the amino acid sequence of SEQ ID NO: 16, SEQ ID NO: 18, SEQ ID NO: 20, SEQ ID NO: 22, SEQ ID NO: 24 or SEQ ID NO: 26.

In some examples, the nucleic acid sequence is human codon optimized.

Also provided herein are chimeric flaviviruses that comprise a nucleic acid chimera disclosed herein. Compositions, such as immunogenic compositions, that include the chimeric flaviviruses are also provided by the present disclosure. In some embodiments, the immunogenic compositions further includes a pharmaceutically acceptable carrier and/or one or more adjuvants.

Further provided herein are methods of eliciting an immune response against ZIKV in a subject by administering to the subject a chimeric flavivirus or immunogenic composition disclosed herein. The immune response may include, for example, induction of ZIKV-specific antibodies (such as IgM and/or IgG antibodies) or induction of a virus-specific T cell response. In some examples, the immune response is a protective immune response.

In some embodiments, the method includes administering one to five doses (such as 1, 2, 3, 4 or 5 doses) of the immunogenic composition to the subject. In some examples, the first 1 or 2 doses is the immunogenic composition of the disclosed live-attenuated chimeric DENV-2/ZKV and the following dose(s) is/are inactivated or non-infectious ZIKV vaccine. In some examples, the method further includes administering a combination of the live-attenuated chimeric DENV-2/ZIKV vaccine disclosed herein with an inactivated or non-infectious ZIKV vaccine (such as the inactivated ZIKV or inactivated chimeric WN/ZIKV) simultaneously. In some examples, the method further includes administering one or more adjuvants to the subject.

Also provided is a method of immunizing a subject against ZIKV by administering to the subject a chimeric flavivirus or immunogenic composition disclosed herein.

In some embodiments of the methods, the subject is a human.

IV. Compositions and Methods for Eliciting an Immune Response

Provided herein are methods of eliciting an immune response in a subject by administering to the subject a chimeric dengue serotype 2/Zika virus (D2/ZKV) disclosed herein. In a particular example, the subject is a human. The chimeric D2/ZKV is used, for examples, to produce an immune response that prevents or inhibits infection with a ZIKV.

In some examples, the method further includes selecting a subject in need of enhanced immunity to ZIKV. Subjects in need of enhanced immunity to ZIKV include subjects who are at risk of ZIKV infection, subjects who have been exposed to one or more ZIKV, and subjects who have previously been vaccinated with ZIKV or other flavivirus vaccines. Residents of, or travelers to, countries or regions where ZIKV is endemic are at risk of contracting ZIKV. Additional factors that contribute to risk of infection with ZIKV include the characteristics of the location, presence of ZIKV in the area, exposure to mosquitos, and lack of preventive measures (such as insect repellant).

One or more chimeric D2/ZIKV are administered to a subject by any of the routes normally used for introducing a composition into a subject. Methods of administration include, but are not limited to, intradermal, intramuscular, intraperitoneal, parenteral, intravenous, subcutaneous, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local.

Immunogenic compositions are administered in any suitable manner, such as with pharmaceutically acceptable carriers. Pharmaceutically acceptable carriers are determined in part by the particular composition being administered, as well as by the particular method used to administer the composition. See, e.g., *Remington: The Science and Practice of Pharmacy*, The University of the Sciences in Philadelphia, Editor, Lippincott, Williams, & Wilkins, Philadelphia, Pa., 21st Edition (2005). Accordingly, there is a wide variety of suitable formulations of pharmaceutical compositions of the present disclosure.

The immunogenic compositions may be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. The formulations may be presented in unit-dose or multi-dose containers, for example, sealed ampules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In some examples, the compositions disclosed herein include one or more adjuvants. In other examples, an adjuvant is not included in the composition, but is separately administered to a subject (for example, in combination with a composition disclosed herein) before, after, or substantially simultaneously with administration of one or more of the compositions disclosed herein. Adjuvants are agents that increase or enhance an immune response in a subject administered an antigen, compared to administration of the antigen in the absence of an adjuvant. One example of an adjuvant is an aluminum salt, such as aluminum hydroxide, aluminum phosphate, aluminum potassium sulfate, or aluminum hydroxyphosphate. Other adjuvants include biological adjuvants, such as cytokines (for example, IL-2, IL-6, IL-12, RANTES, GM-CSF, TNF-α, or IFN-γ), growth factors (for example, GM-CSF or G-CSF), one or more molecules such as OX-40L or 4-1 BBL, immunostimulatory oligonucleotides (for example, CpG oligonucleotides), Toll-like receptor agonists (for example, TLR2, TLR4, TLR7/8, or TLR9 agonists), and bacterial lipopolysaccharides or their derivatives (such as 3D-MPL). Additional adjuvants include oil and water emulsions, squalene, or other agents. In one example, the adjuvant is a mixture of stabilizing detergents, micelle-forming agent, and oil available under the name PROVAX® (IDEC Pharmaceuticals, San Diego, Calif.). One of skill in the art can select a suitable adjuvant or combination of adjuvants to be included in the compositions disclosed herein or administered to a subject in combination with the compositions disclosed herein.

Administration is accomplished by single or multiple doses. The dose administered to a subject in the context of the present disclosure should be sufficient to induce a beneficial therapeutic response in a subject over time, or to inhibit or prevent ZIKV infection. The dose required will vary from subject to subject depending on the species, age, weight and general condition of the subject, the severity of the infection being treated, the particular immunogenic composition being used, and its mode of administration. An appropriate dose can be determined by one of ordinary skill in the art using only routine experimentation. In some examples, the dose of each chimeric virus (such as in an immunogenic composition) administered to the subject is about 100 pfu to about 1000,000 pfu. For example, a dose of the immunogenic composition can contains at least 100 pfu, at least 1000 pfu, at least 5000 pfu, at least 10,000 pfu, at least 50,000 pfu, at least 100,000 pfu, at least 500,000 pfu, or at least 1000,000 pfu of the chimeric virus.

The volume of administration will vary depending on the route of administration. By way of example, intramuscular injections may range from about 0.1 ml to about 1.0 ml. Those of ordinary skill in the art will know appropriate volumes for different routes of administration.

Repeated immunizations may be necessary to produce an immune response in a subject. When administered in multiple doses, the booster doses are administered at various time intervals, such as weeks or months to years. In other examples, the D2/ZKV chimeric viruses are used as a booster following administration of one or more ZIKV vaccines. In one example, a subject is administered a prime dose of a ZIKV vaccine followed by at least one boost dose of a D2/ZKV chimeric virus disclosed herein. In alternative examples, the D2/ZKV chimeric virus is administered first, followed by a booster administration of another ZIKV vaccine, such as a inactivated ZIKV vaccine. In some examples, the boost dose is administered about 14, 30, 60, 90, or more days after administration of the prime dose. Additional boosters can be administered at subsequent time points, if determined to be necessary or beneficial Immunization protocols (such as amount of immunogen, number of doses and timing of administration) can be determined experimentally, for example by using animal models (such as mice or non-human primates), followed by clinical testing in humans.

The following examples are provided to illustrate certain particular features and/or embodiments. These examples should not be construed to limit the disclosure to the particular features or embodiments described.

EXAMPLES

Example 1: Generation and Characterization of Chimeric Flaviviruses

This example describes the construction of chimeric dengue-2/Zika viruses that include the prM protein and at least a portion of the E protein from a ZIKV in an attenuated or wild-type DENV-2 backbone.

Engineering and Deriving Chimeric D2/ZKVs

Using the infectious clones of dengue virus serotype 2 (DENV-2) engineered previously (Kinney et al., *Virology* 230:300-308, 1997; Butrapet et al., *J Virol* 74:3011-3019, 2000), two chimeric DENV-2/Zika viruses (D2/ZKV-P and D2/ZKV-V) were generated. D2/ZKV-P and D2/ZKV-V contain the prM and E genes of a Zika virus (ZIKV) in the genomic background of the parent (P) virus DENV-2 16681 and its vaccine (V) strain PDK-53 strain, respectively. The DENV-2 PDK-53 vaccine strain was originally developed by serial passage of the DENV-2 16681 virus 53 times in primary dog kidney cells. Table 4 provides a summary of the nucleotide and amino acid variation between the two strains (see also PCT Publication No. WO 01/060847, which is herein incorporated by reference in its entirety).

TABLE 4

Nucleotide and Amino Acid Sequence Differences between DENV-2 16681 and its Vaccine Derivative Strain PDK-53

| Genome position | Nucleotide 16681 | Nucleotide PDK-53 | Amino acid 16681 | Amino acid PDK-53 | Protein position | Polyprotein position |
|---|---|---|---|---|---|---|
| 57 | C | T | — | — | | |
| 524 | A | T | Asp | Val | prM-29 | |
| 2055 | C | T | Phe | Phe | E-373 | 653 |
| 2579 | G | A | Gly | Asp | NS1-53 | 828 |
| 4018 | C | T | Leu | Phe | NS2A-181 | 1308 |
| 5270 | A | T | Glu | Val | N53-250 | 1725 |
| 5547 | T | C | Arg | Arg | NS3-342 | 1817 |
| 6599 | G | C | Gly | Ala | NS4A-75 | 2168 |
| 8571 | C | T | Val | Val | NS5-334 | 2825 |

It was previously determined that the three major attenuation determinants of DENV-2 PDK-53 reside in the 5' non-coding region (NCR), NS1 protein, and NS3 protein (Butrapet et al., *J Virol* 74:3011-3019, 2000), which are shown in bold in Table 4. Chimeric viruses containing the prM-E gene region from heterologous flaviviruses, within the DENV-2 PDK-53 genetic backbone, have been shown to express the appropriate heterologous virus-specific E immunogens and retain the attenuated phenotype of the DENV-2 PDK-53 vaccine virus (Huang et al., *J Virol* 74:3020-3028, 2000; Huang et al., *J Virol* 77: 11436-11447, 2003; Kinney et al., *Intervirology* 44:176-197, 2001; Huang et al., *J Virol* 79:7300-7310, 2005). DENV-2 PDK-53-based chimeric D2/D1, D2, D2/D3, D2/D4, and D2/WN viruses were previously generated for a live-attenuated tetravalent DENY vaccine and a WNV vaccine (U.S. Pat. Nos. 7,094,411; 7,641,909; 8,025,887; and 8,673,316, which are herein incorporated by reference in their entirety). The tetravalent DENY vaccine containing chimeric D2/D1, D2, D2/D3, and D2/D4 has been manufactured and characterized for human clinical trials (Huang et al., *PLoS Negl Trop Dis* 7(5):e2243, 2014), and is currently in phase 3 human clinical trials (George et al., *J Infect Dis* 212(7):1032-1041, 2015; Osorio et al., *Lancet Infect Dis* 14:830-838, 2014).

The chimeric D2/ZKV-P and D2/ZKV-V constructs were based on a similar engineering strategy used for generating chimeric D2/WNV (Strategy 1 in FIG. 1). The chimeric D2/ZKV-V, which is based on the DENY-2 PDK-53 vaccine backbone, is used for live-attenuated ZIKV vaccine development. The chimeric D2/ZKV-P, which is based on the parental DENY-2 16681 strain, is used as a parental chimeric virus for virulence and attenuation comparisons with the chimeric D2/ZKV-V vaccine, as well as for ZIKV vaccine development.

Viable chimeric D2/ZKV-P virus was recovered from C6/36 cells transfected with chimeric viral RNA which was in vitro transcribed from engineered chimeric cDNA. Because the DENV-2 PDK-53 vaccine virus does not replicate well in C6/36 cells (which is one of its characteristic attenuation phenotypes), initial efforts in recovering chimeric D2/ZKV-V from C6/36 cells did not yield detectable infectious virus. Also, the first generation of the D2/ZK-P and D2/ZK-V constructs did not generate viable chimeric viruses from transfected Vero cells. The D2/ZK-P virus seed recovered from C6/36 cells also did not infect Vero cells efficiently, suggesting incompatible chimeric genes of the virus for Vero cell infection. Because Vero cells are essential for the manufacture of live-attenuated vaccine viruses, it is necessary to engineer a chimeric virus that replicates well and is stable in Vero cells. D2/ZK-P obtained from C6/36 cells was adapted to grow in Vero cells by serial passage of the virus in Vero cells at a high multiplicity of infection (MOI).

After just one passage in Vero cells at high MOI, successful Vero-adapted D2/ZK-P virus was recovered and sequenced to identify the genetic mutations involved in Vero cell adaption. Further Vero cell passages of the Vero-adapted D2/ZK-P virus resulted in significantly higher titers of D2/ZK-P virus seeds which are also sequenced to identify more mutations that may enhance fitness of the chimera in Vero cells. The necessary Vero-adapted mutation(s) are incorporated into the vaccine D2/ZK-V constructs. In previous studies, various chimeric viruses were modified with mutations for Vero cell adaption to enhance and/or stabilize the chimeric viruses for Vero cell culture, and such modification resulted in successful live-attenuated chimeric dengue viruses and chimeric D2/WN vaccine candidates using the same DENV-2 PDK-53 vaccine backbone.

Chimeric D2/Zika Viruses

Provided below is a list of chimeric D2/ZK viruses for generating live-attenuated ZIKV vaccine candidates:

D2/ZK-P (also referred to as D2/ZK-PS): This chimeric virus includes the parental (P) backbone of D2 16681 and the prM-E genes of Zika virus strain SPH2015 (S). The virus was constructed using Strategy 1 illustrated in FIG. 1. Viable virus was recovered from transfected C6/36 cells, but not from Vero cells, and could not be plaque titrated in Vero cells. Evidence of virus recovery was based on >90% IFA positive C6/36 cells by 4G2, and a strong RT-PCR band from nucleic acid amplified from C6/36 culture fluid.

D2/ZK-P Vero: A Vero cell adapted version of D2/ZK-P. To develop a Vero cell adapted virus, Vero cells were infected with a high MOI of D2/ZK-P virus recovered from C6/36 cells. The first round of adaptation resulted in $7\times10^{6}$ PFU/ml of chimeric virus replicated from Vero cells. The adapted virus was plaque titrated in Vero cells and exhibited clear plaques with mixed sizes. Sequence of the virus identified 7 amino acid mutations (Table 5). Further Vero passages are expected to increase the most adapted chimeric virus in the seed preparation. Plaque purification of larger plaques of the chimera from infected Vero cells is also conducted to further determine the most useful mutation(s) for Vero cell adaption. Four of the identified mutation(s) are engineered into the chimeric constructs to improve D2/ZKV growth in Vero cells (Table 3), and further confirmed as critical mutations for chimeric D2/ZKV adaption and stability in Vero cells (see Example 2). The other 3 mutations at E-191, NS4B-24, and NS4B-245 were found not required for Vero cell adaption or stability.

TABLE 5

Mutations identified from D2/ZK-P Vero cell adapted virus

| NT position on chimeric DENV-2/ZKV | Protein-AA position based on Chimeric DENV-2/ZKV | DENV-2 AA position | ZIKV AA position | AA substitution (WT-Mut) |
|---|---|---|---|---|
| 1610 (A to T) | E-191 | NA | E-191 | His-Leu |
| 2348 (A to G) | E-465 | NA | E-465 | Gln-Arg |
| 2405 (T to C) | E-484 | NA | E-484 | Ile-Thr |
| 2431 (A to T) | E-493 | E-484 | NA | Ile-Phe |
| 3817 (A to C) | NS2A-99 | NS2A-99 | NA | Lys-Asn |
| 6941 (G to A) | NS4B-24 | NS4B-24 | NA | Glu-Gly |
| 7603 (A to T) | NS4B-245 | NS4B-245 | NA | Asn-Leu |

D2/ZK-V (also referred to as D2/ZK-VS): This chimeric virus includes the vaccine (V) strain PDK-53 backbone and the prM-E genes of Zika virus strain SPH2015 (S). The nucleotide and amino acid sequences of this chimeric virus are set forth herein as SEQ ID NO: 1 and SEQ ID NO: 2, respectively. No virus was recovered from C6/36 cells or Vero cells. The vaccine strain backbone is attenuated in C6/36 cells so virus recovery was not expected. The chimera was also not viable in Vero cells (similar to the D2/ZK-P described above). Vero-adaptation mutation(s) identified from D2/ZK-P Vero adapted virus are incorporated into the construct to make viable D2/ZK-V as a live-attenuated vaccine candidate.

D2/ZK-P2A: This chimeric virus includes the parental (P) D2 16681 backbone, but with a mutation that results in a methionine to valine substitution at residue 22 of the NS2A protein, and includes the prM-E gene from Zika virus strain SPH2015. The M22V mutation was identified as a strong Vero cell adaption mutation for the previous D2/WNV chimera. Vero cells were transfected with D2/ZK-P2A to evaluate virus growth. Transfected Vero were cultured at 37° C. or 28° C. to evaluate the temperature sensitivity of the chimeric construct. The results showed the NS2A-22 mutation did not significantly improve the virus stability in Vero cells.

D2/ZK-V2A: This chimeric virus includes the vaccine (V) D2 PDK-53 backbone, but with a mutation that results in a methionine to valine substitution at residue 22 of the NS2A protein, and includes the prM-E gene from Zika virus strain SPH2015. The nucleotide and amino acid sequences of this chimeric virus are set forth herein as SEQ ID NO: 5 and SEQ ID NO: 6, respectively. Vero cells were transfected with D2/ZK-V2A to evaluate virus growth. Transfected Vero cells were cultured at 37° C. or 28° C. to evaluate the temperature sensitivity of the chimeric virus. On day 11 post-transfection, RT-PCR analysis of the Vero-28° C. culture showed a strong positive result, but the Vero-37° C. culture was negative. This result suggested that the NS2A-22 mutation by itself is not sufficient for efficient Vero cell adaption of the chimeric virus.

D2/ZK-5V: This chimeric virus is generated using prM/E junction Strategy 2 shown in FIG. 1. The nucleotide and amino acid sequences of this chimeric virus are set forth herein as SEQ ID NO: 3 and SEQ ID NO: 4, respectively.

The Zika prM-E Gene Differences in Chimeric D2/ZKV Variants

The chimeric D2/ZKV constructs were made with the sequence of the ZIKV SPH2015 strain obtained from Genbank (Accession No. KU321639.1), before the PRVABC59 and R103451 strains were isolated from travelers acquiring ZIKV infection during the 2015 outbreak at CDC's diagnostic lab. The R103451 and PRVABC59 strains are now available as wild-type (wt) ZIKV controls, but the SPH2015 strain is not. There is only 1 amino acid (AA) sequence difference between SPH2015 and PRVABC59 (or R103451) within the prM-E gene region included in the D2/ZIKV chimeric constructs. The difference is at E protein amino acid position 23 position (E-23), with an isoleucine (Ile) in the SPH2015 strain and a valine (Val) in the PRVABC59 and R103451 strains. For the nucleotide sequences of the prM-E, there is one nucleotide difference (silent) between the chimeras and strain R103451, and six silent differences between the chimeras and the PRVABC59 strain.

Attenuation Characterization and Vaccine Development

The D2/ZKV-V vaccine candidate is evaluated for the previously established attenuation phenotypes of DENV-2 PDK-53 based vaccine candidates, which include small plaques in Vero or LLC-MK2 cells, temperature sensitivity in Vero or LLC-MK2 cells, poor growth in mosquito C6/36 cells, mouse neuro-attenuation, and diminished mosquito midgut infection/salivary gland dissemination/transmission (Huang et al., *J. Virol.* 77:11436-11447, 2003; Huang et al., *J. Virol.* 12:7300-7310, 2005; Huang et al., *PLoS Negl Trop Dis* 7(5):e2243, 2014). Vaccine candidates are also tested in a small animal model (mouse) and non-human primate for immunogenicity and protective efficacy.

Vaccine Applications

Based on previous success in DENV and WNV vaccine development using the DENV-2 PDK-53 based chimeric virus platform, it is expected that this platform can be used successfully for the development of a live-attenuated ZIKV vaccine. A chimeric D2/ZKV can be used alone (univalent) or in combination with a live-attenuated tetravalent DENV vaccine based on the same PDK-53 backbone (pentavalent vaccine). Combined vaccination strategies using both live-attenuated and inactivated ZIKV vaccine candidates can be evaluated.

Additional Chimeric Constructs

Additional chimeric D2/ZKV are generated using alternative junction site strategies, incorporating Vero cell adaptation mutations and/or introducing additional mutations to adjust the attenuation level or enhance the fitness/genetic stability of the chimeric D2/ZKV-V.

In one example, a chimeric D2/ZKV is generated using Strategy 2 shown in FIG. 1. In Strategy 2, the prM signal sequence includes the first five amino acids from DENV-2 PDK-53 and the last 13 amino acids from a ZIKV (such as SPH2015).

In other examples, a chimeric D2/ZIKV is generated by incorporating one or more Vero adaption mutations identified from Vero serial passages of D2/ZK-P seeds. In one example, any one of the mutations listed in Table 3 is incorporated into the D2/ZK vaccine virus to improve Vero cell adaption. In other examples, any combinations of the mutations listed in Table 3 are incorporated into the D2/ZKV vaccine to improve growth in Vero cells.

In another example, the chimeric D2/ZKV includes an Ile to Val substitution at E23 to match the sequence of ZIKV strains PRVABC59 and R103451.

Example 2: Chimeric D2/ZK Viruses for Vaccine Development

This example describes the generation and characterization of 10 additional chimeric DENV-2/ZKV (D2/ZK) constructs referred to as D2/ZKV-V2, P3.1, V3.1, V3.2, V3, P4, V4, P5 and V5 (see Table 6).

Based on the mutations identified from Vero cell adapted D2/ZKV-P described in Example 1 (Table 5), some of the mutations were incorporated into the chimeric construct to determine important mutations for Vero cell adaption and stability. Among the 7 mutations, 4 of them (E-465, E-484, E-493, and NS22A-99) were identified for Vero-cell-fitness enhancement of the chimeric D2/ZK viruses (Table 3). Interestingly, all three E mutations were within the transmembrane domain of the E protein, which would not affect the antigenic property of the E protein. In addition, two of them (E-484 and E-493) were near the chimeric E/NS1 junction site, suggesting the mutations might compensate the defect caused by the chimerization between the E proteins of ZIKV and DENV-2 (FIG. 1 shows an example with E-484T and E-493F in D2/ZKV). Table 3 also includes the NS4A-23 mutation that was identified during study of D2/ZKV-V2 construct. Without any Vero-cell-adapted mutations, both D2/ZK-P and D2/ZK-V are incompetent to replicate in Vero cells. It is possible to recover viable D2/ZK-P virus (on D2 16681 backbone) from C6/36 cells, but not D2/ZK-V virus (on D2 PDK-53 backbone).

Ten additional chimeric viruses that are viable in Vero cells were generated. However, each chimeric virus has a different plaque phenotype, growth efficiency and genetic stability. A brief summary of each chimeric virus is provided below:

D2/ZKV-V2: This chimeric virus construct contains E-465R and E-484T mutations, but is still not stable in Vero cells; after 2 passages in Vero cells it acquired multiple mutations. After plaque purification of five clonal V2 viruses, it was determined that three of them had acquired a NS4A-23 N mutation, including one that also acquired a NS2A-99 N mutation, and another clone acquired the E-493 F mutation. Based on these results, the NS4A-23 mutations was included in later constructs. The NS2A-99 and E-493 F mutations were previously identified in the original D2/ZKV-P adapted to Vero cells, which suggests these two mutations play important roles in Vero cell adaption.

D2/ZKV-P3.1 and V3.1: Both of these chimeric viruses were engineered with 3 of the 5 mutations described in Table 3 above—E-493, NS2A-99, and NS4A-23. Both viruses replicated well and produced uniform and clear plaques in Vero cells, however upon further sequencing analysis, it was determined that both recovered viruses acquired the E-465 R mutation. Although the P3.1 and V3.1 viruses were not sufficiently stable for vaccine development, based on the plaque phenotypes and the consistency of the E-465 mutation in both chimeras, it was hypothesized that chimeras containing the E-465R, E-493F, NS2A-99N, and NS4A-23N (RFNN) mutations would be stable for Vero cell amplification and would be potential live-attenuated ZIKV vaccine candidates. The nucleotide and amino acid sequences of the P-RFNN and V-RFNN chimeric viruses are set forth herein as SEQ ID NOs: 15-18.

D2/ZKV-V3.2: This chimeric virus, which has the E-465, E-484, and NS4A-23 mutations, was not stable enough for Vero cell growth. The virus grew poorly in Vero cells, and produced fuzzy pinpoint size plaques.

D2/ZKV-V3: This virus contains one additional NS2A-99 mutation relative to the V3.2 virus, but is still not stable enough for Vero cell growth. After 2-3 passages in Vero cells, the chimera acquired an additional E-493 F mutation (as with V2 described above).

D2/ZKV-P4 and V4: These chimeric viruses were constructed with the E-465, E-484, E-493, and NS2A-99 mutations. They grew well and produced uniform plaques and are therefore candidates for live-attenuated vaccine development. The nucleotide and amino acid sequences of the P4 and V4 chimeric viruses are set forth herein as SEQ ID NOs: 19-22.

D2/ZKV-P5 and V5: These two chimeras, on either the 16681 backbone (P5) or PDK-53 backbone (V5), grew very well in Vero cells and produced plaques that were larger than all other constructs described above. Growth kinetics studies of these two viruses were performed in Vero cells, which confirmed that both viruses replicate efficiently in Vero cells. The V5 virus replicated somewhat slower than the P5 virus, which is consistent with the slower growth of the D2 PDK-53 backbone virus than the D2 16681 virus. Plaque size of both P5 and V5 were smaller than that of the wt ZIKV, suggesting both replicate less efficiently than the wt ZIKV in Vero cells. However, the plaques of V5 virus were slightly smaller than those of P5 virus, which agrees with previous observation that chimeric virus based on the PDK-53 produces smaller plaques than chimeric viruses based on wt D2 16681 backbone. The V5 virus also retained the attenuation phenotype as its D2 PDK-53 backbone in C6/36 cells. In addition, a mouse study was conducted to measure the neurovirulence levels of the D2/ZK-P5 and -V5 viruses (see below). The results indicated both P5 and V5 are fully attenuated for newborn mice. Based on these results, these two viruses are good candidates for live-attenuated vaccine development. The nucleotide and amino acid sequences of the P5 and V5 chimeric viruses are set forth herein as SEQ ID NOs: 23-26.

TABLE 6

| Chimeric DEN-2/Zika viruses | | | | | | | | |
|---|---|---|---|---|---|---|---|---|
| | | Nt and AA position based on chimeric D2/ZIKV genome | | | | | | |
| Virus Names (D2/ZIKV-backbone)* | | Nt | 2348 (A-G) E465 | 2405 (T-C) E484 | 2431 (A-T) E493 | 3819 (G-T) NS2A-99 | 6487 (G-A) NS4A-23 | Growth in |
| 16681 | PDK-53 | AA** | (Q-R) | (I-T) | (I-F) | (K-N) | (D-N) | Vero cells |
| P | V | wt* | Q | I | I | K | D | Not viable in Vero |
| | V2 | | R | T | I | K | D | Not stable, acquired multiple mutations |
| P3.1 | V3.1 | | Q | I | F | N | N | Not stable acquired E465R |
| P-RFNN | V-RFNN | | R | I | F | N | N | Evolved from 3.1 viruses; potential candidates |
| — | V3.2 | | R | T | I | K | N | Poor growth, pinpoint plaques |
| P3 | V3 | | R | T | I | N | N | Not stable, evolved to P5 or V5 like viruses |
| P4 | V4 | | R | T | F | N | D | Uniform plaques; potential candidates |
| P5 | V5 | | R | T | F | N | N | Uniform plaques; potential candidates |

Underline indicates potential live-attenuated ZIKV vaccine candidates

*Chimeric viruses based on D2 16681 parental virus named as D2/ZIKV-P#; Chimeras based on D2 PDK-53 vaccine virus named as D2/ZIKV-V#

**Mutations in bold

Attenuation Characterization

Vaccine candidate viruses were characterized for the previously established attenuation phenotypes of DENV-2 PDK-53. These include small plaques in Vero or LLC-MK2 cells, temperature sensitivity in Vero or LLC-MK2 cells, poor growth in mosquito C6/36 cells, mouse neuro-attenuation, and diminished mosquito midgut infection/salivary gland dissemination/transmission.

Plaque size in Vero cells: The four chimeras V4, V5, P4 and P5 all exhibited smaller plaques than the wt ZIKV. Plaques of the chimeras in the P backbone were somewhat larger than plaques produced from their counterpart V chimeras. In addition, plaques of P5 and V5 were larger than the P4 and V4 versions. The Vero-adapted P-FRNN and V-RFNN (evolved from P3.1 and V3.1) also showed similarly small plaques as P4 and V4 viruses.

Figure 2B:
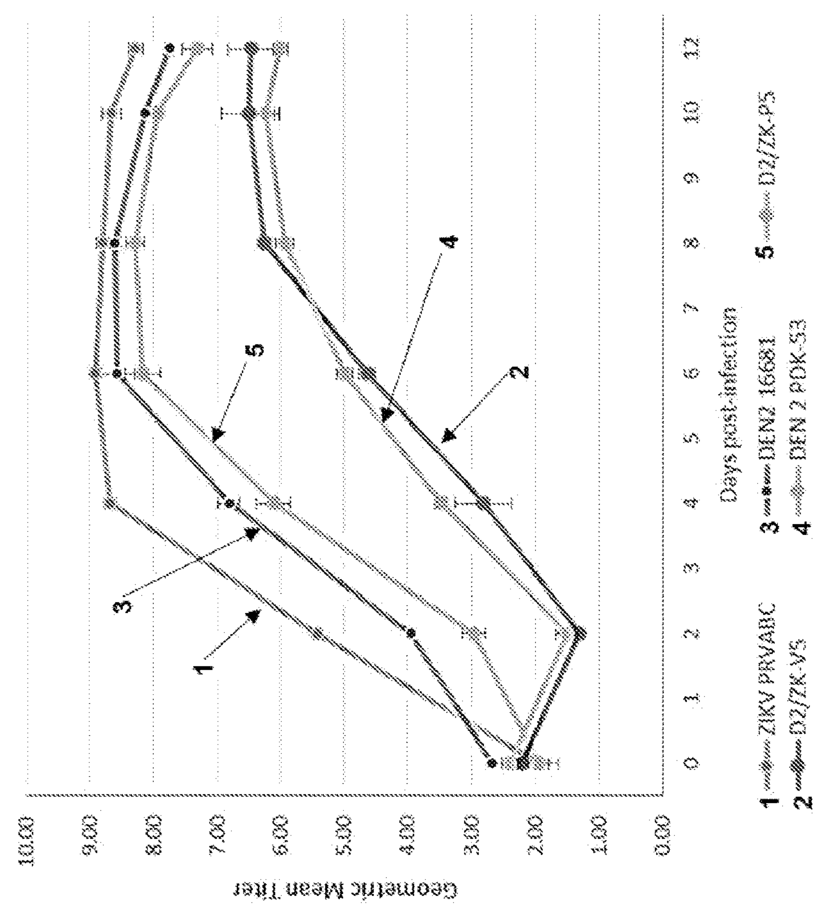
FIGS. 2A-2B are graphs showing growth kinetics of D2/ZK-P5 and D2/ZK-V5.
Figure 2A:
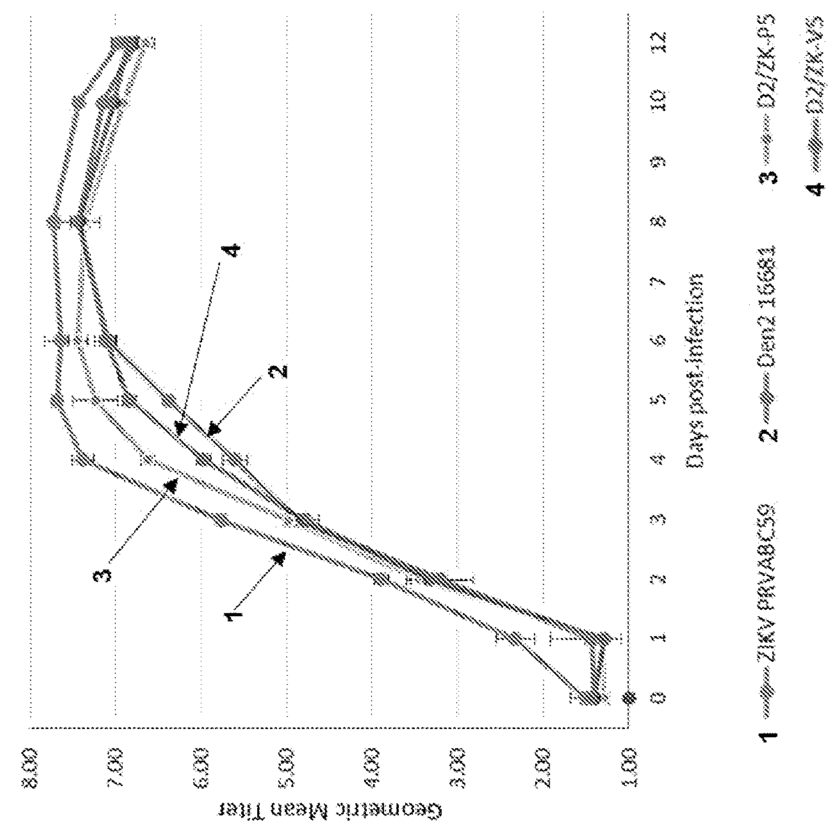

Growth kinetics in Vero cells: Viral growth of P5 and V5 viruses was tested in Vero cells. As shown in FIG. 2A, both viruses replicated efficiently in Vero cells, but V5 was somewhat slower than P5, and both were slower than wt ZIKV.

Growth Kinetics in C6/36 cells: Growth kinetics of the P5 and V5 viruses was evaluated in C6/36 cells. The results are shown in FIG. 2B. Although P5 still grew efficiently in C6/36 cells, the growth was significantly lower than the wt ZIKV PRVABC59, and somewhat lower than its wt DENV-2 16681 backbone virus. The V5 virus retained the attenuation phenotype as its DENV-2 PDK-53 vaccine backbone virus in the C6/36 cells. It is believed that most V viruses will retain the crippled-replication attenuation phenotype of their backbone DENV-2 PDK-53 vaccine, while most P viruses may still replicate well in C6/36 cells. Although the P viruses may not have the in vitro attenuation phenotype in C6/36 cells, they may still be attenuated in whole live mosquitoes due to the chimerization between DENV-2 and ZIKV.

Figure 3:
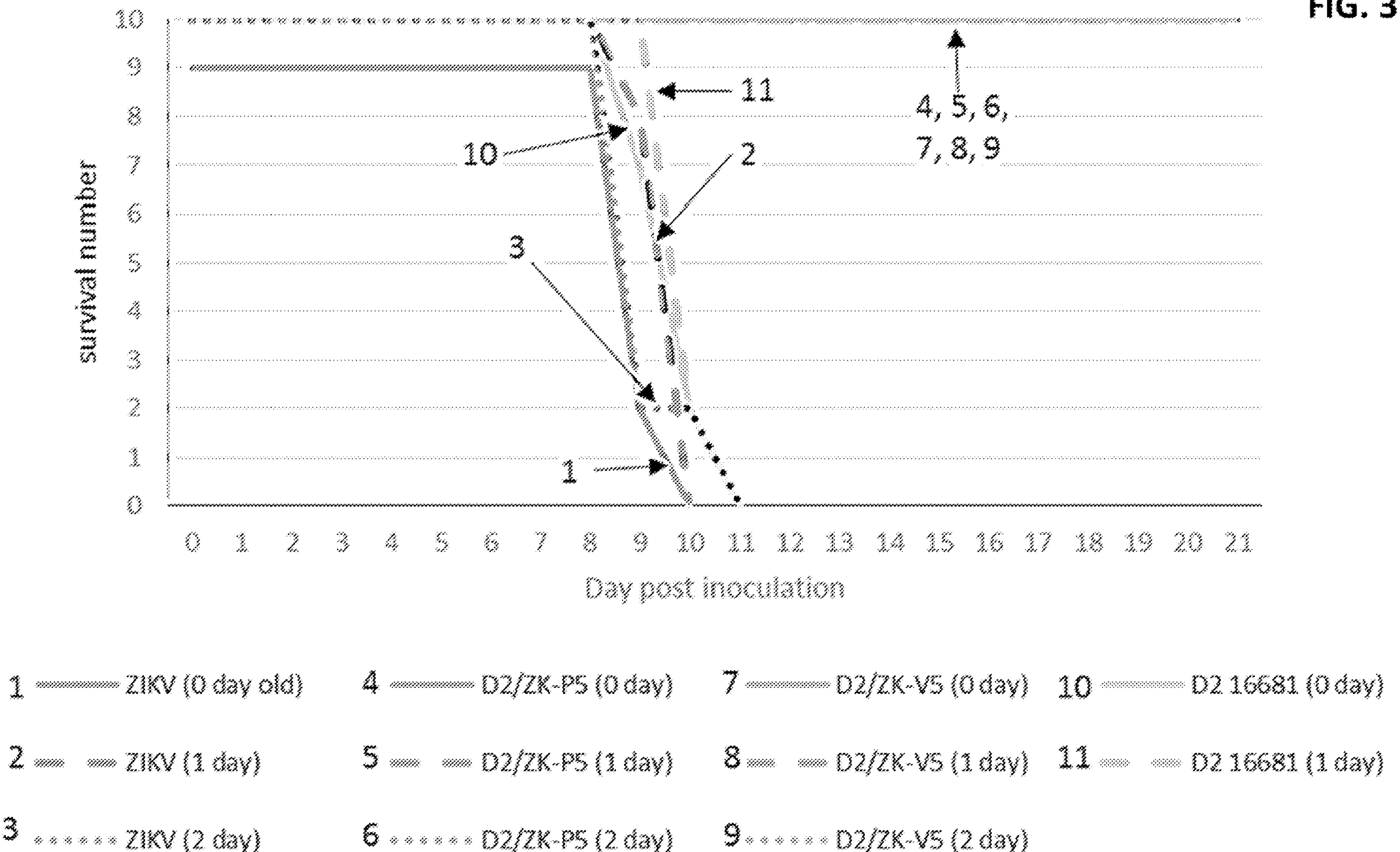
FIG. 3 is a graph showing neurovirulence of wild-type and D2/ZK chimeric viruses in mice. Litters of newborn CD-1 (ICR) mice 0-2 days after birth were placed into groups of 10 according to their age, and inoculated with $10^4$ pfu/30 μl of ZIKV, D2/ZK-P5, D2/ZK-V5 or D2 16681 through intracranial inoculation. All 29 mice (0-, 1-, or 2-days old) challenged with wild-type ZIKV became severely ill or died between 9 and 11 days post-inoculation. The 20 mice (0- or 1-day old) that received wild-type D2 16681 virus also succumbed to virus infection between about days 10 and 11. All 30 mice inoculated with either D2/ZK-P5 or D2/ZK-V5 survived virus inoculation.

Mouse neurovirulence: P5 and V5 viruses were compared with the wt ZIKA and D2 16681 viruses in newborn ICR mice. An initial test in 7-day old ICR (CD-1) mice showed that the newborn mice at 7-days old already developed resistance to wt ZIKV and D2 16681 intracranial challenge. A neurovirulence challenge ICR mouse model for D2 16681 virus using 0-1 day old mice was previously established. Therefore, in the second experiment, 0-2 day old newborn ICR mice were used. Litters of newborn mice (day 0-2 after birth) were grouped in 9-10 newborns/litter inoculated intracranially with $10^4$ pfu of virus. All 29 baby mice (3 litters) inoculated with wt ZIKV died with 8.4±0.49 average survival days (ASD±SD), and all 20 mice (2 litters) inoculated with D2 16681 also died with ASD of 9.05±0.59 (FIG. 3). Strikingly, none of the 30 mice inoculated with either P5 or V5 viruses became ill, and there was no weight loss throughout the experiment.

Immunogenicity and Protective Efficacy of the Vaccine Candidates:

Studies are conducted to evaluate the immunogenicity and protective efficacy of the vaccine candidates. Mice are administered either single or double dose vaccine schedules, and are challenged with a lethal dose of wt ZIKV PRV-ABC59 a month after final immunization. It is expected that the chimeric viruses will induce strong anti-ZIKV neutralization antibodies and protect mice from lethal challenge.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A nucleic acid chimera encoding a chimeric dengue virus serotype 2 (DENV-2)/Zika virus (ZIKV), wherein the ZIKV premembrane (prM) and envelope (E) genes are inserted into the genomic background of a DENV-2 strain, wherein the nucleic acid chimera comprises the following genomic arrangement: DENV-2 5' non-coding region, DENV-2 capsid (C) gene, ZIKV prM/E genes, DENV-2 non-structural (NS) 1-NS5 genes, and DENV-2 3' non-coding region, wherein:

the nucleic acid chimera encodes a modified prM signal sequence comprising the first three amino acids of the DENV-2 prM signal sequence fused to the last 15 amino acids of the ZIKV prM signal sequence; or the first five amino acids of the DENV-2 prM signal sequence fused to the last 13 amino acids of the ZIKV prM signal sequence;

the nucleic acid chimera encodes a chimeric ZIKV/DENV-2 E protein, wherein the last 14 amino acids of the E protein are from DENV-2; and the nucleic acid chimera comprises:

(i) four Vero cell adaptation mutations, wherein the mutations result in:

a glutamine to arginine substitution at residue 465 of the E protein;

an isoleucine to phenylalanine substitution at residue 493 of the E protein;

a lysine to asparagine substitution at residue 99 of the NS2A protein; and an aspartic acid to asparagine substitution at residue 23 of the NS4A protein;

(ii) four Vero cell adaptation mutations, wherein the mutations result in:

a glutamine to arginine substitution at residue 465 of the E protein;

an isoleucine to threonine substitution at residue 484 of the E protein;

an isoleucine to phenylalanine substitution at residue 493 of the E protein; and a lysine to asparagine substitution at residue 99 of the NS2A protein; or (iii) five Vero cell adaptation mutations, wherein the mutations result in:

a glutamine to arginine substitution at residue 465 of the E protein;

an isoleucine to threonine substitution at residue 484 of the E protein;

an isoleucine to phenylalanine substitution at residue 493 of the E protein;

a lysine to asparagine substitution at residue 99 of the NS2A protein; and an aspartic acid to asparagine substitution at residue 23 of the NS4A protein.

2. The nucleic acid chimera of claim 1, wherein the DENV-2 strain is an attenuated DENV-2 strain.

3. The nucleic acid chimera of claim 2, wherein:

the genome of the attenuated DENV-2 comprises a mutation in the 5' non-coding region at nucleotide position 57;

the genome of the attenuated DENV-2 comprises a mutation at nucleotide position 2579 that results in the presence of an aspartate at amino acid residue 53 of the NS1 protein; or the genome of the attenuated DENV-2 comprises a mutation at nucleotide position 5270 that results in the presence of a valine at amino acid residue 250 of the NS3 protein.

4. The nucleic acid chimera of claim 2, wherein the attenuated DENV-2 strain is strain PDK-53.

5. The nucleic acid chimera of claim 1, wherein the DENV-2 strain is a wild-type DENV-2 strain.

6. The nucleic acid chimera of claim 1, wherein the ZIKV is strain SPH2015, PRVABC59 or R103451.

7. The nucleic acid chimera of claim 1, wherein:

the first three amino acids of the DENV-2 prM signal sequence comprises amino acids 101-103 of SEQ ID NO: 12;

the last 15 amino acids of the ZIKV prM signal sequence comprises amino acids 108-122 of SEQ ID NO: 8; or the first three amino acids of the DENV-2 prM signal sequence comprises amino acids 101-103 of SEQ ID NO: 12 and the last 15 amino acids of the ZIKV prM signal sequence comprises amino acids 108-122 of SEQ ID NO: 8.

8. The nucleic acid chimera of claim 1, wherein:

the first five amino acids of the DENV-2 prM signal sequence comprises amino acids 101-105 of SEQ ID NO: 12;

the last 13 amino acids of the ZIKV prM signal sequence comprises amino acids 110-122 of SEQ ID NO: 8; or the first five amino acids of the DENV-2 prM signal sequence comprises amino acids 101-105 of SEQ ID NO: 12 and the last 13 amino acids of the ZIKV prM signal sequence comprises amino acids 110-122 of SEQ ID NO: 8.

9. The nucleic acid chimera of claim 1, wherein the last 14 amino acids of the DENV-2 E protein comprises amino acids 777-790 of SEQ ID NO: 2.

10. The nucleic acid chimera of claim 1, comprising four Vero cell adaptation mutations, wherein the mutations result in:

a glutamine to arginine substitution at residue 465 of the E protein;

an isoleucine to phenylalanine substitution at residue 493 of the E protein;

a lysine to asparagine substitution at residue 99 of the NS2A protein; and an aspartic acid to asparagine substitution at residue 23 of the NS4A protein.

11. The nucleic acid chimera of claim 1, comprising four Vero cell adaptation mutations, wherein the mutations result in:

a glutamine to arginine substitution at residue 465 of the E protein;

an isoleucine to threonine substitution at residue 484 of the E protein;

an isoleucine to phenylalanine substitution at residue 493 of the E protein; and a lysine to asparagine substitution at residue 99 of the NS2A protein.

12. The nucleic acid chimera of claim 1, comprising five Vero cell adaptation mutations, wherein the mutations result in:

a glutamine to arginine substitution at residue 465 of the E protein;

an isoleucine to threonine substitution at residue 484 of the E protein;

an isoleucine to phenylalanine substitution at residue 493 of the E protein;

a lysine to asparagine substitution at residue 99 of the NS2A protein; and an aspartic acid to asparagine substitution at residue 23 of the NS4A protein.

13. The nucleic acid chimera of claim 1, comprising a nucleic acid sequence at least 95% identical to SEQ ID NO: 15, SEQ ID NO: 17, SEQ ID NO: 19, SEQ ID NO: 21, SEQ ID NO: 23 or SEQ ID NO: 25.

14. The nucleic acid chimera of claim 13, comprising the nucleic acid sequence of SEQ ID NO: 15, SEQ ID NO: 17, SEQ ID NO: 19, SEQ ID NO: 21, SEQ ID NO: 23 or SEQ ID NO: 25.

15. The nucleic acid chimera of claim 1, wherein the nucleic acid chimera encodes an amino acid sequence at least 95% identical to SEQ ID NO: 16, SEQ ID NO: 18, SEQ ID NO: 20, SEQ ID NO: 22, SEQ ID NO: 24 or SEQ ID NO: 26.

16. The nucleic acid chimera of claim 15, wherein the nucleic acid chimera encodes the amino acid sequence of SEQ ID NO: 16, SEQ ID NO: 18, SEQ ID NO: 20, SEQ ID NO: 22, SEQ ID NO: 24 or SEQ ID NO: 26.

17. A chimeric flavivirus comprising the nucleic acid chimera of claim 1.

18. An immunogenic composition comprising the chimeric flavivirus of claim 17 and a pharmaceutically acceptable carrier.

19. A method of eliciting an immune response against Zika virus (ZIKV) in a subject, comprising administering to the subject the chimeric flavivirus of claim 17.

20. The method of claim 19, further comprising administering an inactivated Zika virus vaccine.

21. The method of claim 19, wherein the subject is a human.

22. A nucleic acid chimera encoding a chimeric dengue virus serotype 2 (DENV-2)/Zika virus (ZIKV), wherein the ZIKV premembrane (prM) and envelope (E) genes are inserted into the genomic background of a DENV-2 strain, wherein the nucleic acid chimera comprises the following genomic arrangement: DENV-2 5' non-coding region, DENV-2 capsid (C) gene, ZIKV prM/E genes, DENV-2 non-structural (NS) 1-NS5 genes, and DENV-2 3' non-coding region, wherein:

the nucleic acid chimera encodes a modified prM signal sequence comprising the first three amino acids of the DENV-2 prM signal sequence fused to the last 15 amino acids of the ZIKV prM signal sequence; or the first five amino acids of the DENV-2 prM signal sequence fused to the last 13 amino acids of the ZIKV prM signal sequence;

the nucleic acid chimera encodes a chimeric ZIKV/DENV-2 E protein, wherein the last 13 amino acids of the E protein are from DENV-2; and the nucleic acid chimera comprises:

(i) four Vero cell adaptation mutations, wherein the mutations result in:

a glutamine to arginine substitution at residue 465 of the E protein;

an isoleucine to phenylalanine substitution at residue 493 of the E protein;

a lysine to asparagine substitution at residue 99 of the NS2A protein; and an aspartic acid to asparagine substitution at residue 23 of the NS4A protein;

(ii) four Vero cell adaptation mutations, wherein the mutations result in:

a glutamine to arginine substitution at residue 465 of the E protein;

an isoleucine to threonine substitution at residue 484 of the E protein;

an isoleucine to phenylalanine substitution at residue 493 of the E protein; and a lysine to asparagine substitution at residue 99 of the NS2A protein; or (iii) five Vero cell adaptation mutations, wherein the mutations result in:

a glutamine to arginine substitution at residue 465 of the E protein;

an isoleucine to threonine substitution at residue 484 of the E protein;

an isoleucine to phenylalanine substitution at residue 493 of the E protein;

a lysine to asparagine substitution at residue 99 of the NS2A protein; and an aspartic acid to asparagine substitution at residue 23 of the NS4A protein.

23. The nucleic acid chimera of claim 22, wherein the DENV-2 strain is an attenuated DENV-2 strain.

24. The nucleic acid chimera of claim 22, wherein the ZIKV is strain SPH2015, PRVABC59 or R103451.

25. A chimeric flavivirus comprising the nucleic acid chimera of claim 22.

26. An immunogenic composition comprising the chimeric flavivirus of claim 25 and a pharmaceutically acceptable carrier.

27. A method of eliciting an immune response against Zika virus (ZIKV) in a subject, comprising administering to the subject the chimeric flavivirus of claim 25.

* * * * *